US012653168B2

(12) United States Patent
Devalaraja-Narashimha et al.

(10) Patent No.: US 12,653,168 B2
(45) Date of Patent: Jun. 16, 2026

(54) COMPLEMENT FACTOR H GENE KNOCKOUT RAT AS A MODEL OF C3 GLOMERULOPATHY

(71) Applicant: Regeneron Pharmaceuticals, Inc., Tarrytown, NY (US)

(72) Inventors: Kishor Devalaraja-Narashimha, Yorktown Heights, NY (US); Jeffrey D. Lee, New York, NY (US); Lori Morton, Chappaqua, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 851 days.

(21) Appl. No.: 17/275,096

(22) PCT Filed: Sep. 12, 2019

(86) PCT No.: PCT/US2019/050792
§ 371 (c)(1),
(2) Date: Mar. 10, 2021

(87) PCT Pub. No.: WO2020/056122
PCT Pub. Date: Mar. 19, 2020

(65) Prior Publication Data
US 2022/0053741 A1    Feb. 24, 2022

Related U.S. Application Data

(60) Provisional application No. 62/730,690, filed on Sep. 13, 2018.

(51) Int. Cl.
*A01K 67/0276*        (2024.01)

(52) U.S. Cl.
CPC .... *A01K 67/0276* (2013.01); *A01K 2217/075* (2013.01); *A01K 2227/105* (2013.01); *A01K 2267/035* (2013.01); *A01K 2267/0393* (2013.01)

(58) Field of Classification Search
CPC .......... A01K 67/0276; A01K 2217/075; A01K 2227/105; A01K 2267/035; A01K 2267/0393
See application file for complete search history.

(56) References Cited

U.S. PATENT DOCUMENTS

| | | | |
|---|---|---|---|
| 5,942,435 | A | 8/1999 | Wheeler |
| 6,586,251 | B2 | 7/2003 | Economides et al. |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 9,795,121 | B2 | 10/2017 | Hu et al. |
| 10,329,582 | B2 | 6/2019 | Lee et al. |
| 10,385,359 | B2 | 8/2019 | Lee et al. |
| 2008/0078000 | A1 | 3/2008 | Poueymirou et al. |

| | | | |
|---|---|---|---|
| 2012/0159653 | A1* | 6/2012 | Weinstein .......... C12N 15/8509 800/15 |
| 2014/0178879 | A1 | 6/2014 | Economides et al. |
| 2014/0235933 | A1 | 8/2014 | Lee et al. |
| 2014/0310828 | A1 | 10/2014 | Lee et al. |
| 2015/0376628 | A1 | 12/2015 | Schoenherr et al. |
| 2015/0376651 | A1 | 12/2015 | Frendewey et al. |
| 2016/0145646 | A1 | 5/2016 | Frendewey et al. |
| 2018/0243450 | A1 | 8/2018 | Devalaraja-Narashimha et al. |

FOREIGN PATENT DOCUMENTS

| | | |
|---|---|---|
| WO | WO 2014/130706 A1 | 8/2014 |
| WO | WO 2014/172489 A2 | 10/2014 |
| WO | 2015/042557 A1 | 3/2015 |
| WO | 2015/088643 A1 | 6/2015 |
| WO | 2015/200334 A1 | 12/2015 |
| WO | 2015/200805 A2 | 12/2015 |
| WO | 2016/044745 A1 | 3/2016 |
| WO | 2016/081923 A2 | 5/2016 |
| WO | 2017/087780 A1 | 5/2017 |
| WO | 2018/157027 A1 | 8/2018 |
| WO | 2020/056122 A1 | 3/2020 |

OTHER PUBLICATIONS

Vik DP, et. al. J Biol Chem. Feb. 25, 1990;265(6):3193-201 (Year: 1990).*
Fontaine M, et. al. Biochem J. Mar. 15, 1989;258(3):927-30 (Year: 1989).*
Demberg T, et. al. Scand J Immunol. Aug. 2002;56(2):149-60 (Year: 2002).*
Pickering MC, et. al. Nat Genet. Aug. 2002;31(4):424-8 (Year: 2002).*
Klein R. et. al. Arch Ophthalmol. 2009; 127(2):193-199 (Year: 2009).*
Tong, C., et. al. Nature 467, 211-213 (2010) (Year: 2010).*
Riedl, M., Thorner, P. & Licht, C. C3 Glomerulopathy. Pediatr Nephrol 32, 43-57 (2017) (Year: 2017).*
Sengupta P. Int J Prev Med. Jun. 2013;4(6):624-30 (Year: 2013).*
Noris M. et. al. American Journal of Kidney Diseases, vol. 66, Issue 2, 2015, pp. 359-375 (Year: 2015).*
Vik DP, et. al. J Biol Chem. Nov. 15, 1988;263(32):16720-4 (Year: 1988).*
Ren G, et. al. Kidney Int. Sep. 2003;64(3):914-22 (Year: 2003).*
Rats!. Nat Methods 7, 413 (2010) (Year: 2010).*
Bao, Lihua, et. al. Journal of the American Society of Nephrology 22.2 (2011): 285-295 (Year: 2011).*
Pickering, Matthew C., et al. The Journal of experimental medicine 204.6 (2007): 1249-1256 (Year: 2007).*

(Continued)

*Primary Examiner* — Marcia S Noble
*Assistant Examiner* — Zanna Maria Beharry
(74) *Attorney, Agent, or Firm* — Alston & Bird LLP

(57)        ABSTRACT

Rat cells and rats comprising an inactivated Cfh locus and methods of making and using such rat cells and rats are provided. The rats comprising an inactivated Cfh locus model C3 glomerulopathy (C3G). Methods are provided for using such rats comprising an inactivated Cfh locus to assess in vivo efficacy of putative C3G therapeutic agents.

28 Claims, 13 Drawing Sheets
Specification includes a Sequence Listing.

(56) References Cited

OTHER PUBLICATIONS

Migliori, M., et al. International Journal of Immunopathology and Pharmacology 18.4 (2005): 779-790 (Year: 2005).*

Male, Dean A., et al. Molecular immunology 37.1-2 (2000): 41-52 (Year: 2000).*

Obrenović, Radmila, et al. Jugoslovenska medicinska biohemija 25.1 (2006): 21-25 (Year: 2006).*

U.S. Appl. No. 62/730,690, Sep. 13, 2018, Expired

PCT/US2019/050792, Sep. 12, 2019, WO 2020/056122, Expired

Atkinson, et al., "Complement factor H and the hemolytic uremic syndrome," J. Exp. Med. 204(6):1245-1248, (2007).

Ault, et al., "Human Factor H Deficiency: Mutations in Framework Cysteine Residues and Block in H Protein Secretion and Intracellular Catabolism" The Journal of Biological Chemistry, 272(40):25168-25175 (Oct. 3, 1997).

Barbour, et al., "Complement receptor 3 mediates renal protection in experimental C3 glomerulopathy," Kidney Int. 89(4):823-832, (2016).

Barbour, et al., "Dense Deposit Disease and C3 Glomerulopathy," Seminars in Nephrology, 33(6):463-507, (Nov. 2013).

Barbour, et al., "Update on C3 glomerulopathy," Nephrol. Dial. Transplant., 31(5):717-725 (2016).

Barthold, "Genetically altered mice: phenotypes, no phenotypes, and Faux phenotypes," Genetica, 122(1):75-88, (2004).

Birling, et al., "Modeling human disease in rodents by CRISPR/Cas9 genome editing," Mamm. Genome, 28(7-8):291-301, (2017).

Boon, et al., "The spectrum of phenotypes caused by variants in the CFH gene," Mol. Immunol. 46(8-9):1573-1594, (2009).

Brevini, et al., "No. shortcuts to pig embryonic stem cells," Theriogenology, 74(4):544-550, (2010).

Brevini, et al., "Porcine embryonic stem cells: Facts, challenges and hopes," Theriogenology, 68 Suppl. 1:S206-S213, (2007).

Burova, et al., "Characterization of the Anti-PD-1 Antibody REGN2810 and Its Antitumor Activity in Human PD-1 Knock-In Mice," Mol. Cancer Ther., 16(5):861-870, (2017).

Cao, et al., "Isolation and Culture of Primary Bovine Embryonic Stem Cell Colonies by a Novel Method," J. Exp. Zool. A. Ecol. Genet. Physiol., 311(5):368-376, (2009).

Clark, et al., "A future for transgenic livestock," Nat. Rev. Genet., 4(10):825-833, (2003).

Cook, et al., "Histopathology of MPGN and C3 glomerulopathies," Nat. Rev. Nephrol., 11(1):14-22, (Jan. 2015).

Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.

Dennis, "Welfare Issues of Genetically Modified Animals," ILAR J., 43(2):100-109, (2002).

Devalaraja-Narashimha, et al., "Novel approaches for modeling C3 glomerulopathy in mouse and rat," Molecular Immunology, Pergamon, GB, vol. 102, p. 143, (Sep. 16, 2018).

Dragon-Durey, et al., "Heterozygous and Homozygous Factor H Deficiencies Associated with Hemolytic Uremic Syndrome or Membranoproliferative Glomerulonephritis: Report and Genetic Analysis of 16 Cases," J. Am. Soc. Nephrol., 15:787-795, (2004).

Frendewey, et al., "The Loss-of-Allele Assay for ES Cell Screening and Mouse Genotyping," Methods Enzymol., 476:295-307, (2010).

Genoway, "Humanized Mouse Model," retrieved from https://www.genoway.com/services/customized-mouse/knockin-models/humanisation.htm on May 12, 2018.

Gomez, et al., "Derivation of cat embryonic stem-like cells from in vitro-produced blastocysts on homologous and heterologous feeder cells," Theriogenology, 74(4): 498-515, (2010).

Graham, et al., "Resources for the design of CRISPR gene editing experiments," Genome Biol., 16:260, (2015).

Harari, et al., "Bridging the Species Divide: Transgenic Mice Humanized for Type-I Interferon Response," PLoS One, 9(1): e84259, (2014).

Herlitz, et al., "Pathology after Eculizumab in Dense Deposit Disease and C3 GN," J. Am. Soc. Nephrol., 23:1229-1237, (2012).

Herndler-Brandstetter, et al., "Humanized mouse model supports development, function, and tissue residency of human natural killer cells," Proc. Natl. Acad. Sci. U.S.A., 114(45):E9626-E9634, (2017).

Houdebine, "Methods to Generate Transgenic Animals," pp. 31-48 in "Genetic Engineering in Livestock: New Applications and Interdisciplinary Perspectives," Ed. Engelhard et al., (2009).

Jansen, et al., "In situ complement activation in porcine membranoproliferative glomerulonephritis type II," Kidney Int., 53(2):331-349, (1998).

Jean, et al., "Pluripotent genes in avian stem cells," Dev. Growth Differ., 55(1): 41-51, (2013).

Kawamata, et al., "Generation of genetically modified rats from embryonic stem cells," Proc. Natl. Acad. Sci. U.S.A., 7(32):14223-14228, (2010).

Kumar, et al., "Transgenic Mouse Technology: Principles and Methods," Methods Mol. Biol., 590:335-362, (2009).

Le Quintrec, et al., "Eculizumab for Treatment of Rapidly Progressive C3 Glomerulopathy," Am. J. Kidney Dis., 65(3):484-489, (2015).

Levy, et al., "H deficiency in two brothers with atypical dense intramembranous deposit disease," Kidney Int., 30(6):949-956, (1986).

Lute, et al., "Human CTLA4 knock-in mice unravel the quantitative link between tumor immunity and autoimmunity induced by anti-CTLA-4 antibodies," Blood, 106(9):3127-3133, (2005).

Mullins, et al., "Renal disease pathophysiology and treatment: contributions from the rat," Dis. Model Mech. 9(12):1419-1433, (2016).

Mullins, et al., "Transgenesis in the rat and larger mammals," J. Clin. Invest. 97(7):1557-1560, (1996).

Munoz, et al., "Conventional pluripotency markers are unspecific for bovine embryonic-derived cell-lines," Theriogenology, 69(9): 1159-1164, (2008).

Nester, et al., "Complement inhibition in C3 glomerulopathy," Seminars in Immunology, 28:241-249 (2016).

Niemann, "Transgenic farm animals get off the ground. Transgenic Animals in Agriculture, Conference Tahoe City, California, USA. Aug. 24-27, 1997." Transgenic Res., 7(1): 73-75, (1998).

Ortiz, et al., "Translational value of animal models of kidney failure," Eur. J. Pharmacol. 759:205-220, (2015).

Paris, et al., "Equine embryos and embryonic stem cells: defining reliable markers of pluripotency, " Theriogenology, 74(4): 516-524, (2010).

Pickering, et al., "C3 glomerulopathy: consensus report," Kidney International, 84:1079-1089, (2013).

Pickering, et al., "Prevention of C5 activation ameliorates spontaneous and experimental glomerulonephritis in factor H-deficient mice," Proc. Natl. Acad. Sci. U.S.A., 103(25):9649-9654, (Jun. 20, 2006).

Pickering, et al., "Uncontrolled C3 activation causes membranoproliferative glomerulonephritis in mice deficient in complement factor H," Nature Genetics, 31:424-428, (Aug. 2002).

Poueymirou, et al., "F0 generation mice fully derived from gene-targeted embryonic stem cells allowing immediate phenotypic analyses," Nat. Biotechnol., 25(1):91-99, (2007).

Rezza, et al., "Unexpected genomic rearrangements at targeted loci associated with CRISPR/Cas9-mediated knock-in," Sci. Rep., 9(1):3486, (2019).

Ristevski, "Making better transgenic models: conditional, temporal, and spatial approaches," Mol. Biotechnol., 29(2):153-163, (2005).

Rogers, et al., "Disruption of the CFTR Gene Produces a Model of Cystic Fibrosis in Newborn Pigs," Science, 321(5897):1837-1841, (2008).

Rusai, et al., "A rare case: childhood-onset C3 glomerulonephritis due to homozygous factor H deficiency," CEN Case Rep., 2:234-238, (2013).

Servais, et al., "Heterogeneous pattern of renal disease associated with homozygous Factor H deficiency," Human Pathology, 42:1305-1311, (2011).

(56)  References Cited

OTHER PUBLICATIONS

Servais, et al., "Primary glomerulonephritis with isolated C3 deposits: a new entity which shares common genetic risk factors with haemolytic uraemic syndrome," J. Med. Genet., 44:193-199, (2007).

Sigmund, "Viewpoint: Are Studies in Genetically Altered Mice Out of Control?," Arterioscler. Thromb. Vasc. Biol., 20(6):1425-1429, (2000).

Sparta, et al., "Membranoproliferative glomerulonephritis and C3 glomerulopathy in children: change in treatment modality? A report of a case series," Clinical Kidney Journal, 11(4):479-490, (2018).

Valenzuela, et al., "High-throughput engineering of the mouse genome coupled with high-resolution expression analysis," Nat. Biotechnol., 21(6):652-659, (2003).

Vivarelli, "Eculizumab for the Treatment of Dense-Deposit Disease," N. Engl. J. Med., 366(12):1163-1165, (Mar. 22, 2012).

Wakchaure, et al., "Transgenic Animals: A Review on its Various Dimensions and Applications in Animal Biotechnology," International Journal of Emerging Technology and Advanced Engineering, 5(11):210-213, (2015).

Zhao, et al., "Inconsistency between hepatic expression and serum concentration of transthyretin in mice humanized at the transthyretin locus," Genes to Cells, 13:1257-1268, (2008).

Zhou, et al., "Developing tTA transgenic rats for inducible and reversible gene expression," Int. J. Biol. Sci., 5(2):171-181, (2009).

Zipfel, et al., "The role of complement in C3 glomerulopathy," Molecular Immunology, 67:21-30, (2015).

WIPO Application No. PCT/US2019/050792, PCT International Search Report and Written Opinion of the International Searching Authority mailed Nov. 27, 2019.

Alexander, et al., "The C5a receptor has a key role in immune complex glomerulonephritis in complement factor H-deficient mice," Kidney Int., 82(9):961-969, (2012).

Yang et al., "Differential expression of complement genes in mammalian eyes," Invest. Ophthalmol. Vis. Sci. 63(7):4594-F0386, (Jun. 2022).

Demberg, et al., "Rat complement factor H: molecular cloning, sequencing and quantification with a newly established ELISA," Scand. J. Immunol., 56(2):149-160, (2002).

Fontaine, et al., "Truncated forms of human complement factor H," Biochem. J., 258(3):927-930, (1989).

Klein, et al., "Serum cystatin C level, kidney disease markers, and incidence of age-related macular degeneration: the Beaver Dam Eye Study," Arch. Ophthalmol., 127(2):193-199, (2009).

Noris, et al., "Glomerular Diseases Dependent on Complement Activation, Including Atypical Hemolytic Uremic Syndrome, Membranoproliferative Glomerulonephritis, and C3 Glomerulopathy: Core Curriculum 2015," Am. J. Kidney Dis., 66(2):359-375, (2015).

Riedl, et al., "C3 Glomerulopathy," Pediatr. Nephrol., 32(1):43-57, (2017).

Sengupta, "The Laboratory Rat: Relating Its Age With Human's," Int. J. Prev. Med., 4(6):624-630, (2013).

Tong, et al., "Production of p53 gene knockout rats by homologous recombination in embryonic stem cells," Nature, 467(7312):211-213, (2010).

Vik, et al., "Identification and sequence analysis of four complement factor H-related transcripts in mouse liver," J. Biol. Chem., 265(6):3193-3201, (1990).

Dutta et al., Men and mice: Relating their ages, Life Sci. 152:244-248, (2016).

National Kidney Foundation, "What is the Difference Between sCr,eGFR, ACR, and BUN?", Mar. 2, 2018.

* cited by examiner

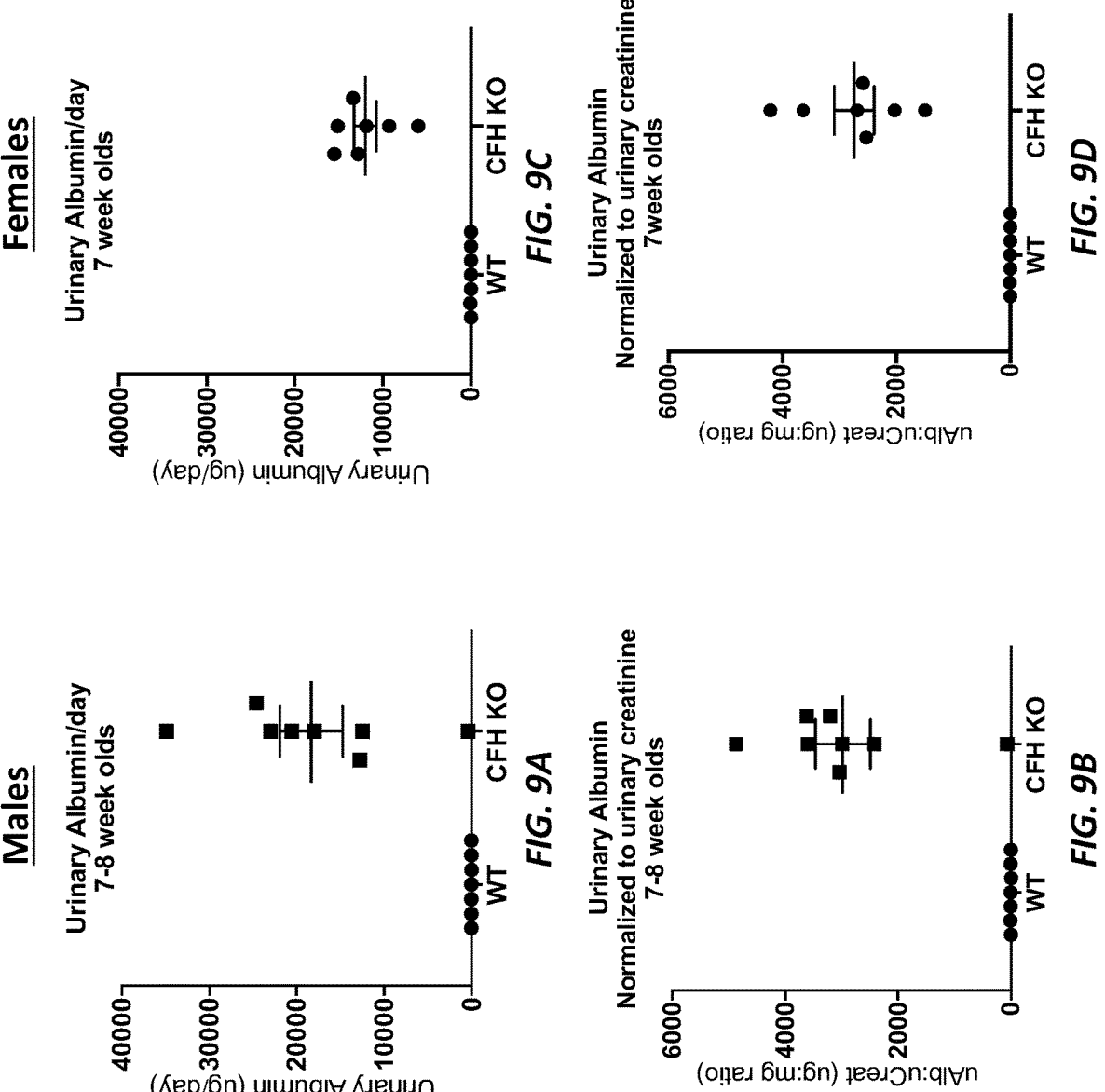

SEQUENCE LISTING

```
<160> NUMBER OF SEQ ID NOS: 26

<210> SEQ ID NO 1
<211> LENGTH: 97474
<212> TYPE: DNA
<213> ORGANISM: Rattus norvegicus
<220> FEATURE:
<221> NAME/KEY: misc_feature
<222> LOCATION: (1)..(189)
<223> OTHER INFORMATION: Exon 1
<220> FEATURE:
<221> NAME/KEY: misc_feature
<222> LOCATION: (59)..(78)
<223> OTHER INFORMATION: rGU1 Target Sequence
<220> FEATURE:
<221> NAME/KEY: misc_feature
<222> LOCATION: (97)..(242)
<223> OTHER INFORMATION: Deleted Sequence in Clone AA8
<220> FEATURE:
<221> NAME/KEY: misc_feature
<222> LOCATION: (132)..(134)
<223> OTHER INFORMATION: Start Codon
<220> FEATURE:
<221> NAME/KEY: misc_feature
<222> LOCATION: (218)..(237)
<223> OTHER INFORMATION: rGU2 Target Sequence
<220> FEATURE:
<221> NAME/KEY: misc_feature
<222> LOCATION: (18159)..(18344)
<223> OTHER INFORMATION: Exon 2
<220> FEATURE:
<221> NAME/KEY: misc_feature
<222> LOCATION: (18640)..(18745)
<223> OTHER INFORMATION: Exon 3
<220> FEATURE:
<221> NAME/KEY: misc_feature
<222> LOCATION: (21167)..(21243)
<223> OTHER INFORMATION: Exon 4
<220> FEATURE:
<221> NAME/KEY: misc_feature
<222> LOCATION: (23369)..(23560)
<223> OTHER INFORMATION: Exon 5
<220> FEATURE:
<221> NAME/KEY: misc_feature
<222> LOCATION: (23995)..(27715)
<223> OTHER INFORMATION: N = A, T, C, or G
<220> FEATURE:
<221> NAME/KEY: misc_feature
<222> LOCATION: (30320)..(30490)
<223> OTHER INFORMATION: Exon 6
<220> FEATURE:
```

```
<221> NAME/KEY: misc_feature
<222> LOCATION: (34023)..(34196)
<223> OTHER INFORMATION: Exon 7
<220> FEATURE:
<221> NAME/KEY: misc_feature
<222> LOCATION: (48039)..(48233)
<223> OTHER INFORMATION: Exon 8
<220> FEATURE:
<221> NAME/KEY: misc_feature
<222> LOCATION: (48597)..(48773)
<223> OTHER INFORMATION: Exon 9
<220> FEATURE:
<221> NAME/KEY: misc_feature
<222> LOCATION: (60274)..(60456)
<223> OTHER INFORMATION: Exon 10
<220> FEATURE:
<221> NAME/KEY: misc_feature
<222> LOCATION: (61569)..(61745)
<223> OTHER INFORMATION: Exon 11
<220> FEATURE:
<221> NAME/KEY: misc_feature
<222> LOCATION: (67016)..(67189)
<223> OTHER INFORMATION: Exon 12
<220> FEATURE:
<221> NAME/KEY: misc_feature
<222> LOCATION: (67904)..(68086)
<223> OTHER INFORMATION: Exon 13
<220> FEATURE:
<221> NAME/KEY: misc_feature
<222> LOCATION: (68172)..(68351)
<223> OTHER INFORMATION: Exon 14
<220> FEATURE:
<221> NAME/KEY: misc_feature
<222> LOCATION: (70591)..(70767)
<223> OTHER INFORMATION: Exon 15
<220> FEATURE:
<221> NAME/KEY: misc_feature
<222> LOCATION: (73304)..(73486)
<223> OTHER INFORMATION: Exon 16
<220> FEATURE:
<221> NAME/KEY: misc_feature
<222> LOCATION: (73657)..(73863)
<223> OTHER INFORMATION: Exon 17
<220> FEATURE:
<221> NAME/KEY: misc_feature
<222> LOCATION: (74428)..(74601)
<223> OTHER INFORMATION: Exon 18
<220> FEATURE:
<221> NAME/KEY: misc_feature
<222> LOCATION: (83593)..(83769)
<223> OTHER INFORMATION: Exon 19
<220> FEATURE:
<221> NAME/KEY: misc_feature
<222> LOCATION: (85396)..(85572)
<223> OTHER INFORMATION: Exon 20
<220> FEATURE:
<221> NAME/KEY: misc_feature
<222> LOCATION: (88223)..(88224)
<223> OTHER INFORMATION: N = A, T, C, or G
<220> FEATURE:
<221> NAME/KEY: misc_feature
<222> LOCATION: (94119)..(94138)
<223> OTHER INFORMATION: rGD3 Target Sequence
<220> FEATURE:
<221> NAME/KEY: misc_feature
<222> LOCATION: (94145)..(94327)
<223> OTHER INFORMATION: Exon 21
<220> FEATURE:
<221> NAME/KEY: misc_feature
<222> LOCATION: (96799)..(97474)
<223> OTHER INFORMATION: Exon 22
<220> FEATURE:
<221> NAME/KEY: misc_feature
<222> LOCATION: (96864)..(96883)
<223> OTHER INFORMATION: rGD2 Target Sequence
<220> FEATURE:
<221> NAME/KEY: misc_feature
<222> LOCATION: (96993)..(96995)
<223> OTHER INFORMATION: Stop Codon
```

-continued

<400> SEQUENCE: 1

```
cctaaactaa ctttcaactt ccctttgggg caagtctgtc tctgctgtaa ccacagttca      60
tagcagagag gaactggatg gtacagcaca tacttctctt cgagtcaact gctcccagat     120
agatccaaga catgagactg tcagcaagaa ttatttggct tatattatgg actgtttgtg     180
tagcagaagg taagcttaaa accaccacct ttctcccttc tgactgagcc gcattataaa     240
acatttgctg ataatatttc tcatagcaat tattcaaatt aagtctagaa aatgtgggta     300
attactagtc tgtaactgaa tggcttttgg tggtaagttt aaaaaccgtg aacctttcac     360
ttgactattg taattgatag ttcagcttga tgtaaaactc aagacagtgc tttaaacatg     420
tttttgcaat ccataattag gcatagacat ttaacttgta gttatcagga aatacaggct     480 cctcttttc tcatgagtgt ccctgaagta ctatatgtaa aactagttag aaatatataa     540
atatccaaag tcaatgaaag cacttacttt tttctttaaa tgggtggatc gatttcaggc     600
ttatttctaa accttcctaa ctacatcact tagctgatat ttccatggtt ttaaaagttt     660
cgtatgtaag accttcaagt atgagataaa aagaaaataa aatttgacat gtaacctgca     720
ttggacggat ctgatttgtt tctggttttg ttttctgtga atacgtgtgg ggcatgtttg     780
tttctgaagc cattttgaag taggtaatgt gactgtcgga gttctttcat gacaataaca     840
gggtctgact ttattattca cttaaattct cccaagactg cttagtttat ccaatgaaag     900
agctttgctt tcccagttta ggaagggtac ctagttgtgg gataaacatt taatcaactc     960
ttctttgtgt tttgattgtt taagataggg tgtcactaca cccttgagct cactgtagtc    1020
ctcttgtcag cagcttccta tgggctgagg ttaccagtga gagtgactgc catgcctgac    1080
ttagcacttt ttatataaag tgaatgacat aactttaata acttccttaa atgtttctct    1140
tagccaatgc attgtaattt gaagctttgc tgtaaccact actcagtaaa gaatactaaa    1200
attatcctct gactggatgt ttaccaaccc acataagaag agtagatatg gtttctcagt    1260
tgtatctttt actaaaattc tgaaaaaaaa atttaagggt attttatact ttttgaaaga    1320
gtaaacattt tcaattatat tttttaatgt tattccttga attttagctt aagagtcttg    1380
tattcagatg ccttatagac taaggcagtc atttccttgt atatgaaaat ataagtattg    1440
ctgaaatgaa atgtgattat attggccagg aattctaaag caatgttgat attaccaagc    1500
ataactaaac tttttatttt gttaaaggca atgttttcat cgcttatttt agtgttctac    1560
ttgaataata atgtttacta agaggttttt aaagatatat aagattaaag aaagaactat    1620
tttatgttta gctaactttt aagtcttaat tgatataaat cgaattaagg tgtctacaca    1680
attacaaagc agaatttcaa tattaaaaag gaagtgccgc gatgtttgcg tgatacttta    1740
acgctaatga tttaaaaatc ctcatttatg ccatggatgt cagctgattt ttttgttatt    1800
gctggatttg aattttcatc agtatgtatt caaatgtggt gccagttctt gctgatgagg    1860
tgggcagtta cactgtgtcc gatactgttt cacagggatt ttcctttcat tcacagatga    1920
aaagagagtt tagtttctaa atcattatgt agggtaacct catggtctcc acaaaatgaa    1980
tgtaaacaga tgggagaagt ttcatggatt ttcagtggac acagtactcc cactttagtc    2040
ttagcttggc tggtgacccg tgtctatctc aaatgtaaac aatttaatca gtctatcaac    2100
ttaagaggaa tttcagcaga agagcttgga tcaattaaaa caattatgta tatgctgcaa    2160
tgtttgctcc tgtttctatt ctattagatg ctggctacta agctgattta aaaaaaaaaa    2220
gtttgtgaaa tgctctcata ttaggctttc tgaaacaggg aagaaaagat ttcataagta    2280
```

-continued

```
ttttctgccc tgataaagat caacattcat ctaaaaccaa tgttagctgg gccagcagga      2340
acggtaaaca caataatgat cttgcttggc aaagaacctg gctacttgag ttcaattcat      2400 gggcccccacc tggtgaaagg gggaaaaaaa gcctctacag actgtcctcc agtttcctca     2460
tacaggcatg gcaactgtat gttacaccca ctcaaattaa aagaaaataa taaccataac      2520
aaaaaattta aactccacta ttaataatta aagaataata accaaaagaa gaactatgaa      2580
cccagcttgt ttgcctccct ccctccgtgc ccctctctct ctctctctct ctctctctct      2640
ctctctgccc cgcggggccg cccccacagc ccctatatc cacaccccca agaggggagg       2700
ggagaaggcc gggcgccacc accccgccc caccaaacaa cccccagac cggccctacc        2760 cacgcgcgga caaccacacc acgccggcga acacccaccc cccacagccg aaccaagcaa      2820
cacacaccac aacccgcgaa ggggacccgt aaccggcccct ctctctctct ctctctctct     2880 ctgtccccccc cctctccttt tccccttttc tacttgccaa gggctttctc atatcttttt      2940
agtgcagtgc ttgactgtat tcacacttct agctgccaag aacagtcaat ggtgcttcct      3000
gcaaaaccac acgctgatca gaattgggtc agatttacag gacaacctgt aacataagag      3060
agttccttgg ttgagccgta taatttcagt tctggggaat ggattatacc caagctttcc      3120
aagcatttta ctctcacaat tgaatattgt atgaaattag gccgcagccc aggattgctg      3180
aaatgaacca attaaacctg tgctgaaaca aaaccaaata accactgcgt gctttctggg      3240
gagataagtg ttttctaatc ctggaggttt aaaggacaaa aaggtccttt caggcttaga      3300
gactttaatc atagaatgga gaattggttt aattctataa tgttttaagt atatgatttt      3360
ttcaaactta gtttaacatt gatgtggaaa aattgatgtt atatacatta attatgagtt      3420
aataatagtt gctttggggg aaatttagag aaaagttaat tattctttta tgtaaaatga      3480
tattatatta tgtcaaaaag tcaagtgatt caatgtaaga tatttatact tttccttaag      3540
aaaaagaatt aatatggagt gtgtcttact tttcccttca ctctgtgtcc aaagttgaaa      3600
gcagctgatt ctgcagcgtt caccacatct taactataaa ccatgtctac agcttttcct      3660
ttggccttag ccatattgaa tatgaaggtt tcacatgtcc caagtgactg aatgaagacg      3720
gatgcagcaa gttgcaatac agaagtgata tgtgcgtcac tgtgtatgta ttgtcacata      3780
cagtactgca tacacagagt tctgtcagta gtatcactgc tgtcctttgt cttcaattac      3840
tttagttctt cgagatagag tcccctgtt tggcccatgc tggtccttaa actcctagtc       3900
ttctggcctt agcctcccta gtactgaaat tcaatatcaa gaatatctta tgcagatttt      3960
ctgttgcttt cattcaacta aattgacagc aatagctgga ccttccttag aaaaatggaa      4020
aaatatttaa atatcaaaac cttctaaaga agcaacctat agttctcttt ttctagacag      4080
aaaataaaaa aaaatccaaa aagtaaaggt caactttaaa acatacatat aagtaatatt      4140
atatatactg atcatgttat atttagaaat atatatgtat atgcatatat gcatataatt      4200
atagttatga aaataagtag tcatggggtg aaagaaagta aaggagatag gtgggcagta      4260
ttggagagac aagaggaaag gggaaatgat gtaattagat tataatctaa aaaatataaa      4320
agaaataaga ataaaaaaga aatggaaatt ttggtggtaa actaaaaaat aacgtgtgga      4380
tttacaaaga gaaaatacat gtctgcatgt cttcaatgct ttcattgaca cagaaaacca      4440
atttcggtat cttgctttta tgctcctta tcacagcaaa aatttataaa catgtcacag        4500
gacaaaccgg gacttttaaa cctttcttgt atttcaaatt ataataaata tttggattta      4560
ttgctgcagt ctctactgtg agcataatgt ttactttctt tctttttta aaatcataat        4620 gttttcaaag ccagaagaca tctgaaaact ctgaagttga ctatctttgg tatttctttg      4680
```

-continued

```
gctttcttgt ttgggacaaa actgaaggaa ttcacaatgt caaccaaacc acctattgcc      4740
attaatagta cctacttgca aagtcctaag tttccattaa ccaaacagca caaaccgaat      4800
ccattgcagt tgtttcgttt ctcccattga ggaaaaaaaa acaacatcct cgtagcctcc      4860
cttttctgaa ccttgaaatt ggaacagtaa tcttttttcac acacaccatg gaggcagtgc     4920
atagatagat ccccacattt ctttaaggaa agtggttgga ttgaataatc aggtgtggga      4980
cagagatgtc aacattgaaa ttcttccttg agtttgaatt ttgagaagag tctaaaagag      5040
gtcaggttga aagaacttgc atcctgtttg ataaggttct tcacacagtc tagcatattt      5100
attaagcttc tcggttgtac tctcccaggc cccagaggtc agaggtccat gtatgccacc      5160
ttctatcaca cttgcttaaa tccaccctag tagatgcaca tgagtattag agatcattat      5220
gtaaactaga cactagggca ctactagttt attacctaaa ttaggcatta atgtcagtgg      5280
agcaagtaac ctctatccct acaacacatg ttttcaggat agaattatat ttccctaaat      5340
catgttactt ggcattgtgc cccaattgtc ttcagtgtct tctttcatgc aactcttaaa      5400
gtatttgaca tgtttatcgt accacaaact caaccaacct gttatttatg tgtaagggac      5460
cacatagtta aatttagtgc tattatgtgt aatttactgt gaaatttcac tgatagagga      5520
tagaactgga aaatggtaag ggacaaaata gaccaaagac attctgagac aggaagcttc      5580
ctaggatgaa atgctgtaac aggtgacaaa gggtggagaa gttgctcgca ggcagggtga      5640
aggtggtcag tgaaaacaag ccttgcttat catcagcaca gtcatgttct aggaatgtgc      5700
atgccctttg ccaggatgct atttaaaact aaaccattta agtagtgcaa agcggaattt      5760
ttctaaggta ggaactgcca cagagtaaat agtctgcctc tttgtcctta gattgctcaa      5820
ttttgaactc tctctcccct tccaaattaa tccatgttta tttcctgact ctgattgtta      5880
gtctttactt cctccttctc tctctccttc cctcactctc tccctcagcc ctccctcctt      5940
cctctctctc tctctctctc tctctctctc tctctcca cacacacaca cacacacaca       6000
cacacacaca cacacacaca cacacacaca cacacactac ctctacctct cgacatttag      6060
gcagatgctg tccaccaaat cctcaaacgc tcagttgact gatgttaact ttagcttttc      6120
tcagagcaca aaacatgaaa aacagataaa gtaattggga aaaaaaatgt actttttttt     6180
ttttggttta aaattagaag aaaaaaaaag tctggttcag ataaagtcaa gcaactaaac      6240
agaaaaaaat tccaaccgtg aaataataaa aagaacacac ggatttgaca gaacactttt      6300
gttttgacat tttcacttag aaagtctagt ttctcacaga gtgttaactg gaaatgggat      6360
agatagagga cgattataga aacacccctt caaaggttcc gagggaactt ttatacttcg      6420
agctaaattc aagtgactct agacttcaaa aaccgcaaca tagacagatg tgcaaactct      6480
gtagagaact ttcagtgcat gcaacaggca ttcaactcca ccagacagtg gtgctcttgc      6540
cactgcctcc tcctcctttt cctcctcttt ttttttccctc aagttgtctc tttctttttcc     6600 tttttccaag tcttgtcttt taagtttccc atttgccact ctcagctgtt ggtggccta      6660 ttgactatat gggtgtacac tgtgggaaag ttcctacagt cttttttgcg ttcgctctct      6720
cctctattca caatcccttt tgaataactt ttaagtactg cgcaatataa tactttccaa      6780
aaggttgtca tttagtggag aggaaaagaa tgaacagtg attgaaatat tcacatacag       6840
tagctcatct tataaactat tatgactcag attttaaaaa gttcctaaag cagaaaactg      6900
aagttgaaaa gatgtgctgt atacacaaaa tgaatttttg ttcagctaca aaaaattatg      6960
aaatttatag gaaaaattga tgaattcaga ctcacaggga gacaaactct gcatgctctc      7020
```

-continued

```
cttcacattt tgattctagt ttttaataca tatactttat atatactgca tatatctttg   7080
tttaatatga cgtgtgtgtg tgtgtgtgtg tgtgtgtgtg tgtgtgtgtg tgacttatgg   7140
atagaagaca tggaactaga agtggaaaaa gaaccgtgga ggaagggaac catgaaaaac   7200
acaagtggat tgaccaagac agaggaggga gacaggtag aaaggtgaag agaagaaat   7260 aaaactgttt ttacaagtca taaaaaaggc tggatatggt ggcacaccat agtccctgta   7320
tgagggaaga aaatacaggg cagttctcta agttcaaggc cagcttaatc tacaaagtga   7380
attcgaggac agtcaggcct acacgaaaaa ctatgtcttg gaagaaaaaa atgcctcact   7440
ataatataat ataaaatata atataatact tcatatatta acttaaaaaa taacatgaaa   7500
taataattgg aatgggaaaa tgggtcagga acaggagagg gtgagggtga cggtaactgg   7560
atacagatgt tctgctgact tagttctatg ttgtttctct gagaaaagtc agacaaagct   7620
ctcaattcac aatcttctct ctccagtatg ctcaaaggac aggcatggag cctcaagtag   7680
ataggctacg gatgctgcat aggagttagt cagaaagacc aaagaggatg ttaacagaaa   7740
aacatcagat atacagaaag aactataggt tctataaagc tgtggggctc atctccacac   7800
ctacaactta acttggctta agtttcacaa ggattagtgg gaggttagga aagaaaaagt   7860
tttccctttt atttattttt gttttgtttt gtttttgatt tttttaattt atatttcaaa   7920
tattatcccc tttcctggtt tcccttcat aaacccccta ctttatcatt ttatcccct   7980 gcccttctt ctatgagggt gttcagccac ccaaccacac acaccttccc gcctcccctc   8040
tctgacattc ccctacacta gggggtcca gccttggcag acccaggggg ttctcctttc   8100
actggtggcc aacaaggcca tcttctgcca catatgcagc tggagccata ggtctgtctg   8160
tgcatactct ttggatggtg gtttagtccc tgggagctct ggttggttgg tattgttgtt   8220
tttatggggt tacaaacccc ttcagctcct tgaatccttt ctctaactcc tccaatgggg   8280
accccattct cagttcaatg gttggctgct agcatcctct gtatttgtca tgctctggca   8340
gagtctctca tgagacagct atattaggct cctgtcagca tgcacttctt gacctcagca   8400
atattgtcga gtttggtgtc tgtatgtata tgggctggat ccccagttgg gacaggttct   8460
gaatggccat ttcttcagac tttgctccaa attttgtctc cctatctcct cctatgaatg   8520
tttttgttcc ccctttcaag aagaactgaa gcatccgcat tttggtcgtc tttcttgagt   8580
ttcatggtgg tctatggatt gtattttggg taagctgggc ttttgggtta atattcactt   8640
ttcagtgagt gcataccagg tgtgtgtgtg tgtgtgtgtg tgtgtgtgtg tgtgtgtgtg   8700
tgtgtgtatg tgtgtgtgtg gttgggttac ctcactcagg atgatatttt ctagttccat   8760
ccatttacct atgaatgtca tgaagtcatt gtttctccctt gttctaatcc ttatcctcgg   8820
catcccactg atacctctca tccactccag tactggagct gctaaaacat tcagccttag   8880
ttactccatc ttgtggctaa actgctttgt gaggcagccg ttcaagccta atgaaaccgt   8940
tcaatgtatg ctaacagttt attttaaaaa gacaatattg aacctggacc cttcttggtg   9000
ttaggagact cttgtgtaaa tgctgccttt ttcagaaatt gacttcaagc tgactcctca   9060
ggaggcaaaa attccaacta ctctggtcga tttcactcag gtttagccat atacctgcct   9120
attatgatct aggtgcttct cgagggtatt agtttttataa agaaaattta taattatttc   9180
tgtatgtttt agaaatagaa atttattttc caatgttcat taaatataac caaaacttaa   9240
atttttgtag tttgttttttt aaagtacttt attgcaattt atatttactt tgttcaaaaa   9300
aattcaacct aaatattctt gcactattta taaattaatc taaatatttt tagtaaacaa   9360
aatactcttt ggatcatata catgcataaa cttaatactc atttatatca ataagaaagc   9420
```

-continued

```
agatgagaaa tttaatgaaa ctaacattct tgctcttccc actttattct tttacttttt      9480
tctgagtaat gtgtatactc caccatctgc taataaatat atttttaaaa tgatgcctct      9540
cattcttttt ccaaaatcct tgtagaagct ataggaagag aaaaaaagat gacctctcca      9600
tctttagtct ttcaaaagtg tgggtacaac tgatgtttta caaaatataa aaattcatta      9660
agacttactt cattgcagca agaacatttc aaagaacaat tctgagacat attggcattc      9720
ggaaaaggaa ttgcacttgg tttgtcagtc ctaattcttt aaaatctgta tatgaaaaac      9780
tggtaatcat gattattaaa acagcaaata tttgctttaa agttccatcg attatagtta      9840
tcttcctcaa gtttaagtaa aactcttgtt ttcagattat caaacctaca cagtcattct      9900
gtttctggaa aacattcaag agtggcattt gcatctaagt aaataggaaa ttaacaaaga      9960
aaattcttaa aaagcaaaat caactattta attaggattg gaccaggttt catttgttgg     10020
aatctgagta aatatttagg tacaagaaaa gtgagtttac tcattcacct ggacatagaa     10080
gctgtcaact tccccgtgtc ttaaaagtct taagttgaat cacccgtctg aaaatgtgtt     10140
catcctttcg aaagcacttc tctactccct atgtaagaac cacctgccct gctttcatta     10200
acaacttctc atttatttca agcaaatgtg tttggtgttt ggtgtacatt taggttgaca     10260
gatggagaac atgaatgagc agaacttgtt cctgtctagt tagaacgcct ggacggctac     10320
tttcagtgga acgtgaaaaa atgtttgcca ccctcaagac acacttaact gttattgtcg     10380
aaatacagtg aacgattact ttaactattt aagccagaac acgagttatg gatacacatt     10440
atgttgagac tctaaacaaa gacaaacagc aactgaaaac agagggattg tttattttcc     10500
cgagagcaac aatttttttt tttttccgaa gaccctggtt ttggcggtgg cagtggtggg     10560
gtattagcgc cacctagtgt ggagaagttt aactactgaa atgatgatca aactaaagct     10620
caaaaaacta gcgaaagact caaaggaaac ccgacagcct aaacaattgc tctattcttc     10680
tataaaacat agcagtcctt ttatttcaca tgctgtgtac catcttgtag atggaagttc     10740
caggtgaaat atacgcagta gggtgatcca ttgcttttta aaagagtaga aaagattagt     10800
aaagtagagc gaattgtcat aaaatcaaga agtaaaagac atgggcaatt tgaacagtat     10860
ttttagaaat aaaatgaata atgagcctag aacctgccat ctaagaagca ccatgctggg     10920
ttttactaac aaccatttaa atatcagggt atttgttaca aagttaagca gcaggcaata     10980
ttaaatgtga ttctatgcct tagcactaat gttccatggt cacaattcca gcgcctggga     11040
gtttaaggca ggaggactat gagatggaga ccaacctggt ctacaaagat tttgtctcaa     11100
aaacaataaa taggcaaagg gaaggataca cggaaggata ggtgcacaac tactgtagta     11160
aaatgttgat tgttggacct gcgtgttagc gtcattggtt ttttactgta aaatcaaact     11220
ttcaaataca ttttgaattt tctgtaaaaa aaaatgttaa gcgaaattct tctctgataa     11280
aacttaagaa cacagctcag gatctccaat ttacttccta tgcccaaact taagtactag     11340
ttgaaaaacg cgagccccaa acttaagtcc agttcaaaaa cacgagccct gttgtctgca     11400
cacttatctt ctgcttctgc cactttcaga aatcttgaaa aagttagtag atatttgaat     11460
ttccatgtct ttacataaca aaaagaagac aatgaaaata aataaagaaa tacaatcaag     11520
aaacacaaac tccccacaaa catttctctcc ctattctttt aattatttgg gaatctcata     11580
tcatacatat ctacaattgc actcatctcc tcttctcaca tttgcccccct tacctgtgag     11640 ctccctcacc cacaaccccg agagagagag agagagagag agagagagga gggaagagcg     11700
aaggaagaga agagagaggg aagggaagag agagggaagg gaagagagag ggaagggaaa     11760
```

-continued

```
agggaagtga agggaaaagg gaaaggacta gccaaggcaa gtattcactg aatcacggtc   11820
aaattcctag tggccaagag aggttttttt ttttttttcct ctgcccgcat ccttggttgc   11880
cagaagccag gagctgaggc aagccatgta gtagctggag cagggtaaat ctagcaatcc   11940
caagcacatg tccctgcctg tactgcagtg ctgtgggcca gtgaaggaca gggccagttc   12000
tctcagaccc atggacatag atagcgtggc ttcaggcaac agcagacatc aacgtggtcc   12060
atggccatat caggaccact gaccaactaa tggccctcag gggatgaatg catggaccac   12120
gagcctccac atggtcttac gccacatcag catgcccccc atctcccgac cccgaggcag   12180
caaagccaga cgacatcact aaggtatcac acagcaatat agatctcata cgtccacatg   12240
gatctcaggt ttcttttggg gctggtgcaa cagcatagac cacagacacc atgatggccc   12300
ttcaaggagg ttgattccag aaagtgaacc tttccttgtc ttgggcctcc attgttgctc   12360
ataacttggg gcatcttgaa actgtgtggc atgttgaggg acagggggtg gggagtatgg   12420
gctacatatg atccaagatg ataagttatg ccaactctac tgggcaatga cagcatgttg   12480
agcttagccc catctcacac ttgtctctag ttctgcttct ctctctaggc acacacctct   12540
ccatgtgtgc ctagttcact tatgtgttca taatagtagt gctgggtggc tttaggtcga   12600
ctcacagcta ccatgtctca accggtactt gcttcccatt atgtacataa catataaata   12660
tatattatat gcatatatgc atatattgta tactactttt aatatattga aaagtaaaag   12720
gaatagaaca aatgctaatt ttattaactt tatatattta aaatatataa cattgtgttc   12780
tgggtgatgc ttgcttcccg ttttacatac atatatacac atatatatat atacatatat   12840
atgtatatat tatatactat ccttagtaaa catattgaaa agtaaaggga atagaataca   12900
ttttgttaac tttttgtatt taaaatatgt gacacatacc attgaattaa ttatgaacat   12960
agtatattac taattattat tcatccatac cacaaaacat agaatttcca gcacctcaga   13020
agatctctgt tggtttcttg catatggaat gaattatttt catagttata ggtacatatt   13080
tgctcttaat tgtttcacct cctatatgtg cctatgtgat ttgtacaaca gcacctcagt   13140
gcatggccac tgtcacccta caccactttg tgctggtcag gaagcacaga gacactgctc   13200
tgagggtgag aaagcacaga ctgagatgtg ggagagccag agctggtttg ggggtcccca   13260
ggcctgtggg gcctgcaaga aggcagggcc ccaggttggg gacagcatct agctcagggc   13320
ttgaggagag ggcagctctg gaccagcagg gattgtcctt agcttggaag aggaaggctt   13380
cttagcagtt gtggttggga gtgctgagaa gcctgctaca ggagacttag ctgctgccct   13440
gtagagctag ttacctggaa agaccacctt catgacattc cccatggtgg tggtagatga   13500
cagagacagt ctgtgtttac ccatattgtt tattggctgt tcattatgga aaatggatgc   13560
atacccactt ctcagggtct gacctaagat taaatacctt tcaacgtctg gaatgtctgg   13620
gaaggaaagc ttattggcta agccctccgg gcctctaggt accttattag cacggagaat   13680
tctgttctgc cttacatgac ctgtcacatt tccttatacg gggagtgtgg cacaaattcc   13740
aggtacaaaa tactcacatt ttcaatgatc attttattca cttcagctga ttcattcttt   13800
aaacttccct tatcttgagg atcagtttcc tttaacctaa agaactttag tgtacattta   13860
taattgttaa agtttctact tcgtttgaga aagtgtccta ttccaaagta aacacagaaa   13920
tctgaaggtt ctcatctaac atccacagtg aaagaaaata tgcaaactct ccctttggag   13980
tctgggatag cttattccac atgatttgtt tccaactcca cctgcgaatt tcctactttt   14040
ccccactgtg taaacagacc atatttttgt tatccattct tcagctgata gacatcctgg   14100
ctgtttctac ttcctggata ttgttggtag agcaacaacg atcatgggtg aacagatatc   14160
```

-continued

```
tctgtggtag ggtatggagt tctttgggag tatgtttaga agagtagtat agttatattc  14220
tatggcagac ctgttgctag cttttgggag aaactttact ctgattttca taatggctgc  14280
agcagtttgc actcccatca gctatgaaaa agttccccct ttcctcacat tccacactga  14340
tatctcttgt cattaattta tttaatctta ttcaggctgg gagaagatga aatcacagag  14400
tagttttaac ttttattccc caaatggcta atgatattaa acatttttaa aagtttctca  14460
attattttta tatcatttcc ttcattgaaa ataaattttg ataaaatata atatattttg  14520
tttatagttt ccccttctcc aactcctccc agatccctct tcccaaccca cccaaatcta  14580
taccatttct ttctctcatt tgtatacaag caggcgtcta aagacaaata ataataataa  14640
aacaaaatta cataaagtaa aagtcaaaca aactttataa gaactctcct gttttttaaaa  14700 tggcttgttc tcattcttga tgctaaggat ggcttttagt agagcctgag aaagttgttt  14760
ggctttttgt tatcattgtt tttataaata gatactagga attttatgca atcattctga  14820
ttttgagttg ataactttag tcatatttgg aaaactttaa atgttcaggt gtcatttctg  14880
ctagttctct catctacctt tgaaccttca gatagatgta gcctgcatct tttgctttct  14940
gcacaaaagt tggcttctgc agatagttct cttttccacca tatttgaaca tttctatctc  15000
aattttcttc aagtggagta catttctttc tgatttcaga tgactgcaga tcaaacaata  15060
taacaatatt atttgtgata ttaattcata acattaagat aacataattt agagccattt  15120
ttattttgaa ctttttaaaat tattttgtc tttttcttaa agttcattaa agatgattga  15180
cttagttatt taaaatatat ttttgctaac taatatctag atcagtgttg attttactgc  15240
ttatttactc ttcatgtcta ttttcctttt tgtatttat ttttttaattt tgtattgtta  15300 ttttacttat ttacatttca aatgtcatcc cttttcccag tttccctcta caaactccta  15360
tcccattccc cttcctcctg cttctatgag ggtgctctcc cacccacaaa cccactcctg  15420
cctcaccacc ttagcattcc cctacactgg ggtattgagt cttcacagga ccaggggtct  15480
cccctcccac taatgccaaa taaggcccat cctctcctac atatgcagct ggaaccgtgg  15540
gtccctccat gtatactctt tggttggtgg tttatgcctt gggagctctg gggggtgtgg  15600
ttagttgata tggttgtttt ctatggggtt gcatcatgct cagtctgatg gttggctgca  15660
agcattggca tctttactgg acaggctctg gcaaagcctc tcgggagaca gttatatcag  15720
gctcctttca gcatgaattt cttggcttca tcaatattgt ctgggtttgg tgtctgcata  15780
tggatggatc cccagttggg gcaatctctg aatggtcttt cctttagtct ctgtgccacg  15840
ctttgtctta tgtcttggaa tatcctcttt gtattttaat tttcataata gttactatat  15900
tttatagaaa atatagtgac taaagtttac gttatgcact catactaaga agaacattta  15960
tcccaagact gaaccccag agaactggat ggttgggggt ggaggggagg atagggaggg  16020
gaacatccat agagaagggg aggaggaggg gttaggggga tgttggcccg gaaactggga  16080 aaggaataa caattgaaat gtaaataaga aatacccaag ttaataaaga tgaaaaaaaa  16140
atgcttggaa accatggggg gggggaataa acgtctattc ttgaacctta aaaaaatgaa  16200
gaacatttat ctttcttact tcaatcatta atttaattaa attgtatctg ggctgcaatt  16260
ttagcttgca ttagctcact tctggtctca aatatttcaa agcaaagacc ttcttatgta  16320
tgagcttttg cacatgtgtt taagcacaaa tctctccttt ctaatagact acaataaatc  16380
tgtcttcttt cctgctatct tgagacatgt tttatattag acactaaaag actcaaatat  16440
tctaatgtgt tgatgaactc accagttctg tattttaagg aggactatta atcttgctgt  16500
```

-continued

```
gacttctgtg agactatagg aacatccagg cttcacttag gaatcaggta attccaataa    16560
gacaactaga ttcagattct gcatgattca gaatgtttca ggttagacac accttcaata    16620
tacatgtctt atttctaaca tcgctaccat tcttgaattc acataacccg ggaccatcaa    16680
ttcacataca gaactaacac atataagaaa tactgtagac ctcagatatg aatagtacag    16740
gcccattcca cctagattta gttcatgaat tttcattgct cttaaaatct gtgctaaggc    16800
actcttataa atacctccac accaactttt ctgcactcca tatttatata gtaggaacat    16860
aactctgttc tatctttta tattatttga atgttgaatg tctccatata gtttcatgtt    16920
aacttatata gaccaatttt aattcagcaa tatggctgct ttagcaaggg atcacataca    16980
aagactttat ctatctagaa tgccacacct ttaatccctc tgggtggaaa tagagatatg    17040 ccccttagtac acacctttaa tcccaaacca tgaaagtaaa gctagttgtt aaaaaaaaaa    17100
gcaaccatgt gtggatgtaa tgtcaaattg aggggcaaag tgatgaatca gagaaagatt    17160
agacagaatg agttagtaat aggatatgcc caactctcac gagaacagac aggaaaaggg    17220
gatgagatga cttaacagtg cagcagggat ggagagagag agagagagag agagagagag    17280
agagagagag agagagagag agagagagag agagaagagg aggaggagga gaaggaggag    17340
gaggaggagg agaaggagga ggaggaggag gaggaggagg aggaggagga gaggagagac    17400
gagacgagac gaggagagga gaggagagga gaggagagga gaggagagaa gagaagagaa    17460
gagaagagaa gagaagagaa gagaagagaa gagaagagaa gagaagagag gagaggagag    17520
gagaggagag gacaagagaa gagaagagga gaagtcctgg agcagagaca ggttgtaggt    17580
taaggcagaa tgagccagag aatgagaagg agccaaaaga ttagaaaaaa ttgtcagagt    17640
ttgtttgaga tcaagcagaa taattcagtg ataactcaag agaagtttga atcagttatg    17700
ttggaaagaa gtttggacca gaacggttga gttgagtcag ccagccagag tttcaaaaga    17760
actggaaagg gtgagcttat tcaacagtaa gcctgcaaga gtacaattat atctggtgaa    17820
tgagttattt tataacctta cttgctttat ttttataagt agaaattatt ctataattca    17880
tggcatgagt ttagaaaata ctgcttagat ttgctactag gaaatatttt gagaatagtt    17940
tattttatcc atagttttgt ttgtttgatt tttttgtttg ttctttacaa cttagaagat    18000
tgcatagtaa attttcataa agtcgtgcac ataaatagct ggatggacct gtaattggta    18060
tgattcaaag aaaaacaaca tgcatattgt ttttgaatag gtatttcaaa tactggtatg    18120 ttttattac ttgtagattg taaaggtcct cctccaagag aaaattcaga aattctctca    18180
ggttcgtggt ctgaacaact atattcagaa ggcactcagg caacctacaa atgccgccct    18240
ggataccgaa cacttggtac tattgtaaaa gtatgcaaga atggagaatg ggtaccttct    18300
aacccatcaa ggatatgtcg gagtaagtac ttcatgtttg taaaacttaa gaaaatttca    18360
gctttgtact aaatccttta cattgtagca atataaatta tattactact gtaactaaag    18420
tgtaatcatt ttaaaatgta cttgtcctaa aaaaaaaaa actaaatatg gaagcgtgaa    18480
gttaccttca attataaaac atgtttttat attttcagtt tctcttctat tcaatgatat    18540
ccaaatgtgc tttcctgact tctacaaaag gtgtatttca tggaccatac actaatatta    18600
tcttcttttt attttagaaa ggccatgtgg gcatcccgga gacacaccct ttgggtcctt    18660
taggctggca gttggatctg aatttgaatt tggtgcaaag gttgtttata catgtgatga    18720
agggtatgtt gttaatatta aaaggcttat ccttgaaacc atgtaggaac gctacaaatt    18780
tgtactttag caagaataaa ttttctatta acatctaaaa tgtaatacag aaataaaact    18840
acgtcatgaa tgcttttaat tggatatcat gtgatctcca taacactgga aagtaagcaa    18900
```

-continued

```
tttatggctg ttctgacata gtgttgaaat aagggtgtat taagttgcta tacacttaat   18960
acacaaaaat taagcattca actcacaagt ccttagtaca ttccactatt gtacaatatc   19020
gtatgagatg ggatagtttt tttttttta tattagggac aatgagaatt gtgaaaacaa    19080
ctacattata tggtaaccct cttaaagaga ttttatagta ttcaaagaaa gcaaaacttt   19140
tatgtgtgaa aaattctttc tcttgaatgc tattttaaa gttgtatgca aattactctt    19200
attccatagg tgcgaaaggc taattttca gaatcattga cttccctctc tgcacagcca    19260
ctggttcgtc attcactcca cagttcttca tttcctatca tacaagaaag ttagagttgt   19320
aacattattc caaataatta taaagaaaag taaacacttt gaatggaatc tttttagttg   19380 cctttattt cctaacttga dacagtgaac tataacggtt tattctattc aagttttaga   19440
attagctcca aaatatccct atgctcaaat gctcaatgtt tgtaacatct tactccgatc   19500
ccctctctta cagaagcaga aaagtgctta tgagcatcat aggattagca ggagaaataa   19560
atatgaccca cccttgcagc acttcaaaat gatcccagat gaccacaaat acccactaga   19620
tgctcatttt tttatttaac ttctccttgt ttcacaacgt gaaggagact tttcaaacta   19680
caattttcaa ggtcactgct gaccttatta tttaaagcca acaaagattt ctttggcctg   19740 gattttcag gttgttccat tcttcacctt tgaattagct catcctaggc cgtagaaact    19800
ctctcatttc tagtcctata ggaaacacca aatacgactc agcagttgtg acttcagtag   19860
gcaagcagac agcacacaca aattggaagc tacagactag tcctttggc aggtcaacac    19920 cagacccaaa ccagcagctg tccaaagctg aaggaaccat tgggcttacc aaccatcctg   19980
acgtaatact gtggaatctg caaattgcca gaggaacttc aggagaattt cttagagaag   20040
cttctcagtg gcagcatagt gaagaatagt gagacagagt aaacaaaatc aatgctcagt   20100
actcgtctcc cactatctgt gtgatcataa ttatactctg tcgtctagag tcctttcatg   20160
tgtgtgcccc agcaaaacat catttgacat aacttacttt ccaaaccgac tagaagtttc   20220
cacttcactt atttacctct gattctggct ctcttcaagt cactgttgcc accttgtatt   20280
tatcaagtgt aaacactgat agaacccatc taggtcaata gctgtgtata ttgattctga   20340
atcaccaata tcaaatcaat caaattactg acaattatcg cgtaaagtcc tcataccacg   20400
taggataaaa ataggtaaaa agcagttcat attcattcaa atttctgttg atgaatgttc   20460
tatctatctt gggataattg cttttttaa acccagaagt gaaaggtaag gataggagag    20520
gcttatttca accctatttt ttttactcat ccttttagt cctgtgcttt tggctaaatt    20580
ttctctgcta aaaataaaca aatataaata aatataaata tagggtttta tgtacttgt    20640 agtagaatga ctccttagga acaataatgt tattgtccaa aaccatcgtg aatgattttg   20700
agatgacact gcaaactgat tttcccccat atggacaacc atttttttc tcctttcccc    20760 tccctccatg aacagaaatc cagtaaggtt ttgtgtagaa ttttatagat tgtctgaagg   20820
aacttagtgt gatggatgga tctctgcagt gaataaaaag tctttaccag gagcttcatt   20880
tcttttctac tggaaaagaa attattctgt ctcctctaca gcaagcatca aggaaacact   20940
taagtccaat atccaaaact aacatattct attgaagtat tttatttcca caaagattta   21000
atagagagat gaaaataata aaagaatgag aaatattttt cccttccaaa tctcttactg   21060
gaggatatcc aagactgcac agagcttcaa actacacaaa aacacatgat gtctcaacac   21120
aaattattat gcttgcattt ttaggtacca actcttaggt gaaattgatt accgtgaatg   21180
tgatgcagat gggtggacca atgatattcc aatatgtgaa ggtaaatgaa aaacagattt   21240
```

-continued

```
gtatgtatgc ctaaagatct aaaatagata agatttccca agctgtgtag aaaaatattc   21300
ttaaagtata tacttaagta tttcatatat ttatgtgtgt gtgtgtgtgt gtgtgtgtgt   21360
gtatatatat atataatttt ataaacttc aattctcttt ttacagtcca gtcattatcc   21420
ccctcccagt ctgccctcat cccagtcccc caccccatct taaagaggat gtcctcatcc   21480
ccttcatccc tgccccacca gaccttccta ctccctgggg cttcaagtct cttcaggatt   21540
aggtgctttt ttctcactga ggccagatca ggcagttctc tgctacatat gtgttgggaa   21600
tctcatattc gctggtgtat gctgcctggt tggtggcttg tctgagagtt ctcgagaggg   21660
tccagattag tctggtcttc ctatgaggtt gtcctcctca gcttctttca gttttttccct  21720 aattcaacca cctgcgtctg actctttcag ctgttttttg ggcctatcag agggcagcca   21780
tgttaggctc ctgttcttaa gtacaccata gcattgataa tagtgtcagg ccttagagcc   21840
tcccctcgag atggatccca atttgggatg attactgagc ctcctttccc tccctcagtc   21900
tcttctccat ttttgtctct gtagttctta tttatatctt ttagtttcta gtataaaaca   21960
taagtacttt gttatagtac tattttgtat ttgtatcaat attctgagaa cactaagtct   22020
agagaatggt gaatttctca ggactactgt agattccttg aggtcttagg cttgacacac   22080
attctcatca atataactta aaactatcta aaacataata gatataaata gagattgata   22140
tacttttatg atcaaagttc tgaatattag aaataccaaa gccatttttt ccattttaca   22200
tttcaaacac taacaataca taagaccatc actagcctat aaaaaaagac cagaatttga   22260
ggtatgtttg tgaagaatga cacccctaat aacatctagc tagttacagg tgtgtaggct   22320
atcacatcca tacattcctg gtagagaatg ttattgaaat acctttcaca attatgatgc   22380
tgtgaaggtt ttatccatag tcttaatttt agaaaaaaaa gggggggagg gaagcaagaa   22440
ttacaaaaga actcttgcct ttcaattctt gctcacatgc tgcttatagg tagagcaaac   22500
agcaagaatg agaaaatgca ggtcttgttt gtaagtttgg cgatagcatg taaataacaa   22560
aggtccatcc aaatgctgta tcctacttcc atgggaagca ataaattaga gaaagaagtg   22620
gagtggaagg agagagggat ggagaatgag aaggcacagt aagttctcct aatgagactt   22680
ttctagtaag gaaatgagaa gatgttcccg gaacgtctgc atcagaattt acatggtgct   22740
tgtttaaaat tgatgtttga ggcccctgaa tggcctgttg agaaagtatc tttgagtgag   22800
aagagcagaa aacctcacta gcatatccat tacatccaaa gtttccttca gaaaagcaac   22860
ttcaaatttc ttcatggcgg agaaattcta aattaaaaaa aaagtttaaa atttttgagc   22920
aatgaggtga aaaggaagga aacattacaa aaagtttttt tcccctatga gaagaaatat   22980
cttcaaaatt cattgattta aaccttatta gaatgcaata tcacgttgct ttgaagaata   23040
aataatacat ttgtattaga ctattccaaa atctcatatg tgttcaccat ttaggagaca   23100
cttgctatca cgaagatgta aactgtcact ctaagtaata gtttttctttt cccattccca  23160 tagaagctga taagcgaact acccgagcta cttagatgtt gtgcaaacag tgatgctgaa   23220
tgtttctcaa acctttaagt cctttccggc aggttgagca ggctgcgtgg tgtttttcatt  23280 catatacgtg tgttttatgt ggaagctggt aaggtctgtt agtaaaagcg atgcctgtat   23340
tttcagttgt gaagtgcttg ccagtgacag aactggagaa tggaagaatt gtgagtggtg   23400
cagccgaacc agaccaggaa tattattttg gacaggtggt acgctttgaa tgcaactccg   23460
gcttcaagat tgaaggacag aaagaaatgc actgctcaga aaatggcctc tggagcaatg   23520
aaaagccaca gtgtgtgggt aagatacaca gatgtgtctg cttcacatat tctagtgaaa   23580
gtatacattt cttttttaaa gtacatttttt aattataata gaattgcaca actcggatgc   23640
```

-continued

```
taatgaagta tgactgtttc cttgtaactg aagttctttg catgaagcct tctattttgc   23700
tttcagaact atatatttca tgcccttgtg tagtctcttt aattgaaata gccaaggtgt   23760
ccatgcttac tgtggcttaa tgacttggac aagatgtaaa cacaggtgtt gcaattcagt   23820
ctagcctcag cgtctctggt gagtgttgta aaactacctt gcagagcata tttttttaat   23880
aaggtttttg gaagctaaag gcttggcatg tgtttacaat cacacattat gatgatattt   23940
tgttttcaat ttatagttag gatgtatatt ttttagaaat ctatttgctg caagnnnnnn   24000
nnnnnnnnnn nnnnnnnnnn nnnnnnnnnn nnnnnnnnnn nnnnnnnnnn nnnnnnnnnn   24060
nnnnnnnnnn nnnnnnnnnn nnnnnnnnnn nnnnnnnnnn nnnnnnnnnn nnnnnnnnnn   24120
nnnnnnnnnn nnnnnnnnnn nnnnnnnnnn nnnnnnnnnn nnnnnnnnnn nnnnnnnnnn   24180
nnnnnnnnnn nnnnnnnnnn nnnnnnnnnn nnnnnnnnnn nnnnnnnnnn nnnnnnnnnn   24240
nnnnnnnnnn nnnnnnnnnn nnnnnnnnnn nnnnnnnnnn nnnnnnnnnn nnnnnnnnnn   24300
nnnnnnnnnn nnnnnnnnnn nnnnnnnnnn nnnnnnnnnn nnnnnnnnnn nnnnnnnnnn   24360
nnnnnnnnnn nnnnnnnnnn nnnnnnnnnn nnnnnnnnnn nnnnnnnnnn nnnnnnnnnn   24420
nnnnnnnnnn nnnnnnnnnn nnnnnnnnnn nnnnnnnnnn nnnnnnnnnn nnnnnnnnnn   24480
nnnnnnnnnn nnnnnnnnnn nnnnnnnnnn nnnnnnnnnn nnnnnnnnnn nnnnnnnnnn   24540
nnnnnnnnnn nnnnnnnnnn nnnnnnnnnn nnnnnnnnnn nnnnnnnnnn nnnnnnnnnn   24600
nnnnnnnnnn nnnnnnnnnn nnnnnnnnnn nnnnnnnnnn nnnnnnnnnn nnnnnnnnnn   24660
nnnnnnnnnn nnnnnnnnnn nnnnnnnnnn nnnnnnnnnn nnnnnnnnnn nnnnnnnnnn   24720
nnnnnnnnnn nnnnnnnnnn nnnnnnnnnn nnnnnnnnnn nnnnnnnnnn nnnnnnnnnn   24780
nnnnnnnnnn nnnnnnnnnn nnnnnnnnnn nnnnnnnnnn nnnnnnnnnn nnnnnnnnnn   24840
nnnnnnnnnn nnnnnnnnnn nnnnnnnnnn nnnnnnnnnn nnnnnnnnnn nnnnnnnnnn   24900
nnnnnnnnnn nnnnnnnnnn nnnnnnnnnn nnnnnnnnnn nnnnnnnnnn nnnnnnnnnn   24960
nnnnnnnnnn nnnnnnnnnn nnnnnnnnnn nnnnnnnnnn nnnnnnnnnn nnnnnnnnnn   25020
nnnnnnnnnn nnnnnnnnnn nnnnnnnnnn nnnnnnnnnn nnnnnnnnnn nnnnnnnnnn   25080
nnnnnnnnnn nnnnnnnnnn nnnnnnnnnn nnnnnnnnnn nnnnnnnnnn nnnnnnnnnn   25140
nnnnnnnnnn nnnnnnnnnn nnnnnnnnnn nnnnnnnnnn nnnnnnnnnn nnnnnnnnnn   25200
nnnnnnnnnn nnnnnnnnnn nnnnnnnnnn nnnnnnnnnn nnnnnnnnnn nnnnnnnnnn   25260
nnnnnnnnnn nnnnnnnnnn nnnnnnnnnn nnnnnnnnnn nnnnnnnnnn nnnnnnnnnn   25320
nnnnnnnnnn nnnnnnnnnn nnnnnnnnnn nnnnnnnnnn nnnnnnnnnn nnnnnnnnnn   25380
nnnnnnnnnn nnnnnnnnnn nnnnnnnnnn nnnnnnnnnn nnnnnnnnnn nnnnnnnnnn   25440
nnnnnnnnnn nnnnnnnnnn nnnnnnnnnn nnnnnnnnnn nnnnnnnnnn nnnnnnnnnn   25500
nnnnnnnnnn nnnnnnnnnn nnnnnnnnnn nnnnnnnnnn nnnnnnnnnn nnnnnnnnnn   25560
nnnnnnnnnn nnnnnnnnnn nnnnnnnnnn nnnnnnnnnn nnnnnnnnnn nnnnnnnnnn   25620
nnnnnnnnnn nnnnnnnnnn nnnnnnnnnn nnnnnnnnnn nnnnnnnnnn nnnnnnnnnn   25680
nnnnnnnnnn nnnnnnnnnn nnnnnnnnnn nnnnnnnnnn nnnnnnnnnn nnnnnnnnnn   25740
nnnnnnnnnn nnnnnnnnnn nnnnnnnnnn nnnnnnnnnn nnnnnnnnnn nnnnnnnnnn   25800
nnnnnnnnnn nnnnnnnnnn nnnnnnnnnn nnnnnnnnnn nnnnnnnnnn nnnnnnnnnn   25860
nnnnnnnnnn nnnnnnnnnn nnnnnnnnnn nnnnnnnnnn nnnnnnnnnn nnnnnnnnnn   25920
nnnnnnnnnn nnnnnnnnnn nnnnnnnnnn nnnnnnnnnn nnnnnnnnnn nnnnnnnnnn   25980
```

-continued

```
nnnnnnnnnn nnnnnnnnnn nnnnnnnnnn nnnnnnnnnn nnnnnnnnnn nnnnnnnnnn   26040
nnnnnnnnnn nnnnnnnnnn nnnnnnnnnn nnnnnnnnnn nnnnnnnnnn nnnnnnnnnn   26100
nnnnnnnnnn nnnnnnnnnn nnnnnnnnnn nnnnnnnnnn nnnnnnnnnn nnnnnnnnnn   26160
nnnnnnnnnn nnnnnnnnnn nnnnnnnnnn nnnnnnnnnn nnnnnnnnnn nnnnnnnnnn   26220
nnnnnnnnnn nnnnnnnnnn nnnnnnnnnn nnnnnnnnnn nnnnnnnnnn nnnnnnnnnn   26280
nnnnnnnnnn nnnnnnnnnn nnnnnnnnnn nnnnnnnnnn nnnnnnnnnn nnnnnnnnnn   26340
nnnnnnnnnn nnnnnnnnnn nnnnnnnnnn nnnnnnnnnn nnnnnnnnnn nnnnnnnnnn   26400
nnnnnnnnnn nnnnnnnnnn nnnnnnnnnn nnnnnnnnnn nnnnnnnnnn nnnnnnnnnn   26460
nnnnnnnnnn nnnnnnnnnn nnnnnnnnnn nnnnnnnnnn nnnnnnnnnn nnnnnnnnnn   26520
nnnnnnnnnn nnnnnnnnnn nnnnnnnnnn nnnnnnnnnn nnnnnnnnnn nnnnnnnnnn   26580
nnnnnnnnnn nnnnnnnnnn nnnnnnnnnn nnnnnnnnnn nnnnnnnnnn nnnnnnnnnn   26640
nnnnnnnnnn nnnnnnnnnn nnnnnnnnnn nnnnnnnnnn nnnnnnnnnn nnnnnnnnnn   26700
nnnnnnnnnn nnnnnnnnnn nnnnnnnnnn nnnnnnnnnn nnnnnnnnnn nnnnnnnnnn   26760
nnnnnnnnnn nnnnnnnnnn nnnnnnnnnn nnnnnnnnnn nnnnnnnnnn nnnnnnnnnn   26820
nnnnnnnnnn nnnnnnnnnn nnnnnnnnnn nnnnnnnnnn nnnnnnnnnn nnnnnnnnnn   26880
nnnnnnnnnn nnnnnnnnnn nnnnnnnnnn nnnnnnnnnn nnnnnnnnnn nnnnnnnnnn   26940
nnnnnnnnnn nnnnnnnnnn nnnnnnnnnn nnnnnnnnnn nnnnnnnnnn nnnnnnnnnn   27000
nnnnnnnnnn nnnnnnnnnn nnnnnnnnnn nnnnnnnnnn nnnnnnnnnn nnnnnnnnnn   27060
nnnnnnnnnn nnnnnnnnnn nnnnnnnnnn nnnnnnnnnn nnnnnnnnnn nnnnnnnnnn   27120
nnnnnnnnnn nnnnnnnnnn nnnnnnnnnn nnnnnnnnnn nnnnnnnnnn nnnnnnnnnn   27180
nnnnnnnnnn nnnnnnnnnn nnnnnnnnnn nnnnnnnnnn nnnnnnnnnn nnnnnnnnnn   27240
nnnnnnnnnn nnnnnnnnnn nnnnnnnnnn nnnnnnnnnn nnnnnnnnnn nnnnnnnnnn   27300
nnnnnnnnnn nnnnnnnnnn nnnnnnnnnn nnnnnnnnnn nnnnnnnnnn nnnnnnnnnn   27360
nnnnnnnnnn nnnnnnnnnn nnnnnnnnnn nnnnnnnnnn nnnnnnnnnn nnnnnnnnnn   27420
nnnnnnnnnn nnnnnnnnnn nnnnnnnnnn nnnnnnnnnn nnnnnnnnnn nnnnnnnnnn   27480
nnnnnnnnnn nnnnnnnnnn nnnnnnnnnn nnnnnnnnnn nnnnnnnnnn nnnnnnnnnn   27540
nnnnnnnnnn nnnnnnnnnn nnnnnnnnnn nnnnnnnnnn nnnnnnnnnn nnnnnnnnnn   27600
nnnnnnnnnn nnnnnnnnnn nnnnnnnnnn nnnnnnnnnn nnnnnnnnnn nnnnnnnnnn   27660
nnnnnnnnnn nnnnnnnnnn nnnnnnnnnn nnnnnnnnnn nnnnnnnnnn nnnnngtggc   27720
aggggtcctg ccgctcctgg gccctccccc acgggagccc agaggcctta tacagtttcc   27780
tcttgggcca gggatgtggg caggggtgag cagtgttggt ggtctcttcc gctctgcagc   27840
ctcaggagtg cccacctgac caggcggttg ggtctctttc tcaccgggtc tgggagcaga   27900
gagctgctgc gggccgggat ctgctgcaag ttttaatttt tttttttttt gattcttttt   27960
tttcggagct ggggaccgaa cccagggcct tgcgcttcct aggtaagcgc tctaccactg   28020
agctaaatcc ccagccccgc aagtttttaat ttttaagaca ttctaatttt tattaatatt   28080
gttaggataa aatatataca tatacatata tcatacaaca cacacagaca tacacacata   28140
tgtattgcat gtttacaatc agtttttaggt atcttaattg aatccactaa gcctttgaat   28200
tttgacaaac tgatataata tattgttact taatatttct tttctttcct cctcctcctc   28260
ctcctcttcc tcttcttcat cttcttcatc ttcttcttct tccccttctt cttcttcttc   28320
ttcttcttct tcttcttctt cttcttcttc ttcttcttct tcttcttctt cttcttcttc   28380
```

-continued

```
ttcttctaga cagcctttca taatgtaatc atggccggcc tgaacctgat atgtagtcca    28440
tatagcttct accttgcagc aggctcctta gagttccgac aagagttttg aaattgcctg    28500
catgtggcac tggtcttata ctatatttat ttttcaatat tatctaacac ctccattatt    28560
ttcaccattc cttagtattg tccaccttag actaaagaag acagtgtttt cttctttca     28620 aatttagttt gcttttgaga ttataactac atcatttctt tcctcaagga ttgactagtt    28680
gctgctaaca actctaacag cactgattca tcatgagaat aatgatatac caatatgtat    28740
agtcaatgtg gcatatattt gacatattga agtttaatgg ctgatatctt ttggacttta    28800
actaattgtc tattgctaat gaaacctagg aaattctgat ccttgagatt atttttaaag    28860
tgcacataag gtatattcag gtgaaaataa agaagacaag catagcagcc cccagaaggc    28920
catgtggaga aagataaaaa aaaaaaaaaa ccagcaaagt atctacagca agatgtgggc    28980
ctgagggtct tctgtgcagc tcagttcaac caaaagtata tcacagcagt tactactgtt    29040
tatgtatgca ttcggaagac gggagggacc tagtcaatat ggtcaatttc aaggacttcc    29100
tgaagctttt gaattgttta cttcctgagc ttccttagag gatgggattt tttagttccc    29160
tttagagcaa tggttctcaa cctgtgaccc cctctgaagt caaacaaacc tttcacatgg    29220
gttgcctaaa accattgtaa aacacagata ttattattaa taatagttgc aaaattacag    29280
ttatgaaata gcaacaaaaa taattttatg gttatgggat cgccacacaa gaggaatggt    29340
attaaaggac caaagcatta gggaggttga aaaccattgc tttatctcat cctattttta    29400
tgggtgcttc tctctgagac ggagtctttt atcttaaaga aaattgctat tcaacaattg    29460
aagagaggta ttaggtcagt aagagtatgg tatggtcata ggccagcaca attcctgcat    29520
atgcttgtca taaataactc acctcttctt cagattgact gggaaaagac aaaacatttc    29580
aaagtgatct tttaaaagtt tccttcgtta taaagaagga aaaatggatt aaaaggatgg    29640
aagaaaatgc tttgaaagac cagttactac tgccatagtc ttagagtagt gtatttgaga    29700
gaactgtgtt aaatgtggtt gctaggactt ttgaaggttt ttttctcccg ttttttgtttt    29760 tgccttttgt ttttatggtt tgcttgtttt gttatttgtg tgtgtgtgtg tgtgtgtgtg    29820
tgtgtgtgtg tgtgtgtgtg tgtgttgtgt gtttgtgtgt atggagaagg caccatgact    29880
tttcaaagat aaaatgaaaa gtgaatctaa tggatttcct tgaaaagctg tcttgaaaat    29940
tactgtcagt aatccaaagt tgtattattt tgaagattat tcaatgaaaa tattaatcta    30000
caaccacgtg tctattttta ttttcacaag agtctgagat tgttactggc tgtcgtttat    30060
ttcaatttgt catcatgttc aatataatta atcatatact tttaatttct tccaaaaatg    30120
aaaatttgaa atgacagata tatgatcaag agggcagtca ggccaaaaca atgtttgttt    30180
ggtcactgat tttgactgat tgacctaatg ggaacaaaac actgtcatta taaaagtatg    30240
ttactcagca gatttcctct tatagtaaac actatacaat tactcttttg catttagaaa    30300
tttcttgcct gccaccacga gttgaaaatg gagatggtat atatctgaaa ccagtttaca    30360
aggagaatga aagattccaa tataaatgta agcaaggttt tgtgtacaaa gaaagagggg    30420
atgctgtctg cacgggttct ggatggaatc ctcagccttc ctgtgaaggt gacattattc    30480
ttattttcta cgtctttat tatataagaa gtagaacagt gaatggaaaa gaaagatggt     30540
gtcacaaatc catgtttagc tgattgcatt gagtctaacc atctgttttc atggtgttta    30600
tgtatcctag tcagagaagt atctcagtag tcctttggca ttaaacctct gcacaagatt    30660
aactccaggt gtcctcctaa atagaccatt tatccactaa aggatcaaac tataacccat    30720
```

-continued

```
gatgtagcta ttttgtattg tcttgtgctt aagaggaact tttcaaacaa tcattccagt   30780
ttcaggtgaa tccagttttc catggaagca ttaggattca atagaatagt catgccacac   30840
caaataacag agcagagcag aatgcctgtt ctgtactgaa ttcacctaaa gctgaaatga   30900
tttttaccta gttaaaatct cttccttaac ctagatttgt tttcaaactg agaaatatat   30960
ttggttccct aaatgtgctt ctacagatgc tacatagcct tgcttctttt gaaccctagg   31020
aaagaggaga ggagtgtgag tagagggaga gaatagagga agggaagaaa ggaagcaggg   31080
aatgaaaaag actctccatt aaagttcatt ttgaccattt ctcaaacaca aagtcaagta   31140
tgaaaagtat agttctgtgt tcttgggggt ctttttcttc agggaaatag gtgacagagg   31200
gtactctcat ctgatagtaa ataagcattt gatgatatga ataaagagac ctgcatctta   31260
actcatatag gcatgcaaat ctctaacaat ggacttcatt ttactgaaga aaactttata   31320
ctcctatatg aaaagtagtt tcttattaat gaaaatagtg catcactctg tacctcagct   31380
gatatgtttg gccaatgcat tgtctttgtt ttcctggagc agaaaaatag cttacttgtg   31440
ttgatgtaca attatctgga aattatcaga acactttaat ctctctgaca ccatatagtg   31500
gaatacatta tttgctgcag ctgactttac aagaatctta gactctataa gacaccaaaa   31560
ttaaaataag ataatataaa aataaataaa ctttgttcca cctgatcata atgtgaacag   31620
ggggtttaaa acaacttccc agagcatttg gatctctagt atatagtaga cagtctctaa   31680
tgacaagcag gaatgatgaa aaataccaca atcttctgaa caatttattt tgatgcatct   31740
gtttcctgta cagagtagat tttgtaaaat tgactttcca atgtaagaga actaaacttg   31800
aaatatccca ttccaaatgt ctctactaaa taatttgaaa taagaaaact gtacatttgg   31860
gaaaatgtac aagggaaaaa agacactatg catttgaaaa attaactaca tatagtcaat   31920
cagacattat caggggttta tgttggcagc ttagggtaat ctccaaaagt cttttttgtta  31980 ataagtttta caaagttctt cccatactgt ttgcttgtcc tcttaaattc ttggacatat   32040
tgttgttgtt tgatatctta tagctgtacc ttaaaaagat actgagtaaa gctgcaatat   32100
taagaaaacc taagtagaaa agcataaact acaatggtcc tatgaaaaca tgacaagcag   32160
agtgctgtga agagaaaaac gatcaaagga acacaatgtt gattcaaaaa ttgttgttaa   32220
gtggcataaa agttaggaga catacttgat ttgagtagtt atcttagggt gaagagacac   32280
catgaccaaa ggaatatta attagggctg gcttacaagt tcagaggttc agtatactat   32340
cgtcaagggg gaaagcttgg cagcatccaa gcaagcatgg ctttgaagaa ggtactgaga   32400
gttctacatc ttgatccaaa ggcagtcagg agaagactgg caaagcccac cctaacagtt   32460
atacatttcc ttcaacaagg ccacacctat tccatcaagg acacacttcc taatagtgtc   32520
actccctggt ccaagtatat tcaaaccatg acagtagtca gatattactt tagctaagtt   32580
tttactacta tatatgtata ttacctgtct tcatgaggga ccccagcaac tgaagcaagg   32640
actgtcgctg actttgttgc ctgtctgtgg atcctatccc ccttgactgg gctgccttgt   32700
ctggcctcag tgagagagga tgtgcctagt tttacagtga cttgatatac cagaatgggc   32760
tggtaaccag ggggccctcc cctttcaga ggagaagggg tagaagggat ggggcaaggg   32820
gctatatgtg gagagactga aaggaaagta gagggcttca ataggg gataa aatttataaa  32880 aaaaagaaat acatatatac tgtggcacaa atttaatacc agtagaaagg ttactgccat   32940
actttcaagg gctaagtgta cacattagca ttatatatgg aaaggcaaaa attcaaataa   33000
cacttaaaac caaagaatta tgtgccagat tgagtataag aatgatgaat aaatctccag   33060
actcttatca taatattttt gttttataag ttaaaatatt agatttagat ggaaaagtat   33120
```

-continued

```
gaatggagga aagttaatga tagagattgc cattttaaaa actggattgc cttcaaattc   33180
tgtatatgag catgattcat ttacctatat ggattttgat taaaactaca gaattattag   33240
cataagagcc agactttaat tatggaggtt atcttgagtg ccataaagga cagaagaaaa   33300
aagaacacta gtgaagaata catgctcata aaaaccaact ataaggcaaa aaagttattt   33360
gtgcagaaac tgtagctact taaaaataat tttttaaatg tagcaatggt atcaattaga   33420
agatctgggt taagatgatt taaggcacat aagacataaa atgtacattt gagaaatggc   33480
ttggtgtttg tgaaggttag attcatgatt ttgaaagtca aaaattacac tatgtttctt   33540
ccttgttcag tagattttcc caaataagtc agaggcacatg ttcaattcaa agagaaagag   33600
gtgtaaaatc ttcatgaata tttagaatta aggacctgtg aatattaata aataggctca   33660
aatgagaatc aaggccagca atttcaatga aagaaataga aactggatgg aaacatgttt   33720
cttgcactga aggtctgtat gatgaagtta ttatcatctt tagaagcata aggtactata   33780
tgggacagca tcaagagaga attagtacca gagaggcaca catacaccag gaggagagag   33840
aagaagtctg actgatatgc ctagcctatg aagatgcatt cttttcaatg tctattatat   33900
agttatcagt acaaataact ggtgtctgcc atttagtttt aatattctta acctaaatga   33960
gattaaatat ttctcattac ttatatctga ttcttttcag aaatgacatg tttgactcca   34020
tatattccaa atggtatcta cacacctcac aggattaaac acagaattga tgatgaaatc   34080
agatatgaat gtaaaaatgg cttctatcct gcaacccgat cacctgtttc aaagtgtaca   34140
attactggct ggatccctgc tccaagatgt agctgtaagc ttcacttata tctttaatct   34200
ccatgatcct gaaattagac taataagcat gcatagaaga aaatatagta atagcaaata   34260
tttaattttt tatctatgta caacacttaa aaatattcta cttttaaaag tcaagaaaaa   34320
ttaacataat attatatttt aatattaaaa tttaaaattg caagtaatat ttaaaataca   34380
ttatagaaaa ctaaaatttt taatttactt ctacttaaat atataggcat ctgtacattt   34440 ttttctttt ttttcatttta tttttttttt attaacttga gtatttctta tttacatttc   34500
gagtgctatt ccctttcccg gtttccgggc caacatcacc ctaaccctg gttgcttggc   34560 attgttgttc ataagaggtc tcgagcccct tcaagcttgc cagttctttc tctgattcct   34620
tcaacggggg tcccgttctc agttcagtgg tttgctgcag gcatttgcct ctgtatttgc   34680
tgtattctgg ctgtgtctct caggagagat ctatatccgg ctcttgtctg cctgcacttc   34740
tttgcttctt gtctaattgg atggttgtat atgtatgggc cacatgtggg gcaggctctg   34800
aatgggtgtt ccttctgtgt ctgtttaat cttgcctct ctattccctg ccaagggtat   34860
tcttgttccc ctttaaaga aggagtgaag cattcacatt ttgatcatcc gtcttgagtt   34920
tcatttgttc taggcatcta gggtaattca agcatttggg ctaatagcca cttatcaatg   34980
agtgcatacc atgtgtgttt tctgtgattg ggttacctca ctcaggatga tattttccag   35040
ttccctccat ttgtctatga atttcataaa gtcattgttt ttgatagctg agtaatattc   35100
cattgtgtag atgtaccaca ttttctgtat ccattcctct gttgaagggc atctgggttc   35160
tttccagctt ctggctatta taaataaggc tgctatgaac atagtggagc acgtgtcttt   35220
tttatatgtt ggggcatctt ttgggtatat gcccaagaga ggtatagctg gatcctcagg   35280
cagttcaatg tccaatttc tgaggaacct ccagattgat ttccagaatg gttgtaccag   35340
tctgcaatcc caccatcaat gcaggagtat tcctctttct ccacatcctt gccatcattt   35400
gctgtcacct gagttttga tcttagccat tctcactgga gtgaggtgaa atctcagggt   35460
```

-continued

```
tgttttgatt tgcatttccc ttatgactaa agatgttgaa catttctttta ggtgtttctc   35520 agccattcgg cattcctcag ctgtgaattc tttgtttagc tctgaacccc attttttaat   35580
agggttattt gtctccctgc ggtctaactt cttgagttct ttgtatattt tggatataag   35640
ccctctatct gttgtaggat tggtaaagat ctttttccaa tctgttggtt gtcgttttgt   35700
cctaaccaca gtgtcctttg ccttacagaa gctttgcagt tttatgtgat cccattggtt   35760
gattcttgat cttagagcat aagccattgg tgtttttgttc aggaaatttt ttccagtgcg   35820
catgtgttcg agattcttcc caacttttttc ttctattagg tttgagtgta tctggtttga   35880
tgtggaggtc cttgatccac ttggacttaa gcttgtacag agtgataagc atggatcgat   35940
ctgcattctt ctacatgttg acctccagtt gaaccagcac cgtttgctga aaaggctatc   36000
ttttttccat tggatggttt tggctcctat gtcaaaaatt aagtgcccat aggtgtgtgg   36060
gttcatttct gggtcttcaa ttctattcca ttggtctatc tgtctgtctc tgtaccaata   36120
ccatgctgtt tttatcacta ttgctctgta atactgcttg agttcaggga tagtgattcc   36180
ccctgaagtc cttttattgt tgaggatagc tttagctatc ctgggttttt tgttattcca   36240
gatgaatttg caaattgttc tgtctaactc tttgaagaat tggattggta ttttgatggg   36300
gattgcattg aatctataga ttgctttttgg taaaatggcc gttttttacta tattaatcct   36360 gccaacccat gagcatggga gatctttcca tcttctgagg tcttcttcaa tttctttctt   36420
cagagtcttg aagttcttat tgcacagatc tttttacttgt ttggttaaag tcacactgag   36480
gtactttata ttatttgggt ctattatgaa gggtgtcatt tccctagttt ctttctcggc   36540
ttgtttctct tttgtgtaga ggaaggctac tgatttatat gagttaattt tatacccagc   36600
cactttgctg aagttgttta tcagctttag tagttctctg gtggaacttt tgggatcact   36660
taaatatata tcatatcatc tgcacatagt gatattttga cttcttcttt tccaatctgt   36720
gtccctttga cctcctttttg ttgtctgatt gctctggcta gaacttcaag aactatattg   36780
aataagtagt gagagagtgg gcagctttgt ctagtccctg attttagtgg gattgcttca   36840
cgtttctctc catttagttt aatgttagca actggtttgc tgtatatggc ttttactgta   36900
tttaggtatg ggccttgaat tcctattctt tccaggactt ttatcatgaa ggggtgttga   36960
attttgtcaa atgctttctc agcatctaat gaaatgatca tgtggttttg ttctttcact   37020
ttgtttatat attggattac gttgataatt ttccgtatat aaaccatcc ctgcatgcct   37080 gggatgaagc ctacttgatc atggtggatg attgtttttga tgtgctttttg gattcggttt   37140 gccagaattt tttgagtatt tttgcattga tatttataag ggaaattggt ctgaagttct   37200
ctttctttgt tgggtctttg ggtggtttag gtataagaat aattgtggct tcatagaacg   37260
aattcagtag cactccattt gtttcaattt tgtggaacaa tttggatagc atatgaggtc   37320
ttctatgaag gtctgataga attctgcact aaacccgtct ggacctgtgc tcttttttggt   37380 tgggagacct ttaatgactg cttctatttc cttaggagtt atggggttgt ttaactggtt   37440
tatctgttcc tgatttaact tcggtacctg gtatctgtct aggaaattgt ccatttcctg   37500
cagattttca agttttgttg aatatatgct tttatagtaa gatctgatga ttttttgtat   37560
ttcctctgaa tctgtagtta agtctccttt ttcatttctg attttgttaa tttggacaca   37620
ctctctgtgt cctctcatta gtctggctaa tggtttatct atcttgttga ttttctcaaa   37680
aaaccaactt ttggttctgt tgattctttc tatggtcctt tttgtttcta ctttgttgat   37740
ttcagctctg agtttgatta tttcctgcct tctactcctc ctgggtgtat ttgcttcttt   37800
ttgttctaga gcttttaggt gtgctgtcaa gctgcttaca tatgctcttt cctgtttctt   37860
```

-continued

```
tctgcaggca ctcagagcta tgagttttcc tcttagctca gctttcattg tgtcccataa   37920
ggttgggtat gttgtacctt cattttcatt aaattctaaa aagtctttaa tttctttctt   37980
tatttcttcc ttgaccaggt tatcgttgag tagagcaatg tgcaacttcc acatatatgt   38040
gggcgttttt cccttattgt tattgaagac agctttaggc cgttgcggtc tgatagcacg   38100
catgggatta tttctatctt tctgtacctg ttgaggcccg ttttttgacc cgtttttaaa   38160
tggtcaattt tggagaaagt accatgagga gctgagaaga atgtatatcc ttttgcttta   38220
ggatagaatg ttctataaat atctgttaag tccatttggc tcatgacttt tcatagtctg   38280
tctacgtctc tgtttaattt ctgtttccat gatctgtcca ttgatgagag tggggtgttg   38340
aaatctccta ctattattgt gtgaggtgca atgtgtgttt tgagctttac taaggtttct   38400
tttacgtttt aggtgccctt gtatttgggg catatatgta ggattgagag ttcatcttag   38460
tggatttttc ctttgttgaa tatgaagtgt ccttccttat ctttttttgat gactttagt   38520 tggaaattga ttttatttga tattagaatg gctactccag cttgcttctt ccgaccattt   38580
gcttgcaaag ttttttttcca gcctttcact ctgaggtaat gtctgtcttt gtctctgagg   38640
tgtgtttccc gtaggcagca gaatgcaggg tcctcgttgc gtatccagtt tgttaatcta   38700
tgtcttttta ttggggagtt gaggccattg atgttgagag atattaagca atagtgatta   38760
ttgcttcctg ttatattcat attttgatat gaggttatgt ttgtgtgctt ttcttctctt   38820
tgttttgttg ccaagacaat tagtttcttg cttcttctag tgtagagttt gcctccttat   38880
gttgggcttt accatttatt attctttgta gtgctggata tgtagaaaga tattgtgtaa   38940
atttggtttt gtcgtggaat atcttggttt ctccatctat gttaattgag tgttttgcag   39000
gatacagtaa cctgggctgg catttgtgtt ctcttagggt ctgtatgaca tctgtccagg   39060
atcttctgac tttcatagtc tctggcgaaa agtctggtgt gattctgata ggtctccttt   39120
tatatgttac ttgacctttt tcccttactg ctttttaatat tctttcttta ttttgtgcgt   39180
ttggtgtttt gactattatg tgacgggggg tgtttctttt ctggtccaat ctatttggag   39240
ttctgtaggc ttcttgtatg cctatgggta tctctttctt taggttaggg aagttttctt   39300
ctatgatttt gttgaagata tttactggtc ctttgagctg ggagtcttca ctctcttcta   39360
tacctattat ccttaggttt gatcttctca ttgagtcctg gatttcctgt atgttttgga   39420
ccagtaactt tttctgcttt acattatctt tgacagttga gtcgatgatt tctatggaat   39480
cttctgctcc tgagattctc tcttctatct cttgtattct gttggtgaag ctcgtatcta   39540
cggctccttg tctcttcttt tgttttttcta tatccaggt tgtttccatg tgttctttct   39600
tgattgcttc tatttccatt tttaattcct tcaactgttt gactgcgttt tcctggaatt   39660
ctttcaggga ttttttgtgat tcctctctgt atgcttctac ttggttattt atgtttttcct   39720 ccatttctct aaaggagttc ttcacgtctt tcttgaagtc ctccagcatc atgatcaaat   39780
aagattttga aactagatct tccttttctg gtgtgtttgg atattccatg tttgctttgg   39840
tgggagaatt gggctctgat gatgccatgt ggtcttggtt tctgttgctt ggattcctgc   39900
gtttgcctct cgccatccga ttatctctag tgttactttg ttctgctatt tctgacagtg   39960
gctagactgt cctataagcc tgtgtgtcag gggtgctgta gacctgtttt cctgttttct   40020
ttcagccagt tatgggaaca gagtgttctg ctttcgggcg tgtagttttt cctctctaca   40080
ggtcttcagc tgttcctgtg ggcctgtgtc ttgagttcac caggcagctt tcttgcagca   40140
gaaaatttgg tcttacctgt ggtcccgagg ctcaggtttg ctcgtggggt gctgtccagg   40200
```

-continued

```
ggctctctgc agcggcagca accaggaaga tctgcgccgc cctttacagg agtttccgtg    40260
caccagggtt ccagatggcg tttggtgttt tcctctggaa tcagtaatgt gggcagagtg    40320
cagtctcttc tggtttccca ggcatgtctg cctctctgaa ggtttagctc tccctcccat    40380
gggatttggg tgcagagaac tgtttatctg gtcggttcct tcaggttctg gtggtgtctt    40440
agacgcaggg gacctgctgc tgctgtgccc ttatccaagg gaacgcagag gccgtataca    40500
gtttcctctt gggccaggga tgtgggttaa gggtgggcag cgttggtggt ctcttctgct    40560
ctgcagtctc aggagtgccc acctgtccag gtggtgaggt ctctctccca tggggtttgg    40620
gagcagcgag ctgctgcggg cagggatccg cgggttttca tctgtacact ttttaactaa    40680
acattttcta agaattgtat gaaattaata ggtaagagac gcaggggacc tgctgctgct    40740
gtgcccttat ccaagggaac gcagaggccg tatacagttt cctcttgggc cagggatgtg    40800
ggttaagggt gggcagcgtt ggtggtctct tctgctctgc agtctcagga gtgcccacct    40860
gtccaggtgg tgaggtctct ctcccatggg gtttgggagc agcgagctgc tgcgggcagg    40920
gatccgcggg ttttcatctg tacacttttt aactaaacat tttctaagaa ttgtatgaaa    40980
ttaataggta agaatattgt caggtaagaa ctgattttac ttatttattt acatcatagt    41040
aaatatcctt caatagtatt tgcctcatag caaacctttg tcatccctcc attttttgtta   41100 gccacatttg aagataactt ggctgctggc tgcatgagtg tggtgctgtc agacattgtc    41160
ttggctctta gtcatcagga gactttgctg ggctgtaggc catatgttca acataccaca    41220
ttcactagga tttggcaaga gggttcaatt ccttatcaga taagcctgtg gatagattga    41280
ttcacaaaat tgattcttgc cttagagtta ctgatcaaag agacattggg gggcctagaa    41340
tccatccata acctacctat accatacaat gttttgcta tggctgtttc ttgtatactg     41400
ggttcaatat gcatatgaag aaggaaatta tgtttatctg tagagagttg ctttgaatga    41460
tgtcggtggc ttctcaacac atgcatacca cagtgttatt tgagtcaaga atatttaatt   41520
cctggaatat tccattcttt tcagatttt gtctatctac atccatatat ttttctttta     41580
tctaacagtc tatgttaaat gtttatcata cgtaaccctg atatcccta aggaataaag      41640 tgtatgacag ataagcagcc aaggatctct tcctactcat ctttctgttg tgatgttaat    41700
attactgaat taactactta gaagaagaat ttattttgtt ttgctgactt gaattcatgg    41760
tcaagttgtt ctgtcatttt catcctgtta ctaggaggtt atttatgtta gggaatgagt    41820
ggtaagtcta agctgcttgg cttatgacca ccagcaagta gagatataag agaatgacca    41880
agatctcaat atcccctca aaggcatagt cccaatgacc taatttattt cactgtgtcc      41940
agaaattctg aaatttataa ccttcctaat agcaccagca atgacaaacc aagcttttaa    42000
ctaaggtgaa attctaggaa atctataata tccaactcaa aagaatgaaa gaagctattt    42060
acactaagaa atagtattga taaatatagt aattgtataa aaattgaatt tttaaaaata   42120
ttaaaattta gatttcttac aaattatttt tcttacttt attggtccta tttatttatt     42180
tattatttgt ttttgtcatt aggttgtttt ttataaaatt tattctctca tatattacat    42240
cctgattgca gtttctttc ccttaatgtc ccaactcctc catccctca acctcattcc       42300 tccccatcca ctcctcctt atttcccttc agaaaatagg gggaccctca gggaaatcaa     42360
ctgattattc catatcagat ttcaatgtgt cagtacaagg caccccagta tgaggacaag    42420
ggtccccaaa ataggcaaaa gaatcaggaa caactgcaac tctctctgtt aggaattcca    42480
caaaacacca ggcttcacaa ctataacaaa tatacagagg gtcaaggtta gatccaggct    42540
ctctgattgt cagttgaatc tcagtaaaac cctgagtcca ggtgagttga ctctgtgagt    42600
```

-continued

```
tttcttgtgg tgtccttggc tgctctgctc ctataatctt tcttctctaa cttcaacagg   42660
attccccaaa ctctaaacta aaggtcagtg gaaaagtacc ttttcttctc ctgagtaatt   42720
gcttcaaagc ctctgctaac ctaggcctag ttctttaatc tttctctagc ctctgtataa   42780
tcttatctag gtcaagaatg tttacagttt ttgaaactta cttgtgaata agatcacatc   42840
gtcctatttc tttctgaact ctggctggct tgttcagctc aactgttctg gcttaaactc   42900
ctctgcaaac tgtttcaaac tgacttcttt ttcagccttt gacttggtgc tatgcttggc   42960
ctcagattaa ccctggcaat ctgtttaat cctccgactc cttcttattc tctggcttct    43020 cttacctta cttgtgacta gcttgttctc tctctgcagc ttgtactggt aaaactgccc    43080
ctccctcacc tctttctctg tgctgccctc tcgtaaagag gtagcctctt tctctctgtt   43140
ctcatgagag ttgggcatat cttattctgt taaatctttc tctgatttaa catctctttc   43200
aaacaagggt gattccttct acaaaataac tttaccttca ttgtttggga ttaaagccct   43260
ttgtagtgtt actaaggact tgtctgtatt ccagccagaa ggattaaagg tatatgctga   43320
ggctgcgcca caccacagct aaaaacaggt ttttcttgta aacaacacaa tcttggattt   43380
cacagtgtta ccaaaagtcc taaaacagtt tgaatctctg catctgtttc tattagttgt   43440
ggagtagagc ctctcctatg atgactgggc taggcaccaa tctataagta cagcagagta   43500
tcattaggca tcattgaatt gacttttttt tctttgccag tcatggttgg ttctattcta   43560
ggtctctggg ccgtacagcc tctggtttct ggtcctcaag tcagtgtcag gcatgggttt   43620
caagctgtac ctgtcattag ttagtcactt tcacaatttc tgtgccacct tcaccccagc   43680
acatcataca ggtgagacaa attgtaggtt gaaggtttta tgtctggttt ggtgtcccaa   43740
aacctttgta gggttatgtc cctgttttca ttactgactt tgttagtttt tatatttaat   43800
ctgtctttca gttagtttgg ctaagggttt gtctatcctg tagattttct caaaagacca   43860
actcttcttt tcatagattc tttgtattgt tctctttgtt tctattttat tgatcttagc   43920
cttataatgt ttcttagccc caagttggtt tatttcctgc tctctactcc tcttccagag   43980
ctttcaggtg tgctgttaag tcacgagtat aagatctctc taatttcttt atgaaggcac   44040
ttagtgctat gtagtttctt cttaacacca cttttattgt gtcccatacg tttggtatgt   44100
tgtgccttca tttttcattga atactagaag ccttaaattc tttatttctt ccttgaccca   44160
gtggtcgttc agtaaagaac tgttcagttt ccatgagttt atggagttta tgttattgtt   44220
caagctcagc tttaatccat gtattctgaa aaaatacagg gggttatttc atttttcttg   44280
tatctgttga gactcgcttt gtgacggagt atatggtcag ttttagataa agtactgtga   44340
gatgttgaga caaaggtgta ttcttttgtc tttgggtgaa atgtttttata gatttctgtt   44400 aagtccattt gattccataat gtcttccagt tccattttttc tgttccttttt ttgtttggat  44460 gacatgtcca ttggtaagag tggggtatgg aagtcttcca ctattaatgt atggtgttca   44520
agatatgtta tgaaatattt ttgttagtta gtttgtttta tgattttttat gattgcggtt   44580 tcccttgcat ttggggcaga tgttcagaac tgagaggtta tactcatgaa atattctttt   44640
tgattagtat gacgtttcct ttgtaccact aatgattaat tggtttgaat aatattttgt   44700
taaatattgg aatggctaca tgatcttgat tctttggtcc atttgctagg gaaatctttt   44760
ctagcctttt attattaagt aatatccact tctgatgttg aggtatattt cctgtatgca   44820
gaagaagggt ggatactgtt ctcacatcca ttttgtgaaa cctgtgccat ttttattgga   44880
gaattgaatc cattgatact gagagctatc aatgactaat gattgttcat tcctattatt   44940
```

-continued

```
ttgatggtgg tggtggcagt gtttgtgttt gagtgtgtgt gtgtgtgtgt gtgtgtgtgt  45000
gtgtgtatgt cttttttttgc tcatatgaga ttgtttattg cctgtggtgt agatgatctt  45060
tttgtgttag ggtacaagtt atttatttct tgggtgtagt tgatctcctt gggttggaat  45120
tttctttcta gtaatttttt ttgtagggct tggctgtgga tagatattgt ttaaacttgg  45180
ctttctcatg gtatatcgtg ttttctccta ctcttattga gtattttgct gactacttca  45240
gtcaggatgc aactgtgatt gttcagaatg cccaggccct tcttgctttc agagtttttca  45300 ctaagaagtc aactatattc tgatagcttt gcctttgtat ttcacttgct ttttttccttt  45360 cacatctttc actaatcatt atttgttttg aatatttagt attttgatta ctgttttgac  45420
aggacttcat tttctttttc catctagttg gtgttctata agcttcttgt gcttttatac  45480
gcatctcctt ctttaggacc tttttctttt attattttgt tgaaaatatt ttctgggcct  45540
tctaaaattt attccttgta agtttcacaa gcacctgatc ccattcttct ttccattctt  45600
ccatatctac tctttttccct tgtaaatgtt cccccaaaac aaaacaaata aaaacaaacc  45660
aacaaacaaa tagacatctt gtcaaggtag ctataggcat tgcagtgtgt cacacaggga  45720
caaaaatctc ttttgtccaa acagctttac ttgcagatat tcatcgcatt tagtcatttc  45780
tttggttcaa gatctctggc ttctagtaca ccacaataca ttctgaatat tttatctttc  45840
acattgctcc aactcgataa acaacacatc atccatatct gtcctttccc cagaatcata  45900
attttgagtg tttttgtatg atgcatttgg cttaactcag gaaatatgtg gaccacttga  45960
attggagctg tattttcgaa cctgatttac tcacgagtgg gtatatacct gaaagcactg  46020
actccctatg tttctgaatc tattagcgta aaatagttcc aaggtgaggg ccaaggttcc  46080
ctatgatctt actacagtca tgcctggata tgagggccca ttcttaagag gtgtctgtaa  46140
ttgttgagag tttgtgattt taatgataat gtttttgttc agaagatatc atagtcttaa  46200
tcactctagc tcttagaacc tatgtgctcc ttcattcaca ggttgcttgt aggggatagt  46260
gctcctgttt tgtttaacac ttcacaatac actcactatt tctagtacct tgtgtattac  46320
tacatctata gttttattat aatttaccag aaaaaagagt cttctctgat gttgacagtg  46380
ttattagcta tgaatataaa catagttact tataaggttg ctcagtgtta agtcaatgta  46440
ttttaatagc agaattaata tgtgtgtctg cactcagatc ttatgacatc cttgccatgg  46500 gctttttaagt aggtttacaa atacaagcct gggatctgtg tagcgcaatg agtcacaaac  46560
ccaactatgt ttgagtttcc ccaatgtaga tttacccaaa tatatctggg ctgcttgtaa  46620
cttaaatata tatgaatttc gtttattcta cactgaactt tctgatactt cctggataag  46680
ataaaaatga ttaatctctc tgtaatgtca ttaaataact ttttctactt aaaatcttta  46740
gtactcactc ctaagggatg tttaattact caccactttc atcaaatctt ttactatttg  46800
ggagaaaatg cattgtaaaa tgataactgg cacaattcag aagatggtga ttgtgaatct  46860
gtgttagaag tgattctaga aattaatctt ttgtgtcatg ttgaagatgt agtaggatga  46920
gatttatcaa taaaaattag aagatcttgg gattgaagat cagtaaaaac tggaatatct  46980
tgcgctgtgt tcataatatt tagaacagtt gtaaaactgg tcaatatatt gatcagcagt  47040
ctgagtagag tgcatcaaca ctgtgatgta tggtccagga atcactgctg atgcagccac  47100
gacctgcatc tggaaagtgt aagatgttaa acaaagctca cttaggtact gaccacctca  47160
ggtgtctgtt actttaagga gtattatgtt tgcttcaaga accatgtata acggagtaaa  47220
cctgtgccca ctggagaatg aagaataggt aaaagtctga ggtctgtggt aataatgata  47280
ctcctactct gaaccatgct ttcttttcatt acttttcaaa acaaaatctc agtgagctaa  47340
```

-continued

```
tttgacttat tgatgtccta tgagaagtgt gattcttaaa attgttaaag aagaacaatt   47400
tttaaaccat gtaaaaatgt gtaaaaaaac tcttgaaata tttaataaaa caaaaactaa   47460
aatgaatgag gaagcttgag gaaatttgtt tgattttttta tgtatttgtt gaaataactt   47520
ttaatgtatt gcatgaggtt ccttgaagca gaatcatact taatataaaa gggatattat   47580
tctcatacta aagtacaaat gataaatagt aatcacaaat aattacatgt aataaagtaa   47640
tcatatatta catataaact taatataatg aacaatatgg catttcaata caaaggtaca   47700
aaaatagctc catatcgttc catgttcata ctatatttta gtttcagtga aaattataaa   47760
taagaaatta tattgaatat taacaagtat ctccaatcca attatctggt ggagtatcag   47820
ctacaacttg acttcatgtt gaaagacatc ctcacaaacc actgttgtct tttgttttat   47880
tttcttatcc cacacattca ctgttctgtc attctgttat tttgattagt ttaaagtaat   47940
ttactgatca agagttttttt ttcctctgat atgagtgttt tatggttgtt ttattttatt   48000 attttttttct ttcaagtgaa accttgtgat tttccacaat tcaaacatgg acgtctgtat   48060
tatgaagaaa gccggagacc ctacttccca gtacctatag gaaaggagta cagctattac   48120
tgtgacaacg ggtttacaac gccttcacag tcatactggg actaccttcg ttgcacagta   48180
aatgggtggg agcctgaagt tccatgcctc agtaagccaa tgcctttata gttaactatg   48240
ttgattcttt taaagagaga gcacatacat aattaagtta ttcataacaa aaataagacc   48300
aacaaaagaa tttgtgagca aaatggctag tttctgttat gaaatgtttc ttcatgaaac   48360
atgcaatagg gactatggaa atatctttat cacttgcata ttttattttt acaaacgaaa   48420
gataaatgct attctcttaa atgtttgtta ttaattttat ttttgaatga tgtgcatact   48480
cattaaacag ttttaaagat aacatttatc ttagtttatt tttaaacaaa ttaaagattt   48540
tattttttta atttttaatt attatgtttc ttagggcaat gtattttcca ttatgtggaa   48600
tatggagaat cttatactg gcaaagaaga tatatagagg gtcagctgc aaaagtccag   48660 tgtcacagtg gctatagtct tccaaatggt caagatacaa tattatgtac agaaaatggc   48720
tggtcccctc ctcccaaatg cgtccgtatc agtaagtaac taatacttag atcgcaagaa   48780
gatcgtgact ctctgtccca tctgtatttg tttttattgg ctaatttttta tgtacatttc   48840 aaatgttatt cttttttcctg gtttcccata cataagcccc ctatccaatc cccctcacac   48900
ttctttgagg gtgttcccct tccccaagaa cccatccttt cccacttccc taccctgaca   48960
ttcccctact aatacttaga tcgcaagaag atcgtgactc tctgtcccat ctgtatttgt   49020
ttttattggc taattttttat gtacatttca aatgttattc tttttcctgg tttcccatac   49080
ataagccccc tatccaatcc ccctcacact tctttgaggg tgttcccctt ccccaagaac   49140
ccatcctttc ccacttccct accctgacat tcccctacac tggagggccc agccttagca   49200
aaaccaagga cttctcccct cattggtgcc caacaaagcc atccttgtta tatacagcta   49260
catatgcatc tggagccatg agtctgtcca aatgtcctct ttgggcagtt gtttagacct   49320
tgggaactct ggttggttgg tagtgttgtt cttatggggt tttaagaccc ttcagctcct   49380
tcaatccttc ctctaattcc tccagtgagg accccattct cagttcaatg gttggctgct   49440
agcattctcc tctgtatttg tcacactctg gttgagcctc tcaggagaca actatatcat   49500
gttcctgtca gcatgcactt cttggctcca tcaatattgt ctaggtttag tatgcatgtg   49560
tgtttatata tatatatatg tatatataca ggtgtagtat gcataagtat atatgtatat   49620
gtctatgttt atttgttgga tccccaggtg gatcaggctc tgaatgtcca ttccttcagt   49680
```

-continued

```
gtctgctcca aacttggtct caatatctct tcctacaaat tttcttctat tagttcgaga   49740
gtatctagct tcatgtggag gttcttgact aactttgact taaggatttt tgcagggtga   49800
tgaaaatggg tcgatttgcg ttcttctaca tgctgacctc caggataacc agcaccatct   49860
ggtgattcca ctgaatgatt ttagttcctt tgtcaaatat taagtgacca caggtgtgtg   49920
agttcatttt tgggtcttca attctactcc aatgatctac ttgcttgtct ctgtatcatt   49980
attgctctgt aaaacagctt gaggtcatgg atgagattac caaagaacct tttttattat   50040
tgaggatagt tttcactatc ttggattttt ttgttagtcc aaatgaattt gcaaattgct   50100
ctttctatgt ctatgaagaa tttagttggg attttgatag ggattgcatt gaatttgtag   50160
attgcttttg gcaaaatggc cattttact gtattaatcc ccccaaacca caagcatggg   50220
aaggttctcc atcttctgag atctttgatt tctttcttca gagacttgaa gtaattgtaa   50280
gatctttcac ttgtttgagt agagtcacaa caaggtattg tacgtaactt gtgaccattg   50340
tgaagggtgt catttcccta atttcttttt cagcctggtt atcctttgag tagaggaagg   50400
gtactaattt atttgagtta aatttatacc cagccaattg gctgaagtta tcatgcttag   50460
tagtttgctg atggaacttt tggggtcact taaggatagt attatatcat ctgcaaatag   50520
tgatattttg actcttcctt tccaatttgt atcccattga cctttgttg tttgattgct   50580 ctgaccaaaa ctttgagtac tatattgaat aagtagggag agagtgggca gccttgtcta   50640
gtccctgatt ttagtgggat tgcttcaagt ttctctccat atagtttgat gttggctact   50700
ggtttgctgt atattgcttt taatatgttt gggtatcggc cttgaattcc tgatctttct   50760
acggcttcta tcatgaaggg gtgttgaatt ttgtcaaatg ctttctcagc atctaatgaa   50820
atgatcacat ggtttttttc tttgagtttg ttaatataga ggattacgtt gatgaatttc   50880
tgtattttga accatccctg catccctgag atgatgccta cttgatcatg agggacgatt   50940
attttgatgt gttcttggat tctattgaca agaattttat tgagtatttt tgcatcaata   51000
ttcataaggg aaattggtct gaagttgtct ttctttgttg ggtctttctg tggtttaggt   51060
attagtgtaa ttgtgacttc atagaaggaa ttcggtagtg ccctgtttct cttttgtgga   51120
atagcttgga aagtgtgaat atgaggtctt ctatgaaggt ctgatagaat ctgcaccta   51180 actcatctgg tcctgggccc tttttttctt aggagacctt taataactgc ttctatttct   51240
ttaggagtta tggggttgtt tagatggttt atctgttcct gatttaacat tatacatggt   51300
atttgtctag aaaattgtcc atttcctcga tattgaatat aggcttttgt agtaggatct   51360
gatgattttt ttaatttcct cagattcttt cgttatgtct ccattttcat cttgaatttt   51420
gttaattgga aatactctct gtgacctctg gtttatctgg ctaagggttt atctatctgg   51480
ttgattttct caaagaacta tctcctggtt ttgttgattc ttttttttttt cttccttta   51540 ttgaatatat tttttttcaga gggaaaatgt ttattagttt catagtttta tacctttcag   51600 cttatttttaa cttggtctct ggagcatttg gaagactagc tgcttacatc agagcagtgc   51660
tgaaatagag acaactataa atccagagac aaacatagcc ttcaaagtta tttagcccta   51720
cttctaaaca gatagtctat aatatttatt ctcaataact gtaaagaaac ttatattctc   51780
cccctcccac aaaacatcac tgaaagacga aagaattggt tccatgtatg accttcttgt   51840
ttgaccagtg gcttcattag ggtcatttac aggagcatgc caagaagtta cttaaaagaa   51900
tagtaatgat tcaactgaag tttcattaaa gatatgtctc atcacagaat gcttttcaat   51960
tcataaatca cctctagaat gctatccaca ccatcgagaa tcctgtgatc tcctctcaat   52020
ctataataac atattggctt ggggagggtt tatgaaagaa tagtggggtg tgtgtgtgtg   52080
```

-continued

```
tgagtgtgtg tgtgtgtgtg tgtgtgagac aaaaaaattg atttaaagtt aacttctaag    52140
tcccagctaa caaccaatgt tctgatcaga gagctttcag aatagactct attttctcta    52200
tattctgctc caaacaactt tcctgatggc tgtctttcta taagtagttt gctttgcatg    52260
acacagcttt ctcttactat tccttttttt ttttaactta agtatttctt atttacaatt    52320
cgagtgttat tccttttccc ggtttctggg ccgacatccc ctaacccctc ccctcccct    52380 tctttatgag tgttcccctc cccatcctcc ccccattgct gccctccccc caacaatcac    52440
gtttgctggg ggttcagtct tagcagtccc cttccacagg tgatcttact aggatattca    52500
ttgctaccta tgaggtcaga gtccagggtc agtccatgta gagtctttag gtagtggctt    52560
agtccctgga agctctggtt gcttggcatt gttgtacata tggggtctcg agcccctta    52620 aggtcttcca cttctttctc tgattgcttc aacgggggtc ctattctcca ttcagtggtt    52680
tgctgctggc attcacctct gttttagctg tattctggct gtgtgtctct caggagagat    52740
ctacatccgg ctcctgtctg cctacacttc tttgcttcat ccatcttgtc taattgggtg    52800
gctgtatatg tataggccac atgtggggca ggctctgaat gggtattcct tctgtcactg    52860
ttttaatctt tgcctcccta ttcgctgcca agggtattct tgttcccctt ttaaagaagg    52920
agtgaagcat tcacattttg atcatccatc ttgagtttct tgtgttctat gcatctaggg    52980
taattcaagc atttgagcta atagccactt atcaatgagt gcataccatg tgtgtttttc    53040
tgtgaatggg ttacgtcatt cacgatgata ttttcctgat ccatccattt gcctatgaat    53100
ttcataaatg cattgttttt gatagctgag taatattcca ttgtgtagat gtaccacatt    53160
ttttctgtat ccattcctct gttgaagggc atctgggttc tttccagctt ctggctaata    53220
taaataaggc tgctatgaac atagtagagc acaagtcttt ttatatatcc gggcatcttt    53280
tcggtatatg cccaagagag gtataactgg atcctcaggt agttcaatgt ccaatattgt    53340
gaggaacctc cagactgatt tccagaatgg ttttaccagt ctgcaatccc accaacaatg    53400
gaggagtgtt cctctttctc cacatgctca ccagcatttg ttgtcacctg agattttgat    53460
cttagccatt ctcactggtg tgaggtgaaa tctcagggtt gttttgattt gcatttccct    53520
tatgactaaa gatgttgaac atttctttag gtgtttctca gccattcggc attcctcagc    53580
tgtgaattct ttgtttagtt ctgaacccca tttttaata agattatttg tctccctgcg    53640
gtctaatttc ttgagttctt tgtatatttt ggatataagg cctctatctg ttgtatgatt    53700
ggtaaagatc ttttcccaat ctgttggttg ccgttttgtc ctaaccacag tgtcctttgc    53760
cttacagaag ctttgcagtt ttatgagatc ccatttgtcg attcttgatc ttagagtata    53820
agccattggt gtttttgttca ggaaatgttt tccagtgccc atgtgttcca gatgcttccc    53880 tagttttct tctattagtt agagtgtatc tggtttgatg tggaggtcct tgatccactt    53940
ggacttaagg tttgtacagg gtgataagca tggattgatc tgcattcttc tacatgttga    54000
cctccagtta aaccagcacc atttgctgaa aatgctatct tttttccatt ggatggtttt    54060
ggctcctttg tcaaaaatca agtgcccata ggtgtttggg ttcatttctg ggtcttcaat    54120
tctgttccat tggtctatct gtctgtctct gtaccaatac catgcagttt ttatcactat    54180
tgctctgtaa tactgcttga gttcagggaa agtgattccc cctgaagtcc tattattgtt    54240
gaggttagtt ttagctatcc tgggtttttt gttattccag atgaacttgc aaattgttct    54300
gtctaactct ttgaagaaat ggattggtat tttgatgggg attgcattga atctgtagat    54360
cgcttttggt aaaatggcca ttttgctata taaatcctac caatccatga gcctgggaga    54420
```

-continued

```
tctttccatc ttctgaggtc ttcttcaatt tctttcttca gagtcttgaa gttcttattg   54480
tacagatctt ttacttgctt ggttaaagtc acactgaggt attttatatt atttgggtct   54540
attatgaagg gtgtcatttc cctaatttct ttctcagctt gtttctcttt tatgtagagg   54600
aaggctactg atttatttga gttaatttta tacccagcca ctttgctgaa gttgtttatc   54660
agctttagta gatctctggt ggaactcttg ggatcactta aatatattat catatcatct   54720
gcaaatagtg atattttgac ttcttcttat ccaatcggta tccccttgat ctccttttgt   54780
tgtctgattg ctctggctag aacttcaaga actatattga ataagtaggg agagagtggg   54840
cagccttgtt tagtccctga tttcagtgtg attgcttcaa gtttctctcc atttagttta   54900
atgttagcaa ctggtttgcc gtatatagct tttactatgt ttaggtatgg gccttgaatt   54960
cctattcttt ccaggacttt tatcatgaag gggtgttgaa ttttgtcaaa tgctttccca   55020
ggatctaatg agatgatcat gttgtttgt tctttcagtt tgtttatata atggatcacg    55080
ttgatggttt tccgtatatt aaaccatccc tgcatgcctg ggatgaagcc tacttgatca   55140
tggtggatga ttgtttttgat gtgctcttga attcggtttg ccagaatttt ttgagtattt   55200
ttgcgttgat atttataagg gaaattggtc tgaagttctc tttctttctt gggtctttgt   55260
gcggtttagg tataaaagta attgtggctt catagaagga attcggtagt gctccatctg   55320
tttcaatttt gtggaatagt ttggatagta ttagtttgag gtcttctatg agggtctgat   55380
agaattctgc actaaacccg gctggacctg ggctcttttt cgttgggata cctttattga   55440
ctgcttctat ttccttagga gttatggggt tgtttaactg gtttatatgt tcctgattta   55500
acttcagtac ctggtatttg tctaggaaat tgtccaagtg tttcttttct ggtccaatct   55560
atttggagtt ctgtaggctt cttgtatgct tatgggtatc tctttcttta ggttagggaa   55620
gttttcttct atgattttgt tgaagatatt tactggtcct ttgagttggg agtcttcact   55680
ctcttctatt cctattatcc ttaggtttga tcttctcatt gagtcctgga tttcctgtat   55740
gttttggacc agtagctttt tctgctttac attatctttc acagttgagt cgatagtttt   55800
ctatagaatc ttctgctcct gagatcctct cttctatctc ttgtattctg ttggtgaagc   55860
tcgtatctac ggctccttgt ctcttctttt ggttttctat atccattgtt gtttccatgt   55920
gttctttctt gattgcttct atttccattt ttaattcctt caactgtttg attgtgtttt   55980
cctggaattc tttcagggat ttttgtgatt cctctctgta ggcttctact tctttatgtt   56040
ttcctgcatt tctctaaggg agctcttcat gtctttcttg aagtcctcca gcatcgtgat   56100
caaatatgat tttgaaacta gatcttgctt ttctggtgtg cttggatatt ctgtgtttgc   56160
tttgttggga gaattgggct ctgatgatgc catgtactct tggtttctgt tgcttgggtt   56220
cctgcgctta cctatcgcca tcagattatc tctagtgtta ctttgttctt ctatttctga   56280
cagtggctag actgtcctta taagcctgtg tgtcaggaat gctgtagacc tgttttcctc   56340
ttttctttca gcaagttatg ggaacagagt cttctgcttt cggccgtgta gtctttcctg   56400
tctactggtc ttcagctgtt cctgtgggcg tgtgtcctga gtccattagg caggtcactt   56460
ggagccgaaa agttggtctt gcctctggtc ttgggccaaa atttgctttc cgtgagggct   56520
gcaatcaaag ggcttgctca gccttctctc aggcctagat ggcactagaa cttttcctct   56580
agagtcagaa atatgggcag agagtagtct cctctggttt cccaggtttg tctgcccctc   56640
tgaaggtcta gctctccctt ccatgggatt tgaatacagg gagctgtttg accgggtccc   56700
ttcagaactg ggcgcagtct ggaacctagc gctcctgcag cttgagtgac catatcttcc   56760
tgttcccaga ggccctgtac agtttcttct tgggtcaggg atgtgggcaa gggtgggcag   56820
```

```
tactggaagt ctctcctgcc ttgcagtctc aggagtgccc acctgtttgg ttgatgagct   56880
ctctctccca cggggtttgg gaacagggag ctgtgggcca ggatcagcga ggtttgggcc   56940
ccagctagaa accagaagtg tctggtccca gaagaatttt gcctttgtgt atcctgaatc   57000
cagcaggcag gtcacttgga gcagaaaagt tggtcttacc tcttgtctcg ggcctgaagt   57060
cgctcctcgg agctggtttt cagctctcca tcagggcagc aaccaaaagg gcctgccccg   57120
ccttctctca ggaccctgtg cacaggggggc ccagatggtg ctagaccttt ttctctagat   57180
tcagaaatgt gggcagagag tagtttcctc tgccttccca ggcatgtctg ttcctctgaa   57240
ggtctagctt tccctcccat gggatttggg tgcagggagc tgtttgacca agcgctcctg   57300
cagcttgagt gccctatct tccttttcac agaggcccta tacagtttca tcttgggcca   57360
gggatgtggg cgagggtggg tagtactgga ggtctctcct gccctgcagt ctcaggagtg   57420
cccacctgtc tgggtgatga gctgtctctc ccctggggtt tgggaggagg gaactgtggg   57480
ccaggatctc ttcacctatt cttaacatta ataattcaac acacacacac acacacacac   57540
acacacacac acacagcccc tagtgagtca ctatactgct ggtagcctga atgtatgttt   57600
tatgcttgat cacttgggat tagataactt atcagagaga ggcttattct tagagtagat   57660
tgaattttca gcaagtatta attacctgtt gttcttcatt gagagggtta gtgattatga   57720
aaatttctcc atatgcattg aaatgtcaac tggtattgta gtaaactcac atagacaatc   57780
atagttttga aatttcatgg gctctgcctg cctgtcatat atagaaagct tttctcatag   57840
taggcatcct agttttttgcc cttaaattct ttctgctcct tctcaaatga tgattccca   57900 agccttaggt ttgtttagtg actactactt acataagact taatatctta taatattaga   57960
cattaaattt atttgttcct aaacagctac atttaaaata tttaaacgaa agtgcaagtt   58020
gtagaaattt attgttaaga aatatactat ttctattaat aaatatagta tgtaatattt   58080
acattaggtt taaaatatct agatgtttga gcactttgaa gaaatgtctt gctatggtct   58140
cttgccatgt gactttttaga gtaagcttgc tcatgcatga aaaattcatt tctggattca   58200 atttttgagaa aattgataca gcaccattaa ttttttctat taataactac gatatgtcta   58260
tgatttagtt agacccttag tctcttgtgg cactgttctg ttttatgcag caacttcagt   58320
agatggatag ctaatagacg tttttcaaatt gtagtaattg tattcatgtt atctatttt   58380 cttgggtata gtttatggtt ttcattaatt ctattcattt tatcttgcca aattaattga   58440
cgtgaatgtt cataatattc tccaattatt tttgaaattt atgtaaaagc acataatgat   58500
acaattccca tcattgctga taatgttaat ttgatctttc tctacctttt ccctaccttt   58560
ctctgctatg tctgcttaaa agatgattaa tttaggtgtc tttcatagga tcgagatgta   58620
aagttaattc tgctttgtgt tatttttaaat gacatgactc ccactcccaa ttctactccc   58680 cctttctttta aattttctgc tttttcctaa tgtcttaatg agatctcagg caactgatgt   58740
gagcccgtgt tccttgtcca tttgaatgtt gagtgcagcc agattttgt tatcatccca   58800 catagttgtg tgtgttaatt tatctattgg tacttggata caatgggtga acattatcag   58860
tttattgttg gggaaataat tcagtgccac aaatgtatat gttttcattc acctctgcca   58920
caatcccttg aataataaag cagcactcca tgaaaactttt ttgctagtgc ttgggcttgg   58980
aaaattgcag aataaaaata ctgagtttga tttttcctttg aaattatttt agattggttt   59040
gccacacatt ttttgtacaa cttgagtgtt cagaatatca ataaaactct ccaggggggat   59100 gtctttctaa aggattatgg tgattacacg aatctttact gtctacacct ttgaatatct   59160
```

-continued

```
tgaattgttg gtgttctggg tacctttttcc tgtaatttttt ggggtagtta ttcttctcat    59220
gttcttcatc agagaatctt gtaatgtgct agactgtgct gatagaggat ggcaattgag    59280
aaatgcagag ttccgctcca tattttcttt gttcttgctt ttctatgcca cacgttcagt    59340
gactccagtc tttttgagca aagtaatttt tgttgcttaa attcaataaa atacccattt    59400 ttcttctttta gttcacaatt tgcaattttc tggaaaactc tcctttacat aaagccacct    59460
caataatgaa catcattaat ctgttgcctc tggtactggt aattttcaac taaatatgtt    59520
cttatcattt gagtctgcta cactatttta tttttgtttc tttataattt tattatatcc    59580
ttttacagca acaaaatctc attacttttt ctaatcttta ttaacctttg aacaaccatt    59640
ctattttagg catgcagctg aaattattgg cactggagtc tgtagtaact ttggatatat    59700
tttttaagat catcattcga ctccagaatc cctagtggga tgaaatgaga tctaggttcc    59760
taagagatcc aattattctt aagcagaaag aaaaaaaatg aaagaatgaa tgaataaaaa    59820
aagagagaaa gaaaggaaga gagaaagaaa gaaagaaaaa agaaagagaa aaagaaagaa    59880
agagagaaag aaaatattgt ccagagttct gatggtctat aagatatata ttcatttgga    59940
caaaaatgtt aaacatattt aagaacatat tataaatcct ttcaattttta ctttgttaga    60000 aaaaaacttt ctcagaggac tatgatgatg tatgtttaaa acgaaaggtt tgttgttttt    60060
tcttttcttt ttcttttttcgt ttcttttttt tgtttttttt tgtttttttt tcttttttttg    60120 gcctagtgat gggaaagact ttgattattt catgtacaaa tgactaatga ctacttctgc    60180
acctttaata ttgtagatcc ctaggctgcc atgcctatac tcacctcttt tcttacttttt    60240 taccctttta gagacttgtt cagtatcaga tatagaaatt gaaatgggt tttttttctga    60300 atctgattat acatatgctc taaatagaaa aacacggtat agatgtaaac agggatatgt    60360
aacaaatacc ggagaaatat caggaataat tacttgtctt caagatggat ggtcacctcg    60420
accctcatgc attagtgagt attttattat attgttgcaa ttatactaat gatgcatagg    60480
agtttagtgt tattctttttt gtatatgatt gatattcttt catttgtaaa cagctttcaa    60540
acttcaagaa aaaatacaca gcattttttt tatttagaca ttcctgcatt gtaaaatatc    60600
agttcatttg ccttttttcta ggctctaaaa tagcctagtt ttaaatctag tgaagaagtc    60660
tttgaccaga tgcaaattcc tgaatatatg ataaccttat aatatgtacg tgacactatg    60720
agttacgatc tatttcagaa catctccctt ttagaagatc tttttaaata ttttgatatt    60780
ggaaagaaag aaatgcttcc aggcaccagg aaattttggt atttggaaac attcttttgt    60840
tttaggacat acagttaatg aggattttct aggattaaca attagctcat ctagtcttat    60900
ttataagaaa aatacccagt gctatttttc aagatgtatt caatttatac cttattgttt    60960
aaggtatgat ttaaagtatt cactaagttc ataattttttc gtctactgtg attttacagg    61020
atttaattaa agaaaaggaa attaaaatta ttcccatata acattcattt atattaaatt    61080
ataattggta aggatttatt gaatttttttt actgtgaaag ggaaaaccct tgatataata    61140
tctgcttaaa ttcaattcat ctactttcct atattttatg agtcatttga tgtactaatt    61200
ataggacctt aattcgcaaa atgctatcat actttcctaa aattatgtat ttgcacttgt    61260
ctattttttg gagtatgtga taagtataag aaaaattgag ctgagaaatg atttctaaaa    61320 taaaattttta taaaagctta agaaaggaga tgaatgttac atagagtata tctcaatttt    61380
aataactttc aagaaaataa attattactg gtctccttag tttccttcaa tacagtattt    61440
aatttgctat catatattaa tttataaaga cttttttctc atgagaatta tttctacttg    61500
ctattgacac attagaaatg acattgtctc tcttatttttg cattagagtc ttgtgatatg    61560
```

-continued

```
cctgtatttg agaatgctat gactaagaat aataacacat ggtttaaact caatgacaaa   61620
ttagactatg aatgtcacat tggatatgaa aatgaatata aacataccaa aggctctata   61680
acatgtactt atgatggatg gtctagtaca ccctcctgtt atggtaagta ctattttctc   61740
tggaatattt ttagataaaa ataaatgttt gtgttattaa taactgaatg ttctagaatc   61800
ttccttatga gttaatgtag cctaagaaaa aggactgtta tgaaagctat cgataataat   61860
atttacattt attatatcat tacattcatt tatttatcct gtgtgtatac atgcacacat   61920
atgtgtgttt ctggaagtgt gtatactgca ttatacaggt aggtgtcaga gaacttgtga   61980
gagtcagttc cctctttcat catatggatc tgagggattg aagaggactc caggcctaaa   62040
ggcaagcact cttactgact gagccatctt tctggcctga taatctgttt ttaaaaaatt   62100
ctatattcat cagttgtata tggcactgga ttatgattct agcaattagg accctgaatc   62160
aagagatttt taagtttgaa ggtatattgg actacatact aagttctgtt tctaaaacca   62220
aacaaaccaa aaatttcatt aaattaatga ttcctttgtg tggcctgtgt gtatcatgta   62280
tctctgattt gaggacaatt cttttgttat tcaagctctt atgtagacta ggtctccatt   62340
atcaaattta tgatctgaag catgaaacta ggtaatgaaa acttgaggcc tggagagatg   62400
gctcagcagg taagagcatg ggctgctctt ccagagatcc tgagttcaat tcccagcaac   62460
cacatcatgg ctcacaatga aggaggtaga agtatggcat tcttgaaatc taggccagtc   62520
tgggctatgt aggaattgta agtggtaagt gcaggaattg taggaataca gctctgaagg   62580
gaaaagcttc cccaatggag atgctgcagc tctgagtgtc tcagtgcaag tatgacagct   62640
ctgaagggaa aggtatcctg gcagtaggga gctaaggaaa accacaaact tacactgcac   62700
aaaacaaacc tggcacaaga actttattgg gaaaaacata agaaagctgt ttctgctcca   62760
gattaaagca gcaaagaaca agctcagtga ttggtgagat tttgagttta tcttgggctt   62820
ccaccccatc cctaccctcc agaaaggaac ttggccatta gcacctcaag gggctagact   62880
gccattatag tagtctggag gtggggcttg gtcacttgcg tgacttcaag ggacttacct   62940
taagatggtg gctgcctctg tttgaccaac atacaacagg aaactgagca ggagacagat   63000
aaatataagt tgtttttttt tccgggggtc tggggtaggg gtgggttttg gaggataaac   63060
atttccaagg tggggaatgg tgagattttc aagatcaaga ctggtgggta ttcacactca   63120
gggcttggta gggtttccta tttagggatt ggtaggtttg ggtaggtttt aagccatgaa   63180
atgggctcag aacttttacc ctaaatgaag acatctcaca aacagacaaa cagcaacaaa   63240
tgatgtacat agtaagaaaa aaatcaaact aaacaaacgg tgatcactag tttctctctg   63300
attataagca gttcaacatt atgaaatcag gactttctat aatacaatac taaagtagaa   63360
tggaagggga gggatattag tttcacaata caatactttg cctaaggatc agtactaaca   63420
ctacaagtat aaaataaaat ataatataaa attatttata tactattctg atgtgtgaga   63480
attttttttc tgtgaagtca atatacaaac atctactcac cccaagaaag agcccatgac   63540
agaccaatgt acagatacca ctaatttcca acttcatgaa ccttgagtca ttgtgtccag   63600
ttgcaaaatc cccaaagaga ctacccggaa ctgcaacttc cacacacgca caggagagtc   63660
tttattcaag ctcgagcttg ggctacgtac cttcctgatg aataggaag gagagagata   63720 cttgagtcta ggggcttagg gcttatatag ggaaaaatct caagctggag tcttcaagcc   63780
ttggcattac atgtttgggt aaaggggtaa aggaatgtta accttcagac tgatatcatc   63840 aggggggagac cacacattta aaagaggcat cttgtccttg gaatgattta tgttttttta   63900
```

-continued

```
acttattatt gtgaccagtt ttcctgttgt tgcaagctgg ccactgctgt tatatctatt    63960
ttcaactgct gggaagggtt ggttgtctct tttccagagc ccaagatggg ggccatatca    64020
cttcaaggac agcagttttc tccaaggaca gcagcttttc ccaaggacag caattttctc    64080
caaggacaag atcttaaaat tgaatttaaa ggaaaagatg gaatccctcc tgctgccttt    64140
tgccttttca gagtttttatt aaggttgctt tcagaaatat gaatgagggt gttctcatag    64200
gagaagaaat ggctcaaaga cagctacatc accaaagcct acccagtatg gctgacaatt    64260
cacaaaacac aatggatcat ataacataat gtgtaggcag cacatagatt gaggagtgtc    64320 tttttcaagtg agtcagctga tgaagcacct accactgggt aggatccttc ttctaggaag    64380
ttaattatct cattctttgc tccatctagg gagctctgag ctccttcctt gcagtttttgc    64440 ttgtctgagt gattctcacc aattcagcta gcttgtttac tctggaagta aggggcctgc    64500
taaatctgct tagtttcagg gactccctga agctattttg agttgtttac ttccctcctt    64560
aaggagcttc cctgcagtat ggagtatttc agtctcaagg aaactgttgc ccaacaaatt    64620
cccatggtct ttcaatgtct ccaggtctga caggtgattg taaagcagag gagaattgca    64680
caaattattt tttcactttta agacagagta ttatggtatg tttgctaaac aatttgtata    64740
aaataagcaa agagaataca caaataggtg caaaacaaaa aatagttata gatgattata    64800
ttgtgccatt caaatccact tggaaagagc acacacgtag attcaattca agtttaggtt    64860
aaatgaattt cttcttattt ctatcaacac agaaggggga ggaagggagg gtttataaag    64920
ttggattcct aaagttgcat attacaatta gccatgaaat ctgcagctgg accaaaaagt    64980 gttttttgcat ccctcagttg ttctttacct ttgtatgcca ataaaaagat cacttcatcc    65040
ctgtcccaca aaagcaaaaa acaaactgtc aaacatctta caacaggaac tctagtaacc    65100
tatctaaact tttctgtttt ctttactttt cttttttactt attcttctct cttacaataa    65160
atatatcctg attgtagcct cccttcccce aactcctccc tgttcccact ttcccttctc    65220
taccagacct actgctcctc cctttccctt cagaaaagag caggcgattc atgaatatta    65280
atcaaatatg acataacaag atataataag cctaggcata agcccttatt tcaaggctgg    65340
atgaaacaac caagtaggat aatggtctca agagcaggca aaagaattag agacacccat    65400
gactcccatt gttaggagtc ccacaaaatt cccaagctaa agaacactat gcaaaggacc    65460
tagcacagac ccatacaggc tctttgattt cagctcctgt ctctgtagcc tctatgagtc    65520
ctacttagtt gattctgtgg cccacgtttt tctgctgtta ccattccaca cacaaaattc    65580
attctattgc cccttcccag ggtgatttcc ttcttacttc tctccacttc ttacttagcc    65640 tcccttttgtc tgtgtgctgt cacatgatta gcctttactt agctctaata actacttatg    65700
aatacataat tattttttgtc tttccaggtc tggttgcctc actcaggata tgtttttcta    65760
gttccatcat ttgcctgaaa atttcatgat ggcatttctc taacatcttt cataatatac    65820
cattatataa atataccaca tttttatgca ctcttcagtt gaggggacat ctaggtttct    65880
aagctatcca gtctctgttt gctggccctc aggttagtgc ctggcatggc tctttctcac    65940
tgcattggga tgaagctgta ccaatcattg attggccact cctgcaagtt ctgcagccgt    66000
atcttgcagg agaaatagtc ggctgaagat tttgtggcag ggttggtgcc ccaattcctc    66060
aactggaaat cttggttaga aaagttggct ggttcaggct ccttaaaccc cagtactagg    66120
agtctttact aggctcacac tcaaagattc cttggaattt cccttgcact aaggtttggt    66180
cttgtccctg aaatacccca aattctaatc atctctttca atactttctc actccaccac    66240
acctgatttc tcctcttacc atcccttcag ttttgaacat agcagttgtc ttttatgaat    66300
```

-continued

```
gactctaatt aaaaattatg acttttaata tatacattgg aaagaaagga gatttttaag   66360
gcagaaatgt gttatttatt tatttacata ttttttggtaa cactcaacaa tgacaaaaat   66420
tgaagaaaaa attttcata caggagaatg tgtcatacat tcttaatttg agtcagaata   66480
attcacaatt aattaattaa aaccagaatt ataaaactgg tttaatgtaa aggtttttgca   66540 caactttttt atagtctact taatcataaa atatactata ttttcctaac ttcagataaa   66600
ttagaaatta ttttatatat tttagtttct cattatatta aactgaaatg atttcaatat   66660
atgatgtaga tatagtatga cactaatttc aaatctgaag gaaagaattt tgtgttgtag   66720
aataggaaag ttattacttt aacattaata tttatctgca gcagctcaga tccactggaa   66780
gacagttggt tttattaaat cagttttgtg attaatacat tatgctttgt tatgtttctc   66840
agagacgtcc acattgactt agaggctata ttaaagctag gacacaatgt ttttcctaag   66900
gaagagggtt tctgaagctt ccctgtgaat gtacatgaga aagataaaaa tacttatcaa   66960
tgattaatgg tatattctaa ttatcttttc aagaaagaga atgcagcatt cccctgttac   67020
accaagactt agttgttttt cccagagaag taaaatacaa agttggagat tcgttgagtt   67080
tctcttgccg ttcaggacac agagttggag cagatttagt gcaatgctac cactttggat   67140
ggtcccctaa tttcccaacg tgtgaaggtc agtatctgtt ttatatttga tgaactaaga   67200
tcagaagttt attttttttc ctcttttagt attccccagt tatcaagtat gtctataata   67260
taaaaatctt cagagaaatg aacattcatt cagatacaca gccacatgtt tatgaggtta   67320
atttgaagct aacttgcttc tttaaatgtg ttatccatgt gtttacacat gcagacatga   67380
tggctgagac tgatgggatt tctttcattt tgcctatatt accattagtg ctggtgtttt   67440
tataccatag gccttcccgc atattgtata gagtacgtcc aaacctgtaa aagcaggttg   67500
taattaattc aaaaccaggt tcaatatcta tttaaaatag atacgaggta caatgctgat   67560
tttttttaca atgtggtaaa tgtatgataa aatagtacca gtcaatgtga aaatcattat   67620
aatcaacaca acaattactg agtgattgca tgtatcttca ggctgtcagg tttatcaaaa   67680
attcttccac ctccaatata tttgcaatgc tattgcaaca gttgtattaa agttgtgaaa   67740
tgtaaattta gtgtaaatac tatttagaaa agtgtaaaag aaagttatat agtgtataca   67800
tttaaatttt ctccatttac taaaatttta gactgtaaga tggacatttt cttttatatt   67860
tatacagtat ttctgtaaca ggccaagtaa aatcatgtga ccaacctctt gaaatcccga   67920
atggggaaat aaagggaaca aaaaaagttg aatacagcca tggtgacgtg gtggaatatg   67980
attgcaaacc tagatttcta ctgaagggac ccaataaaat ccagtgtgtt gacgggaagt   68040
ggacaacctt gccgatatgc gttggtaatt aaaataatta acacttaaaa attgttttgc   68100
atctcatgtg acgttttaat tataagtaac ttaagtgaaa tacctacaga gtatgagaga   68160
acatgtggag accttcctgc acttgagcat ggctctgtcc agttatctgt ccctccctac   68220
caccacggag attcagtgga gttcacttgt gcagaaacct tcacaatgat tgggcatgca   68280
gtagttttct gcattagtgg aaggtggacc gagcttcctc aatgtgttgg taagtatgtg   68340
tgcataaaat ggatacttca taaagtttaa tatttatatt gcagaaatat ttgctactgt   68400
gtacttctga agtaagtagt cattttggaa atatctagtc ttaaataata tgaatccaaa   68460
ctttcattgt ttatattttg atggatgtct acaggtgaac agaaattctt aacatacaat   68520
atataaaagt ttgttcatta ccacaagata aatctagttg ttaattataa attgtcatgt   68580
gactgacatg tgaatattaa cacccaagta ggtttgacta tggtacaaaa aagatcattg   68640
```

-continued

```
ttttttattgt atgagactct cctctcagga cttggaaagg taagaattaa agtctgctaa   68700
tcacccattt cctactctca ttatagactt accctgaagc atgtctgtaa tgtttgtgtt   68760
tattctacag actgcattct aaagtcaatg tgccaaagtt gggactctcc accctgccat   68820
cagctgtaga actcagggat tagatgggaa acataatccc atatatgact ccacttcaca   68880
ctgattcccc atgttccttt gctgattcag tcttaatgag ttactggaag aatcttggtg   68940
tctacatttt cttttctctg aaatggaagt ttttcattga ttgaccttgg tcatccaggc   69000
ttcactattt gttggagttt tggatattct ttaatgccag ggaaacatgg agctcctttg   69060
gaacgggcac ctattcttgt gctgcttaat gatatgctct ctctgcccag acacccaaac   69120
ttcataacag tttgccatgt aaatgaatac ctttactaca tatcaatcat aacaattttt   69180
gctcagcaag cagattttgc caaacccatc ttcatcattg ctttaaaact gtttaacact   69240
ttcataagaa gaaagatcag atataatatc atatataaaa actgaatcct tcattttata   69300
ttagtttatg cttattttta tgtactctat tgtactctag tatttgttca tatatcagag   69360
gtttagtttg gtttatctgc ctgcagccac cttaatatga ctccagttat gtcttcctgg   69420
attgcaaagt taatgttatg atacaaatat ttttaccttg acactctacc ttactttttct  69480 ccaaacccctt ggctttcacc tgatgaataa gagattcaga agcaaatcaa ccacacagtc  69540
accatgcccc tttgactttc ttcttttttcc tttacagaaa ttggctttgt gtgtgtgtgt   69600
gtgtgtgtgt gtgtgtgtgt gtgtgtgtgt gtaccaatct ttagtaaggg acgaattctc   69660
aggagtcttt agtgtttgca tcactctatc aacattttaa atattataca actttgtcta   69720
attatttact tttatttgta ctgtgtttat tttattttag atttcaaatt attgataaaa   69780
attatccatg acctatacag aaatgtcaaa ttcaaaagga ctctcatttt caccaaataa   69840
ttaaaatgta tagtacacta aaatgcttcc atatatatat acatatatcc ttatttaact   69900
tataaaacaa ccatacaatc agaacaattt attattataa cttaatattg ctgtattata   69960
gaataacgtc atatgaaaat atatcttata gactcatatg tagggtgtat aaaggagata   70020
gatgttgact acaagcccct aatatcctat accaattctc tctcataaaa tagtttgaaa   70080
tatttgtatt ctatacaata taaattaaat gttattttct tgtatcacat ctattaaaaa   70140
agatgtcccg atatcttatc aacacatttt ttattttaaa attttttaaca ttttaacatt  70200 atgaaaaaat ctgagagtaa tgaatttgca tattttttata ggtttttaagt ctatgaccaa  70260 agctggtcat atcataatca tttcttatgt agagcatctg agaaagtgtt ttttttaatgc  70320 ttttgtaatt gtctagtacc caagttcctt catgacacaa aatgtctctg agacataaat   70380
gagtgggcat gatatctagt tcttatacta taggccactt tcgcatggtg agtctcaaca   70440
ttttagttgg cagaatttat agtactaagt tgtgtttcat tgtacattta ctgcatgcac   70500
attttaatgt agtagctcac tcacttctta taagtgtttt tattttttcat gaaaatattt   70560 tcatacagca acagatcaac tggagaagtg taaagccccg aagtcaactg gcatagatgc   70620
aattcatcca aataagaatg aatttaatca taactttagt gtgagttaca gatgtagaca   70680
aaagcaggag tatgaacatt caatctgcat caatggaaga tgggatcctg aaccaaactg   70740
tacaagtaag ttcttcttgg cattgtgttc tcatgagtgt tctagccttt tctcaactag   70800
agcagttgtg tctttatttta cttaaaaaat ttttcctcaa attttatggg taaaacctgt   70860
atttatatta tttttacctc tccctcttcc cactccaact caactccttt tgtgtccctc   70920 caatttttata tccaatttat gtcctcttct tgaagtatat gtgtaagcat acataatata  70980
tgcataatat atacaaatga aacttgtata tataaattca acctgattag tccattcagt   71040
```

-continued

```
gtttctccta tgtgtatgtg ctaagactaa gtgcatgggt ttcaataacc tatttgtttg   71100
ctccagagag aaggctgatt attccactct agacagccat taatcacctg taggggaagg   71160
gtcatgtagc attttcccta tccatactaa tttgtcagtt ggtaatgtca tcatggatat   71220
cttgttgggt gaccacactt ttgagatttc atgagttcat ctactctgcc atatatgaag   71280
atattatctt ctaacacatt ttctggaaaa aatatttttt aatctagagg ttgatttaga   71340
aattacaata tcatgcttgt tagtgaccta tagtgtaaaa cacagaaaca aacttgctca   71400
acatggcttt tcctatgtgt cataatggat tcttaccatt ccactacatg tgattaattt   71460
atcacaacaa atgtgttatg cctctcctat gcttcatcat catgtctttc ggtatgattg   71520
tgtgttctgt cagaccaacc atttatttaa ctctcctaac aatcagctta cctggaaaac   71580
ctcgatttat ttgacacctt ctattctatg ttactgggca acagggccat tctactacta   71640
tttctgcttc cctatttgtc tttatcaccg ttgttgtgga ggccctgtct catttgatat   71700
tttaaatatt tcttaaagac gaaagttcac agaaagtatt tccatgccat tctaaaatta   71760
aacctactac aggcatgtta atgcagtgca tgtgttgttt tgaaattgtc tatgttagga   71820
tatcatttct ggtgtcattt tgattatagt attaagatag taattgcttt tctcttatgt   71880
atggctagct agttgttcaa agaatgtatt tactacgtag tgctgatttc tatttattcc   71940
actctactta agcaaaaata taaaaagaat gaaattatta gtaaccacta agaaagtacc   72000
ctttcatatt atgaatctga gaggagagtc tgagtgatga atgtgaggtg tcttgatttt   72060
gtagctacgt agtgaaaaac ttgtcagaag cactacatta tcctggctgc gaaccatccg   72120
ttttcacatg tgtaactagt tcaggttaaa tggaatgtcc agcataattg aaattttgta   72180
caacatagta taaaccactt tgggtcacac tccatattct tgttgaccaa gaaccaaggt   72240
taagttaact atcaattgtg ataactaatt cttatttgct atctgacaga gtccacaatt   72300
tcctaagaaa aacgtatctg agcatgtttg taggggcgtt tctagtttag gttaactgag   72360
gaggaacaat acactgtatg tgtagatggc accattttat gggcagggtt cctagcataa   72420
ataaaaagag aaaggtgact gtgaatcctg agtatagata cagtatgagc aacagcctca   72480
catgtctact gccattgctt tcctgcgcga tgagctaact taaactattc cttcttcttt   72540
tctaccctcc ttcctatctt ccttcctacc ttccttcctt tcttagcttc ttttgtcaag   72600
tgcttcatca cagaaatgag aaaagtcact agtatatcaa gtaaatgaaa gtaccacttt   72660
tcctaatcaa cttttcattta taaaatagtc cctgaggatt tttaatgtaa gtcaacatat   72720
tagattataa atagtcatag acagctctag aaaaatattc atgtaagctt aatcttaaca   72780
taatatattt tttatgactc acttaaaata ttttaaaatc tagaaatgat tgaagtatgt   72840
tttataaaaa tatataaaac tgcattaaaa tgaatgagaa aaaatttgga gtacaagaat   72900
tgctatatta aattgctata caattgaaat atgcaaaata tagacaattt ttttgcaact   72960
caacaatcag atttatatgc taaattctca atccacaata gattcacaca gtaaacttac   73020
aagcaatcga taaggatata aactgccaac ctagatgaga taaatttgcc tacagaaatc   73080
catgccaaca accttggcaa tactatatat atatatatgt atacatatat atgtatatat   73140
gtgtgtatat atatgtatat atgcatatat agagagagac agttattaaa tttcattact   73200
aacttacttt ttaatgaaaa ttatcacttc aataatttaa gatattctct ttagtaaaga   73260
actctgatta ttttttttcta ggaaatgaga aaagattctg ccctcctccc ccacagattc   73320
caaatgccca agtgattgaa accacagtga aatacttgga tggagagaaa gtatctgttc   73380
```

```
tttgccaaga tggttaccta actcagggcc cagaagaaat ggtgtgtaaa catggaaggt   73440
ggcagtcgtt accacgctgc acgggtcagt agataggatt tactttgcac cattagaacg   73500
taggtgaggg gtgggtattg aaaaaaaaag ggcatactat aaatgttctg gacacattat   73560
tcaaattgtg tatatttatt tctaatgtaa gtttttattt cggcttgact atttcatttc   73620
tgttctctat gtagaaaaaa ttccatgttc ccagcccoct aaaattgaac atggatctat   73680
taagtcgccc aggtcctcag aagagagaga tttaattgag tccagcagtt atgaacacgg   73740
aactacattc agctatgtct gtgatgatgg attcaggata tctgaagaaa atagggtaac   73800
ctgcaacatg ggaaaatgga gctctctgcc tcgttgtgtt ggtgagactg acatgaaaat   73860
tcaattttca ttttcaatat gtcattacca atattctact cttatccaag ccagagagaa   73920
agaataattt aggatagcac atatatacat ttatatattt tactatacat ttatacttgc   73980
acactataat ctatgctgtt ttagttcatt gtgccatttc tgtagacata tactttcact   74040
cttgcattac cgtttttaaa tatgatgtat tacagactcc atgtgctcat gtgaattcta   74100
ctgtttgatt tgccaccaag tattaaagtc caaagtatct tttgcctaaa atgtcctccc   74160
cactcccatc ccacaataca tggtattttc tgatatttgt aatactttca agttgtttaa   74220
cagatgcaag acaacagaat gtgctattag gaagcactgc ccaccttcct tatgatgatg   74280
catctttcat attaacactt ccttcttgta cccctacaca cagaactgat acatacaagc   74340
aaatttctgt attagtgcaa tgtggaattg tttaactatg taactctcat ttgtgtcttt   74400
ttcaggaata ccttgtggac ccccaccttc aattcctctt ggtattgttt ctcatgaact   74460
agaaagttac caatatggag aggaggttac atacaattgt tctgaaggct ttggaattga   74520
tggaccagca tttattaaat gtgtaggagg acagtggtct gaaccaccca aatgcataag   74580 tacatttaa ttttcattct tttgtctagt atataataca attcaatcta tatgtggtac   74640
aattaagaag ctaagtcata ctttgattcc atatctcctc ctatgaatat gtttgtttcc   74700
cctctaagaa aaactgaagc atcctcactt tggttatcct tcttgagctt catgtggtct   74760
gttgattgta tctttgggta aactaaggtt ttggactaat acccacttat cagtgaatac   74820
atagtatgtg tgtttttttg tgattggggtt gcctcactaa ggatgatact tcctttttttt  74880 attttttatta tttttatctt tgttaacttg agtatttctt atttacattt ctattgttat   74940 tcccttctc ggtttccggg ccaacatccc cctaactcct ccccttcccc tttcatatag    75000 gcttccctc cccatcctcc ctctattacc accctcccccc cccaaaatca cattcactag   75060
gtgttcagtc ttggcaggac ccagggcttc ccttccact ggtgctctta ctaggatatt    75120
cattgctacc tatgaggtca gagtccaggg tcagtccatg tacagtcttt gggtagtggc   75180
ttagtcccta gaagctctgg ttgcttggca ttgttgttca tatggggtcg cgagcccctt   75240
caagttcttc cagtcctttc tctgattcct tcaaaagagg tcccgttctt agttcagtgg   75300
tttgctgctg gcatttgtct ctgtatttgt tgtattctag gtatgtctct caggagagat   75360
atatatcagg ttcctgttgg actgcacctt ttgcttcatc cgtcatatct agtttgatgg   75420
ctgtatatgt atgggccaca tgtagggcag gctctgaatg ggtgttcctt ctgcctctgt   75480
tctaaacttt gcctccctat tccctgccaa gggtattctt gttcccgttt aaagaaggag   75540
tgaagcattc acattttggt catccttctt gagtttcatg tgttctgtga atctagagca   75600
attcaggcat ttgggataat agccacttat caatgagtgc ataccatgtg tgttttttctg  75660 tgattgggtt agctcactca ggatgatatt ttccagttcc atccatttgc ctatgaattt   75720
cataaagtca ttgtttttga tagctgagta atattccaat gtgtagatgt accacatttt   75780
```

-continued

```
ctgtatccat tcctctgttg aagggcatct gggttctttc cagcttctgg ctattataaa   75840
taaggctgct gtgaacatag gggaacacgt gtctttttta tatgttgggg catcttttgg   75900
atatatgccc aagagacgta tagctgggtc ctcaggtagt tcaatgtcca attttctgag   75960
gaaaccccag actgatttcc agaatggttt taccagtttg taatcccaac aacaagggag   76020
gggtgttcct ccttctccac atcctggcca gcatttgctg acacctcagt ttttgatctt   76080
agccattctc actggtgtga ggtgaaatct cagggttgtt ttgatttgca tttcccttat   76140
gactaaagat gttgaacatt tctttaggtg tttctcagcc attcggcatt cctcagcagt   76200
gaataatttg tttagctctg aaccccattt tttagtaggg ttatttgtct ccctgtggtc   76260
taacttcttg aattctttga atattttgga tataagccct ctatctgttg taggattggt   76320
aaagatcttt tcccaatctg ttggttgtcg ttttgtccta acaacaatgt cctttgcctt   76380
acagaagctt tgcagcttta agagatccca tttgtcgatt cttgatctta gagcataagc   76440
cattggtgtt ttgttcagga aatttttccc agtgcccatg tgttcgagat gcttccctaa   76500
tttttcatct attagtttga gtgtatctgg tttgatgtgg aggtccttga tccacttaaa   76560
cttaagccct gtacagggtg ataagcatgc atcgatatgc attcttctac atactgacct   76620
ccagttgaac cagcaccatt tgctgaaaat gctatctttt ttccattgga tggttttagc   76680
tcctttgtca aaaatcaagt gcccatatgt gtgtgggctc atctcagggt cttcaattcc   76740
atttcattgg tctatctttc tgtctctgta ccaataccat gcagttttta tcactattgc   76800
tctgtaatac tgcttgagtt cagggatagt gattcccca gaagtccttt cattgttgag   76860
gatagttcta gctatcctgg gttttttgtt attccagatg aaaattgcaa ttgttctgtc   76920
taactctctg aagaattgga ttggtagttt gatggggatt gcattgaatc tgtagatttc   76980
ttttggcaaa atggccattt ttactatttt aatcctgtca gtccatgagc atgggattct   77040
ttccgtcttc tgaggtcttc ttcaatttct ttcttcagag gcttgaagtt ctcatcatac   77100
agatcattta tttgcttgat taaagtgaca ccgagggatt ttatattatt tgggactatt   77160
atgaagggtg acgtttcctt aatttccttc tcagcttctt tctctttcat gtaggggaaa   77220
gctactgatt tatttgaatt aattttaacc cagccacatt gctgaaagtg tttaacaggt   77280
ttagtagttc ccttgggatc acttaaatat actatcatat catcagcata tagtgttatt   77340
ttgaattctt cttttccaat ctgtatcctc ttgatctcct tttgttgtct gattgctctg   77400
gctagaactt caagaacaat attgaataag taaggagaga gtgggcaacc ttgtctagtc   77460
cctgatttta gtgggattgc ttcacgtttc tctccattta gtttaatgtt agctactggt   77520
ttgctgtata tggcttttac tatgtttagg tatggacctt gaattcctat tcttttccag   77580
gacttttatc atgaaggggt gttgaatttt gtgaaatgct ttctcagcat ctaatgaaat   77640
gatcatgtgg ttttgttctt tcactttgtt tatataatgg attacgttga taattttctg   77700
tataataaac catccctaca tgcctgcgat gaagcctact tgatcatggt ggatgaatgt   77760
tttgatgtgc tcttggattc ggtttgccag aattttttga gtattttttgc gttgatattt   77820 ataagggaaa ttggtctgaa gttctctttc tttgttgggt ctttgtgtgg tttatccatc   77880
ttgacctggg ctcttttttgg ttgggagacc tttaatgact gcttctattt agttcagagt   77940
tatggggttg tttaaatggt ttatctgttc ctgatttaac tttggtacct ggtatctgtc   78000
taggaaattg tccatttcct gcagattttc aagttttgtt gaatataggc ttctgtagta   78060
ggatcttatg attttttgaa tttcttctga ttctgtagtt atgtctccct tttcatttct   78120
```

-continued

```
gattttgtta atttggacac actctctgtg gtctctcatt agtctgacta agggttaatc    78180
tatcttgttg atttttctcaa agaaccagct tttggttctg ttgattcttt gtatagtcct    78240
ttttgtttct acttggttga tttcagctct gagtttgatt attttctgcc ttctacgcct    78300
cctgggtgta tttgcttctt tttgttctag agcttttagg tgtgctgtca agctactgat    78360
atatgttctc tcctgtttct ttctgtaggc acttagagct ataagttttc ctcttagcac    78420
cgcttccatt gtgtcccata attttgggta tgctatactt tcattttcat taaattctaa    78480
gaagtcttta atttctttat ttcttccttg accatgttat cattgagtac agcattgttc    78540
aacttccatg tatatgtgga cgttcttccc ctattgttat tgaagaccag ctttagcctg    78600
tgatggtctg ataggacaaa tgggattatt tctatctttc tgtatctttt gaggcctgtt    78660
ttatgactta ctacatggtc aattttggag aaagtaccat gaggtggtga gaagaagtta    78720
tatccttttg ttttaggata gaatgttcta taaatatctg ttaagtccat ttggttcatg    78780
acttctctta gtctgtctat gtctctgttt aatttgtttc catgacctgt ccattgatga    78840
gagtgtgtgt gtgtgtgtgt gtgtgtgtgt gtgtgtgtgt gtgtgtgtgt gtgtgtaatc    78900
tactatcatt gtgtgaggtg caatgtgtgt tttgagcttt agtaaggttt cttttatgta    78960
tgtagatgcc ttgtatttag agcatagata cttaggattg agagttcatc ttggtggatt    79020
tttcctttga tgaatagaaa gtgtccttcc ttaccttttt tgatgacttt tagttgaaaa    79080 tcaatttat ttgatattag aatggctact ccagcttcct tcttcagacc ccttgcctgg    79140
aaagttgttt ttcagccttt cacactgagg tagtttcttt ctttgtctct gaggtatgtt    79200
tcctgtagac agcagaatgc caggtcctca ttgcatatca ggttcattaa tctatgtctt    79260
tttattgggg cattgagacg tttgatattg agagatatta aggaatactg attattgctt    79320
cctgttatat tcatatttgg atgtgaggtt atgtttgtgt gcttttcttc tctttgtttt    79380
gttgccaaga cgattagttt cttgcttttt ctagggtgta gcttgcctcc ttttgttggg    79440
ctttaccatt tatcctttgg agtgctgagt ttgtagaaag atattgtgta aatttggttt    79500
tgtcatggaa tatcttggtt tctccatcaa tgttaattga gaattttgca ggatacagta    79560
acctgggctg gcacttgtgt tctcttaggg tctgtatgac atctgtccgg gatcttctgg    79620
ctttcatagt gtctggtgag aagtctggtg tgattttgat aagtctgcct ttatatgtta    79680
cttgacattt ttccttactg cttttaatat tctttctttta ttttgtgcat ttggtatttt    79740
gactgttatg tgatggcagg agtttctttt ctgatccaat atatttggag ttctgtagga    79800
ttcttgcttg tttatgggca tctctttctt taggttaggg aagttttctt ctatgatttt    79860
gttgaagata tttactggtc ctttgagctg ggaagtcttc actcttttct atacctattt    79920
atcttctcat tgagtcctgg atttcctgta tgtttggac cagtagcttt ttccatttta    79980
cactatcttt accccttgtgt caatgatttc tatggaatct tctgctcctg agattctttc    80040
ttctgtctct tgtattctgt tggtgatgct tgtatctatg gctccttgtc tcttcctttg    80100
gttttctata tccagggttg tttccatttc agctttcttt attgcttcta tttccctttt    80160
taattccttc acctctttga ttttgttttc ctggaattct ttctgggatt tttgtgattc    80220
ctctctatag ggttctactt gtttatttat gttttactgc atttctttaa gggagttctt    80280
catgtctttc ttgaagtcct ccagcatcat tatcaaatgt gattttaaat ctagatcttg    80340
cttttctggt gtgtttggat attcagtgtt tgctttggtg ggagaattgg gctctgatga    80400
taccgtatag tcttggtttc tgttgcctgg gttcctgcgc ttgcctcttg ccatctagtt    80460
gtctctggtt ttatcttctg ctatttctaa cagtggctag accttcctat agggctatgt    80520
```

-continued

```
gtcaggagtg ctgtagacct gtttcccttt tttcgttcag ctagttgtgg gaacagagtg   80580
ttctttaggg tgtgtagtct ttcctgccta gtggtcttcg ctgttcctgt gggactgtcc   80640
tgagtccacc aggcaggtca cttggatcag aaaagttggt cttacctgtg gtcctgtgtc   80700
tcaagttgct cgtgggggc tgcttttgag ctctctgtga gggtggcaac caggagggtc   80760
tgtgcagcct tttccatgag cccccgagta ctggggtccc agacggcatt aggtgttttc   80820
ctctggagtc tgaaatgtgg gcagagtgta gtctcttctg gcctcccagg cgtgtctgcc   80880
cctctgaaag tttagctctc tctcccatgg gatttggctg cagagagctg ttgattggtc   80940
ccttcaggtc aggtgggtat ctggatccca ggggacctgc tgctccagtg cccctgtctt   81000
ccatttccca gagactgtat acagtttcct cttgggccag ggatgtgggc aggggtgggc   81060
agtattggtg gtctcttctg ctctgcagtc tcaggagtgc ccacctgtcc agatggtgag   81120
ctctccctcc cacaggattt gggtgcagag agctgttgat ccggtccttt caggtccagg   81180
cgatgtctgg agcacagggg acctgcagct ccagtgcccc tatcttccag ttcccagagg   81240
ccgtatacag tttcctcttg ggccgcggat gtgggccggg gtgggcagta ttggtggtct   81300
ctccctctct gcattctcag gagtgcccac ctgtctgggc ggcgagctct ctctcccagg   81360
ggtttgggag cagtgaagtg tggccgggat cagcgagatt cgggctccag ctaaaaacca   81420
gaagtgtcct gttccagagg aattttgcct cagtgtgtcc tgagtccacc aggcaggtcg   81480
cttggagcat aaaagttggt cttacctgtg gtcttgaagc tcaagttgct tgtgaggggg   81540
ctgcttttga gctctctgtg agggcggcaa ccaggagggc ctgcaccgcc ttttcctgga   81600 gccctgtgc accgggatcc cagatggcat taggtgtttt cctctggagt cagaaatgtg   81660
ggcagagtgt agtctctttt tgcttcccag gagtgtctgc ccctctgaag gtttagctct   81720
ccctcccatg ggatttgggt gcagagaact gttgagcagt cccttcaggt ccgggcagca   81780
tctggaacga gggggacctg ctgctccagt gccctgtct tccagttcca ggaggccta   81840 tacagtttcc tcttgggcca cggatgtggg caggggtggg cagtgttggt agtctctccc   81900
actctgcagt ctcaggagtg cccacctgtc tgggtggtga gctctctgtc ccacagggtt   81960
tgggagttgg gagctgtggg ccgggatcag tgaggttagg aggatgatac tttctagttc   82020
catccatttg cctatgaatg tcatgaatca ttgtttttag ttgctgagta atactccatt   82080
gtgtagatgt accacatttt ctttatttat tccactgttg aggaacatct gggttctttc   82140
cagcttctgg ttattataaa taaggttgct atgaatatag gagaatatgt gtcctggtta   82200
tatgttggaa catcttttgg gtatatgccc aagagaggta tagctgggta ctcaggtagg   82260
tcaatgtcca attttctgag gaacctccag actgatttcc agaatggttg taacagcttg   82320
caatcccaac aacaatggaa gagtgctcct ctttctccac atccttgcca gcatctgttg   82380
tcacctgagt tttttatctt aagaatgtcc attcagatac tgccccacct ggggatccag   82440
ccaatatata tacagccacc aaacccagtc actatatgcc aagagctgca tgctgacagg   82500
aacctggtat ggaagtctcc tgagaggctc tgccaaagca taacaaatac agagatggac   82560
tgagaactgg gtgcatattg gaggagttag agaaaggatt gaaggagctg aaggtgtttg   82620
caacccccta agaacaacga tacccaccaa ccagagcttt caggaactaa atcactgtcc   82680
aaagagtaca catggacaga cccatggctc cagttgcata tgtagcagag gatggccttg   82740
ttggccacca atgggaggag aaaaccctTG tcctgtcaag gctcatcctc caaccctttc   82800
ctatctgaca ttcccacccc ccccccagt ttaggcgact gtaagatagg aaagggttgg   82860
```

-continued

```
aggatgggca ggggaacacc ctcatagaag aaagtggaga gggaatggga caggggggtttt   82920 gtgggcagga aactggaaag tgggatggca tttgaaatgt aaaaataaaa atatccaata   82980
aaaaaactaa tgaaggagaa tcgggtatag ttaaaaaaaa aaagaaacga agccataatt   83040
ctagcatata aaaagttttt gctgcataat ttgaatgctg gaagacaaat acgatatgag   83100
tcaaaacaaa atttttcctt tccagcccac ctaagttgtt tttgttccat gtagtctgag   83160
atatctgaat tatcagaatt ctcagaatcc aggaacacac aggctcctct aaacagtctc   83220
atcactacaa tgacagtttt agagcaatgc cactacaatt acatatgctc taaatttttc   83280 aaataaattat gagtaagtta cattttataa agtcaaacat aaatactcta attttggaaa   83340
gtacaagaaa aattgaatgc aaaatttaaa atttcaaaaa ttataaccat caggattctg   83400
tgtctatctt atttattttc ataaatatag aagaacgtca gtgtaactaa gtaaaaaatg   83460
gaaaacctac tgtatgtatt gttttctatg aagttaacta ttgtttcata tatcgtatgt   83520
tctacaactt cctgaaaaca aacacccaca tactcttta ttttttttaag aaactgattg   83580 tgacaacttg cccacatttg aaattgccaa accgacagaa aagaaaaaaa aatcatacag   83640
gtcaggagaa caagtgacat tcagatgtcc acctccgtat cgaatggatg gctctgacat   83700
tgtcacatgt gttaatacga agtggattgg acagccggta tgcaaaggta tttgaatggg   83760
tttttaacat gcatttattc tagtgtcaaa gaatgacata actgaaaatg gtgcagagat   83820
tacttttaaa gtaagatcaa gtttgtttgt atcaaataat aaaagcattg aattaaaaaa   83880
actgatggct aagctgatag catgatggtg ttcagagttt gatttcatgg tcagcatcat   83940
cagtatcatt agaatacaaa cattttgaaa atgtaaatta acagctagga gtacatgcta   84000
gatatcctaa ataggacgac atctaaagat gagaccttca atctcctttt agggatctgt   84060
gtatgactaa gtttggaatg tgctgtaggc tgtcaatatt tgttaatatg ttgttaaata   84120
attagccttc aattgaaatc ttgcttatat ctcattttat caaattcatt ggaatattag   84180
gatattttat ttgattatca ctttcttatg actatattat tcttaaaaca atgttctttt   84240
tcctctaaca ttgcaaatag attttttttct cacataatac atatcctgat tgtttttctct   84300 tccctccact catttcagct ccttcctacc cctttttttca tctaatttttt cccctttctg   84360 tatttcagga gaaaggaaag tcttctaagg agtaatacta ataaaacaaa aatgaaacaa   84420
atacagtagg aggtaacaaa caaataattt tagggaaaac agcataagaa aatagataag   84480
aaacaaaata gacaaaatgt cccactttat acacctagga atcccttaag aatactcacc   84540
tgaaaaccat aatatatatt gaacagcatg caaagtacct tcctgtacca aagatgcttc   84600 ccttagggggt gaaggctcta tgtaggcatc agtgacactt tgctatgatc agtgagttgc   84660
atatttgttg ttttttcacag tgtagacttg ccttcaggtt gtgtggtata atctgtagtc   84720
ttctcaacag cctgcctgtg ttattcggaa gtttccatgt gaccccctctg gtacacattt   84780 aattagatgt aaccttatca cagtactaga agcttcatta gtgacatgat atgtccctcg   84840
gggctctgtc tccttacact tttggtgatt gcacttatat ttcctttata tatgtatgta   84900
ttttagaaag cttatattga attaggtttt gataatatcc ctcaaatgac acttaacttt   84960
tgctgttcct ctctgtattc tgattttttgt ctacccttct tgacatccat aactatctac   85020
tctatttctc catcctaagg agacagtact ttgcccccaa ttccttaggc ctacacctaa   85080
attctgttgt tctgtggatt gtaaagtgac tttcattggc tttcagctaa tatctacata   85140
tcagcaaata tatacatgtg tgtctttctg ggtctgagtt cttcactcag gatgaatttt   85200
tgtctattac ccatcatttta cctgtgacat tcatgatttc attttttgcat gtaaataaat   85260
```

-continued

```
gtagcaaatt ttctttatcc attcagcaag tcagaaatat atttggaatc ttatgcatta  85320
attggacact caagatgagc aaataggtac taatacttta ttttactctt tagataattc  85380
ctgtgtgaat ccaccacatg tgccaaatgc tactatacta acaaggcaca agactaaata  85440
tccatctggt gacaaagtac gttatgactg taataaacct tttgaattat ttggggaagt  85500
ggaagtgatg tgccaaaacg ggatttggac agaaccaccg aaatgcaaag gtagggcatc  85560 atttcccta atgtttattt gacaatgcaa tttagttatt gtacattagt gaaaggaaac  85620
tgaagcaatt tttaaacttt ttttaacttt tacaattatt ttatttattt acatcccaaa  85680
tgatgtcctc tccctgtccc cactccaaga actctttccc ccatacccct ctacttcacc  85740
tctgagatgg tgcttaccca tccctcttgc ctggggcatc aatttttaa aggattaggt  85800 gcatcctatc ccttcgaggc cagaaaaggg agtcctctgc tatatgtctg ccaggagctt  85860
gtaattagcc tctgtatgct ctttggtttt gtggcatagt ctgcgagctg caagtggtga  85920
gtggtccatg ttagttgaca ctgttggtct tcctatgggg ttcccattcc cctcaacttc  85980
tttaatacag cccctgacac ttccataggt caactgctgg tagagtttat tagaggaaag  86040
ccatgctagg ctcctgtctg caagcacaac atagcatcag taatagcatc agtgcttggt  86100
gaccctcccc acctccatga gacagaactc acattgggcc agcaactagt caataattcc  86160
ttcagtctct gctcctttt tgtctctgca tttctttcag agaggaacaa tttggagtca  86220
aaattttgaa gttggtttgg ttgtcacacc cctcctctgg gtgtcctatt gaactattgg  86280
acttcaggtt cctcttccca ccattgagta ttttgcttaa ggtcacccac attaaaacct  86340
gggagtctct ccaccctggg tttctaggat tttaagcagt ttctgttgat tccctgtctc  86400
tggaaaattt atgtttccac ttattttct ggtctgctgg gcttctcttc cgttttgccc  86460
catatctgac cctgccccac cccatgcccc cgttatccct tcccctccct tctcccacct  86520
aggtaacccc ctccctctac ctcccatgat tattttgcct catattctaa ggtaaatttg  86580
aagcatccca catttgggct ttccttcttg tttaacttct taagctatat gggggaaccc  86640
catgggaatt ctggactttt taactaatac cccttaccaa tgagtccata ccatgaatgt  86700
cctttgagtc ttggtttctc agtcaaaata atttttcttt tcttttata ttttgtttac  86760 tcttttttac actccaaatt ttattcccct ctttgtccac cctccgactg ttccacatca  86820
catatgtcct cccttcccct gccccctgcct tccatctagg aggatgtccc ctacacccca  86880 ccccacccc agatctctaa actccctgga gcctccagtc tcttgaaggt taggtgcatc  86940
ttctttgatt gaacacagac ctggaagtct agtgctgtat atttgttgag ggtctcatat  87000
cagctggtgt atgctaccag gttggtggta cagtgtctga gagatctcag gggtccaggt  87060
tagttgagac agctggtctt cctatgggac caccctaatc atcatcttct ttcaagcatt  87120
tccctaattc aaccacatgg atcagcatct tctgtccact ggttgagtct aatatctgca  87180
tctgaatttt ccagcttctt gttgggtctt tcgggtggca gtcatgagag gtcccttttt  87240
gtgagtgctc catatcctta gaattactgt cagaccttat agcctcccct tgagctgggt  87300
cccaatttgg gcctatcaac agatttcctt tccctcaggc tcttctccat ttttgtccct  87360
gtagttctta cagataggaa catttctgag ttacagtttt tttgactgtg ggatagcaac  87420
cccatccctc cactttatcc tttctcttcc tactggaggt agactctaca agttccctct  87480
ccccactgta gggcatttcc tctaaggtcc tgccttttgg gacctgagag tctctcatgg  87540
ccaaggtgtc tggtaatttta tatagggttc cctccatctt ctacctccag aggttgctta  87600
```

-continued

```
tttccatttt tttctgctaa cccaaaggac ttcagtcctg ttttccctgc ctccaatatg   87660
tgatcatgtc atccttttca ctcgctcatc caagtacctc tctctcctga ctgccccatg   87720
attgcatggg gtgttcaaat ctcctattat tattgtgtga ggtgttatgt gtgcttcaag   87780
cttcagtaag tttttttta ataactgtat gttgccttgc atttggagaa tagatattca   87840
ggattaagag ttcatcttgg tagatttttt tcctttgatg aatatgaagt gtctgttctt   87900 atccttttg ataacttttg gtagaaagtt ggttttattt gctattagaa tgtctactcc   87960
aacttgtttc ttggaaccaa atgcttggaa aattgttttt cagcctttta ttctgcggta   88020
gtatctatct acagtcacta gagtgtgttt cctttaggca gcaaaatgct gggtcctctt   88080
tctctatcca gtctgttatt ggggaattgg gtccattggt gttaagagat attaaggaat   88140
agtgattgtt gttgtgtagc tctcttcttt tggtttcgtt gtaaggagat tactttcttg   88200 cttttttctag ggtgtagttt ttnntgtgga aatatattgt ataaatttgg tttggtcatg   88260
gaatatcttt tttctccacc tgtgttaatc aaaagttttg ctggatatag tagcatggac   88320
tggcatttgt attctcttag ggtttgtatg aaatctgccc agtatcttct ggctttcata   88380
ttctctggtg agaagtctgg tgtaactgtt ttaggtctgt ctttatatgt tacttgacct   88440
ttttcactta ctgcttttaa tattctttct tcgttttgtg catttggtgt tttgtctatt   88500
acgtgacagg aatttctttt ctgttcaaat ctatatggaa ttctgtaggc ttcttgtatg   88560
tttatgggaa tttcttttctt taggttaggg aagtttctt ctataatttt gttgaagata   88620
ttactggccc tttatgttgg gagtctttgg tctcttctat gcctattatc cttaggttga   88680
tcttctcatt gcttcctgaa gtttctagag gttttgggtt aggagctttt tgcattttac   88740
attatctttg acatttgtgt cgatgttttc tatggtatct tctgcccctg agattctctc   88800
ttctatctcc tgaatctctg ttggtgatgc ttgcatctat gactcctgat ctctttccta   88860
ggctttctgt ctccctttgt gatttcctta ttgtttctat ttcaattttt aaatcctgaa   88920 tagtttgct caattccttc acctgttcgg ttgtgttttt ctgtaactct ttaaggaatt   88980
tttgggtttc ctctttaagg gcttctgctt gtttacctgc attgtcctgt atttctttat   89040
gggagttatt tatgcccttc ttaaagttct ctatcatcac catgagatgt aattttaaat   89100
ccaaatcttg cttttccagt gtgtttggac atccagtatt ttctttggtg ggagaacttg   89160
gctctgatga taccaagtag tctttgtttc tgttgctttg gttcctgtgc atgcttcttc   89220
ccatcagttt gtctctgctg ttagcttgtc ttgctctctc tgacagtggt ttgaccctcc   89280
tgtaagctat gtgtcagcat tcctgcagac ctgtttcctt tcagtcagat ctgggaagag   89340
agagctgttc ctggttgtgt gtcctgaagc ctccaagagg gttgcatgga gcagaagagt   89400 tggtttacc tctgttctct ggtgtgtcag ggctccaggc tattggcttt cagctctggg   89460
ctcaggcaga aaccggattg attctgcccc tgactattcc taggttcttg tattcagagg   89520
gctctagaca gatttctctt gggacaggaa tgtgagcaga agtgggggtc ttccctgatc   89580
tctcaggatt gtctgcactt ctgagggtcc agctgtctcc ctcacaggat ttgggtacag   89640
agaactgcag gacctgttca ggaccttgtg caggcagaaa ctggtagtgg actgtccaag   89700
aagacttctg tctttgtgtg tcctgaggcc accaggtgtc cacttggagc agaagagttg   89760
gtcttacctc tgctctctgg tgtgtcatca ctcctgatga ctggctttca gttttgggtg   89820
caggcagaaa caggaagaga cctgcccctg actgctctaa tttcttgtgc ccagagagca   89880
gaggaggcac tagacaggtt cctgttgggc caagaatgtg agcagaagtc ggggtctccc   89940
ctgagctctc aggattatct gcacttctga gggtccagct gtctccccga taggatttgg   90000
```

-continued

```
gtacagagaa ctgcaggacc agttcaggtc cttgtgcagg cagaaactgg aagtgtactg   90060
tcccagactg ctcctgcctt tgtgtgtcct gaggccacca ggcagatttc ttggagcaga   90120
agagttggcc ctccctctgc tcttagatgt gcaggcgctc ctggaaaccg actttcagct   90180
ctggatacag gcaaaaacca taagtttcct ccgctgaatg ctcccaggtt actgtgctta   90240
gaggtcacag agggcactag gaaggttcct gttgggccag gaatgtgagc agaggtgggg   90300
gtctctcctg agctctcggg attgtctgca cttctgagag tccaattctc tctcccacga   90360
tatttgggta cagaaatgtg ggaccaggtc agccctgggt gcaggtgcct atttctatta   90420
ttcttagatt tgatattttc attgtacctg gatttcctgg atgcttcatg ttgcaagatt   90480
tttatgtctt gactttcctt tgacagtgtg tcaatatctt ctaaaatatc ttctacatct   90540
gaaaattcta tataatatct cttatattct gttgttgatg ctttcatcca taattcctga   90600
cctcttttct aggttttcca attcaagcac tgcctctctt tgtgttttct ttatagtttc   90660
tacttccact tttagctctt ggaccacatt cttcaattgc ttcacctgat ttctttcttt   90720
cttttccccc ctgtatttct ttaaggaatt tatttgtttc ccctttaaag gcttctaccc   90780
gtttacctat gttttcctgt ttgtctttcc atgacttact tctatcctct ttaaaggatg   90840
ctattatctt catggatagt atattaggtc agcttcctgt ttttcaagtt tgttgttgca   90900
cacaaggctt gctgaagtga gagaattggt ttctgatgac gccaaagtat attgacttct   90960
gtttcttatg gtcttgggct tgcctctagc aaactggtca tctctggtgt tagctgttct   91020
gggtgtctct gtcttcatcc tacttcctat gtccctgggt tgctagagtt ctctgggtag   91080
gcttgtgttt ctggctgtag ctgaccactg gtgaagactt cagaatgtga ggtcttaata   91140
ggggcatgta cactagtgac ctgctgccct ggctacagag acaatctgct gatctgttgc   91200
cctgtgtgca gcagatctct ttggaggcct tcagactgtg gggtctgttg ctcagtgtgt   91260
agcagaattc gcggaggact tcacactggt cagttatcct gcatgtacca gaactcgtga   91320
gaggccttca gactgtagta tctttagagg agcagacaag ctgatgatct gccattgcag   91380
aaggtgcagg atggaaagca ttcttgtttg ggagggtccc ttacttattg ccctgtgtgc   91440
tgcagaactc ctgagaggcc atcaggctgt gataccttca gaagagcagc caagctggta   91500
ggggtcttat ttctcttttt atttcttgtt ttggaggagt ggttctcaag aatttaacag   91560
tggcatgcat ttttattact tttgaacaca tagtctgagt atgctatctc taatagtttc   91620
ctaaccatct gttactcaag tcaaccaggc tgatatttta tataagtaga aactgaactt   91680
atcttcaaaa tccaattaca ttttccattt tttgtgtttt ccttaaaaat tccttcggag   91740
ttttctctta catatattaa atgccaccct ttttttattt tatttttttc agagtccatg   91800
atttatttgt ttactctcct tcctgggatt gcccttttcaa taaatccct ttctttgctt   91860 ttcattgtta ttcatcaatt ttttcttctt attattttat ttacttacat tccaaacatt   91920 ggccccttc ccagtaccat atcctcaagt tattcattgt ccccctttcc tttgcttctg   91980
agagtgtgct ccctgacaca cccacctacc tacacctcac ccctaccagc atcccttctc   92040 ccctctttc agatttctac aggatttggc tgttcctctc ctactgaggt cagataaggc   92100
agccctctgc cacatatgta ccaggagcta tggatcagtc catgaatact cttttgttgg   92160
tggcttagac tctgggatct ctgaggtgtt ctggttattt gatactgttg ttctttctgt   92220
gataccacaa tccccttcag caccatcaat cctttgctta actcatccat agacatccca   92280
gacctcattc actgttggct gtaaatattt ccatctgttt cagtcagctg ctaaatagag   92340
```

-continued

```
cctctcatgg gacagccatg ctgggcttct ctctgcaagt acaacatggt gtcaaagttt   92400
ggtgcctata catgggatgc atctcaagtt gagagggtca ctggatgggc tttccttcag   92460
gctctccaca attttttctcc ctgtgtttcc tttagacagg aacaattctt ggtcgaacat   92520
ttataaggtg actgggtgac cccattcctc aactgggtgc catgtctacc tactgttggt   92580
ctctttaggt tccaactcct cacttttgga cattctgatt aagcttatcc ccattggatc   92640
ctaagagccc cctctcatat ctttgatgtc tgagtctttc tagggattct ccagttcccc   92700
caaccattca ctggtgcata tttctgttca ttcttctggc cctctagaat tctgtcctgt   92760 gtcccccat attttatcca gaccttcctc ttctccctcc tcatcccctc tgccattcat    92820
gtccctccct ccctctgcct cctatgatta tttttaacac tcttcttata tgcaagtttt   92880
cacttgaaac acaaatctaa ttttatgaaa acaaagatca cctactatat agccctaatc    92940
ttacagttaa atttgtccta ctcttaattt ttatttttca cttatataat gaattctggt   93000
agttattctt tagggaggac tctctgatgg agataaatcc cctttatctc ttttatctga   93060
taatgtctca tcaatgtctt tattcaaaag gcaaacaaca caggatatag aacttaaggc    93120
ttacactcat tttcttttcc ttactatggt ctgcatggtg agaggatagg agtcactttc    93180
tttgggatct gggtccagtg tggttgatga tgacttccta ctgattttg tccaagatgt    93240 tttcttaag cagtttcagt agagagatct ccaggagttt catgggactt gtcctatttg    93300
actttactca gttcttgaat atgtacagtc atctattatg gagaattgtt ttcattttcc    93360
ttcatagtaa aacattaatt ttgcttgaat attgaatatt ttgttttac ctaaaaatat    93420 ttgaattttt ttcagtttca tgatgttcct cttgaggtca tactgaacat aatcagtact   93480
tttgatttca tattttttcct gtgtcctcac aagaacaatc agtagtctaa aagaaaaaca   93540
tataacacaa cagtgtgaca ttagatgagt ttggaatttc tttgctagaa ttttcaatgt   93600
ctcatctctt catataatgt ttactaaaaa ttctatgtcc aagcttttca gatataccta   93660
gttaaagtat atcatagatg tctatgctta ttttaaccat atcagaaacc cagaaaacct   93720
cattagcctt ctgttacatt ataggctttc aagtcttgtt ttaaatgtac ttatacaaaa   93780
tgataaagag tgggaatata tacagtcata tactattgag tttcttcaaa aaaaaatgcc   93840
tatctacatt ggccatagca cctaatcctt ctcaggttca gaagctgtta agagatttac   93900
tactacttga agttttcagg cagacatgtt tgctgtagtt aagaaatgtt tcaggtgaga   93960
aaaaaagaag aacttgtaac tctcagttta tatgattaat ctttcttcaa ataatcattt   94020
atacagccag aaatcactaa agacttaata cttaatgttt ttggttctgc ttgagcctgt    94080
agttttactt gatattcaaa cattcaaatg ttgtctcctt agattcaaca gggaaatgtg   94140
ggcctcctcc acctattgac aatggagaca tcacctcctt gtcattacca gtatatgcac   94200
cattatcatc agttgaatat caatgccaga actattatct acttaaggga aataagatag   94260
taacatgtag aaatggaaag tggtctcagc caccaacctg cttacgtaag taccttattc   94320
acatagatta taagaaattc tgttttatat tgtgggtatt tttctgttta taatataaca   94380
ttcacaaaat aaaagtactg ttttgtttgt gtttcagtat caaacatcag catgtgataa   94440
aacaagatta ttagattctt tttataaaaa atacctgtta aataaaattg tatatattat   94500
tcttaataat tgttttttttc taatatgtat taacatctac aaaactgggt gccagcataa   94560
cattatataa ctgttgtctc agtcagtgtt ctattgtttt aaagaggaac tatgaccatg   94620
gcaactcttt taaaagaaac catttgttgg gggttgctta caattttgga aatttattct    94680
actctcaaca tgtttgggag catggtggca cagaggtaaa catgatggtg aagaagtagc    94740
```

-continued

```
taagtattcc atatctggct ctgcagggag cagaaagtga taggcatact tctaacaagt  94800
ctatgcaaac tcccacaagg ccgtagccat aatacttcac aagtaccacc attctccaat  94860
gaaaaatctg tatgtgtatc tatggaggtc attccttttc aaataagcac atctgtatac  94920
atcttgcagt tattaaatcc atacaacatc tcctttcctt agataaggca actgacatct  94980
attaatcact gttatgcatt ctaaagtaat tctctctgtg agaaagagca caaagtagtt  95040
gtctttctgt gttggttata tttgacttaa tgtccttcaa tgcccttttc taagtaaaat  95100
aataaaatat atctttaatg acttaatatt ttacatttaa atataccatg atgtcattat  95160
aaattcacca attagtatta gttcagcttt cttcacctta ccaacttcca tgtagcagtt  95220
tagaataaac atatagatcc aggttgagta ctttgatttt atttcctttg cgtacattcc  95280
agaagaaaca ataggaacaa tacataaata tctatttta aatttgtaag aaatctcaat  95340
ttttatccat agtaacttca caaaatcata ttcctgtcaa tggtttgtga agtgttcacc  95400
acacactaat gagcagttgt aattttagg gctccttcct ctggtgctac tttaactgag  95460
ttaaaagata tcttactatg gctttcaat ggaatgacag caatgatatt tatgtgtttt  95520
tcttagaagt atctattcat ttatccagat ttgatcagct tattttcct ttaaaatgtg  95580 ctttaccaca gactaatata gttcagcgaa aggttatcag cagactggaa tattttcaa  95640 ttatttaagt ataatttatg acagatatag tgcaaagcct tttcacaatc aatttactaa  95700
aaaaggtgtt ctaacttcta acagaccagc aaggcccaaa gcaatgaaat caaattatat  95760
aaaaacaaaa caaaagcaaa taaatatatt tatgcacttt gtacgaaatg gaggtcacat  95820
ctttatgctt tcttgaccca ggacacccc ctaaaagata tgtaaatacc taaaaataaa  95880
gaatagacaa ccatatactt caattaaact tgctgccaat ttcttaggtg tattgactat  95940
gctctgtgat atgcaccagt accacaatgg gatcaaatcc acaggtcaaa gtttgctttt  96000
tgccttgtga tttggagtcc cagccaaaca cacagtgtca aaaccatgaa atgtttccct  96060
gttgtgcttc ctgatacttt cagtggtttg ttcttatatc aatgtctttg accaaatttc  96120
agttgaattt gcccataatg acaaacagat ataaaatttc aatcatcgcc atatggatat  96180
caattatcat tttatcattt attaaatatg atatcagttc attaacataa gttttgggaa  96240 agttattaa gatcagtaac ctgtagatgc atagatcaat tttcaaatca cttttctcat  96300
tcattggagt cttccgagtg ttctggttac tgtgggggtc ctggtgtata ttgaaataaa  96360
gtattatggt atctcctgat ttttcctttc tgttctagtt acagttgtct attcattcta  96420
ttgtagttcc atacaagttt tagatttta tccctattag tatgaaaaat gttattgata  96480
tttcagtgtc agctcacaga gtctgctatt agccatagga tatgtggaca tgtctatacc  96540
tatattaatt cttacaaccc attaatatac aagctttctc tatttctgtc ttttcagatt  96600
attttaccag ttaactaata tttttgattg aagtttcac ttctgtttat aaattcatag  96660
ctgaattaat tttgaagata ctgaaaatga cattgcattt atagttaatt ctcagaaaaa  96720 tggaatttt ctatagaaag ggggtgattt ctgtaggttt atatattaat tgttgaactt  96780
tggtaattta tctttcagat gcatgtgtga taccagaaga tattatggaa aaacataata  96840
tagttctcag atggagggaa aatgcaaaga tttattccca atcaggggag aatattgaat  96900
tcatgtgtaa acctggatat agaaaattca gaggatcacc tccgtttcgt acaaagtgca  96960
ttgagggtca catcaattat cccacttgtg tataaaatcg ctatacaatt attagtaaac  97020
cttatggatg aacctttgtt tagaaatgca catgtatatt actaatacag tttgaattta  97080
```

-continued

```
catttgaaat attgtttagc tcatttcttc taataagtat ataaacttttt tttatatggt    97140 ggttaatcag taactttaca gactgttgcc acaaagcaag aacattgcat tcaaaactcc    97200
taatccaaaa tatgatatgt ccaaggacaa actatgtcta agcaagaaaa taaatgttag    97260
ttcttcaatg tctgtttta ttcaggactt ttcagatttt cttggatacc ttttgttgtt    97320
aggttctgat tcacagtgag tggaagacac actgactctg acttcaaatt agtattactt    97380
gccaatacat aacaaccaaa ctatcataat atcacaaatg tatacagcta attactgtgt    97440
cctacctttg tatcaataaa gaaatctaag aaag                                97474

<210> SEQ ID NO 2
<211> LENGTH: 4236
<212> TYPE: DNA
<213> ORGANISM: Rattus norvegicus

<400> SEQUENCE: 2
acagcacata cttctcttcg agtcaactgc tcccagatag atccaagaca tgagactgtc      60
agcaagaatt atttggctta tattatggac tgtttgtgta gcagaagatt gtaaaggtcc     120
tcctccaaga gaaaattcag aaattctctc aggttcgtgg tctgaacaac tatattcaga     180
aggcactcag gcaacctaca aatgccgccc tggataccga acacttggta ctattgtaaa     240
agtatgcaag aatggagaat gggtaccttc taacccatca aggatatgtc ggaaaaggcc     300
atgtgggcat cccggagaca caccctttgg gtcctttagg ctggcagttg gatctgaatt     360
tgaatttggt gcaaaggttg tttatacatg tgatgaaggg taccaactct taggtgaaat     420
tgattaccgt gaatgtgatg cagatgggtg gaccaatgat attccaatat gtgaagttgt     480
gaagtgcttg ccagtgacag aactggagaa tggaagaatt gtgagtggtg cagccgaacc     540
agaccaggaa tattattttg gacaggtggt acgctttgaa tgcaactccg gcttcaagat     600
tgaaggacag aaagaaatgc actgctcaga aaatggcctc tggagcaatg aaaagccaca     660
gtgtgtggaa atttcttgcc tgccaccacg agttgaaaat ggagatggta tatatctgaa     720
accagtttac aaggagaatg aaagattcca atataaatgt aagcaaggtt ttgtgtacaa     780
agaaagaggg gatgctgtct gcacgggttc tggatggaat cctcagcctt cctgtgaaga     840
aatgacatgt ttgactccat atattccaaa tggtatctac acacctcaca ggattaaaca     900
cagaattgat gatgaaatca gatatgaatg taaaaatggc ttctatcctg caacccgatc     960
acctgtttca aagtgtacaa ttactggctg gatccctgct ccaagatgta gcttgaaacc    1020
ttgtgatttt ccacaattca aacatggacg tctgtattat gaagaaagcc ggagacccta    1080
cttcccagta cctataggaa aggagtacag ctattactgt gacaacgggt ttacaacgcc    1140
ttcacagtca tactgggact accttcgttg cacagtaaat gggtgggagc ctgaagttcc    1200
atgcctcagg caatgtattt tccattatgt ggaatatgga gaatctttat actggcaaag    1260
aagatatata gagggtcagt ctgcaaaagt ccagtgtcac agtggctata gtcttccaaa    1320
tggtcaagat acaatattat gtacagaaaa tggctggtcc cctcctccca aatgcgtccg    1380
tatcaagact tgttcagtat cagatataga aattgaaaat gggtttttttt ctgaatctga    1440 ttatacatat gctctaaata gaaaaacacg gtatagatgt aaacagggat atgtaacaaa    1500
taccggagaa atatcaggaa taattacttg tcttcaagat ggatggtcac ctcgaccctc    1560
atgcattaag tcttgtgata tgcctgtatt tgagaatgct atgactaaga ataataacac    1620
atggtttaaa ctcaatgaca aattagacta tgaatgtcac attggatatg aaaatgaata    1680
taaacatacc aaaggctcta aacatgtac ttatgatgga tggtctagta caccctcctg    1740
```

```
ttatgaaaga gaatgcagca ttcccctgtt acaccaagac ttagttgttt ttcccagaga    1800
agtaaaatac aaagttggag attcgttgag tttctcttgc cgttcaggac acagagttgg    1860
agcagattta gtgcaatgct accactttgg atggtcccct aatttcccaa cgtgtgaagg    1920
ccaagtaaaa tcatgtgacc aacctcttga aatcccgaat ggggaaataa agggaacaaa    1980
aaaagttgaa tacagccatg gtgacgtggt ggaatatgat tgcaaaccta gatttctact    2040
gaagggaccc aataaaatcc agtgtgttga cgggaagtgg acaaccttgc cgatatgcgt    2100
tgagtatgag agaacatgtg gagaccttcc tgcacttgag catggctctg tccagttatc    2160
tgtccctccc taccaccacg gagattcagt ggagttcact tgtgcagaaa ccttcacaat    2220
gattgggcat gcagtagttt tctgcattag tggaaggtgg accgagcttc ctcaatgtgt    2280
tgcaacagat caactggaga agtgtaaagc cccgaagtca actggcatag atgcaattca    2340
tccaaataag aatgaattta atcataactt tagtgtgagt tacagatgta gacaaaagca    2400
ggagtatgaa cattcaatct gcatcaatgg aagatgggat cctgaaccaa actgtacaag    2460
aaatgagaaa agattctgcc ctcctccccc acagattcca aatgcccaag tgattgaaac    2520
cacagtgaaa tacttggatg gagagaaagt atctgttctt tgccaagatg gttacctaac    2580
tcagggccca gaagaaatgg tgtgtaaaca tggaaggtgg cagtcgttac cacgctgcac    2640
ggaaaaaatt ccatgttccc agcccctaa aattgaacat ggatctatta gtcgcccag      2700 gtcctcagaa gagagagatt taattgagtc cagcagttat gaacacggaa ctacattcag    2760
ctatgtctgt gatgatggat tcaggatatc tgaagaaaat agggtaacct gcaacatggg    2820
aaaatggagc tctctgcctc gttgtgttgg aataccttgt ggaccccac cttcaattcc     2880 tcttggtatt gtttctcatg aactagaaag ttaccaatat ggagaggagg ttacatacaa    2940
ttgttctgaa ggctttggaa ttgatggacc agcatttatt aaatgtgtag gaggacagtg    3000
gtctgaacca cccaaatgca taaaaactga ttgtgacaac ttgcccacat ttgaaattgc    3060
caaaccgaca gaaaagaaaa aaaatcata caggtcagga gaacaagtga cattcagatg      3120
tccacctccg tatcgaatgg atggctctga cattgtcaca tgtgttaata cgaagtggat    3180
tggacagccg gtatgcaaag ataattcctg tgtgaatcca ccacatgtgc caaatgctac    3240
tatactaaca aggcacaaga ctaaatatcc atctggtgac aaagtacgtt atgactgtaa    3300
taaacctttt gaattatttg gggaagtgga agtgatgtgc caaaacggga tttggacaga    3360
accaccgaaa tgcaaagatt caacagggaa atgtgggcct cctccaccta ttgacaatgg    3420
agacatcacc tccttgtcat taccagtata tgcaccatta tcatcagttg aatatcaatg    3480
ccagaactat tatctactta agggaaataa gatagtaaca tgtagaaatg gaaagtggtc    3540
tcagccacca acctgcttac atgcatgtgt gataccagaa gatattatgg aaaaacataa    3600
tatagttctc agatggaggg aaaatgcaaa gatttattcc caatcagggg agaatattga    3660
attcatgtgt aaacctggat atagaaaatt cagaggatcc cctccgtttc gtacaaagtg    3720
cattgagggt cacatcaatt atcccacttg tgtataaaat cgctatacaa ttattagtaa    3780
accttatgga tgaacctttg tttagaaatg cacatgtata ttactaatac agtttgaatt    3840
tacatttgaa atattgttta gctcatttct tctaataagt atataaactt ttttttatatg   3900 gtggttaatc agtaactta cagactgttg ccacaaagca agaacattgc attcaaaact      3960
cctaatccaa aatatgatat gtccaaggac aaactatgtc taagcaagaa aataaatgtt    4020
agttcttcaa tgtctgtttt tattcaggac ttttcagatt ttcttggata cctttttgttg   4080
```

-continued

```
ttaggttctg attcacagtg agtggaagac acactgactc tgacttcaaa ttagtattac    4140
ttgccaatac ataacaacca aactatcata atatcacaaa tgtatacagc taattactgt    4200
gtcctacctt tgtatcaata aagaaatcta agaaag                              4236
```

```
<210> SEQ ID NO 3
<211> LENGTH: 1235
<212> TYPE: PRT
<213> ORGANISM: Rattus norvegicus

<400> SEQUENCE: 3

Met Arg Leu Ser Ala Arg Ile Ile Trp Leu Ile Leu Trp Thr Val Cys
1               5                   10                  15

Val Ala Glu Asp Cys Lys Gly Pro Pro Pro Arg Glu Asn Ser Glu Ile
                20                  25                  30

Leu Ser Gly Ser Trp Ser Glu Gln Leu Tyr Ser Glu Gly Thr Gln Ala
            35                  40                  45

Thr Tyr Lys Cys Arg Pro Gly Tyr Arg Thr Leu Gly Thr Ile Val Lys
        50                  55                  60

Val Cys Lys Asn Gly Glu Trp Val Pro Ser Asn Pro Ser Arg Ile Cys
65                  70                  75                  80

Arg Lys Arg Pro Cys Gly His Pro Gly Asp Thr Pro Phe Gly Ser Phe
                85                  90                  95

Arg Leu Ala Val Gly Ser Glu Phe Glu Phe Gly Ala Lys Val Val Tyr
            100                 105                 110

Thr Cys Asp Glu Gly Tyr Gln Leu Leu Gly Glu Ile Asp Tyr Arg Glu
        115                 120                 125

Cys Asp Ala Asp Gly Trp Thr Asn Asp Ile Pro Ile Cys Glu Val Val
        130                 135                 140

Lys Cys Leu Pro Val Thr Glu Leu Glu Asn Gly Arg Ile Val Ser Gly
145                 150                 155                 160

Ala Ala Glu Pro Asp Gln Glu Tyr Tyr Phe Gly Gln Val Val Arg Phe
                165                 170                 175

Glu Cys Asn Ser Gly Phe Lys Ile Glu Gly Gln Lys Glu Met His Cys
            180                 185                 190

Ser Glu Asn Gly Leu Trp Ser Asn Glu Lys Pro Gln Cys Val Glu Ile
        195                 200                 205

Ser Cys Leu Pro Pro Arg Val Glu Asn Gly Asp Gly Ile Tyr Leu Lys
        210                 215                 220

Pro Val Tyr Lys Glu Asn Glu Arg Phe Gln Tyr Lys Cys Lys Gln Gly
225                 230                 235                 240

Phe Val Tyr Lys Glu Arg Gly Asp Ala Val Cys Thr Gly Ser Gly Trp
                245                 250                 255

Asn Pro Gln Pro Ser Cys Glu Glu Met Thr Cys Leu Thr Pro Tyr Ile
            260                 265                 270

Pro Asn Gly Ile Tyr Thr Pro His Arg Ile Lys His Arg Ile Asp Asp
        275                 280                 285

Glu Ile Arg Tyr Glu Cys Lys Asn Gly Phe Tyr Pro Ala Thr Arg Ser
    290                 295                 300

Pro Val Ser Lys Cys Thr Ile Thr Gly Trp Ile Pro Ala Pro Arg Cys
305                 310                 315                 320

Ser Leu Lys Pro Cys Asp Phe Pro Gln Phe Lys His Gly Arg Leu Tyr
                325                 330                 335

Tyr Glu Glu Ser Arg Arg Pro Tyr Phe Pro Val Pro Ile Gly Lys Glu
            340                 345                 350
```

-continued

```
Tyr Ser Tyr Tyr Cys Asp Asn Gly Phe Thr Thr Pro Ser Gln Ser Tyr
    355             360             365

Trp Asp Tyr Leu Arg Cys Thr Val Asn Gly Trp Glu Pro Glu Val Pro
    370             375             380

Cys Leu Arg Gln Cys Ile Phe His Tyr Val Glu Tyr Gly Glu Ser Leu
385             390             395             400

Tyr Trp Gln Arg Arg Tyr Ile Glu Gly Gln Ser Ala Lys Val Gln Cys
            405             410             415

His Ser Gly Tyr Ser Leu Pro Asn Gly Gln Asp Thr Ile Leu Cys Thr
            420             425             430

Glu Asn Gly Trp Ser Pro Pro Pro Lys Cys Val Arg Ile Lys Thr Cys
            435             440             445

Ser Val Ser Asp Ile Glu Ile Glu Asn Gly Phe Phe Ser Glu Ser Asp
    450             455             460

Tyr Thr Tyr Ala Leu Asn Arg Lys Thr Arg Tyr Arg Cys Lys Gln Gly
465             470             475             480

Tyr Val Thr Asn Thr Gly Glu Ile Ser Gly Ile Ile Thr Cys Leu Gln
            485             490             495

Asp Gly Trp Ser Pro Arg Pro Ser Cys Ile Lys Ser Cys Asp Met Pro
            500             505             510

Val Phe Glu Asn Ala Met Thr Lys Asn Asn Asn Thr Trp Phe Lys Leu
            515             520             525

Asn Asp Lys Leu Asp Tyr Glu Cys His Ile Gly Tyr Glu Asn Glu Tyr
    530             535             540

Lys His Thr Lys Gly Ser Ile Thr Cys Thr Tyr Asp Gly Trp Ser Ser
545             550             555             560

Thr Pro Ser Cys Tyr Glu Arg Glu Cys Ser Ile Pro Leu Leu His Gln
            565             570             575

Asp Leu Val Val Phe Pro Arg Glu Val Lys Tyr Lys Val Gly Asp Ser
            580             585             590

Leu Ser Phe Ser Cys Arg Ser Gly His Arg Val Gly Ala Asp Leu Val
            595             600             605

Gln Cys Tyr His Phe Gly Trp Ser Pro Asn Phe Pro Thr Cys Glu Gly
    610             615             620

Gln Val Lys Ser Cys Asp Gln Pro Leu Glu Ile Pro Asn Gly Glu Ile
625             630             635             640

Lys Gly Thr Lys Lys Val Glu Tyr Ser His Gly Asp Val Val Glu Tyr
            645             650             655

Asp Cys Lys Pro Arg Phe Leu Leu Lys Gly Pro Asn Lys Ile Gln Cys
            660             665             670

Val Asp Gly Lys Trp Thr Thr Leu Pro Ile Cys Val Glu Tyr Glu Arg
            675             680             685

Thr Cys Gly Asp Leu Pro Ala Leu Glu His Gly Ser Val Gln Leu Ser
    690             695             700

Val Pro Pro Tyr His His Gly Asp Ser Val Glu Phe Thr Cys Ala Glu
705             710             715             720

Thr Phe Thr Met Ile Gly His Ala Val Val Phe Cys Ile Ser Gly Arg
            725             730             735

Trp Thr Glu Leu Pro Gln Cys Val Ala Thr Asp Gln Leu Glu Lys Cys
            740             745             750

Lys Ala Pro Lys Ser Thr Gly Ile Asp Ala Ile His Pro Asn Lys Asn
    755             760             765
```

-continued

```
Glu Phe Asn His Asn Phe Ser Val Ser Tyr Arg Cys Arg Gln Lys Gln
770                 775                 780

Glu Tyr Glu His Ser Ile Cys Ile Asn Gly Arg Trp Asp Pro Glu Pro
785                 790                 795                 800

Asn Cys Thr Arg Asn Glu Lys Arg Phe Cys Pro Pro Pro Gln Ile
                805                 810                 815

Pro Asn Ala Gln Val Ile Glu Thr Thr Val Lys Tyr Leu Asp Gly Glu
                820                 825                 830

Lys Val Ser Val Leu Cys Gln Asp Gly Tyr Leu Thr Gln Gly Pro Glu
                835                 840                 845

Glu Met Val Cys Lys His Gly Arg Trp Gln Ser Leu Pro Arg Cys Thr
        850                 855                 860

Glu Lys Ile Pro Cys Ser Gln Pro Pro Lys Ile Glu His Gly Ser Ile
865                 870                 875                 880

Lys Ser Pro Arg Ser Ser Glu Glu Arg Asp Leu Ile Glu Ser Ser Ser
                885                 890                 895

Tyr Glu His Gly Thr Thr Phe Ser Tyr Val Cys Asp Asp Gly Phe Arg
                900                 905                 910

Ile Ser Glu Glu Asn Arg Val Thr Cys Asn Met Gly Lys Trp Ser Ser
                915                 920                 925

Leu Pro Arg Cys Val Gly Ile Pro Cys Gly Pro Pro Pro Ser Ile Pro
        930                 935                 940

Leu Gly Ile Val Ser His Glu Leu Glu Ser Tyr Gln Tyr Gly Glu Glu
945                 950                 955                 960

Val Thr Tyr Asn Cys Ser Glu Gly Phe Gly Ile Asp Gly Pro Ala Phe
                965                 970                 975

Ile Lys Cys Val Gly Gly Gln Trp Ser Glu Pro Pro Lys Cys Ile Lys
                980                 985                 990

Thr Asp Cys Asp Asn Leu Pro Thr  Phe Glu Ile Ala Lys  Pro Thr Glu
                995                 1000                1005

Lys Lys  Lys Lys Ser Tyr Arg  Ser Gly Glu Gln Val  Thr Phe Arg
    1010                1015                1020

Cys Pro  Pro Pro Tyr Arg Met  Asp Gly Ser Asp Ile  Val Thr Cys
    1025                1030                1035

Val Asn  Thr Lys Trp Ile Gly  Gln Pro Val Cys Lys  Asp Asn Ser
    1040                1045                1050

Cys Val  Asn Pro Pro His Val  Pro Asn Ala Thr Ile  Leu Thr Arg
    1055                1060                1065

His Lys  Thr Lys Tyr Pro Ser  Gly Asp Lys Val Arg  Tyr Asp Cys
    1070                1075                1080

Asn Lys  Pro Phe Glu Leu Phe  Gly Glu Val Glu Val  Met Cys Gln
    1085                1090                1095

Asn Gly  Ile Trp Thr Glu Pro  Pro Lys Cys Lys Asp  Ser Thr Gly
    1100                1105                1110

Lys Cys  Gly Pro Pro Pro  Ile Asp Asn Gly Asp  Ile Thr Ser
    1115                1120                1125

Leu Ser  Leu Pro Val Tyr Ala  Pro Leu Ser Ser Val  Glu Tyr Gln
    1130                1135                1140

Cys Gln  Asn Tyr Tyr Leu Leu  Lys Gly Asn Lys Ile  Val Thr Cys
    1145                1150                1155

Arg Asn  Gly Lys Trp Ser Gln  Pro Pro Thr Cys Leu  His Ala Cys
    1160                1165                1170

Val Ile  Pro Glu Asp Ile Met  Glu Lys His Asn Ile  Val Leu Arg
```

```
        1175              1180              1185

Trp Arg  Glu Asn Ala Lys Ile  Tyr Ser Gln Ser Gly  Glu Asn Ile
    1190              1195              1200

Glu Phe  Met Cys Lys Pro Gly  Tyr Arg Lys Phe Arg  Gly Ser Pro
    1205              1210              1215

Pro Phe  Arg Thr Lys Cys Ile  Glu Gly His Ile Asn  Tyr Pro Thr
    1220              1225              1230

Cys Val
    1235

<210> SEQ ID NO 4
<211> LENGTH: 97328
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(96)
<223> OTHER INFORMATION: Exon 1
<220> FEATURE:
<221> NAME/KEY: misc_feature
<222> LOCATION: (18013)..(18198)
<223> OTHER INFORMATION: Exon 2
<220> FEATURE:
<221> NAME/KEY: misc_feature
<222> LOCATION: (18494)..(18599)
<223> OTHER INFORMATION: Exon 3
<220> FEATURE:
<221> NAME/KEY: misc_feature
<222> LOCATION: (21021)..(21097)
<223> OTHER INFORMATION: Exon 4
<220> FEATURE:
<221> NAME/KEY: misc_feature
<222> LOCATION: (23223)..(23414)
<223> OTHER INFORMATION: Exon 5
<220> FEATURE:
<221> NAME/KEY: misc_feature
<222> LOCATION: (23849)..(27569)
<223> OTHER INFORMATION: N = A, T, C, or G
<220> FEATURE:
<221> NAME/KEY: misc_feature
<222> LOCATION: (30174)..(30344)
<223> OTHER INFORMATION: Exon 6
<220> FEATURE:
<221> NAME/KEY: misc_feature
<222> LOCATION: (33877)..(34050)
<223> OTHER INFORMATION: Exon 7
<220> FEATURE:
<221> NAME/KEY: misc_feature
<222> LOCATION: (47893)..(48087)
<223> OTHER INFORMATION: Exon 8
<220> FEATURE:
<221> NAME/KEY: misc_feature
<222> LOCATION: (48451)..(48627)
<223> OTHER INFORMATION: Exon 9
<220> FEATURE:
<221> NAME/KEY: misc_feature
<222> LOCATION: (60128)..(60310)
<223> OTHER INFORMATION: Exon 10
<220> FEATURE:
<221> NAME/KEY: misc_feature
<222> LOCATION: (61423)..(61599)
<223> OTHER INFORMATION: Exon 11
<220> FEATURE:
<221> NAME/KEY: misc_feature
<222> LOCATION: (66870)..(67043)
<223> OTHER INFORMATION: Exon 12
<220> FEATURE:
<221> NAME/KEY: misc_feature
<222> LOCATION: (67758)..(67940)
<223> OTHER INFORMATION: Exon 13
<220> FEATURE:
<221> NAME/KEY: misc_feature
```

-continued

```
<222> LOCATION: (68026)..(68205)
<223> OTHER INFORMATION: Exon 14
<220> FEATURE:
<221> NAME/KEY: misc_feature
<222> LOCATION: (70445)..(70621)
<223> OTHER INFORMATION: Exon 15
<220> FEATURE:
<221> NAME/KEY: misc_feature
<222> LOCATION: (73158)..(73340)
<223> OTHER INFORMATION: Exon 16
<220> FEATURE:
<221> NAME/KEY: misc_feature
<222> LOCATION: (73511)..(73717)
<223> OTHER INFORMATION: Exon 17
<220> FEATURE:
<221> NAME/KEY: misc_feature
<222> LOCATION: (74282)..(74455)
<223> OTHER INFORMATION: Exon 18
<220> FEATURE:
<221> NAME/KEY: misc_feature
<222> LOCATION: (83447)..(83623)
<223> OTHER INFORMATION: Exon 19
<220> FEATURE:
<221> NAME/KEY: misc_feature
<222> LOCATION: (85250)..(85426)
<223> OTHER INFORMATION: Exon 20
<220> FEATURE:
<221> NAME/KEY: misc_feature
<222> LOCATION: (88077)..(88078)
<223> OTHER INFORMATION: N = A, T, C, or G
<220> FEATURE:
<221> NAME/KEY: misc_feature
<222> LOCATION: (93999)..(94181)
<223> OTHER INFORMATION: Exon 21
<220> FEATURE:
<221> NAME/KEY: misc_feature
<222> LOCATION: (96653)..(97328)
<223> OTHER INFORMATION: Exon 22
<220> FEATURE:
<221> NAME/KEY: misc_feature
<222> LOCATION: (96847)..(96849)
<223> OTHER INFORMATION: Stop Codon

<400> SEQUENCE: 4
cctaaactaa ctttcaactt ccctttgggg caagtctgtc tctgctgtaa ccacagttca         60
tagcagagag gaactggatg gtacagcaca tacttcattt gctgataata tttctcatag        120
caattattca aattaagtct agaaaatgtg ggtaattact agtctgtaac tgaatggctt        180
ttggtggtaa gtttaaaaac cgtgaacctt tcacttgact attgtaattg atagttcagc        240
ttgatgtaaa actcaagaca gtgctttaaa catgtttttg caatccataa ttaggcatag        300
acatttaact tgtagttatc aggaaataca ggctcctctt tttctcatga gtgtccctga        360
agtactatat gtaaaactag ttagaaatat ataaatatcc aaagtcaatg aaagcactta        420
cttttttctt taaatgggtg gatcgatttc aggcttattt ctaaaccttc ctaactacat        480
cacttagctg atatttccat ggttttaaaa gtttcgtatg taagacccttc aagtatgaga       540 taaaaagaaa ataaaatttg acatgtaacc tgcattggac ggatctgatt tgtttctggt        600 tttgtttttct gtgaatacgt gtggggcatg tttgtttctg aagccatttt gaagtaggta       660
atgtgactgt cggagttctt tcatgacaat aacagggtct gactttatta ttcacttaaa        720
ttctcccaag actgcttagt ttatccaatg aaagagcttt gctttcccag tttaggaagg        780
gtacctagtt gtgggataaa catttaatca actcttcttt gtgttttgat tgtttaagat        840
agggtgtcac tacacccttg agctcactgt agtcctcttg tcagcagctt cctatgggct        900
gaggttacca gtgagagtga ctgccatgcc tgacttagca cttttttatat aaagtgaatg       960 acataacttt aataacttcc ttaaatgttt ctcttagcca atgcattgta atttgaagct       1020
```

-continued

```
ttgctgtaac cactactcag taaagaatac taaaattatc ctctgactgg atgtttacca     1080
acccacataa gaagagtaga tatggtttct cagttgtatc ttttactaaa attctgaaaa     1140
aaaaatttaa gggtatttta tacttttttga aagagtaaac attttcaatt atatttttta     1200
atgttattcc ttgaatttta gcttaagagt cttgtattca gatgccttat agactaaggc     1260
agtcatttcc ttgtatatga aaatataagt attgctgaaa tgaaatgtga ttatattggc     1320
caggaattct aaagcaatgt tgatattacc aagcataact aaactttta ttttgttaaa     1380 ggcaatgttt tcatcgctta ttttagtgtt ctacttgaat aataatgttt actaagaggt     1440
ttttaaagat atataagatt aaagaaagaa ctattttatg tttagctaac ttttaagtct     1500
taattgatat aaatcgaatt aaggtgtcta cacaattaca aagcagaatt tcaatattaa     1560
aaaggaagtg ccgcgatgtt tgcgtgatac tttaacgcta atgatttaaa aatcctcatt     1620
tatgccatgg atgtcagctg attttttttgt tattgctgga tttgaatttt catcagtatg     1680
tattcaaatg tggtgccagt tcttgctgat gaggtgggca gttacactgt gtccgatact     1740
gtttcacagg gattttcctt tcattcacag atgaaaagag agtttagttt ctaaatcatt     1800
atgtagggta acctcatggt ctccacaaaa tgaatgtaaa cagatgggag aagtttcatg     1860
gattttcagt ggacacagta ctcccacttt agtcttagct tggctggtga cccgtgtcta     1920
tctcaaatgt aaacaattta atcagtctat caacttaaga ggaatttcag cagaagagct     1980
tggatcaatt aaaacaatta tgtatatgct gcaatgtttg ctcctgtttc tattctatta     2040
gatgctggct actaagctga tttaaaaaaa aaaagtttgt gaaatgctct catattaggc     2100
tttctgaaac agggaagaaa agatttcata agtattttct gccctgataa agatcaacat     2160
tcatctaaaa ccaatgttag ctgggccagc aggaacggta aacacaataa tgatcttgct     2220
tggcaaagaa cctggctact tgagttcaat tcatgggccc cacctggtga aaggggggaaa     2280 aaaagcctct acagactgtc ctccagtttc ctcatacagg catggcaact gtatgttaca     2340
cccactcaaa ttaaagaaa ataataacca taacaaaaaa tttaaactcc actattaata     2400
attaaagaat aataaccaaa agaagaacta tgaacccagc ttgtttgcct ccctccctcc     2460
gtgcccctct ctctctctct ctctctctct ctctctctct gccccgcggg gccgccccca     2520 cagccccta tatccacacc cccaagaggg gaggggagaa ggccgggcgc caccaccccc     2580
gccccaccaa acaacccccc agaccggccc tacccacgcg cggacaacca caccacgccg     2640
gcgaacaccc accccccaca gccgaaccaa gcaacacaca ccacaacccg cgaaggggac     2700
ccgtaaccgg ccctctctct ctctctctct ctctctgtcc cccccctctc cttttcccct     2760
tttctacttg ccaagggctt tctcatatct ttttagtgca gtgcttgact gtattcacac     2820
ttctagctgc caagaacagt caatggtgct tcctgcaaaa ccacacgctg atcagaattg     2880
ggtcagattt acaggacaac ctgtaacata agagagttcc ttggttgagc cgtataattt     2940
cagttctggg gaatggatta tacccaagct ttccaagcat tttactctca caattgaata     3000
ttgtatgaaa ttaggccgca gcccaggatt gctgaaatga accaattaaa cctgtgctga     3060
aacaaaacca aataaccact gcgtgctttc tggggagata agtgttttct aatcctggag     3120
gtttaaagga caaaaaggtc ctttcaggct tagagacttt aatcatagaa tggagaattg     3180
gtttaattct ataatgtttt aagtatatga ttttttcaaa cttagtttaa cattgatgtg     3240
gaaaaattga tgttatatac attaattatg agttaataat agttgctttg ggggaaattt     3300
agagaaaagt taattattct tttatgtaaa atgatattat attatgtcaa aaagtcaagt     3360
gattcaatgt aagatatttta tacttttcct taagaaaaag aattaatatg gagtgtgtct     3420
```

-continued

```
tactttttccc ttcactctgt gtccaaagtt gaaagcagct gattctgcag cgttcaccac      3480
atcttaacta taaaccatgt ctacagcttt tcctttggcc ttagccatat tgaatatgaa      3540
ggtttcacat gtcccaagtg actgaatgaa gacggatgca gcaagttgca atacagaagt      3600
gatatgtgcg tcactgtgta tgtattgtca catacagtac tgcatacaca gagttctgtc      3660
agtagtatca ctgctgtcct ttgtcttcaa ttactttagt tcttcgagat agagtccccc      3720
tgtttggccc atgctggtcc ttaaactcct agtcttctgg ccttagcctc cctagtactg      3780
aaattcaata tcaagaatat cttatgcaga ttttctgttg ctttcattca actaaattga      3840
cagcaatagc tggaccttcc ttagaaaaat ggaaaaatat ttaaatatca aaaccttcta      3900
aagaagcaac ctatagttct ctttttctag acagaaaata aaaaaaaatc caaaaagtaa      3960
aggtcaactt taaaacatac atataagtaa tattatatat actgatcatg ttatatttag      4020
aaatatatat gtatatgcat atatgcatat aattatagtt atgaaaataa gtagtcatgg      4080
ggtgaaagaa agtaaaggag ataggtgggc agtattggag agacaagagg aaaggggaaa      4140
tgatgtaatt agattataat ctaaaaaata taaagaaat aagaataaaa aagaaatgga      4200
aattttggtg gtaaactaaa aaataacgtg tggatttaca aagagaaaat acatgtctgc      4260
atgtcttcaa tgctttcatt gacacagaaa accaatttcg gtatcttgct tttatgctcc      4320
tttatcacag caaaaattta taaacatgtc acaggacaaa ccgggacttt taaacctttc      4380
ttgtatttca aattataata aatatttgga tttattgctg cagtctctac tgtgagcata      4440
atgtttactt tctttctttt tttaaaatca taatgttttc aaagccagaa gacatctgaa      4500
aactctgaag ttgactatct ttggtatttc tttggctttc ttgtttggga caaaactgaa      4560
ggaattcaca atgtcaacca aaccacctat tgccattaat agtacctact tgcaaagtcc      4620
taagtttcca ttaaccaaac agcacaaacc gaatccattg cagttgtttc gtttctccca      4680
ttgaggaaaa aaaaacaaca tcctcgtagc ctccctttc tgaaccttga aattggaaca      4740
gtaatctttt tcacacacac catggaggca gtgcatagat agatccccac atttctttaa      4800
ggaaagtggt tggattgaat aatcaggtgt gggacagaga tgtcaacatt gaaattcttc      4860
cttgagtttg aattttgaga agagtctaaa agaggtcagg ttgaaagaac ttgcatcctg      4920
tttgataagg ttcttcacac agtctagcat atttattaag cttctcggtt gtactctccc      4980
aggccccaga ggtcagaggt ccatgtatgc caccttctat cacacttgct taaatccacc      5040
ctagtagatg cacatgagta ttagagatca ttatgtaaac tagacactag ggcactacta      5100
gtttattacc taaattaggc attaatgtca gtggagcaag taacctctat ccctacaaca      5160
catgttttca ggatagaatt atatttccct aaatcatgtt acttggcatt gtgccccaat      5220
tgtcttcagt gtcttctttc atgcaactct taaagtattt gacatgttta tcgtaccaca      5280
aactcaacca acctgttatt tatgtgtaag ggaccacata gttaaattta gtgctattat      5340
gtgtaattta ctgtgaaatt tcactgatag aggatagaac tggaaaatgg taagggacaa      5400
aatagaccaa agacattctg agacaggaag cttcctagga tgaaatgctg taacaggtga      5460
caaagggtgg agaagttgct cgcaggcagg gtgaaggtgg tcagtgaaaa caagccttgc      5520
ttatcatcag cacagtcatg ttctaggaat gtgcatgccc tttgccagga tgctatttaa      5580
aactaaacca tttaagtagt gcaaagcgga attttttctaa ggtaggaact gccacagagt      5640
aaatagtctg cctctttgtc cttagattgc tcaattttga actctctctc cccttccaaa      5700
ttaatccatg tttatttcct gactctgatt gttagtcttt acttcctcct tctctctctc      5760
```

-continued

```
cttccctcac tctctccctc agccctccct ccttcctctc tctctctctc tctctctctc   5820
tctctctctc tccacacaca cacacacaca cacacacaca cacacacaca cacacacaca   5880
cacacacaca ctacctctac ctctcgacat ttaggcagat gctgtccacc aaatcctcaa   5940
acgctcagtt gactgatgtt aactttagct tttctcagag cacaaaacat gaaaaacaga   6000
taaagtaatt gggaaaaaaa atgttacttt tttttttttgg tttaaaatta gaagaaaaaa   6060
aaagtctggt tcagataaag tcaagcaact aaacagaaaa aaattccaac cgtgaaataa   6120
taaaaagaac acacggattt gacagaacac ttttgttttg acattttcac ttagaaagtc   6180
tagtttctca cagagtgtta actggaaatg ggatagatag aggacgatta tagaaacacc   6240
ccttcaaagg ttccgaggga acttttatac ttcgagctaa attcaagtga ctctagactt   6300
caaaaaccgc aacatagaca gatgtgcaaa ctctgtagag aactttcagt gcatgcaaca   6360
ggcattcaac tccaccagac agtggtgctc ttgccactgc ctcctcctcc ttttcctcct   6420
cttttttttc cctcaagttg tctctttctt ttccttttc caagtcttgt cttttaagtt   6480
tcccatttgc cactctcagc tgttggtggc cctattgact atatgggtgt acactgtggg   6540
aaagttccta cagtcttttt tgcgttcgct ctctcctcta ttcacaatcc cttttgaata   6600
acttttaagt actgcgcaat ataatacttt ccaaaaggtt gtcatttagt ggagaggaaa   6660
agaatgaaca gtgtattgaa atattccacat acagtagctc atcttataaa ctattatgac   6720
tcagatttta aaaagttcct aaagcagaaa actgaagttg aaaagatgtg ctgtatacac   6780
aaaatgaatt tttgttcagc tacaaaaaat tatgaaattt ataggaaaaa ttgatgaatt   6840
cagactcaca gggagacaaa ctctgcatgc tctccttcac attttgattc tagtttttaa   6900
tacatatact ttatatatac tgcatatatc tttgtttaat atgacgtgtg tgtgtgtgtg   6960
tgtgtgtgtg tgtgtgtgtg tgtgtgactt atggatagaa gacatggaac tagaagtgga   7020
aaaagaaccg tggaggaagg gaaccatgaa aaacacaagt ggattgacca agacagagga   7080
gggagacagg gtagaaaggt gaagagaaga aaataaaact gtttttacaa gtcataaaaa   7140
aggctggata tggtggcaca ccatagtccc tgtatgaggg aagaaaatac agggcagttc   7200
tctaagttca aggccagctt aatctacaaa gtgaattcga ggacagtcag gcctacacga   7260
aaaactatgt cttggaagaa aaaaatgcct cactataata taatataaaa tataatataa   7320
tacttcatat attaacttaa aaaataacat gaaataataa ttggaatggg aaaatgggtc   7380
aggaacagga gagggtgagg gtgacggtaa ctggatacag atgttctgct gacttagttc   7440
tatgttgttt ctctgagaaa agtcagacaa agctctcaat tcacaatctt ctctctccag   7500
tatgctcaaa ggacaggcat ggagcctcaa gtagataggc tacggatgct gcataggagt   7560
tagtcagaaa gaccaaagag gatgttaaca gaaaaacatc agatatacag aaagaactat   7620
aggttctata aagctgtggg gctcatctcc acacctacaa cttaacttgg cttaagtttc   7680
acaaggatta gtgggaggtt aggaaagaaa aagttttccc ttttatttat ttttgttttg   7740
ttttgttttt gattttttta atttatattt caaatattat cccctttcct ggtttccctt   7800
tcataaaccc cctactttat cattttatcc ccctgcccct tcttctatga gggtgttcag   7860
ccacccaacc acacacacct tcccgcctcc cctctctgac attcccctac actagggggg   7920
tccagccttg gcaggaccca ggggttctcc tttcactggt ggccaacaag gccatcttct   7980
gccacatatg cagctggagc cataggtctg tctgtgcata ctctttggat ggtggtttag   8040
tccctgggag ctctggttgg ttggtattgt tgttttttatg gggttacaaa ccccttcagc   8100
tccttgaatc ctttctctaa ctcctccaat ggggaccccca ttctcagttc aatggttggc   8160
```

-continued

```
tgctagcatc ctctgtattt gtcatgctct ggcagagtct ctcatgagac agctatatta   8220
ggctcctgtc agcatgcact tcttgacctc agcaatattg tcgagtttgg tgtctgtatg   8280
tatatgggct ggatccccag ttgggacagg ttctgaatgg ccatttcttc agactttgct   8340
ccaaattttg tctccctatc tcctcctatg aatgtttttg ttcccccttt caagaagaac   8400
tgaagcatcc gcattttggt cgtctttctt gagtttcatg gtggtctatg gattgtattt   8460
tgggtaagct gggctttggg gttaatattc acttttcagt gagtgcatac caggtgtgtg   8520
tgtgtgtgtg tgtgtgtgtg tgtgtgtgtg tgtgtgtgtg tatgtgtgtg tgtggttggg   8580
ttacctcact caggatgata ttttctagtt ccatccattt acctatgaat gtcatgaagt   8640
cattgttttc ccttgttcta atccttatcc tcggcatccc actgatacct ctcatccact   8700
ccagtactgg agctgctaaa acattcagcc ttagttactc catcttgtgg ctaaactgct   8760
ttgtgaggca gccgttcaag cctaatgaaa ccgttcaatg tatgctaaca gtttatttta   8820
aaaagacaat attgaacctg gacccttctt ggtgttagga gactcttgtg taaatgctgc   8880
ctttttcaga aattgacttc aagctgactc ctcaggaggc aaaaattcca actactctgg   8940
tcgatttcac tcaggtttag ccatatacct gcctattatg atctaggtgc ttctcgaggg   9000
tattagtttt ataaagaaaa tttataatta tttctgtatg ttttagaaat agaaatttat   9060
tttccaatgt tcattaaata taaccaaaac ttaaattttt gtagtttgtt ttttaaagta   9120
ctttattgca atttatattt actttgttca aaaaaattca acctaaatat tcttgcacta   9180
tttataaatt aatctaaata ttttttagtaa acaaaatact ctttggatca tatacatgca   9240
taaacttaat actcatttat atcaataaga aagcagatga gaaatttaat gaaactaaca   9300
ttcttgctct tcccacttta ttcttttact tttttctgag taatgtgtat actccaccat   9360
ctgctaataa atatattttt aaaatgatgc ctctcattct ttttccaaaa tccttgtaga   9420
agctatagga agagaaaaaa agatgacctc tccatcttta gtctttcaaa agtgtgggta   9480
caactgatgt tttacaaaat ataaaaattc attaagactt acttcattgc agcaagaaca   9540
tttcaaagaa caattctgag acatattggc attcggaaaa ggaattgcac ttggtttgtc   9600
agtcctaatt ctttaaaatc tgtatatgaa aaactggtaa tcatgattat taaaacagca   9660
aatatttgct ttaaagttcc atcgattata gttatcttcc tcaagtttaa gtaaaactct   9720
tgttttcaga ttatcaaacc tacacagtca ttctgtttct ggaaaacatt caagagtggc   9780
atttgcatct aagtaaatag gaaattaaca aagaaaattc ttaaaaagca aaatcaacta   9840
tttaattagg attggaccag gtttcatttg ttggaatctg agtaaatatt taggtacaag   9900
aaaagtgagt ttactcattc acctggacat agaagctgtc aacttccccg tgtcttaaaa   9960
gtcttaagtt gaatcacccg tctgaaaatg tgttcatcct ttcgaaagca cttctctact   10020
ccctatgtaa gaaccacctg ccctgctttc attaacaact tctcatttat ttcaagcaaa   10080
tgtgtttggt gtttggtgta catttaggtt gacagatgga gaacatgaat gagcagaact   10140
tgttcctgtc tagttagaac gcctggacgg ctactttcag tggaacgtga aaaaatgttt   10200
gccaccctca agacacactt aactgttatt gtcgaaatac agtgaacgat tactttaact   10260
atttaagcca gaacacgagt tatggataca cattatgttg agactctaaa caaagacaaa   10320
cagcaactga aaacagaggg attgtttatt ttcccgagag caacaatttt ttttttttc   10380 cgaagaccct ggttttggcg gtggcagtgg tggggtatta gcgccaccta gtgtggagaa   10440
gtttaactac tgaaatgatg atcaaactaa agctcaaaaa actagcgaaa gactcaaagg   10500
```

-continued

```
aaacccgaca gcctaaacaa ttgctctatt cttctataaa acatagcagt cctttttattt   10560 cacatgctgt gtaccatctt gtagatggaa gttccaggtg aaatatacgc agtagggtga   10620
tccattgctt tttaaaagag tagaaaagat tagtaaagta gagcgaattg tcataaaatc   10680
aagaagtaaa agacatgggc aatttgaaca gtatttttag aaataaaatg aataatgagc   10740
ctagaacctg ccatctaaga agcaccatgc tgggtttttac taacaaccat ttaaatatca   10800
gggtatttgt tacaaagtta agcagcaggc aatattaaat gtgattctat gccttagcac   10860
taatgttcca tggtcacaat tccagcgcct gggagtttaa ggcaggagga ctatgagatg   10920
gagaccaacc tggtctacaa agattttgtc tcaaaaacaa taaataggca aagggaagga   10980
tacacggaag gataggtgca caactactgt agtaaaatgt tgattgttgg acctgcgtgt   11040
tagcgtcatt ggtttttac tgtaaaatca aactttcaaa tacattttga attttctgta   11100
aaaaaaaatg ttaagcgaaa ttcttctctg ataaaactta agaacacagc tcaggatctc   11160
caatttactt cctatgccca aacttaagta ctagttgaaa aacgcgagcc ccaaacttaa   11220
gtccagttca aaaacacgag ccctgttgtc tgcacactta tcttctgctt ctgccacttt   11280
cagaaatctt gaaaaagtta gtagatattt gaatttccat gtctttacat aacaaaaaga   11340
agacaatgaa aataaataaa gaaatacaat caagaaacac aaactcccca caaacatttt   11400
ctccctattc ttttaattat ttgggaatct catatcatac atatctacaa ttgcactcat   11460
ctcctcttct cacatttgcc cccttacctg tgagctccct cacccacaac cccgagagag   11520
agagagagag agagagagag aggagggaag agcgaaggaa gagaagagag agggaaggga   11580
agagagaggg aagggaagag agagggaagg gaaaagggaa gtgaagggaa aagggaaagg   11640
actagccaag gcaagtattc actgaatcac ggtcaaattc ctagtggcca agagaggttt   11700 ttttttttt tcctctgccc gcatccttgg ttgccagaag ccaggagctg aggcaagcca   11760
tgtagtagct ggagcagggt aaatctagca atcccaagca catgtccctg cctgtactgc   11820
agtgctgtgg gccagtgaag gacagggcca gttctctcag acccatggac atagatagcg   11880
tggcttcagg caacagcaga catcaacgtg gtccatggcc atatcaggac cactgaccaa   11940
ctaatggccc tcaggggatg aatgcatgga ccacgagcct ccacatggtc ttacgccaca   12000
tcagcatgcc ccccatctcc cgaccccgag gcagcaaagc cagacgacat cactaaggta   12060
tcacacagca atatagatct catacgtcca catggatctc aggtttcttt tggggctggt   12120
gcaacagcat agaccacaga caccatgatg gcccttcaag gaggttgatt ccagaaagtg   12180
aacctttcct tgtcttgggc ctccattgtt gctcataact tggggcatct tgaaactgtg   12240
tggcatgttg agggacaggg ggtgggggagt atgggctaca tatgatccaa gatgataagt   12300
tatgccaact ctactgggca atgacagcat gttgagctta gccccatctc acacttgtct   12360
ctagttctgc ttctctctct aggcacacac ctctccatgt gtgcctagtt cacttatgtg   12420
ttcataatag tagtgctggg tggctttagg tcgactcaca gctaccatgt ctcaaccggt   12480
acttgcttcc cattatgtac ataacatata aatatatatt atatgcatat atgcatatat   12540
tgtatactac ttttaatata ttgaaaagta aaaggaatag aacaaatgct aatttatta   12600 actttatata tttaaaatat ataacattgt gttctgggtg atgcttgctt cccgtttac   12660 atacatatat acacatatat atatatacat atatgtgtat atattatata ctatccttag   12720
taaacatatt gaaaagtaaa gggaatagaa tacattttgt taacttttg tatttaaaat   12780 atgtgacaca taccattgaa ttaattatga acatagtata ttactaatta ttattcatcc   12840
ataccacaaa acatagaatt tccagcacct cagaagatct ctgttggttt cttgcatatg   12900
```

-continued

```
gaatgaatta ttttcatagt tataggtaca tatttgctct taattgtttc acctcctata   12960
tgtgcctatg tgatttgtac aacagcacct cagtgcatgg ccactgtcac cctacaccac   13020
tttgtgctgg tcaggaagca cagagacact gctctgaggg tgagaaagca cagactgaga   13080
tgtgggagag ccagagctgg tttggggggtc cccaggcctg tggggcctgc aagaaggcag   13140
ggccccaggt tggggacagc atctagctca gggcttgagg agagggcagc tctggaccag   13200
cagggattgt ccttagcttg gaagaggaag gcttcttagc agttgtggtt gggagtgctg   13260
agaagcctgc tacaggagac ttagctgctg ccctgtagag ctagttacct ggaaagacca   13320
ccttcatgac attccccatg gtggtggtag atgacagaga cagtctgtgt ttacccatat   13380
tgtttattgg ctgttcatta tggaaaatgg atgcataccc acttctcagg gtctgaccta   13440
agattaaata cctttcaacg tctggaatgt ctgggaagga aagcttattg gctaagccct   13500
ccgggcctct aggtacctta ttagcacgga gaattctgtt ctgccttaca tgacctgtca   13560
catttcctta tacggggagt gtggcacaaa ttccaggtac aaaatactca cattttcaat   13620
gatcatttta ttcacttcag ctgattcatt ctttaaactt cccttatctt gaggatcagt   13680
ttcctttaac ctaaagaact ttagtgtaca tttataattg ttaaagtttc tacttcgttt   13740
gagaaagtgt cctattccaa agtaaacaca gaaatctgaa ggttctcatc taacatccac   13800
agtgaaagaa aatatgcaaa ctctcccttt ggagtctggg atagcttatt ccacatgatt   13860
tgtttccaac tccacctgcg aatttcctac ttttccccac tgtgtaaaca gaccatattt   13920
ttgttatcca ttcttcagct gatagacatc ctggctgttt ctacttcctg gatattgttg   13980
gtagagcaac aacgatcatg ggtgaacaga tatctctgtg gtagggtatg gagttctttg   14040
ggagtatgtt tagaagagta gtatagttat attctatggc agacctgttg ctagcttttg   14100
ggagaaactt tactctgatt ttcataatgg ctgcagcagt ttgcactccc atcagctatg   14160
aaaaagttcc ccctttcctc acattccaca ctgatatctc ttgtcattaa tttatttaat   14220
cttattcagg ctgggagaag atgaaatcac agagtagttt taactttat tccccaaatg    14280 gctaatgata ttaaacattt ttaaaagttt ctcaattatt tttatatcat ttccttcatt   14340
gaaaataaat tttgataaaa tataatatat tttgtttata gtttcccctt ctccaactcc   14400
tcccagatcc ctcttcccaa cccacccaaa tctataccat ttctttctct catttgtata   14460
caagcaggcg tctaaagaca aataataata ataaaacaaa attacataaa gtaaaagtca   14520
aacaaacttt ataagaactc tcctgttttt aaaatggctt gttctcattc ttgatgctaa   14580
ggatggcttt tagtagagcc tgagaaagtt gtttggcttt ttgttatcat tgttttttata   14640 aatagatact aggaatttta tgcaatcatt ctgattttga gttgataact ttagtcatat   14700
ttggaaaact ttaaatgttc aggtgtcatt tctgctagtt ctctcatcta cctttgaacc   14760
ttcagataga tgtagcctgc atcttttgct ttctgcacaa aagttggctt ctgcagatag   14820
ttctctttcc accatatttg aacatttcta tctcaatttt cttcaagtgg agtacatttc   14880
tttctgattt cagatgactg cagatcaaac aatataacaa tattatttgt gatattaatt   14940
cataacatta agataacata atttagagcc attttattt tgaactttta aaattatttt    15000
tgtctttttc ttaaagttca ttaaagatga ttgacttagt tatttaaaat atatttttgc   15060
taactaatat ctagatcagt gttgatttta ctgcttattt actcttcatg tctattttcc   15120
tttttgtatt ttattttttta attttgtatt gttattttac ttatttacat ttcaaatgtc   15180
atcccttttc ccagtttccc tctacaaact cctatcccat tcccttcct cctgcttcta    15240
```

-continued

```
tgagggtgct ctcccaccca caaacccact cctgcctcac caccttagca ttcccctaca   15300
ctggggtatt gagtcttcac aggaccaggg gtctcccctc ccactaatgc caaataaggc   15360
ccatcctctc ctacatatgc agctggaacc gtgggtccct ccatgtatac tctttggttg   15420
gtggtttatg ccttgggagc tctggggggt gtggttagtt gatatggttg ttttctatgg   15480
ggttgcatca tgctcagtct gatggttggc tgcaagcatt ggcatcttta ctggacaggc   15540
tctggcaaag cctctcggga gacagttata tcaggctcct ttcagcatga atttcttggc   15600
ttcatcaata ttgtctgggt ttggtgtctg catatggatg gatccccagt tggggcaatc   15660
tctgaatggt ctttccttta gtctctgtgc cacgctttgt cttatgtctt ggaatatcct   15720
ctttgtattt taattttcat aatagttact atattttata gaaaatatag tgactaaagt   15780
ttacgttatg cactcatact aagaagaaca tttatcccaa gactgaaccc ccagagaact   15840
ggatggttgg gggtggaggg gaggataggg aggggaacat ccatagagaa ggggaggagg   15900
aggggttagg gggatgttgg cccggaaact gggaaaggga ataacaattg aaatgtaaat   15960
aagaaatacc caagttaata aagatgaaaa aaaaatgctt ggaaaccatg gggggggggga  16020 ataaacgtct attcttgaac cttaaaaaaa tgaagaacat ttatctttct tacttcaatc   16080
attaatttaa ttaaattgta tctgggctgc aattttagct tgcattagct cacttctggt   16140
ctcaaatatt tcaaagcaaa gaccttctta tgtatgagct tttgcacatg tgtttaagca   16200
caaatctctc ctttctaata gactacaata aatctgtctt ctttcctgct atcttgagac   16260 atgtttata ttagacacta aaagactcaa atattctaat gtgttgatga actcaccagt   16320
tctgtatttt aaggaggact attaatcttg ctgtgacttc tgtgagacta taggaacatc   16380
caggcttcac ttaggaatca ggtaattcca ataagacaac tagattcaga ttctgcatga   16440
ttcagaatgt ttcaggttag acacaccttc aatatacatg tcttatttct aacatcgcta   16500
ccattcttga attcacataa cccgggacca tcaattcaca tacagaacta acacatataa   16560
gaaatactgt agacctcaga tatgaatagt acaggcccat tccacctaga tttagttcat   16620
gaattttcat tgctcttaaa atctgtgcta aggcactctt ataaatacct ccacaccaac   16680
ttttctgcac tccatattta tatagtagga acataactct gttctatctt tttatattat   16740
ttgaatgttg aatgtctcca tatagtttca tgttaactta tatagaccaa ttttaattca   16800
gcaatatggc tgctttagca agggatcaca tacaaagact ttatctatct agaatgccac   16860
acctttaatc cctctgggtg gaaatagaga tatgccctta gtacacacct ttaatcccaa   16920
accatgaaag taaagctagt tgttaaaaaa aaaagcaacc atgtgtggat gtaatgtcaa   16980
attgaggggc aaagtgatga atcagagaaa gattagacag aatgagttag aataggata   17040 tgcccaactc tcacgagaac agacaggaaa aggggatgag atgacttaac agtgcagcag   17100
ggatggagag agagagagag agagagagag agagagagag agagagagag agagagagag   17160
agagagagaa gaggaggagg aggagaagga ggaggaggag gaggagaagg aggaggagga   17220
ggaggaggag gaggaggagg aggagaggag agacgagacg agacgaggag aggagaggag   17280
aggagaggag aggagaggag agaagagaag agaagagaag agaagagaag agaagagaag   17340
agaagagaag agaagagaag agaggagagg agaggagagg agaggacaag agaagagaag   17400
aggagaagtc ctggagcaga gacaggttgt aggttaaggc agaatgagcc agagaatgag   17460
aaggagccaa aagattagaa aaaattgtca gagtttgttt gagatcaagc agaataattc   17520
agtgataact caagagaagt ttgaatcagt tatgttggaa agaagtttgg accagaacgg   17580
ttgagttgag tcagccagcc agagtttcaa aagaactgga aagggtgagc ttattcaaca   17640
```

-continued

```
gtaagcctgc aagagtacaa ttatatctgg tgaatgagtt attttataac cttacttgct   17700
ttatttttat aagtagaaat tattctataa ttcatggcat gagtttagaa aatactgctt   17760
agatttgcta ctaggaaata ttttgagaat agtttatttt atccatagtt ttgtttgttt   17820
gatttttttg tttgttcttt acaacttaga agattgcata gtaaattttc ataaagtcgt   17880
gcacataaat agctggatgg acctgtaatt ggtatgattc aaagaaaaac aacatgcata   17940
ttgtttttga ataggtattt caaatactgg tatgttttta ttacttgtag attgtaaagg   18000
tcctcctcca agagaaaatt cagaaattct ctcaggttcg tggtctgaac aactatattc   18060
agaaggcact caggcaacct acaaatgccg ccctggatac cgaacacttg gtactattgt   18120
aaaagtatgc aagaatggag aatgggtacc ttctaaccca tcaaggatat gtcggagtaa   18180
gtacttcatg tttgtaaaac ttaagaaaat ttcagctttg tactaaatcc tttacattgt   18240
agcaatataa attatattac tactgtaact aaagtgtaat cattttaaaa tgtacttgtc   18300
ctaaaaaaaa aaaaactaaa tatggaagcg tgaagttacc ttcaattata aaacatgttt   18360
ttatattttc agtttctctt ctattcaatg atatccaaat gtgctttcct gacttctaca   18420
aaaggtgtat ttcatggacc atacactaat attatcttct tttattttta gaaaggccat   18480
gtgggcatcc cggagacaca ccctttgggt cctttaggct ggcagttgga tctgaatttg   18540
aatttggtgc aaaggttgtt tatacatgtg atgaagggta tgttgttaat attaaaaggc   18600
ttatccttga aaccatgtag gaacgctaca aatttgtact ttagcaagaa taaattttct   18660
attaacatct aaaatgtaat acagaaataa aactacgtca tgaatgcttt taattggata   18720
tcatgtgatc tccataacac tggaaagtaa gcaatttatg gctgttctga catagtgttg   18780
aaataagggt gtattaagtt gctatacact taatacacaa aaattaagca ttcaactcac   18840
aagtccttag tacattccac tattgtacaa tatcgtatga gatgggatag ttttttttt   18900 tttatattag ggacaatgag aattgtgaaa acaactacat tatatggtaa ccctcttaaa   18960
gagattttat agtattcaaa gaaagcaaaa cttttatgtg tgaaaaattc tttctcttga   19020
atgctatttt taaagttgta tgcaaattac tcttattcca taggtgcgaa aggctaattt   19080
ttcagaatca ttgacttccc tctctgcaca gccactggtt cgtcattcac tccacagttc   19140
ttcatttcct atcatacaag aaagttagag ttgtaacatt attccaaata attataaaga   19200
aaagtaaaca ctttgaatgg aatctttta gttgccttt atttcctaac ttgagacagt   19260
gaactataac ggtttattct attcaagttt tagaattagc tccaaaatat ccctatgctc   19320
aaatgctcaa tgtttgtaac atcttactcc gatcccctct cttacagaag cagaaaagtg   19380
cttatgagca tcataggatt agcaggagaa ataaatatga cccacccttg cagcacttca   19440
aaatgatccc agatgaccac aaatacccac tagatgctca tttttttatt taacttctcc   19500
ttgtttcaca acgtgaagga gacttttcaa actacaattt tcaaggtcac tgctgacctt   19560
attatttaaa gccaacaaag atttctttgg cctggatttt tcaggttgtt ccattcttca   19620
cctttgaatt agctcatcct aggccgtaga aactctctca tttctagtcc tataggaaac   19680
accaaatacg actcagcagt tgtgacttca gtaggcaagc agacagcaca cacaaattgg   19740
aagctacaga ctagtccttt tggcaggtca acaccagacc caaaccagca gctgtccaaa   19800
gctgaaggaa ccattgggct taccaaccat cctgacgtaa tactgtggaa tctgcaaatt   19860
gccagaggaa cttcaggaga atttcttaga gaagcttctc agtggcagca tagtgaagaa   19920
tagtgagaca gagtaaacaa aatcaatgct cagtactcgt ctcccactat ctgtgtgatc   19980
```

-continued

```
ataattatac tctgtcgtct agagtccttt catgtgtgtg ccccagcaaa acatcatttg    20040
acataactta ctttccaaac cgactagaag tttccacttc acttatttac ctctgattct    20100
ggctctcttc aagtcactgt tgccaccttg tatttatcaa gtgtaaacac tgatagaacc    20160
catctaggtc aatagctgtg tatattgatt ctgaatcacc aatatcaaat caatcaaatt    20220
actgacaatt atcgcgtaaa gtcctcatac cacgtaggat aaaaataggt aaaaagcagt    20280
tcatattcat tcaaatttct gttgatgaat gttctatcta tcttgggata attgcttttt    20340
ttaaacccag aagtgaaagg taaggatagg agaggcttat ttcaacccta tttttttttac    20400 tcatcctttt tagtcctgtg cttttggcta aattttctct gctaaaaata aacaaatata    20460
aataaatata aatatagggt tttatgtact ttgtagtaga atgactcctt aggaacaata    20520
atgttattgt ccaaaaccat cgtgaatgat tttgagatga cactgcaaac tgattttccc    20580
ccatatggac aaccattttt tttctccttt cccctccctc catgaacaga aatccagtaa    20640
ggttttgtgt agaattttat agattgtctg aaggaactta gtgtgatgga tggatctctg    20700
cagtgaataa aaagtcttta ccaggagctt catttctttt ctactggaaa agaaattatt    20760
ctgtctcctc tacagcaagc atcaaggaaa cacttaagtc caatatccaa aactaacata    20820
ttctattgaa gtattttatt tccacaaaga tttaatagag agatgaaaat aataaaagaa    20880
tgagaaatat ttttcccttc caaatctctt actggaggat atccaagact gcacagagct    20940
tcaaactaca caaaaacaca tgatgtctca acacaaatta ttatgcttgc attttttaggt    21000 accaactctt aggtgaaatt gattaccgtg aatgtgatgc agatgggtgg accaatgata    21060
ttccaatatg tgaaggtaaa tgaaaaacag atttgtatgt atgcctaaag atctaaaata    21120
gataagattt cccaagctgt gtagaaaaat attcttaaag tatatactta agtatttcat    21180
atatttatgt gtgtgtgtgt gtgtgtgtgt gtgtgtatat atatatataa ttttatataa    21240
cttcaattct cttttttacag tccagtcatt atcccccctcc cagtctgccc tcatcccagt    21300
cccccacccc atcttaaaga ggatgtcctc atccccttca tccctgcccc accagacctt    21360
cctactccct ggggcttcaa gtctcttcag gattaggtgc ttttttctca ctgaggccag    21420
atcaggcagt tctctgctac atatgtgttg ggaatctcat attcgctggt gtatgctgcc    21480
tggttggtgg cttgtctgag agttctcgag agggtccaga ttagtctggt cttcctatga    21540
ggttgtcctc ctcagcttct ttcagttttt ccctaattca accacctgcg tctgactctt    21600
tcagctgttt tttgggccta tcagagggca gccatgttag gctcctgttc ttaagtacac    21660
catagcattg ataatagtgt caggccttag agcctcccct cgagatggat cccaatttgg    21720
gatgattact gagcctcctt tccctccctc agtctcttct ccattttttgt ctctgtagtt    21780 cttatttata tcttttagtt tctagtataa aacataagta ctttgttata gtactatttt    21840
gtatttgtat caatattctg agaacactaa gtctagagaa tggtgaattt ctcaggacta    21900
ctgtagattc cttgaggtct taggcttgac acacattctc atcaatataa cttaaaacta    21960
tctaaaacat aatagatata aatagagatt gatatacttt tatgatcaaa gttctgaata    22020
ttagaaatac caaagccatt ttttccattt tacatttcaa acactaacaa tacataagac    22080
catcactagc ctataaaaaa agaccagaat ttgaggtatg tttgtgaaga atgacacccc    22140
taataacatc tagctagtta caggtgtgta ggctatcaca tccatacatt cctggtagag    22200
aatgttattg aaatacccttt cacaattatg atgctgtgaa ggttttatcc atagtcttaa    22260
ttttagaaaa aaaaggggggg gagggaagca agaattacaa aagaactctt gcctttcaat    22320
tcttgctcac atgctgctta taggtagagc aaacagcaag aatgagaaaa tgcaggtctt    22380
```

-continued

```
gtttgtaagt ttggcgatag catgtaaata acaaaggtcc atccaaatgc tgtatcctac    22440
ttccatggga agcaataaat tagagaaaga agtggagtgg aaggagagag ggatggagaa    22500
tgagaaggca cagtaagttc tcctaatgag acttttctag taaggaaatg agaagatgtt    22560
cccggaacgt ctgcatcaga atttacatgg tgcttgttta aaattgatgt ttgaggcccc    22620
tgaatggcct gttgagaaag tatctttgag tgagaagagc agaaaacctc actagcatat    22680
ccattacatc caaagtttcc ttcagaaaag caacttcaaa tttcttcatg gcggagaaat    22740
tctaaattaa aaaaaaagtt taaaattttt gagcaatgag gtgaaaagga aggaaacatt    22800
acaaaaagtt tttttcccct atgagaagaa atatcttcaa aattcattga tttaaacctt    22860
attagaatgc aatatcacgt tgctttgaag aataaataat acatttgtat tagactattc    22920
caaaatctca tatgtgttca ccatttagga gacacttgct atcacgaaga tgtaaactgt    22980
cactctaagt aatagttttc ttttcccatt cccatagaag ctgataagcg aactacccga    23040
gctacttaga tgttgtgcaa acagtgatgc tgaatgtttc tcaaaccttt aagtcctttc    23100
cggcaggttg agcaggctgc gtggtgtttt cattcatata cgtgtgtttt atgtggaagc    23160
tggtaaggtc tgttagtaaa agcgatgcct gtattttcag ttgtgaagtg cttgccagtg    23220
acagaactgg agaatggaag aattgtgagt ggtgcagccg aaccagacca ggaatattat    23280
tttggacagg tggtacgctt tgaatgcaac tccggcttca agattgaagg acagaaagaa    23340
atgcactgct cagaaaatgg cctctggagc aatgaaaagc cacagtgtgt gggtaagata    23400
cacagatgtg tctgcttcac atattctagt gaaagtatac atttcttttt taaagtacat    23460
ttttaattat aatagaattg cacaactcgg atgctaatga agtatgactg tttccttgta    23520
actgaagttc tttgcatgaa gccttctatt ttgctttcag aactatatat ttcatgccct    23580
tgtgtagtct ctttaattga aatagccaag gtgtccatgc ttactgtggc ttaatgactt    23640
ggacaagatg taaacacagg tgttgcaatt cagtctagcc tcagcgtctc tggtgagtgt    23700
tgtaaaacta ccttgcagag catatttttt taataaggtt tttggaagct aaaggcttgg    23760
catgtgttta caatcacaca ttatgatgat attttgtttt caatttatag ttaggatgta    23820
tattttttag aaatctattt gctgcaagnn nnnnnnnnnn nnnnnnnnnn nnnnnnnnnn    23880
nnnnnnnnnn nnnnnnnnnn nnnnnnnnnn nnnnnnnnnn nnnnnnnnnn nnnnnnnnnn    23940
nnnnnnnnnn nnnnnnnnnn nnnnnnnnnn nnnnnnnnnn nnnnnnnnnn nnnnnnnnnn    24000
nnnnnnnnnn nnnnnnnnnn nnnnnnnnnn nnnnnnnnnn nnnnnnnnnn nnnnnnnnnn    24060
nnnnnnnnnn nnnnnnnnnn nnnnnnnnnn nnnnnnnnnn nnnnnnnnnn nnnnnnnnnn    24120
nnnnnnnnnn nnnnnnnnnn nnnnnnnnnn nnnnnnnnnn nnnnnnnnnn nnnnnnnnnn    24180
nnnnnnnnnn nnnnnnnnnn nnnnnnnnnn nnnnnnnnnn nnnnnnnnnn nnnnnnnnnn    24240
nnnnnnnnnn nnnnnnnnnn nnnnnnnnnn nnnnnnnnnn nnnnnnnnnn nnnnnnnnnn    24300
nnnnnnnnnn nnnnnnnnnn nnnnnnnnnn nnnnnnnnnn nnnnnnnnnn nnnnnnnnnn    24360
nnnnnnnnnn nnnnnnnnnn nnnnnnnnnn nnnnnnnnnn nnnnnnnnnn nnnnnnnnnn    24420
nnnnnnnnnn nnnnnnnnnn nnnnnnnnnn nnnnnnnnnn nnnnnnnnnn nnnnnnnnnn    24480
nnnnnnnnnn nnnnnnnnnn nnnnnnnnnn nnnnnnnnnn nnnnnnnnnn nnnnnnnnnn    24540
nnnnnnnnnn nnnnnnnnnn nnnnnnnnnn nnnnnnnnnn nnnnnnnnnn nnnnnnnnnn    24600
nnnnnnnnnn nnnnnnnnnn nnnnnnnnnn nnnnnnnnnn nnnnnnnnnn nnnnnnnnnn    24660
nnnnnnnnnn nnnnnnnnnn nnnnnnnnnn nnnnnnnnnn nnnnnnnnnn nnnnnnnnnn    24720
```

-continued

```
nnnnnnnnnn nnnnnnnnnn nnnnnnnnnn nnnnnnnnnn nnnnnnnnnn nnnnnnnnnn    24780
nnnnnnnnnn nnnnnnnnnn nnnnnnnnnn nnnnnnnnnn nnnnnnnnnn nnnnnnnnnn    24840
nnnnnnnnnn nnnnnnnnnn nnnnnnnnnn nnnnnnnnnn nnnnnnnnnn nnnnnnnnnn    24900
nnnnnnnnnn nnnnnnnnnn nnnnnnnnnn nnnnnnnnnn nnnnnnnnnn nnnnnnnnnn    24960
nnnnnnnnnn nnnnnnnnnn nnnnnnnnnn nnnnnnnnnn nnnnnnnnnn nnnnnnnnnn    25020
nnnnnnnnnn nnnnnnnnnn nnnnnnnnnn nnnnnnnnnn nnnnnnnnnn nnnnnnnnnn    25080
nnnnnnnnnn nnnnnnnnnn nnnnnnnnnn nnnnnnnnnn nnnnnnnnnn nnnnnnnnnn    25140
nnnnnnnnnn nnnnnnnnnn nnnnnnnnnn nnnnnnnnnn nnnnnnnnnn nnnnnnnnnn    25200
nnnnnnnnnn nnnnnnnnnn nnnnnnnnnn nnnnnnnnnn nnnnnnnnnn nnnnnnnnnn    25260
nnnnnnnnnn nnnnnnnnnn nnnnnnnnnn nnnnnnnnnn nnnnnnnnnn nnnnnnnnnn    25320
nnnnnnnnnn nnnnnnnnnn nnnnnnnnnn nnnnnnnnnn nnnnnnnnnn nnnnnnnnnn    25380
nnnnnnnnnn nnnnnnnnnn nnnnnnnnnn nnnnnnnnnn nnnnnnnnnn nnnnnnnnnn    25440
nnnnnnnnnn nnnnnnnnnn nnnnnnnnnn nnnnnnnnnn nnnnnnnnnn nnnnnnnnnn    25500
nnnnnnnnnn nnnnnnnnnn nnnnnnnnnn nnnnnnnnnn nnnnnnnnnn nnnnnnnnnn    25560
nnnnnnnnnn nnnnnnnnnn nnnnnnnnnn nnnnnnnnnn nnnnnnnnnn nnnnnnnnnn    25620
nnnnnnnnnn nnnnnnnnnn nnnnnnnnnn nnnnnnnnnn nnnnnnnnnn nnnnnnnnnn    25680
nnnnnnnnnn nnnnnnnnnn nnnnnnnnnn nnnnnnnnnn nnnnnnnnnn nnnnnnnnnn    25740
nnnnnnnnnn nnnnnnnnnn nnnnnnnnnn nnnnnnnnnn nnnnnnnnnn nnnnnnnnnn    25800
nnnnnnnnnn nnnnnnnnnn nnnnnnnnnn nnnnnnnnnn nnnnnnnnnn nnnnnnnnnn    25860
nnnnnnnnnn nnnnnnnnnn nnnnnnnnnn nnnnnnnnnn nnnnnnnnnn nnnnnnnnnn    25920
nnnnnnnnnn nnnnnnnnnn nnnnnnnnnn nnnnnnnnnn nnnnnnnnnn nnnnnnnnnn    25980
nnnnnnnnnn nnnnnnnnnn nnnnnnnnnn nnnnnnnnnn nnnnnnnnnn nnnnnnnnnn    26040
nnnnnnnnnn nnnnnnnnnn nnnnnnnnnn nnnnnnnnnn nnnnnnnnnn nnnnnnnnnn    26100
nnnnnnnnnn nnnnnnnnnn nnnnnnnnnn nnnnnnnnnn nnnnnnnnnn nnnnnnnnnn    26160
nnnnnnnnnn nnnnnnnnnn nnnnnnnnnn nnnnnnnnnn nnnnnnnnnn nnnnnnnnnn    26220
nnnnnnnnnn nnnnnnnnnn nnnnnnnnnn nnnnnnnnnn nnnnnnnnnn nnnnnnnnnn    26280
nnnnnnnnnn nnnnnnnnnn nnnnnnnnnn nnnnnnnnnn nnnnnnnnnn nnnnnnnnnn    26340
nnnnnnnnnn nnnnnnnnnn nnnnnnnnnn nnnnnnnnnn nnnnnnnnnn nnnnnnnnnn    26400
nnnnnnnnnn nnnnnnnnnn nnnnnnnnnn nnnnnnnnnn nnnnnnnnnn nnnnnnnnnn    26460
nnnnnnnnnn nnnnnnnnnn nnnnnnnnnn nnnnnnnnnn nnnnnnnnnn nnnnnnnnnn    26520
nnnnnnnnnn nnnnnnnnnn nnnnnnnnnn nnnnnnnnnn nnnnnnnnnn nnnnnnnnnn    26580
nnnnnnnnnn nnnnnnnnnn nnnnnnnnnn nnnnnnnnnn nnnnnnnnnn nnnnnnnnnn    26640
nnnnnnnnnn nnnnnnnnnn nnnnnnnnnn nnnnnnnnnn nnnnnnnnnn nnnnnnnnnn    26700
nnnnnnnnnn nnnnnnnnnn nnnnnnnnnn nnnnnnnnnn nnnnnnnnnn nnnnnnnnnn    26760
nnnnnnnnnn nnnnnnnnnn nnnnnnnnnn nnnnnnnnnn nnnnnnnnnn nnnnnnnnnn    26820
nnnnnnnnnn nnnnnnnnnn nnnnnnnnnn nnnnnnnnnn nnnnnnnnnn nnnnnnnnnn    26880
nnnnnnnnnn nnnnnnnnnn nnnnnnnnnn nnnnnnnnnn nnnnnnnnnn nnnnnnnnnn    26940
nnnnnnnnnn nnnnnnnnnn nnnnnnnnnn nnnnnnnnnn nnnnnnnnnn nnnnnnnnnn    27000
nnnnnnnnnn nnnnnnnnnn nnnnnnnnnn nnnnnnnnnn nnnnnnnnnn nnnnnnnnnn    27060
nnnnnnnnnn nnnnnnnnnn nnnnnnnnnn nnnnnnnnnn nnnnnnnnnn nnnnnnnnnn    27120
```

-continued

```
nnnnnnnnnn nnnnnnnnnn nnnnnnnnnn nnnnnnnnnn nnnnnnnnnn nnnnnnnnnn   27180
nnnnnnnnnn nnnnnnnnnn nnnnnnnnnn nnnnnnnnnn nnnnnnnnnn nnnnnnnnnn   27240
nnnnnnnnnn nnnnnnnnnn nnnnnnnnnn nnnnnnnnnn nnnnnnnnnn nnnnnnnnnn   27300
nnnnnnnnnn nnnnnnnnnn nnnnnnnnnn nnnnnnnnnn nnnnnnnnnn nnnnnnnnnn   27360
nnnnnnnnnn nnnnnnnnnn nnnnnnnnnn nnnnnnnnnn nnnnnnnnnn nnnnnnnnnn   27420
nnnnnnnnnn nnnnnnnnnn nnnnnnnnnn nnnnnnnnnn nnnnnnnnnn nnnnnnnnnn   27480
nnnnnnnnnn nnnnnnnnnn nnnnnnnnnn nnnnnnnnnn nnnnnnnnnn nnnnnnnnnn   27540
nnnnnnnnnn nnnnnnnnnn nnnnnnnnng tggcaggggt cctgccgctc ctgggccctc   27600
ccccacggga gcccagaggc cttatacagt ttcctcttgg gccagggatg tgggcagggg   27660
tgagcagtgt tggtggtctc ttccgctctg cagcctcagg agtgcccacc tgaccaggcg   27720
gttgggtctc tttctcaccg ggtctgggag cagagagctg ctgcgggccg ggatctgctg   27780
caagttttaa tttttttttt ttttgattct ttttttttcgg agctggggac cgaacccagg   27840
gccttgcgct tcctaggtaa gcgctctacc actgagctaa atccccagcc ccgcaagttt   27900
taatttttaa gacattctaa ttttttattaa tattgttagg ataaaatata tacatataca   27960
tatatcatac aacacacaca gacatacaca catatgtatt gcatgtttac aatcagtttt   28020
aggtatctta attgaatcca ctaagccttt gaattttgac aaactgatat aatatattgt   28080
tacttaatat ttcttttctt tcctcctcct cctcctcctc ttcctcttct tcatcttctt   28140
catcttcttc ttcttcccct tcttcttctt cttcttcttc ttcttcttct tcttcttctt   28200
cttcttcttc ttcttcttct tcttcttctt cttcttcttc tagacagcct ttcataatgt   28260
aatcatggcc ggcctgaacc tgatatgtag tccatatagc ttctaccttg cagcaggctc   28320
cttagagttc cgacaagagt tttgaaattg cctgcatgtg gcactggtct tatactatat   28380
ttatttttca atattatcta acacctccat tattttcacc attccttagt attgtccacc   28440
ttagactaaa gaagacagtg ttttcttctt ttcaaattta gtttgctttt gagattataa   28500
ctacatcatt tctttcctca aggattgact agttgctgct aacaactcta acagcactga   28560
ttcatcatga gaataatgat ataccaatat gtatagtcaa tgtggcatat atttgacata   28620
ttgaagttta atggctgata tcttttggac tttaactaat tgtctattgc taatgaaacc   28680
taggaaattc tgatccttga gattattttt aaagtgcaca taaggtatat tcaggtgaaa   28740
ataaagaaga caagcatagc agcccccaga aggccatgtg gagaaagata aaaaaaaaaa   28800
aaaaccagca aagtatctac agcaagatgt gggcctgagg gtcttctgtg cagctcagtt   28860
caaccaaaag tatatcacag cagttactac tgtttatgta tgcattcgga agacgggagg   28920
gacctagtca atatggtcaa tttcaaggac ttcctgaagc ttttgaattg tttacttcct   28980
gagcttcctt agaggatggg attttttagt tccctttaga gcaatggttc tcaacctgtg   29040
accccctctg aagtcaaaca aacctttcac atgggttgcc taaaaccatt gtaaaacaca   29100
gatattatta ttaataatag ttgcaaaatt acagttatga aatagcaaca aaaataattt   29160
tatggttatg ggatcgccac acaagaggaa tggtattaaa ggaccaaagc attagggagg   29220
ttgaaaacca ttgctttatc tcatcctatt tttatgggtg cttctctctg agacggagtc   29280
ttttatctta aagaaaattg ctattcaaca attgaagaga ggtattaggt cagtaagagt   29340
atggtatggt cataggccag cacaattcct gcatatgctt gtcataaata actcacctct   29400
tcttcagatt gactgggaaa agacaaaaca tttcaaagtg atctttttaaa agtttccttc   29460
```

-continued

```
gttataaaga aggaaaaatg gattaaaagg atggaagaaa atgctttgaa agaccagtta   29520
ctactgccat agtcttagag tagtgtattt gagagaactg tgttaaatgt ggttgctagg   29580
acttttgaag gtttttttct cccgtttttg tttttgcctt ttgtttttat ggtttgcttg   29640
ttttgttatt tgtgtgtgtg tgtgtgtgtg tgtgtgtgtg tgtgtgtgtg tgtgtgtgtt   29700
gtgtgtttgt gtgtatggag aaggcaccat gacttttcaa agataaaatg aaaagtgaat   29760
ctaatggatt tccttgaaaa gctgtcttga aaattactgt cagtaatcca aagttgtatt   29820
attttgaaga ttattcaatg aaaatattaa tctacaacca cgtgtctatt tttattttca   29880
caagagtctg agattgttac tggctgtcgt ttatttcaat ttgtcatcat gttcaatata   29940
attaatcata tactttttaat ttcttccaaa aatgaaaatt tgaaatgaca gatatatgat   30000
caagagggca gtcaggccaa aacaatgttt gtttggtcac tgattttgac tgattgacct   30060
aatgggaaca aaacactgtc attataaaag tatgttactc agcagatttc ctcttatagt   30120
aaacactata caattactct tttgcattta gaaatttctt gcctgccacc acgagttgaa   30180
aatggagatg gtatatatct gaaaccagtt tacaaggaga atgaaagatt ccaatataaa   30240
tgtaagcaag gtttttgtgta caaagaaaga ggggatgctg tctgcacggg ttctggatgg   30300
aatcctcagc cttcctgtga aggtgacatt attcttatttt tctacgtctt ttattatata   30360
agaagtagaa cagtgaatgg aaaagaaaga tggtgtcaca aatccatgtt tagctgattg   30420
cattgagtct aaccatctgt tttcatggtg tttatgtatc ctagtcagag aagtatctca   30480
gtagtccttt ggcattaaac ctctgcacaa gattaactcc aggtgtcctc ctaaatagac   30540
catttatcca ctaaaggatc aaactataac ccatgatgta gctattttgt attgtcttgt   30600
gcttaagagg aacttttcaa acaatcattc cagtttcagg tgaatccagt tttccatgga   30660
agcattagga ttcaatagaa tagtcatgcc acaccaaata acagagcaga gcagaatgcc   30720
tgttctgtac tgaattcacc taaagctgaa atgattttta cctagttaaa atctcttcct   30780
taacctagat ttgtttttcaa actgagaaat atatttggtt ccctaaatgt gcttctacag   30840
atgctacata gccttgcttc tttttgaaccc taggaaagag gagaggagtg tgagtagagg   30900
gagagaatag aggaagggaa gaaaggaagc agggaatgaa aaagactctc cattaaagtt   30960
cattttgacc atttctcaaa cacaaagtca agtatgaaaa gtatagttct gtgttcttgg   31020
gggtcttttt cttcagggaa ataggtgaca gagggtactc tcatctgata gtaaataagc   31080
atttgatgat atgaataaag agacctgcat cttaactcat ataggcatgc aaatctctaa   31140
caatggactt cattttactg aagaaaactt tatactccta tatgaaaagt agtttcttat   31200
taatgaaaat agtgcatcac tctgtacctc agctgatatg tttggccaat gcattgtctt   31260
tgttttcctg gagcagaaaa atagcttact tgtgttgatg tacaattatc tggaaattat   31320
cagaacactt taatctctct gacaccatat agtggaatac attatttgct gcagctgact   31380
ttacaagaat cttagactct ataagacacc aaaattaaaa taagataata taaaaataaa   31440
taaactttgt tccacctgat cataatgtga acagggggtt taaaacaact tcccagagca   31500
tttggatctc tagtatatag tagacagtct ctaatgacaa gcaggaatga tgaaaaatac   31560
cacaatcttc tgaacaattt attttgatgc atctgtttcc tgtacagagt agattttgta   31620
aaattgactt tccaatgtaa gagaactaaa cttgaaatat cccattccaa atgtctctac   31680
taaataattt gaaataagaa aactgtacat ttgggaaaat gtacaaggga aaaaagacac   31740
tatgcatttg aaaaattaac tacatatagt caatcagaca ttatcagggg tttatgttgg   31800
cagcttaggg taatctccaa aagtcttttt gttaataagt tttacaaagt tcttcccata   31860
```

-continued

```
ctgtttgctt gtcctcttaa attcttggac atattgttgt tgtttgatat cttatagctg   31920
taccttaaaa agatactgag taaagctgca atattaagaa aacctaagta gaaaagcata   31980
aactacaatg gtcctatgaa aacatgacaa gcagagtgct gtgaagagaa aaacgatcaa   32040
aggaacacaa tgttgattca aaaattgttg ttaagtggca taaaagttag gagacatact   32100
tgatttgagt agttatctta gggtgaagag acaccatgac caaaggaata tttaattagg   32160
gctggcttac aagttcagag gttcagtata ctatcgtcaa gggggaaagc ttggcagcat   32220
ccaagcaagc atggctttga agaaggtact gagagttcta catcttgatc caaaggcagt   32280
caggagaaga ctggcaaagc ccaccctaac agttatacat ttccttcaac aaggccacac   32340
ctattccatc aaggacacac ttcctaatag tgtcactccc tggtccaagt atattcaaac   32400
catgacagta gtcagatatt actttagcta agtttttact actatatatg tatattacct   32460
gtcttcatga gggaccccag caactgaagc aaggactgtc gctgactttg ttgcctgtct   32520
gtggatccta tcccccttga ctgggctgcc ttgtctggcc tcagtgagag aggatgtgcc   32580
tagttttaca gtgacttgat ataccagaat gggctggtaa ccaggggcc ctcccctttt   32640 cagaggagaa ggggtagaag ggatggggca aggggctata tgtggagaga ctgaaaggaa   32700
agtagagggc ttcaataggg ataaaattta taaaaaaaag aaatacatat atactgtggc   32760
acaaatttaa taccagtaga aaggttactg ccatactttc aagggctaag tgtacacatt   32820
agcattatat atggaaaggc aaaaattcaa ataacactta aaaccaaaga attatgtgcc   32880
agattgagta taagaatgat gaataaatct ccagactctt atcataatat ttttgtttta   32940
taagttaaaa tattagattt agatggaaaa gtatgaatgg aggaaagtta atgatagaga   33000
ttgccatttt aaaaactgga ttgccttcaa attctgtata tgagcatgat tcatttacct   33060
atatggattt tgattaaaac tacagaatta ttagcataag agccagactt taattatgga   33120
ggttatcttg agtgccataa aggacagaag aaaaaagaac actagtgaag aatacatgct   33180
cataaaaacc aactataagg caaaaaagtt atttgtgcag aaactgtagc tacttaaaaa   33240
taatttttta aatgtagcaa tggtatcaat tagaagatct gggttaagat gatttaaggc   33300
acataagaca taaaatgtac atttgagaaa tggcttggtg tttgtgaagg ttagattcat   33360
gattttgaaa gtcaaaaatt acactatgtt tcttccttgt tcagtagatt ttcccaaata   33420
agtcagagga catgttcaat tcaaagagaa agaggtgtaa aatcttcatg aatatttaga   33480
attaaggacc tgtgaatatt aataaatagg ctcaaatgag aatcaaggcc agcaatttca   33540
atgaaagaaa tagaaactgg atggaaacat gtttcttgca ctgaaggtct gtatgatgaa   33600
gttattatca tctttagaag cataaggtac tatatgggac agcatcaaga gagaattagt   33660
accagagagg cacacataca ccaggaggag agagaagaag tctgactgat atgcctagcc   33720
tatgaagatg cattcttttc aatgtctatt atatagttat cagtacaaat aactggtgtc   33780
tgccatttag ttttaatatt cttaacctaa atgagattaa atatttctca ttacttatat   33840
ctgattcttt tcagaaatga catgtttgac tccatatatt ccaaatggta tctacacacc   33900
tcacaggatt aaacacagaa ttgatgatga aatcagatat gaatgtaaaa atggcttcta   33960
tcctgcaacc cgatcacctg tttcaaagtg tacaattact ggctggatcc ctgctccaag   34020
atgtagctgt aagcttcact tatatctta atctccatga tcctgaaatt agactaataa   34080
gcatgcatag aagaaaatat agtaaatagca aatatttaat tttttatcta tgtacaacac   34140
ttaaaaatat tctactttta aaagtcaaga aaaattaaca taatattata ttttaatatt   34200
```

-continued

```
aaaatttaaa attgcaagta atatttaaaa tacattatag aaaactaaaa tttttaattt    34260
acttctactt aaatatatag gcatctgtac attttttttc ttttttttca tttatttttt    34320
ttttattaac ttgagtattt cttatttaca tttcgagtgc tattcccttt cccggtttcc    34380
gggccaacat caccctaacc cctggttgct tggcattgtt gttcataaga ggtctcgagc    34440
cccttcaagc ttgccagttc tttctctgat tccttcaacg ggggtcccgt tctcagttca    34500
gtggtttgct gcaggcattt gcctctgtat ttgctgtatt ctggctgtgt ctctcaggag    34560
agatctatat ccggctcttg tctgcctgca cttctttgct tcttgtctaa ttggatggtt    34620
gtatatgtat gggccacatg tggggcaggc tctgaatggg tgttccttct gtgtctgttt    34680
taatctttgc ctctctattc cctgccaagg gtattcttgt tccccttta aagaaggagt     34740 gaagcattca cattttgatc atccgtcttg agtttcattt gttctaggca tctagggtaa    34800
ttcaagcatt tgggctaata gccacttatc aatgagtgca taccatgtgt gttttctgtg    34860
attgggttac ctcactcagg atgatatttt ccagttccct ccatttgtct atgaatttca    34920
taaagtcatt gttttgata gctgagtaat attccattgt gtagatgtac cacattttct     34980
gtatccattc ctctgttgaa gggcatctgg gttctttcca gcttctggct attataaata    35040
aggctgctat gaacatagtg gagcacgtgt cttttttata tgttggggca tcttttgggt    35100
atatgcccaa gagaggtata gctggatcct caggcagttc aatgtccaat tttctgagga    35160
acctccagat tgatttccag aatggttgta ccagtctgca atcccaccat caatgcagga    35220
gtattcctct ttctccacat ccttgccatc atttgctgtc acctgagttt ttgatcttag    35280
ccattctcac tggagtgagg tgaaatctca gggttgtttt gatttgcatt tcccttatga    35340
ctaaagatgt tgaacatttc tttaggtgtt tctcagccat tcggcattcc tcagctgtga    35400
attctttgtt tagctctgaa ccccattttt taatagggtt atttgtctcc ctgcggtcta    35460
acttcttgag ttctttgtat attttggata taagccctct atctgttgta ggattggtaa    35520
agatcttttc ccaatctgtt ggttgtcgtt ttgtcctaac cacagtgtcc tttgccttac    35580
agaagctttg cagttttatg tgatcccatt ggttgattct tgatcttaga gcataagcca    35640
ttggtgtttt gttcaggaaa tttttttccag tgcgcatgtg ttcgagattc ttcccaactt    35700
tttcttctat taggtttgag tgtatctggt ttgatgtgga ggtccttgat ccacttggac    35760
ttaagcttgt acagagtgat aagcatggat cgatctgcat tcttctacat gttgacctcc    35820
agttgaacca gcaccgtttg ctgaaaaggc tatctttttt ccattggatg gtttttggctc    35880 ctatgtcaaa aattaagtgc ccataggtgt gtgggttcat ttctgggtct tcaattctat    35940
tccattggtc tatctgtctg tctctgtacc aataccatgc tgtttttatc actattgctc    36000
tgtaatactg cttgagttca gggatagtga ttcccctga agtccttta ttgttgagga     36060 tagctttagc tatcctgggt tttttgttat tccagatgaa tttgcaaatt gttctgtcta    36120
actctttgaa gaattggatt ggtattttga tggggattgc attgaatcta tagattgctt    36180
ttggtaaaat ggccgttttt actatattaa tcctgccaac ccatgagcat gggagatctt    36240
tccatcttct gaggtcttct tcaatttctt tcttcagagt cttgaagttc ttattgcaca    36300 gatctttttac ttgtttggtt aaagtcacac tgaggtactt tatattattt gggtctatta    36360
tgaagggtgt catttcccta gtttctttct cggcttgttt ctcttttgtg tagaggaagg    36420
ctactgattt atatgagtta attttatacc cagccacttt gctgaagttg tttatcagct    36480
ttagtagttc tctggtggaa cttttgggat cacttaaaata tatatcatat catctgcaca    36540
tagtgatatt ttgacttctt cttttccaat ctgtgtccct ttgacctcct tttgttgtct    36600
```

-continued

```
gattgctctg gctagaactt caagaactat attgaataag tagtgagaga gtgggcagct   36660
ttgtctagtc cctgatttta gtgggattgc ttcacgtttc tctccattta gtttaatgtt   36720
agcaactggt ttgctgtata tggctttttac tgtatttagg tatgggcctt gaattcctat   36780
tctttccagg acttttatca tgaaggggtg ttgaattttg tcaaatgctt tctcagcatc   36840
taatgaaatg atcatgtggt tttgttcttt cactttgttt atatattgga ttacgttgat   36900
aattttccgt atattaaacc atccctgcat gcctgggatg aagcctactt gatcatggtg   36960
gatgattgtt ttgatgtgct tttggattcg gtttgccaga attttttgag tatttttgca   37020
ttgatattta taagggaaat tggtctgaag ttctctttct ttgttgggtc tttgggtggt   37080
ttaggtataa gaataattgt ggcttcatag aacgaattca gtagcactcc atttgtttca   37140
attttgtgga acaatttgga tagcatatga ggtcttctat gaaggtctga tagaattctg   37200
cactaaaccc gtctggacct gtgctctttt tggttgggag acctttaatg actgcttcta   37260
tttccttagg agttatgggg ttgtttaact ggttatctg ttcctgattt aacttcggta   37320
cctggtatct gtctaggaaa ttgtccattt cctgcagatt ttcaagtttt gttgaatata   37380 tgctttata gtaagatctg atgatttttt gtatttcctc tgaatctgta gttaagtctc   37440
ctttttcatt tctgattttg ttaatttgga cacactctct gtgtcctctc attagtctgg   37500
ctaatggttt atctatcttg ttgattttct caaaaaacca acttttggtt ctgttgattc   37560
tttctatggt ccttttttgtt tctactttgt tgatttcagc tctgagtttg attatttcct   37620
gccttctact cctcctgggt gtatttgctt ctttttgttc tagagctttt aggtgtgctg   37680
tcaagctgct tacatatgct ctttcctgtt tctttctgca ggcactcaga gctatgagtt   37740
ttcctcttag ctcagctttc attgtgtccc ataaggttgg gtatgttgta ccttcatttt   37800
cattaaattc taaaaagtct ttaatttctt tctttattc ttccttgacc aggttatcgt   37860
tgagtagagc aatgtgcaac ttccacatat atgtgggcgt ttttcccta ttgttattga   37920 agacagcttt aggccgttgc ggtctgatag cacgcatggg attatttcta tctttctgta   37980
cctgttgagg cccgtttttt gacccgtttt taaatggtca attttggaga aagtaccatg   38040
aggagctgag aagaatgtat atccttttgc tttaggatag aatgttctat aaatatctgt   38100
taagtccatt tggctcatga cttttcatag tctgtctacg tctctgttta atttctgttt   38160
ccatgatctg tccattgatg agagtggggt gttgaaatct cctactatta ttgtgtgagg   38220
tgcaatgtgt gttttgagct ttactaaggt ttcttttacg ttttaggtgc ccttgtattt   38280
ggggcatata tgtaggattg agagttcatc ttagtggatt tttcctttgt tgaatatgaa   38340
gtgtccttcc ttatctttt tgatgacttt tagttggaaa ttgattttat ttgatattag   38400
aatggctact ccagcttgct tcttccgacc atttgcttgc aaagtttttt tccagccttt   38460
cactctgagg taatgtctgt ctttgtctct gaggtgtgtt tcccgtaggc agcagaatgc   38520
agggtcctcg ttgcgtatcc agtttgttaa tctatgtctt tttattgggg agttgaggcc   38580
attgatgttg agagatatta agcaatagtg attattgctt cctgttatat tcatattttg   38640
atatgaggtt atgtttgtgt gctttttcttc tctttgtttt gttgccaaga caattagttt   38700
cttgcttctt ctagtgtaga gtttgcctcc ttatgttggg ctttaccatt tattattctt   38760
tgtagtgctg gatatgtaga aagatattgt gtaaatttgg ttttgtcgtg gaatatcttg   38820
gtttctccat ctatgttaat tgagtgtttt gcaggataca gtaacctggg ctggcatttg   38880
tgttctctta gggtctgtat gacatctgtc caggatcttc tgactttcat agtctctggc   38940
```

-continued

```
gaaaagtctg gtgtgattct gataggtctc cttttatatg ttacttgacc tttttcccctt    39000 actgctttta atattctttc tttattttgt gcgtttggtg ttttgactat tatgtgacgg    39060
ggggtgtttc ttttctggtc caatctattt ggagttctgt aggcttcttg tatgcctatg    39120
ggtatctctt tctttaggtt agggaagttt tcttctatga ttttgttgaa gatatttact    39180
ggtcctttga gctgggagtc ttcactctct tctataccta ttatccttag gtttgatctt    39240
ctcattgagt cctggatttc ctgtatgttt tggaccagta actttttctg cttttacatta    39300 tctttgacag ttgagtcgat gatttctatg gaatcttctg ctcctgagat tctctcttct    39360
atctcttgta ttctgttggt gaagctcgta tctacggctc cttgtctctt cttttgtttt    39420
tctatatcca gggttgtttc catgtgttct ttcttgattg cttctatttc catttttaat    39480
tccttcaact gtttgactgc gttttcctgg aattctttca gggattttttg tgattcctct    39540 ctgtatgctt ctacttggtt atttatgttt tcctccattt ctctaaagga gttcttcacg    39600
tctttcttga agtcctccag catcatgatc aaataagatt ttgaaactag atcttccttt    39660
tctggtgtgt ttggatattc catgtttgct ttggtgggag aattgggctc tgatgatgcc    39720
atgtggtctt ggtttctgtt gcttggattc ctgcgtttgc ctctcgccat ccgattatct    39780
ctagtgttac tttgttctgc tatttctgac agtggctaga ctgtcctata agcctgtgtg    39840
tcaggggtgc tgtagacctg ttttcctgtt ttctttcagc cagttatggg aacagagtgt    39900
tctgctttcg ggcgtgtagt ttttcctctc tacaggtctt cagctgttcc tgtgggcctg    39960
tgtcttgagt tcaccaggca gctttcttgc agcagaaaat ttggtcttac ctgtggtccc    40020
gaggctcagg tttgctcgtg gggtgctgtc caggggctct ctgcagcggc agcaaccagg    40080
aagatctgcg ccgcccttta caggagtttc cgtgcaccag ggttccagat ggcgtttggt    40140
gttttcctct ggaatcagta atgtgggcag agtgcagtct cttctggttt cccaggcatg    40200
tctgcctctc tgaaggttta gctctccctc ccatgggatt tgggtgcaga gaactgttta    40260
tctggtcggt tccttcaggt tctggtggtg tcttagacgc aggggacctg ctgctgctgt    40320
gcccttatcc aagggaacgc agaggccgta tacagtttcc tcttgggcca gggatgtggg    40380
ttaagggtgg gcagcgttgg tggtctcttc tgctctgcag tctcaggagt gcccacctgt    40440
ccaggtggtg aggtctctct cccatggggt ttgggagcag cgagctgctg cgggcaggga    40500 tccgcgggt tcatctgta cacttttttaa ctaaacattt tctaagaatt gtatgaaatt    40560
aataggtaag agacgcaggg gacctgctgc tgctgtgccc ttatccaagg gaacgcagag    40620
gccgtataca gttcctctt gggccaggga tgtgggttaa gggtgggcag cgttggtggt    40680
ctcttctgct ctgcagtctc aggagtgccc acctgtccag gtggtgaggt ctctctccca    40740
tggggtttgg gagcagcgag ctgctgcggg caggatccg cgggtttttca tctgtacact    40800 ttttaactaa acattttcta agaattgtat gaaattaata ggtaagaata ttgtcaggta    40860
agaactgatt ttacttattt atttacatca tagtaaatat ccttcaatag tatttgcctc    40920
atagcaaacc tttgtcatcc ctccattttt gttagccaca tttgaagata acttggctgc    40980
tggctgcatg agtgtggtgc tgtcagacat tgtcttggct cttagtcatc aggagacttt    41040
gctgggctgt aggccatatg ttcaacatac cacattcact aggatttggc aagagggttc    41100
aattccttat cagataagcc tgtggataga ttgattcaca aaattgattc ttgccttaga    41160
gttactgatc aaagagacat tgggggggcct agaatccatc cataacctac ctataccata    41220
caatgttttt gctatggctg tttcttgtat actgggttca atatgcatat gaagaaggaa    41280
attatgttta tctgtagaga gttgctttga atgatgtcgg tggcttctca acacatgcat    41340
```

-continued

```
accacagtgt tatttgagtc aagaatattt aattcctgga atattccatt cttttcagat   41400
ttttgtctat ctacatccat atatttttct tttatctaac agtctatgtt aaatgtttat   41460
catacgtaac cctgatatcc cctaaggaat aaagtgtatg acagataagc agccaaggat   41520
ctcttcctac tcatctttct gttgtgatgt taatattact gaattaacta cttagaagaa   41580
gaatttattt tgttttgctg acttgaattc atggtcaagt tgttctgtca ttttcatcct   41640
gttactagga ggttatttat gttagggaat gagtggtaag tctaagctgc ttggcttatg   41700
accaccagca agtagagata taagagaatg accaagatct caatatcccc ttcaaaggca   41760
tagtcccaat gacctaattt atttcactgt gtccagaaat tctgaaattt ataaccttcc   41820
taatagcacc agcaatgaca aaccaagctt ttaactaagg tgaaattcta ggaaatctat   41880
aatatccaac tcaaaagaat gaaagaagct atttacacta agaaatagta ttgataaata   41940
tagtaattgt ataaaaattg aatttttaaa aatattaaaa tttagatttc ttacaaatta   42000 ttttttcttac ttttattggt cctatttatt tatttattat ttgttttttgt cattaggttg   42060 ttttttataa aatttattct ctcatatatt acatcctgat tgcagtttct tttcccttaa   42120
tgtcccaact cctccatccc ctcaacctca ttcctcccca tccactcctc ctttatttcc   42180
cttcagaaaa taggggacc ctcagggaaa tcaactgatt attccatatc agatttcaat   42240
gtgtcagtac aaggcacccc agtatgagga caagggtccc caaataggc aaagaatca   42300 ggaacaactg caactctctc tgttaggaat tccacaaaac accaggcttc acaactataa   42360
caaatataca gagggtcaag gttagatcca ggctctctga ttgtcagttg aatctcagta   42420
aaaccctgag tccaggtgag ttgactctgt gagtttctt gtggtgtcct tggctgctct   42480
gctcctataa tctttcttct ctaacttcaa caggattccc caaactctaa actaaaggtc   42540
agtggaaaag tacctttct tctcctgagt aattgcttca aagcctctgc taacctaggc   42600
ctagttcttt aatctttctc tagcctctgt ataatcttat ctaggtcaag aatgtttaca   42660
gtttttgaaa cttacttgtg aataagatca catcgtccta tttctttctg aactctggct   42720
ggcttgttca gctcaactgt tctggcttaa actcctctgc aaactgtttc aaactgactt   42780 cttttttcagc ctttgacttg gtgctatgct tggcctcaga ttaaccctgg caatctgttt   42840
taatcctccg actccttctt attctctggc ttctcttacc tttacttgtg actagcttgt   42900
tctctctctg cagcttgtac tggtaaaact gcccctccct cacctctttc tctgtgctgc   42960
cctctcgtaa agaggtagcc tctttctctc tgttctcatg agagttgggc atatcttatt   43020
ctgttaaatc tttctctgat ttaacatctc tttcaaacaa gggtgattcc ttctacaaaa   43080
taactttacc ttcattgttt tggattaaag ccctttgtag tgttactaag gacttgtctg   43140
tattccagcc agaaggatta aaggtatatg ctgaggctgc gccacaccac agctaaaaac   43200
aggtttttct tgtaaacaac acaatcttgg atttcacagt gttaccaaaa gtcctaaaac   43260
agtttgaatc tctgcatctg tttctattag ttgtggagta gagcctctcc tatgatgact   43320
gggctaggca ccaatctata agtacagcag agtatcatta ggcatcattg aattgacttt   43380 ttttttctttg ccagtcatgg ttggttctat tctaggtctc tgggccgtac agcctctggt   43440
ttctggtcct caagtcagtg tcaggcatgg gtttcaagct gtacctgtca ttagttagtc   43500
actttcacaa tttctgtgcc accttcaccc cagcacatca tacaggtgag acaaattgta   43560
ggttgaaggt tttatgtctg gtttggtgtc ccaaaacctt tgtagggtta tgtccctgtt   43620
ttcattactg actttgttag ttttttatatt taatctgtct ttcagttagt ttggctaagg   43680
```

-continued

```
gtttgtctat cctgtagatt ttctcaaaag accaactctt cttttcatag attctttgta   43740
ttgttctctt tgtttctatt ttattgatct tagccttata atgtttctta gccccaagtt   43800
ggtttatttc ctgctctcta ctcctcttcc agagctttca ggtgtgctgt taagtcacga   43860
gtataagatc tctctaattt cttttatgaag gcacttagtg ctatgtagtt tcttcttaac   43920
accactttta ttgtgtccca tacgtttggt atgttgtgcc ttcattttca ttgaatacta   43980
gaagccttaa attctttatt tcttccttga cccagtggtc gttcagtaaa gaactgttca   44040
gtttccatga gtttatggag tttatgttat tgttcaagct cagctttaat ccatgtattc   44100
tgaaaaaata caggggggtta tttcatttttt cttgtatctg ttgagactcg ctttgtgacg   44160
gagtatatgg tcagttttag ataaagtact gtgagatgtt gagacaaagg tgtattcttt   44220
tgtctttggg tgaaatgttt tatagatttc tgttaagtcc atttgattca taatgtcttc   44280
cagttccatt tttctgttcc ttttttgttt ggatgacatg tccattggta agagtggggt   44340
atggaagtct tccactatta atgtatggtg ttcaagatat gttatgaaat atttttgtta   44400
gttagtttgt tttatgattt ttatgattgc ggtttccctt gcatttgggg cagatgttca   44460
gaactgagag gttatactca tgaaatattc tttttgatta gtatgacgtt tcctttgtac   44520
cactaatgat taattggttt gaataatatt ttgttaaata ttggaatggc tacatgatct   44580
tgattctttg gtccatttgc tagggaaatc ttttctagcc ttttattatt aagtaatatc   44640
cacttctgat gttgaggtat atttcctgta tgcagaagaa gggtggatac tgttctcaca   44700
tccattttgt gaaacctgtg ccatttttat tggagaattg aatccattga tactgagagc   44760
tatcaatgac taatgattgt tcattcctat tattttgatg gtggtggtgg cagtgtttgt   44820
gtttgagtgt gtgtgtgtgt gtgtgtgtgt gtgtgtgtgt atgtcttttt ttgctcatat   44880
gagattgttc attgcctgtg gtgtagatga tctttttgtg ttagggtaca agttatttat   44940
ttcttgggtg tagttgatct ccttgggttg gaattttctt tctagtaatt ttttttgtag   45000
ggcttggctg tggatagata ttgtttaaac ttggctttct catggtatat cgtgttttct   45060
cctactctta ttgagtattt tgctgactac ttcagtcagg atgcaactgt gattgttcag   45120
aatgcccagg cccttcttgc tttcagagtt ttcactaaga agtcaactat attctgatag   45180
ctttgccttt gtatttcact tgcttttttc cttttcacatc tttcactaat cattatttgt   45240
tttgaatatt tagtattttg attactgttt tgacaggact tcattttctt tttccatcta   45300
gttggtgttc tataagcttc ttgtgctttt atacgcatct ccttctttag gaccttttc   45360 ttttattatt ttgttgaaaa tattttctgg gccttctaaa atttattcct tgtaagtttc   45420
acaagcacct gatcccattc ttctttccat tcttccatat ctactctttt cccttgtaaa   45480 tgttcccca aaacaaaaca aataaaaaca aaccaacaaa caaatagaca tcttgtcaag   45540
gtagctatag gcattgcagt gtgtcacaca gggacaaaaa tctcttttgt ccaaacagct   45600
ttacttgcag atattcatcg catttagtca tttctttggt tcaagatctc tggcttctag   45660
tacaccacaa tacattctga atattttatc tttcacattg ctccaactcg ataaacaaca   45720
catcatccat atctgtcctt tccccagaat cataattttg agtgtttttg tatgatgcat   45780
ttggcttaac tcaggaaata tgtggaccac ttgaattgga gctgtatttt cgaacctgat   45840
ttactcacga gtgggtatat acctgaaagc actgactccc tatgtttctg aatctattag   45900
cgtaaaatag ttccaaggtg agggccaagg ttccctatga tcttactaca gtcatgcctg   45960
gatatgaggg cccattctta agaggtgtct gtaattgttg agagtttgtg attttaatga   46020
taatgttttt gttcagaaga tatcatagtc ttaatcactc tagctcttag aacctatgtg   46080
```

-continued

```
ctccttcatt cacaggttgc ttgtaggGga tagtgctcct gttttgttta acacttcaca    46140
atacactcac tatttctagt accttgtgta ttactacatc tatagtttta ttataattta    46200
ccagaaaaaa gagtcttctc tgatgttgac agtgttatta gctatgaata taaacatagt    46260
tacttataag gttgctcagt gttaagtcaa tgtattttaa tagcagaatt aatatgtgtg    46320
tctgcactca gatcttatga catccttgcc atgggctttt aagtaggttt acaaatacaa    46380
gcctgggatc tgtgtagcgc aatgagtcac aaacccaact atgtttgagt ttccccaatg    46440
tagatttacc caaatatatc tgggctgctt gtaacttaaa tatatatgaa tttcgtttat    46500
tctacactga actttctgat acttcctgga taagataaaa atgattaatc tctctgtaat    46560
gtcattaaat aacttttttct acttaaaatc tttagtactc actcctaagg gatgtttaat    46620
tactcaccac tttcatcaaa tcttttacta tttgggagaa aatgcattgt aaaatgataa    46680
ctggcacaat tcagaagatg gtgattgtga atctgtgtta gaagtgattc tagaaattaa    46740
tcttttgtgt catgttgaag atgtagtagg atgagattta tcaataaaaa ttagaagatc    46800
ttgggattga agatcagtaa aaactggaat atcttgcgct gtgttcataa tatttagaac    46860
agttgtaaaa ctggtcaata tattgatcag cagtctgagt agagtgcatc aacactgtga    46920
tgtatggtcc aggaatcact gctgatgcag ccacgacctg catctggaaa gtgtaagatg    46980
ttaaacaaag ctcacttagg tactgaccac ctcaggtgtc tgttacttta aggagtatta    47040
tgtttgcttc aagaaccatg tataacggag taaacctgtg cccactggag aatgaagaat    47100
aggtaaaagt ctgaggtctg tggtaataat gatactccta ctctgaacca tgctttcttt    47160
cattactttt caaaacaaaa tctcagtgag ctaatttgac ttattgatgt cctatgagaa    47220
gtgtgattct taaaattgtt aaagaagaac aatttttaaa ccatgtaaaa atgtgtaaaa    47280
aaactcttga aatatttaat aaaacaaaaa ctaaaatgaa tgaggaagct tgaggaaatt    47340
tgtttgattt tttatgtatt tgttgaaata acttttaatg tattgcatga ggttccttga    47400
agcagaatca tacttaatat aaaagggata ttattctcat actaaagtac aaatgataaa    47460
tagtaatcac aaataattac atgtaataaa gtaatcatat attacatata aacttaatat    47520
aatgaacaat atggcatttc aatacaaagg tacaaaaata gctccatatc gttccatgtt    47580
catactatat tttagtttca gtgaaaatta taaataagaa attatattga atattaacaa    47640
gtatctccaa tccaattatc tggtggagta tcagctacaa cttgacttca tgttgaaaga    47700
catcctcaca aaccactgtt gtcttttgtt ttattttctt atcccacaca ttcactgttc    47760
tgtcattctg ttattttgat tagtttaaag taatttactg atcaagagtt ttttttcctc    47820
tgatatgagt gttttatggt tgttttattt tattattttt ttctttcaag tgaaaccttg    47880
tgattttcca caattcaaac atggacgtct gtattatgaa gaaagccgga gaccctactt    47940
cccagtacct ataggaaagg agtacagcta ttactgtgac aacgggttta caacgccttc    48000
acagtcatac tgggactacc ttcgttgcac agtaaatggg tgggagcctg aagttccatg    48060
cctcagtaag ccaatgcctt tatagttaac tatgttgatt ctttttaaaga gagagcacat    48120 acataattaa gttattcata acaaaaataa gaccaacaaa agaatttgtg agcaaaatgg    48180
ctagtttctg ttatgaaatg tttcttcatg aaacatgcaa tagggactat ggaaatatct    48240
ttatcacttg catattttat ttttacaaac gaaagataaa tgctattctc ttaaatgttt    48300
gttattaatt ttattttttga atgatgtgca tactcattaa acagttttaa agataacatt    48360
tatcttagtt tattttttaaa caaattaaag attttatttt tttaatttttt aattattatg    48420
```

-continued

```
tttcttaggg caatgtattt tccattatgt ggaatatgga gaatctttat actggcaaag   48480
aagatatata gagggtcagt ctgcaaaagt ccagtgtcac agtggctata gtcttccaaa   48540
tggtcaagat acaatattat gtacagaaaa tggctggtcc cctcctccca aatgcgtccg   48600
tatcagtaag taactaatac ttagatcgca agaagatcgt gactctctgt cccatctgta   48660
tttgttttta ttggctaatt tttatgtaca tttcaaatgt tattcttttt cctggtttcc   48720
catacataag ccccctatcc aatcccctc acacttcttt gagggtgttc cccttcccca   48780
agaacccatc ctttcccact tccctaccct gacattcccc tactaatact tagatcgcaa   48840
gaagatcgtg actctctgtc ccatctgtat ttgtttttat tggctaattt ttatgtacat   48900
ttcaaatgtt attctttttc ctggtttccc atacataagc ccctatcca atcccccctca   48960 cacttctttg agggtgttcc ccttccccaa gaacccatcc tttcccactt ccctaccctg   49020
acattcccct acactggagg gcccagcctt agcaaaacca aggacttctc ccctcattgg   49080
tgcccaacaa agccatcctt gttatataca gctacatatg catctggagc catgagtctg   49140
tccaaatgtc ctctttgggc agttgtttag accttgggaa ctctggttgg ttggtagtgt   49200
tgttcttatg gggttttaag acccttcagc tccttcaatc cttcctctaa ttcctccagt   49260
gaggacccca ttctcagttc aatggttggc tgctagcatt ctcctctgta tttgtcacac   49320
tctggttgag cctctcagga gacaactata tcatgttcct gtcagcatgc acttcttggc   49380
tccatcaata ttgtctaggt ttagtatgca tgtgtgttta tatatatata tatgtatata   49440
tacaggtgta gtatgcataa gtatatatgt atatgtctat gtttatttgt tggatcccca   49500
ggtggatcag gctctgaatg tccattcctt cagtgtctgc tccaaacttg gtctcaatat   49560
ctcttcctac aaattttctt ctattagttc gagagtatct agcttcatgt ggaggttctt   49620
gactaacttt gacttaagga tttttgcagg gtgatgaaaa tgggtcgatt tgcgttcttc   49680
tacatgctga cctccaggat aaccagcacc atctggtgat tccactgaat gattttagtt   49740
cctttgtcaa atattaagtg accacaggtg tgtgagttca tttttgggtc ttcaattcta   49800
ctccaatgat ctacttgctt gtctctgtat cattattgct ctgtaaaaca gcttgaggtc   49860
atggatgaga ttaccaaaga acctttttta ttattgagga tagttttcac tatcttggat   49920 tttttttgtta gtccaaatga atttgcaaat tgctctttct atgtctatga agaatttagt   49980
tgggattttg atagggattg cattgaattt gtagattgct tttggcaaaa tggccatttt   50040
tactgtatta atccccccaa accacaagca tgggaaggtt ctccatcttc tgagatcttt   50100
gatttctttc ttcagagact tgaagtaatt gtaagatctt tcacttgttt gagtagagtc   50160
acaacaaggt attgtacgta acttgtgacc attgtgaagg gtgtcatttc cctaatttct   50220
ttttcagcct ggttatcctt tgagtagagg aagggtacta atttatttga gttaaattta   50280
tacccagcca atttgctgaa gttatcatgc ttagtagttt gctgatggaa cttttggggt   50340
cacttaagga tagtattata tcatctgcaa atagtgatat tttgactctt cctttccaat   50400
ttgtatccca ttgacctttt gttgtttgat tgctctgacc aaaactttga gtactatatt   50460
gaataagtag ggagagagtg ggcagccttg tctagtccct gattttagtg ggattgcttc   50520
aagtttctct ccatatagtt tgatgttggc tactggtttg ctgtatattg cttttaatat   50580
gtttgggtat cggccttgaa ttcctgatct ttctacggct tctatcatga aggggtgttg   50640
aattttgtca aatgctttct cagcatctaa tgaaatgatc acatggtttt tttctttgag   50700
tttgttaata tagaggatta cgttgatgaa tttctgtatt ttgaaccatc cctgcatccc   50760
tgagatgatg cctacttgat catgagggac gattattttg atgtgttctt ggattctatt   50820
```

-continued

```
gacaagaatt ttattgagta tttttgcatc aatattcata agggaaattg gtctgaagtt    50880
gtctttcttt gttgggtctt tctgtggttt aggtattagt gtaattgtga cttcatagaa    50940
ggaattcggt agtgccctgt ttctcttttg tggaatagct tggaaagtgt gaatatgagg    51000
tcttctatga aggtctgata gaattctgca cctaactcat ctggtcctgg gccctttttt    51060
tcttaggaga cctttaataa ctgcttctat ttctttagga gttatggggt tgtttagatg    51120
gtttatctgt tcctgattta acattataca tggtatttgt ctagaaaatt gtccatttcc    51180
tcgatattga atataggctt ttgtagtagg atctgatgat ttttttaatt tcctcagatt    51240
ctttcgttat gtctccattt tcatcttgaa ttttgttaat tggaaatact ctctgtgacc    51300
tctggtttat ctggctaagg gtttatctat ctggttgatt ttctcaaaga actatctcct    51360
ggttttgttg attctttttt ttttcttcct tttattgaat atattttttt cagagggaaa    51420
atgtttatta gtttcatagt tttatacctt tcagcttatt ttaacttggt ctctggagca    51480
tttggaagac tagctgctta catcagagca gtgctgaaat agagacaact ataaatccag    51540
agacaaacat agccttcaaa gttatttagc cctacttcta aacagatagt ctataatatt    51600
tattctcaat aactgtaaag aaacttatat tctcccctc ccacaaaaca tcactgaaag    51660
acgaaagaat tggttccatg tatgaccttc ttgtttgacc agtggcttca ttagggtcat    51720
ttacaggagc atgccaagaa gttacttaaa agaatagtaa tgattcaact gaagtttcat    51780
taaagatatg tctcatcaca gaatgctttt caattcataa atcacctcta gaatgctatc    51840
cacaccatcg agaatcctgt gatctcctct caatctataa taacatattg gcttggggag    51900
ggtttatgaa agaatagtgg ggtgtgtgtg tgtgtgagtg tgtgtgtgtg tgtgtgtgtg    51960
agacaaaaaa attgatttaa agttaacttc taagtcccag ctaacaacca atgttctgat    52020
cagagagctt tcagaataga ctctattttc tctatattct gctccaaaca actttcctga    52080
tggctgtctt tctataagta gtttgctttg catgacacag ctttctctta ctattccttt    52140
ttttttttaa cttaagtatt tcttatttac aattcgagtg ttattccttt tcccggtttc    52200
tgggccgaca tcccctaacc cctcccctc cccttcttta tgagtgttcc cctccccatc    52260 ctcccccat tgctgccctc cccccaacaa tcacgtttgc tgggggttca gtcttagcag    52320
tccccttcca caggtgatct tactaggata ttcattgcta cctatgaggt cagagtccag    52380
ggtcagtcca tgtagagtct ttaggtagtg gcttagtccc tggaagctct ggttgcttgg    52440
cattgttgta catatggggt ctcgagcccc ttcaaggtct tccacttctt tctctgattg    52500
cttcaacggg ggtcctattc tccattcagt ggtttgctgc tggcattcac ctctgtttta    52560
gctgtattct ggctgtgtgt ctctcaggag agatctacat ccggctcctg tctgcctaca    52620
cttctttgct tcatccatct tgtctaattg ggtggctgta tatgtatagg ccacatgtgg    52680
ggcaggctct gaatgggtat tccttctgtc actgttttaa tctttgcctc cctattcgct    52740
gccaagggta ttcttgttcc ccttttaaag aaggagtgaa gcattcacat tttgatcatc    52800
catcttgagt ttcttgtgtt ctatgcatct agggtaattc aagcatttga gctaatagcc    52860
acttatcaat gagtgcatac catgtgtgtt tttctgtgaa tgggttacgt cattcacgat    52920
gatattttcc tgatccatcc atttgcctat gaatttcata aatgcattgt ttttgatagc    52980
tgagtaatat tccattgtgt agatgtacca cattttttct gtatccattc ctctgttgaa    53040
gggcatctgg gttctttcca gcttctggct aatataaaata aggctgctat gaacatagta    53100
gagcacaagt cttttatat atccgggcat cttttcggta tatgcccaag agaggtataa    53160
```

-continued

```
ctggatcctc aggtagttca atgtccaata ttgtgaggaa cctccagact gatttccaga    53220 atggtttttac cagtctgcaa tcccaccaac aatggaggag tgttcctctt tctccacatg    53280
ctcaccagca tttgttgtca cctgagattt tgatcttagc cattctcact ggtgtgaggt    53340
gaaatctcag ggttgttttg atttgcattt cccttatgac taaagatgtt gaacatttct    53400
ttaggtgttt ctcagccatt cggcattcct cagctgtgaa ttctttgttt agttctgaac    53460
cccatttttt aataagatta tttgtctccc tgcggtctaa tttcttgagt tctttgtata    53520
ttttggatat aaggcctcta tctgttgtat gattggtaaa gatcttttcc caatctgttg    53580
gttgccgttt tgtcctaacc acagtgtcct ttgccttaca gaagctttgc agttttatga    53640
gatcccattt gtcgattctt gatcttagag tataagccat tggtgttttg ttcaggaaat    53700
gttttccagt gcccatgtgt tccagatgct tccctagttt ttcttctatt agttagagtg    53760
tatctggttt gatgtggagg tccttgatcc acttggactt aaggtttgta cagggtgata    53820
agcatggatt gatctgcatt cttctacatg ttgacctcca gttgaaccag caccatttgc    53880
tgaaaatgct atctttttc cattggatgg ttttggctcc tttgtcaaaa atcaagtgcc    53940
cataggtgtt tgggttcatt tctgggtctt caattctgtt ccattggtct atctgtctgt    54000
ctctgtacca ataccatgca gtttttatca ctattgctct gtaatactgc ttgagttcag    54060
ggaaagtgat tcccctgaa gtcctattat tgttgaggtt agttttagct atcctgggtt    54120
ttttgttatt ccagatgaac ttgcaaattg ttctgtctaa ctctttgaag aaatggattg    54180
gtattttgat ggggattgca ttgaatctgt agatcgcttt tggtaaaatg gccattttgc    54240
tatataaatc ctaccaatcc atgagcctgg gagatctttc catcttctga ggtcttcttc    54300
aatttctttc ttcagagtct tgaagttctt attgtacaga tcttttactt gcttggttaa    54360
agtcacactg aggtatttta tattatttgg gtctattatg aagggtgtca tttccctaat    54420
ttctttctca gcttgtttct cttttatgta gaggaaggct actgatttat ttgagttaat    54480
tttataccca gccactttgc tgaagttgtt tatcagcttt agtagatctc tggtggaact    54540
cttgggatca cttaaatata ttatcatatc atctgcaaat agtgatattt tgacttcttc    54600
ttatccaatc ggtatcccct tgatctcctt ttgttgtctg attgctctgg ctagaacttc    54660
aagaactata ttgaataagt agggagagag tgggcagcct tgtttagtcc ctgatttcag    54720
tgtgattgct tcaagtttct ctccatttag tttaatgtta gcaactggtt tgccgtatat    54780
agcttttact atgtttaggt atgggccttg aattcctatt ctttccagga cttttatcat    54840
gaaggggtgt tgaattttgt caaatgcttt cccaggatct aatgagatga tcatgttgtt    54900
ttgttctttc agtttgttta tataatggat cacgttgatg gttttccgta tattaaacca    54960
tccctgcatg cctgggatga agcctacttg atcatggtgg atgattgttt tgatgtgctc    55020
ttgaattcgg tttgccagaa ttttttgagt atttttgcgt tgatatttat aagggaaatt    55080
ggtctgaagt tctctttctt tcttgggtct ttgtgcggtt taggtataaa agtaattgtg    55140
gcttcataga aggaattcgg tagtgctcca tctgtttcaa ttttgtggaa tagtttggat    55200
agtattagtt tgaggtcttc tatgagggtc tgatagaatt ctgcactaaa cccggctgga    55260
cctgggctct ttttcgttgg gataccttta ttgactgctt ctatttcctt aggagttatg    55320
gggttgttta actggtttat atgttcctga tttaacttca gtacctggta tttgtctagg    55380
aaattgtcca agtgtttctt ttctggtcca atctatttgg agttctgtag gcttcttgta    55440
tgcttatggg tatctctttc tttaggttag ggaagttttc ttctatgatt ttgttgaaga    55500
tatttactgg tcctttgagt tgggagtctt cactctcttc tattcctatt atccttaggt    55560
```

-continued

```
ttgatcttct cattgagtcc tggatttcct gtatgttttg gaccagtagc tttttctgct   55620
ttacattatc tttcacagtt gagtcgatag ttttctatag aatcttctgc tcctgagatc   55680
ctctcttcta tctcttgtat tctgttggtg aagctcgtat ctacggctcc ttgtctcttc   55740
ttttggtttt ctatatccat tgttgtttcc atgtgttctt tcttgattgc ttctatttcc   55800
atttttaatt ccttcaactg tttgattgtg ttttcctgga attctttcag ggattttgt    55860 gattcctctc tgtaggcttc tacttcttta tgttttcctg catttctcta agggagctct   55920
tcatgtcttt cttgaagtcc tccagcatcg tgatcaaata tgattttgaa actagatctt   55980
gcttttctgg tgtgcttgga tattctgtgt ttgctttgtt gggagaattg ggctctgatg   56040
atgccatgta ctcttggttt ctgttgcttg ggttcctgcg cttacctatc gccatcagat   56100
tatctctagt gttactttgt tcttctattt ctgacagtgg ctagactgtc cttataagcc   56160
tgtgtgtcag gaatgctgta gacctgtttt cctcttttct ttcagcaagt tatgggaaca   56220
gagtcttctg ctttcggccg tgtagtcttt cctgtctact ggtcttcagc tgttcctgtg   56280
ggcgtgtgtc ctgagtccat taggcaggtc acttggagcc gaaaagttgg tcttgcctct   56340
ggtcttgggc caaaatttgc tttccgtgag ggctgcaatc aaagggcttg ctcagccttc   56400
tctcaggcct agatggcact agaacttttc ctctagagtc agaaatatgg gcagagagta   56460
gtctcctctg gtttcccagg tttgtctgcc cctctgaagg tctagctctc ccttccatgg   56520
gatttgaata cagggagctg tttgaccggg tcccttcaga actgggcgca gtctggaacc   56580
tagcgctcct gcagcttgag tgaccatatc ttcctgttcc cagaggccct gtacagtttc   56640
ttcttgggtc agggatgtgg gcaagggtgg gcagtactgg aagtctctcc tgccttgcag   56700
tctcaggagt gcccacctgt ttggttgatg agctctctct cccacggggt ttgggaacag   56760
ggagctgtgg gccaggatca gcgaggtttg ggccccagct agaaaccaga agtgtctggt   56820
cccagaagaa ttttgccttt gtgtatcctg aatccagcag gcaggtcact tggagcagaa   56880
aagttggtct tacctcttgt ctcgggcctg aagtcgctcc tcggagctgg ttttcagctc   56940
tccatcaggg cagcaaccaa aagggcctgc cccgccttct ctcaggaccc tgtgcacagg   57000
gggcccagat ggtgctagac ctttttctct agattcagaa atgtgggcag agagtagttt   57060
cctctgcctt cccaggcatg tctgttcctc tgaaggtcta gctttccctc ccatgggatt   57120
tgggtgcagg gagctgtttg accaagcgct cctgcagctt gagtgcccct atcttccttt   57180
tcacagaggc cctatacagt ttcatcttgg gccagggatg tgggcgaggg tgggtagtac   57240
tggaggtctc tcctgccctg cagtctcagg agtgcccacc tgtctgggtg atgagctgtc   57300
tctcccctgg ggtttgggag gagggaactg tgggccagga tctcttcacc tattcttaac   57360
attaataatt caacacacac acacacacac acacacacac acacacacag cccctagtga   57420
gtcactatac tgctggtagc ctgaatgtat gttttatgct tgatcacttg ggattagata   57480
acttatcaga gagaggctta ttcttagagt agattgaatt ttcagcaagt attaattacc   57540
tgttgttctt cattgagagg gttagtgatt atgaaaattt ctccatatgc attgaaatgt   57600
caactggtat tgtagtaaac tcacatagac aatcatagtt ttgaaatttc atgggctctg   57660
cctgcctgtc atatatagaa agcttttctc atagtaggca tcctagtttt tgcccttaaa   57720
ttctttctgc tccttctcaa atgatgattc cccaagcctt aggtttgttt agtgactact   57780
acttacataa gacttaatat cttataatat tagacattaa atttatttgt tcctaaacag   57840
ctacatttaa aatatttaaa cgaaagtgca agttgtagaa atttattgtt aagaaatata   57900
```

-continued

```
ctatttctat taataaatat agtatgtaat atttacatta ggtttaaaat atctagatgt   57960
ttgagcactt tgaagaaatg tcttgctatg gtctcttgcc atgtgacttt tagagtaagc   58020
ttgctcatgc atgaaaaatt catttctgga ttcaattttg agaaaattga tacagcacca   58080
ttaatttttt ctattaataa ctacgatatg tctatgattt agttagaccc ttagtctctt   58140
gtggcactgt tctgttttat gcagcaactt cagtagatgg atagctaata gacgttttca   58200
aattgtagta attgtattca tgttatctat ttttcttggg tatagtttat ggttttcatt   58260
aattctattc attttatctt gccaaattaa ttgacgtgaa tgttcataat attctccaat   58320
tatttttgaa atttatgtaa aagcacataa tgatacaatt cccatcattg ctgataatgt   58380
taatttgatc tttctctacc ttttccctac ctttctctgc tatgtctgct taaaagatga   58440
ttaatttagg tgtctttcat aggatcgaga tgtaaagtta attctgcttt gtgttatttt   58500
aaatgacatg actcccactc ccaattctac tccccctttc tttaaatttt ctgctttttc   58560
ctaatgtctt aatgagatct caggcaactg atgtgagccc gtgttccttg tccatttgaa   58620
tgttgagtgc agccagattt ttgttatcat cccacatagt tgtgtgtgtt aatttatcta   58680
ttggtacttg gatacaatgg gtgaacatta tcagtttatt gttggggaaa taattcagtg   58740
ccacaaatgt atatgttttc attcacctct gccacaatcc cttgaataat aaagcagcac   58800
tccatgaaaa ctttttgcta gtgcttgggc ttggaaaatt gcagaataaa aatactgagt   58860
ttgattttcc tttgaaatta ttttagattg gtttgccaca cattttttgt acaacttgag   58920
tgttcagaat atcaataaaa ctctccaggg ggatgtcttt ctaaaggatt atggtgatta   58980
cacgaatctt tactgtctac acctttgaat atcttgaatt gttggtgttc tgggtacctt   59040
ttcctgtaat ttttggggta gttattcttc tcatgttctt catcagagaa tcttgtaatg   59100
tgctagactg tgctgataga ggatggcaat tgagaaatgc agagttccgc tccatatttt   59160
ctttgttctt gcttttctat gccacacgtt cagtgactcc agtctttttg agcaaagtaa   59220
tttttgttgc ttaaattcaa taaaataccc atttttcttc tttagttcac aatttgcaat   59280
tttctggaaa actctccttt acataaagcc acctcaataa tgaacatcat taatctgttg   59340
cctctggtac tggtaatttt caactaaata tgttcttatc atttgagtct gctacactat   59400
tttatttttg tttctttata attttattat atcctttttac agcaacaaaa tctcattact   59460
ttttctaatc tttattaacc tttgaacaac cattctattt taggcatgca gctgaaatta   59520
ttggcactgg agtctgtagt aactttggat atattttta agatcatcat tcgactccag   59580
aatccctagt gggatgaaat gagatctagg ttcctaagag atccaattat tcttaagcag   59640
aaagaaaaaa aatgaaagaa tgaatgaata aaaaagaga gaaagaaagg aagagagaaa   59700
gaaagaaaga aaaagaaag agaaaagaa agaaagagag aaagaaaata ttgtccagag   59760
ttctgatggt ctataagata tatattcatt tggacaaaaa tgttaaacat atttaagaac   59820
atattataaa tcctttcaat tttactttgt tagaaaaaaa ctttctcaga ggactatgat   59880
gatgtatgtt taaaacgaaa ggtttgttgt ttttctttt ctttttctttt tcgtttcttt   59940 ttttgtttt tttttgtttt tttttctttt tttggcctag tgatgggaaa gactttgatt   60000
atttcatgta caaatgacta atgactactt ctgcaccttt aatattgtag atccctaggc   60060
tgccatgcct atactcacct cttttcttac tttttaccct tttagagact tgttcagtat   60120
cagatataga aattgaaaat gggttttttt ctgaatctga ttatacatat gctctaaata   60180
gaaaaacacg gtatagatgt aaacagggat atgtaacaaa taccggagaa atatcaggaa   60240
taattacttg tcttcaagat ggatggtcac ctcgaccctc atgcattagt gagtattta   60300
```

-continued

```
ttatattgtt gcaattatac taatgatgca taggagttta gtgttattct ttttgtatat   60360
gattgatatt ctttcatttg taaacagctt tcaaacttca agaaaaaata cacagcattt   60420
tttttattta gacattcctg cattgtaaaa tatcagttca tttgcctttt tctaggctct   60480
aaaatagcct agttttaaat ctagtgaaga agtctttgac cagatgcaaa ttcctgaata   60540
tatgataacc ttataatatg tacgtgacac tatgagttac gatctatttc agaacatctc   60600
ccttttagaa gatctttta aatattttga tattggaaag aaagaaatgc ttccaggcac   60660
caggaaattt tggtatttgg aaacattctt ttgttttagg acatacagtt aatgaggatt   60720
ttctaggatt aacaattagc tcatctagtc ttatttataa gaaaaatacc cagtgctatt   60780
tttcaagatg tattcaattt ataccttatt gtttaaggta tgatttaaag tattcactaa   60840
gttcataatt tttcgtctac tgtgatttta caggatttaa ttaaagaaaa ggaaattaaa   60900
attattccca tataacattc atttatatta aattataatt ggtaaggatt tattgaattt   60960
ttttactgtg aaagggaaaa cccttgatat aatatctgct taaattcaat tcatctactt   61020
tcctatattt tatgagtcat ttgatgtact aattatagga ccttaattcg caaaatgcta   61080
tcatactttc ctaaaattat gtatttgcac ttgtctattt tttggagtat gtgataagta   61140
taagaaaaat tgagctgaga aatgatttct aaaataaaat tttataaaag cttaagaaag   61200
gagatgaatg ttacatagag tatatctcaa ttttaataac tttcaagaaa ataaattatt   61260
actggtctcc ttagtttcct tcaatacagt atttaatttg ctatcatata ttaatttata   61320 aagactttt tctcatgaga attatttcta cttgctattg acacattaga aatgacattg   61380
tctctcttat tttgcattag agtcttgtga tatgcctgta tttgagaatg ctatgactaa   61440
gaataataac acatggttta aactcaatga caaattagac tatgaatgtc acattggata   61500
tgaaaatgaa tataaacata ccaaaggctc tataacatgt acttatgatg gatggtctag   61560
tacaccctcc tgttatggta agtactattt tctctggaat attttttagat aaaaataaat   61620 gtttgtgtta ttaataactg aatgttctag aatcttcctt atgagttaat gtagcctaag   61680
aaaaaggact gttatgaaag ctatcgataa taatatttac atttattata tcattacatt   61740
catttattta tcctgtgtgt atacatgcac acatatgtgt gtttctggaa gtgtgtatac   61800
tgcattatac aggtaggtgt cagagaactt gtgagagtca gttccctctt tcatcatatg   61860
gatctgaggg attgaagagg actccaggcc taaaggcaag cactcttact gactgagcca   61920
tctttctggc ctgataatct gttttttaaaa aattctatat tcatcagttg tatatggcac   61980
tggattatga ttctagcaat taggaccctg aatcaagaga tttttaagtt tgaaggtata   62040
ttggactaca tactaagttc tgtttctaaa accaaacaaa ccaaaaattt cattaaatta   62100
atgattcctt tgtgtggcct gtgtgtatca tgtatctctg atttgaggac aattcttttg   62160
ttattcaagc tcttatgtag actaggtctc cattatcaaa tttatgatct gaagcatgaa   62220
actaggtaat gaaaacttga ggcctggaga gatggctcag caggtaagag catgggctgc   62280
tcttccagag atcctgagtt caattcccag caaccacatc atggctcaca atgaaggagg   62340
tagaagtatg gcattcttga aatctaggcc agtctgggct atgtaggaat tgtaagtggt   62400
aagtgcagga attgtaggaa tacagctctg aagggaaaag cttccccaat ggagatgctg   62460
cagctctgag tgtctcagtg caagtatgac agctctgaag ggaaaggtat cctggcagta   62520
gggagctaag gaaaaccaca aacttacact gcacaaaaca aacctggcac aagaacttta   62580
ttgggaaaaa cataagaaag ctgtttctgc tccagattaa agcagcaaag aacaagctca   62640
```

-continued

```
gtgattggtg agattttgag tttatcttgg gcttccaccc catccctacc ctccagaaag    62700
gaacttggcc attagcacct caaggggcta gactgccatt atagtagtct ggaggtgggg    62760
cttggtcact tgcgtgactt caagggactt accttaagat ggtggctgcc tctgtttgac    62820
caacatacaa caggaaactg agcaggagac agataaatat aagttgtttt ttttttccggg    62880 ggtctggggg tagggtgggt tttggaggat aaacatttcc aaggtgggga atggtgagat    62940
tttcaagatc aagactggtg ggtattcaca ctcagggctt ggtagggttt cctatttagg    63000
gattggtagg tttgggtagg ttttaagcca tgaaatgggc tcagaacttt taccctaaat    63060
gaagacatct cacaaacaga caaacagcaa caaatgatgt acatagtaag aaaaaaatca    63120
aactaaacaa acggtgatca ctagtttctc tctgattata agcagttcaa cattatgaaa    63180
tcaggacttt ctataataca atactaaagt agaatggaag gggagggata ttagtttcac    63240
aatacaatac tttgcctaag gatcagtact aacactacaa gtataaaata aaatataata    63300
taaaattatt tatatactat tctgatgtgt gagaattttt tttctgtgaa gtcaatatac    63360
aaacatctac tcaccccaag aaagagccca tgacagacca atgtacagat accactaatt    63420
tccaacttca tgaaccttga gtcattgtgt ccagttgcaa aatccccaaa gagactaccc    63480
ggaactgcaa cttccacaca cgcacaggag agtctttatt caagctcgag cttgggctac    63540
gtaccttcct gatggaatag gaaggagaga gatacttgag tctaggggct tagggcttat    63600
ataggggaaa atctcaagct ggagtcttca agccttggca ttacatgttt gggtaaaggg    63660
gtaaaggaat gttaaccttc agactgatat catcagggggg agaccacaca tttaaaagag    63720
gcatcttgtc cttggaatga tttatgtttt tttaacttat tattgtgacc agttttcctg    63780
ttgttgcaag ctggccactg ctgttatatc tattttcaac tgctgggaag ggttggttgt    63840
ctcttttcca gagcccaaga tggggggccat atcacttcaa ggacagcagt tttctccaag    63900
gacagcagct tttcccaagg acagcaattt tctccaagga caagatctta aaattgaatt    63960
taaaggaaaa gatggaatcc ctcctgctgc cttttgcctt ttcagagttt tattaaggtt    64020
gctttcagaa atatgaatga gggtgttctc ataggagaag aaatggctca aagacagcta    64080
catcaccaaa gcctacccag tatggctgac aattcacaaa acacaatgga tcatataaca    64140
taatgtgtag gcagcacata gattgaggag tgtcttttca agtgagtcag ctgatgaagc    64200
acctaccact gggtaggatc cttcttctag gaagttaatt atctcattct ttgctccatc    64260
tagggagctc tgagctcctt ccttgcagtt ttgcttgtct gagtgattct caccaattca    64320
gctagcttgt ttactctgga agtaaggggc ctgctaaatc tgcttagttt cagggactcc    64380
ctgaagctat tttgagttgt ttacttccct ccttaaggag cttccctgca gtatggagta    64440
tttcagtctc aaggaaactg ttgcccaaca aattcccatg gtctttcaat gtctccaggt    64500
ctgacaggtg attgtaaagc agaggagaat tgcacaaatt attttttcac tttaagacag    64560
agtattatgg tatgtttgct aaacaatttg tataaaataa gcaaagagaa tacacaaata    64620
ggtgcaaaac aaaaaatagt tatagatgat tatattgtgc cattcaaatc cacttggaaa    64680
gagcacacac gtagattcaa ttcaagttta ggttaaatga atttcttctt atttctatca    64740
acacagaagg gggaggaagg gagggtttat aaagttggat tcctaaagtt gcatattaca    64800
attagccatg aaatctgcag ctggaccaaa aagtgttttt gcatccctca gttgttcttt    64860
acctttgtat gccaataaaa agatcacttc atccctgtcc cacaaaagca aaaaacaaac    64920
tgtcaaacat cttacaacag gaactctagt aacctatcta aacttttctg ttttctttac    64980
ttttcttttt acttattctt ctctcttaca ataaatatat cctgattgta gcctcccttc    65040
```

-continued

```
ccccaactcc tccctgttcc cactttccct tctctaccag acctactgct cctcccttc   65100 ccttcagaaa agagcaggcg attcatgaat attaatcaaa tatgacataa caagatataa   65160
taagcctagg cataagccct tatttcaagg ctggatgaaa caaccaagta ggataatggt   65220
ctcaagagca ggcaaaagaa ttagagacac ccatgactcc cattgttagg agtcccacaa   65280
aattcccaag ctaaagaaca ctatgcaaag gacctagcac agacccatac aggctctttg   65340
atttcagctc ctgtctctgt agcctctatg agtcctactt agttgattct gtggcccacg   65400
tttttctgct gttaccattc cacacacaaa attcattcta ttgcccccttc ccagggtgat   65460 ttccttctta cttctctcca cttcttactt agcctcccctt tgtctgtgtg ctgtcacatg   65520
attagccttt acttagctct aataactact tatgaataca taattatttt tgtctttcca   65580
ggtctggttg cctcactcag gatatgtttt tctagttcca tcatttgcct gaaaatttca   65640
tgatggcatt tctctaacat ctttcataat ataccattat ataaatatac cacatttttta   65700 tgcactcttc agttgagggg acatctaggt ttctaagcta tccagtctct gtttgctggc   65760
cctcaggtta gtgcctggca tggctctttc tcactgcatt gggatgaagc tgtaccaatc   65820
attgattggc cactcctgca agttctgcag ccgtatcttg caggagaaat agtcggctga   65880
agattttgtg gcagggttgg tgccccaatt cctcaactgg aaatcttggt tagaaaagtt   65940
ggctggttca ggctccttaa accccagtac taggagtctt tactaggctc acactcaaag   66000
attccttgga atttcccttg cactaaggtt tggtcttgtc cctgaaatac cccaaattct   66060
aatcatctct ttcaatactt tctcactcca ccacacctga tttctcctct taccatccct   66120
tcagttttga acatagcagt tgtctttttat gaatgactct aattaaaaat tatgacttttt   66180 aatatataca ttggaaagaa aggagatttt taaggcagaa atgtgttattt tatttatttta   66240 catatttttg gtaacactca acaatgacaa aaattgaaga aaaaatttt catacaggag   66300 aatgtgtcat acattcttaa tttgagtcag aataattcac aattaattaa ttaaaaccag   66360
aattataaaa ctggtttaat gtaaaggttt tgcacaactt ttttatagtc tacttaatca   66420
taaaatatac tatattttcc taacttcaga taaattagaa attattttat atattttagt   66480
ttctcattat attaaactga aatgatttca atatatgatg tagatatagt atgacactaa   66540
tttcaaatct gaaggaaaga attttgtgtt gtagaatagg aaagttatta ctttaacatt   66600
aatatttatc tgcagcagct cagatccact ggaagacagt tggtttttatt aaatcagttt   66660 tgtgattaat acattatgct ttgttatgtt tctcagagac gtccacattg acttagaggc   66720
tatattaaag ctaggacaca atgttttttcc taaggaagag ggtttctgaa gcttccctgt   66780
gaatgtacat gagaaagata aaaatactta tcaatgatta atggtatatt ctaattatct   66840
tttcaagaaa gagaatgcag cattcccctg ttacaccaag acttagttgt ttttcccaga   66900
gaagtaaaat acaaagttgg agattcgttg agtttctctt gccgttcagg acacagagtt   66960
ggagcagatt tagtgcaatg ctaccacttt ggatggtccc ctaatttccc aacgtgtgaa   67020
ggtcagtatc tgttttatat ttgatgaact aagatcagaa gtttattttt tttcctctttt   67080 tagtattccc cagttatcaa gtatgtctat aatataaaaa tcttcagaga aatgaacatt   67140
cattcagata cacagccaca tgtttatgag gttaatttga agctaacttg cttctttaaa   67200
tgtgttatcc atgtgtttac acatgcagac atgatggctg agactgatgg gatttctttc   67260
attttgccta tattaccatt agtgctggtg tttttatacc ataggccttc ccgcatattg   67320
tatagagtac gtccaaacct gtaaaagcag gttgtaatta attcaaaacc aggttcaata   67380
```

-continued

```
tctatttaaa atagatacga ggtacaatgc tgattttttt tacaatgtgg taaatgtatg   67440
ataaaatagt accagtcaat gtgaaaatca ttataatcaa cacaacaatt actgagtgat   67500
tgcatgtatc ttcaggctgt caggtttatc aaaaattctt ccacctccaa tatatttgca   67560
atgctattgc aacagttgta ttaaagttgt gaaatgtaaa tttagtgtaa atactattta   67620
gaaaagtgta aaagaaagtt atatagtgta tacatttaaa ttttctccat ttactaaaat   67680
tttagactgt aagatggaca ttttctttta tatttataca gtatttctgt aacaggccaa   67740
gtaaaatcat gtgaccaacc tcttgaaatc ccgaatgggg aaataaaggg aacaaaaaaa   67800
gttgaataca gccatggtga cgtggtggaa tatgattgca aacctagatt tctactgaag   67860
ggacccaata aaatccagtg tgttgacggg aagtggacaa ccttgccgat atgcgttggt   67920
aattaaaata attaacactt aaaaattgtt ttgcatctca tgtgacgttt taattataag   67980
taacttaagt gaaatacccta cagagtatga gagaacatgt ggagaccttc ctgcacttga   68040
gcatggctct gtccagttat ctgtccctcc ctaccaccac ggagattcag tggagttcac   68100
ttgtgcagaa accttcacaa tgattgggca tgcagtagtt ttctgcatta gtggaaggtg   68160
gaccgagctt cctcaatgtg ttggtaagta tgtgtgcata aaatggatac ttcataaagt   68220
ttaatattta tattgcagaa atatttgcta ctgtgtactt ctgaagtaag tagtcatttt   68280
ggaaatatct agtcttaaat aatatgaatc caaactttca ttgtttatat tttgatggat   68340
gtctacaggt gaacagaaat tcttaacata caatatataa aagtttgttc attaccacaa   68400
gataaatcta gttgttaatt ataaattgtc atgtgactga catgtgaata ttaacaccca   68460
agtaggtttg actatggtac aaaaaagatc attgttttta ttgtatgaga ctctcctctc   68520
aggacttgga aaggtaagaa ttaaagtctg ctaatcaccc atttcctact ctcattatag   68580
acttaccctg aagcatgtct gtaatgtttg tgtttattct acagactgca ttctaaagtc   68640
aatgtgccaa agttgggact ctccaccctg ccatcagctg tagaactcag ggattagatg   68700
ggaaacataa tcccatatat gactccactt cacactgatt ccccatgttc ctttgctgat   68760
tcagtcttaa tgagttactg gaagaatctt ggtgtctaca ttttcttttc tctgaaatgg   68820
aagtttttca ttgattgacc ttggtcatcc aggcttcact atttgttgga gttttggata   68880
ttctttaatg ccagggaaac atggagctcc tttggaacgg gcacctattc ttgtgctgct   68940
taatgatatg ctctctctgc ccagacaccc aaacttcata acagtttgcc atgtaaatga   69000 ataccttttac tacatatcaa tcataacaat ttttgctcag caagcagatt ttgccaaacc   69060
catcttcatc attgctttaa aactgtttaa cactttcata agaagaaaga tcagatataa   69120
tatcatatat aaaaactgaa tccttcattt tatattagtt tatgcttatt tttatgtact   69180
ctattgtact ctagtatttg ttcatatatc agaggtttag tttggtttat ctgcctgcag   69240
ccaccttaat atgactccag ttatgtcttc ctggattgca aagttaatgt tatgatacaa   69300 atattttac cttgacactc taccttactt ttctccaaac ccttggcttt cacctgatga   69360
ataagagatt cagaagcaaa tcaaccacac agtcaccatg cccctttgac tttcttcttt   69420
ttcctttaca gaaattggct ttgtgtgtgt gtgtgtgtgt gtgtgtgtgt gtgtgtgtgt   69480
gtgtgtacca atctttagta agggacgaat tctcaggagt ctttagtgtt tgcatcactc   69540
tatcaacatt ttaaatatta tacaactttg tctaattatt tacttttatt tgtactgtgt   69600
ttattttatt ttagatttca aattattgat aaaaattatc catgacctat acagaaatgt   69660
caaattcaaa aggactctca ttttcaccaa ataattaaaa tgtatagtac actaaaatgc   69720
ttccatatat atatacatat atccttattt aacttataaa acaaccatac aatcagaaca   69780
```

-continued

```
atttattatt ataacttaat attgctgtat tatagaataa cgtcatatga aaatatatct   69840
tatagactca tatgtagggt gtataaagga gatagatgtt gactacaagc ccctaatatc   69900
ctataccaat tctctctcat aaaatagttt gaaatatttg tattctatac aatataaatt   69960
aaatgttatt ttcttgtatc acatctatta aaaaagatgt cccgatatct tatcaacaca   70020
ttttttattt taaaattttt aacattttaa cattatgaaa aaatctgaga gtaatgaatt   70080
tgcatatttt tataggtttt aagtctatga ccaaagctgg tcatatcata atcatttctt   70140
atgtagagca tctgagaaag tgttttttta atgcttttgt aattgtctag tacccaagtt   70200
ccttcatgac acaaaatgtc tctgagacat aaatgagtgg gcatgatatc tagttcttat   70260
actataggcc actttcgcat ggtgagtctc aacattttag ttggcagaat ttatagtact   70320
aagttgtgtt tcattgtaca tttactgcat gcacatttta atgtagtagc tcactcactt   70380
cttataagtg tttttatttt tcatgaaaat attttcatac agcaacagat caactggaga   70440
agtgtaaagc cccgaagtca actggcatag atgcaattca tccaaataag aatgaattta   70500
atcataactt tagtgtgagt tacagatgta gacaaaagca ggagtatgaa cattcaatct   70560
gcatcaatgg aagatgggat cctgaaccaa actgtacaag taagttcttc ttggcattgt   70620
gttctcatga gtgttctagc cttttctcaa ctagagcagt tgtgtcttta tttacttaaa   70680 aaattttttcc tcaaatttta tgggtaaaac ctgtatttat attattttta cctctccctc   70740
ttcccactcc aactcaactc cttttgtgtc cctccaattt tatatccaat ttatgtcctc   70800
ttcttgaagt atatgtgtaa gcatacataa tatatgcata atatatacaa atgaaacttg   70860
tatatataaa ttcaacctga ttagtccatt cagtgtttct cctatgtgta tgtgctaaga   70920
ctaagtgcat gggtttcaat aacctatttg tttgctccag agagaaggct gattattcca   70980
ctctagacag ccattaatca cctgtagggg aagggtcatg tagcattttc cctatccata   71040
ctaatttgtc agttggtaat gtcatcatgg atatcttgtt gggtgaccac acttttgaga   71100
tttcatgagt tcatctactc tgccatatat gaagatatta tcttctaaca cattttctgg   71160
aaaaaatatt ttttaatcta gaggttgatt tagaaattac aatatcatgc ttgttagtga   71220
cctatagtgt aaaacacaga aacaaacttg ctcaacatgg cttttcctat gtgtcataat   71280
ggattcttac cattccacta catgtgatta atttatcaca acaaatgtgt tatgcctctc   71340
ctatgcttca tcatcatgtc tttcggtatg attgtgtgtt ctgtcagacc aaccatttat   71400
ttaactctcc taacaatcag cttacctgga aaacctcgat ttatttgaca ccttctattc   71460
tatgttactg ggcaacaggg ccattctact actatttctg cttccctatt tgtctttatc   71520
accgttgttg tggaggccct gtctcatttg atattttaaa tatttcttaa agacgaaagt   71580
tcacagaaag tatttccatg ccattctaaa attaaaccta ctacaggcat gttaatgcag   71640
tgcatgtgtt gttttgaaat tgtctatgtt aggatatcat ttctggtgtc attttgatta   71700
tagtattaag atagtaattg cttttctctt atgtatggct agctagttgt tcaaagaatg   71760
tatttactac gtagtgctga tttctattta ttccactcta cttaagcaaa aatataaaaa   71820
gaatgaaatt attagtaacc actaagaaag tacccttttca tattatgaat ctgagaggag   71880
agtctgagtg atgaatgtga ggtgtcttga ttttgtagct acgtagtgaa aaacttgtca   71940
gaagcactac attatcctgg ctgcgaacca tccgtttttca catgtgtaac tagttcaggt   72000
taaatggaat gtccagcata attgaaattt tgtacaacat agtataaacc actttgggtc   72060
acactccata ttcttgttga ccaagaacca aggttaagtt aactatcaat tgtgataact   72120
```

-continued

```
aattcttatt tgctatctga cagagtccac aatttcctaa gaaaaacgta tctgagcatg    72180
tttgtagggg cgtttctagt ttaggttaac tgaggaggaa caatacactg tatgtgtaga    72240
tggcaccatt ttatgggcag ggttcctagc ataaataaaa agagaaaggt gactgtgaat    72300
cctgagtata gatacagtat gagcaacagc ctcacatgtc tactgccatt gctttcctgc    72360
gcgatgagct aacttaaact attccttctt cttttctacc ctccttccta tcttccttcc    72420
taccttcctt cctttcttag cttcttttgt caagtgcttc atcacagaaa tgagaaaagt    72480
cactagtata tcaagtaaat gaaagtacca cttttcctaa tcaactttca tttataaaat    72540
agtccctgag gatttttaat gtaagtcaac atattagatt ataaatagtc atagacagct    72600
ctagaaaaat attcatgtaa gcttaatctt aacataatat attttttatg actcacttaa    72660
aatattttaa aatctagaaa tgattgaagt atgttttata aaaatatata aaactgcatt    72720
aaaatgaatg agaaaaaatt tggagtacaa gaattgctat attaaattgc tatacaattg    72780
aaatatgcaa aatatagaca attttttttgc aactcaacaa tcagatttat atgctaaatt    72840
ctcaatccac aatagattca cacagtaaac ttacaagcaa tcgataagga tataaactgc    72900
caacctagat gagataaatt tgcctacaga aatccatgcc aacaaccttg gcaatactat    72960
atatatatat atgtatacat atatatgtat atatgtgtgt atatatatgt atatatgcat    73020
atatagagag agacagttat taaatttcat tactaactta cttttttaatg aaaattatca    73080 cttcaataat ttaagatatt ctctttagta aagaactctg attattttt tctaggaaat     73140 gagaaaagat tctgccctcc tccccacag attccaaatg cccaagtgat tgaaaccaca     73200
gtgaaatact tggatggaga gaaagtatct gttctttgcc aagatggtta cctaactcag    73260
ggcccagaag aaatggtgtg taaacatgga aggtggcagt cgttaccacg ctgcacgggt    73320
cagtagatag gatttacttt gcaccattag aacgtaggtg aggggtgggt attgaaaaaa    73380
aaagggcata ctataaatgt tctggacaca ttattcaaat tgtgtatatt tatttctaat    73440
gtaagttttt atttcggctt gactatttca tttctgttct ctatgtagaa aaaattccat    73500
gttcccagcc ccctaaaatt gaacatggat ctattaagtc gcccaggtcc tcagaagaga    73560
gagatttaat tgagtccagc agttatgaac acggaactac attcagctat gtctgtgatg    73620
atggattcag gatatctgaa gaaaataggg taacctgcaa catgggaaaa tggagctctc    73680
tgcctcgttg tgttggtgag actgacatga aaattcaatt ttcattttca atatgtcatt    73740
accaatattc tactcttatc caagccagag agaaagaata atttaggata gcacatatat    73800
acatttatat attttactat acatttatac ttgcacacta taatctatgc tgttttagtt    73860
cattgtgcca tttctgtaga catatacttt cactcttgca ttaccgtttt taaatatgat    73920
gtattacaga ctccatgtgc tcatgtgaat tctactgttt gatttgccac caagtattaa    73980
agtccaaagt atcttttgcc taaaatgtcc tccccactcc catcccacaa tacatggtat    74040
tttctgatat ttgtaatact ttcaagttgt ttaacagatg caagacaaca gaatgtgcta    74100
ttaggaagca ctgcccacct tccttatgat gatgcatctt tcatattaac acttccttct    74160
tgtaccccta cacacagaac tgatacatac aagcaaattt ctgtattagt gcaatgtgga    74220
attgtttaac tatgtaactc tcatttgtgt cttttttcagg aataccttgt ggaccccac    74280 cttcaattcc tcttggtatt gtttctcatg aactagaaag ttaccaatat ggagaggagg    74340
ttacatacaa ttgttctgaa ggctttggaa ttgatggacc agcatttatt aaatgtgtag    74400
gaggacagtg gtctgaacca cccaaatgca taagtacatt ttaattttca ttcttttgtc    74460
tagtatataa tacaattcaa tctatatgtg gtacaattaa gaagctaagt catactttga    74520
```

-continued

```
ttccatatct cctcctatga atatgtttgt ttcccctcta agaaaaactg aagcatcctc     74580
actttggtta tccttcttga gcttcatgtg gtctgttgat tgtatctttg ggtaaactaa     74640
ggttttggac taatacccac ttatcagtga atacatagta tgtgtgtttt tttgtgattg     74700
ggttgcctca ctaaggatga tacttccttt ttttattttt attattttta tctttgttaa     74760
cttgagtatt tcttatttac atttctattg ttattccct tctcggtttc cgggccaaca      74820 tcccctaac tcctcccctt ccccttcat ataggcttcc cctccccatc ctccctctat       74880
taccaccctc ccccccaaa atcacattca ctaggtgttc agtcttggca ggacccaggg       74940
cttccccttc cactggtgct cttactagga tattcattgc tacctatgag gtcagagtcc     75000
agggtcagtc catgtacagt ctttgggtag tggcttagtc cctagaagct ctggttgctt     75060
ggcattgttg ttcatatggg gtcgcgagcc ccttcaagtt cttccagtcc tttctctgat     75120
tccttcaaaa gaggtcccgt tcttagttca gtggtttgct gctggcattt gtctctgtat     75180
ttgttgtatt ctaggtatgt ctctcaggag agatatatat caggttcctg ttggactgca     75240
ccttttgctt catccgtcat atctagtttg atggctgtat atgtatgggc cacatgtagg     75300
gcaggctctg aatgggtgtt ccttctgcct ctgttctaaa cttttgcctcc ctattccctg    75360 ccaagggtat tcttgttccc gtttaaagaa ggagtgaagc attcacattt tggtcatcct     75420
tcttgagttt catgtgttct gtgaatctag agcaattcag gcatttggga taatagccac     75480
ttatcaatga gtgcatacca tgtgtgtttt tctgtgattg ggttagctca ctcaggatga     75540
tattttccag ttccatccat ttgcctatga atttcataaa gtcattgttt ttgatagctg     75600
agtaatattc caatgtgtag atgtaccaca ttttctgtat ccattcctct gttgaagggc     75660
atctgggttc tttccagctt ctggctatta taaataaggc tgctgtgaac ataggggaac     75720
acgtgtcttt tttatatgtt ggggcatctt ttggatatat gcccaagaga cgtatagctg     75780
ggtcctcagg tagttcaatg tccaattttc tgaggaaacc ccagactgat ttccagaatg     75840
gttttaccag tttgtaatcc caacaacaag ggaggggtgt tcctccttct ccacatcctg     75900
gccagcattt gctgacacct cagttttttga tcttagccat tctcactggt gtgaggtgaa     75960
atctcagggt tgttttgatt tgcatttccc ttatgactaa agatgttgaa catttcttta     76020
ggtgtttctc agccattcgg cattcctcag cagtgaataa tttgtttagc tctgaacccc     76080
attttttagt agggttattt gtctccctgt ggtctaactt cttgaattct ttgaatattt     76140
tggatataag ccctctatct gttgtaggat tggtaaagat ctttttccaa tctgttggtt     76200 gtcgtttttgt cctaacaaca atgtcctttg ccttacagaa gctttgcagc tttaagagat    76260
cccatttgtc gattcttgat cttagagcat aagccattgg tgttttgttc aggaaatttt     76320
tcccagtgcc catgtgttcg agatgcttcc ctaatttttc atctattagt ttgagtgtat     76380
ctggtttgat gtggaggtcc ttgatccact taaacttaag ccctgtacag ggtgataagc     76440
atgcatcgat atgcattctt ctacatactg acctccagtt gaaccagcac catttgctga     76500
aaatgctatc ttttttccat tggatggttt tagctccttt gtcaaaaatc aagtgcccat     76560
atgtgtgtgg gctcatctca gggtcttcaa ttccatttca ttggtctatc tttctgtctc     76620
tgtaccaata ccatgcagtt tttatcacta ttgctctgta atactgcttg agttcaggga     76680
tagtgattcc cccagaagtc ctttcattgt tgaggatagt tctagctatc ctgggttttt     76740
tgttattcca gatgaaattg caaattgttc tgtctaactc tctgaagaat tggattggta     76800
gtttgatggg gattgcattg aatctgtaga tttctttttgg caaaatggcc atttttacta    76860
```

-continued

```
ttttaatcct gtcagtccat gagcatggga ttctttccgt cttctgaggt cttcttcaat   76920
ttctttcttc agaggcttga agttctcatc atacagatca tttatttgct tgattaaagt   76980
gacaccgagg gattttatat tatttgggac tattatgaag ggtgacgttt ccttaatttc   77040
cttctcagct tctttctctt tcatgtaggg gaaagctact gatttatttg aattaatttt   77100
aacccagcca cattgctgaa agtgtttaac aggtttagta gttcccttgg gatcacttaa   77160
atatactatc atatcatcag catatagtgt tattttgaat tcttctttc caatctgtat    77220 cctcttgatc tccttttgtt gtctgattgc tctggctaga acttcaagaa caatattgaa   77280
taagtaagga gagagtgggc aaccttgtct agtccctgat tttagtggga ttgcttcacg   77340
tttctctcca tttagtttaa tgttagctac tggtttgctg tatatggctt ttactatgtt   77400
taggtatgga ccttgaattc ctattctttt ccaggacttt tatcatgaag gggtgttgaa   77460
ttttgtgaaa tgctttctca gcatctaatg aaatgatcat gtggttttgt tctttcactt   77520
tgtttatata atggattacg ttgataattt tctgtataat aaaccatccc tacatgcctg   77580
cgatgaagcc tacttgatca tggtggatga atgtttgat gtgctcttgg attcggtttg    77640
ccagaatttt ttgagtattt ttgcgttgat atttataagg gaaattggtc tgaagttctc   77700
tttctttgtt gggtctttgt gtggtttatc catcttgacc tgggctcttt ttggttggga   77760
gacctttaat gactgcttct atttagttca gagttatggg gttgtttaaa tggtttatct   77820
gttcctgatt taactttggt acctggtatc tgtctaggaa attgtccatt tcctgcagat   77880
tttcaagttt tgttgaatat aggcttctgt agtaggatct tatgattttt tgaatttctt   77940
ctgattctgt agttatgtct cccttttcat ttctgatttt gttaatttgg acacactctc   78000
tgtggtctct cattagtctg actaagggtt aatctatctt gttgattttc tcaaagaacc   78060
agcttttggt tctgttgatt ctttgtatag tccttttgt ttctacttgg ttgatttcag    78120
ctctgagttt gattattttc tgccttctac gcctcctggg tgtatttgct tcttttgtt    78180 ctagagcttt taggtgtgct gtcaagctac tgatatatgt tctctcctgt ttctttctgt   78240
aggcacttag agctataagt tttcctctta gcaccgcttc cattgtgtcc cataattttg   78300
ggtatgctat actttcattt tcattaaatt ctaagaagtc tttaatttct ttatttcttc   78360
cttgaccatg ttatcattga gtacagcatt gttcaacttc catgtatatg tggacgttct   78420
tcccctattg ttattgaaga ccagctttag cctgtgatgg tctgatagga caaatgggat   78480
tatttctatc tttctgtatc tttttgaggcc tgttttatga cttactacat ggtcaatttt   78540
ggagaaagta ccatgaggtg gtgagaagaa gttatatcct tttgtttttag gatagaatgt   78600 tctataaata tctgttaagt ccatttggtt catgacttct cttagtctgt ctatgtctct   78660
gtttaatttg tttccatgac ctgtccattg atgagagtgt gtgtgtgtgt gtgtgtgtgt   78720
gtgtgtgtgt gtgtgtgtgt gtgtgtgtgt aatctactat cattgtgtga ggtgcaatgt   78780
gtgttttgag ctttagtaag gtttctttta tgtatgtaga tgccttgtat ttagagcata   78840
gatacttagg attgagagtt catcttggtg gattttttcct ttgatgaata gaaagtgtcc   78900
ttccttacct tttttgatga cttttagttg aaaatcaatt ttatttgata ttagaatggc   78960
tactccagct tccttcttca gaccccttgc ctggaaagtt gttttttcagc ctttcacact   79020 gaggtagttt ctttctttgt ctctgaggta tgtttcctgt agacagcaga atgccaggtc   79080
ctcattgcat atcaggttca ttaatctatg tcttttttatt ggggcattga gacgtttgat  79140
attgagagat attaaggaat actgattatt gcttcctgtt atattcatat ttggatgtga   79200
ggttatgttt gtgtgcttttt cttctctttg ttttgttgcc aagacgatta gtttcttgct   79260
```

-continued

```
ttttctaggg tgtagcttgc ctccttttgt tgggctttac catttatcct ttggagtgct   79320
gagtttgtag aaagatattg tgtaaatttg gttttgtcat ggaatatctt ggtttctcca   79380
tcaatgttaa ttgagaattt tgcaggatac agtaacctgg gctggcactt gtgttctctt   79440
agggtctgta tgacatctgt ccgggatctt ctggctttca tagtgtctgg tgagaagtct   79500
ggtgtgattt tgataagtct gcctttatat gttacttgac attttttcctt actgctttta  79560 atattctttc tttattttgt gcatttggta ttttgactgt tatgtgatgg caggagtttc   79620
ttttctgatc caatatattt ggagttctgt aggattcttg cttgtttatg ggcatctctt   79680
tctttaggtt agggaagttt tcttctatga tttttgttgaa gatatttact ggtcctttga   79740
gctgggaagt cttcactctt ttctatacct atttatcttc tcattgagtc ctggatttcc   79800
tgtatgtttt ggaccagtag ctttttttccat tttacactat ctttacccctt gtgtcaatga  79860 tttctatgga atcttctgct cctgagattc tttcttctgt ctcttgtatt ctgttggtga   79920
tgcttgtatc tatggctcct tgtctcttcc tttggttttc tatatccagg gttgtttcca   79980
tttcagcttt ctttattgct tctatttccc tttttaattc cttcacctct ttgattttgt   80040
tttcctggaa ttctttctgg gattttttgtg attcctctct ataggggtct acttgtttat   80100
ttatgtttta ctgcatttct ttaagggagt tcttcatgtc tttcttgaag tcctccagca   80160
tcattatcaa atgtgatttt aaatctagat cttgcttttc tggtgtgttt ggatattcag   80220
tgtttgcttt ggtgggagaa ttgggctctg atgataccgt atagtcttgg tttctgttgc   80280
ctgggttcct gcgcttgcct cttgccatct agttgtctct ggttttatct tctgctattt   80340
ctaacagtgg ctagaccttc ctatagggct atgtgtcagg agtgctgtag acctgtttcc   80400
cttttttcgt tcagctagtt gtgggaacag agtgttctttt agggtgtgta gtctttcctg   80460
cctagtggtc ttcgctgttc ctgtgggact gtcctgagtc caccaggcag gtcacttgga   80520
tcagaaaagt tggtcttacc tgtggtcctg tgtctcaagt tgctcgtggg gggctgcttt   80580
tgagctctct gtgagggtgg caaccaggag ggtctgtgca gcctttttcca tgagccccccg  80640 agtactgggg tcccagacgg cattaggtgt tttcctctgg agtctgaaat gtgggcagag   80700
tgtagtctct tctggcctcc caggcgtgtc tgccctctg aaagtttagc tctctctccc    80760
atgggatttg gctgcagaga gctgttgatt ggtcccttca ggtcaggtgg gtatctggat   80820
cccaggggac ctgctgctcc agtgcccctg tcttccattt cccagagact gtatacagtt   80880
tcctcttggg ccagggatgt gggcaggggt gggcagtatt ggtggtctct tctgctctgc   80940
agtctcagga gtgcccacct gtccagatgg tgagctctcc ctcccacagg atttgggtgc   81000
agagagctgt tgatccggtc ctttcaggtc caggcgatgt ctggagcaca ggggacctgc   81060
agctccagtg cccctatctt ccagttccca gaggccgtat acagtttcct cttgggccgc   81120
ggatgtgggc cggggtgggc agtattggtg gtctctccct ctctgcattc tcaggagtgc   81180
ccacctgtct gggcggcgag ctctctctcc caggggtttg ggagcagtga agtgtggccg   81240
ggatcagcga gattcgggct ccagctaaaa accagaagtg tcctgttcca gaggaatttt   81300
gcctcagtgt gtcctgagtc caccaggcag gtcgcttgga gcataaaagt tggtcttacc   81360
tgtggtcttg aagctcaagt tgcttgtgag ggggctgctt ttgagctctc tgtgagggcg   81420
gcaaccagga gggcctgcac cgcctttttcc tggagccccct gtgcaccggg atcccagatg   81480
gcattaggtg ttttcctctg gagtcagaaa tgtgggcaga gtgtagtctc tttttgcttc   81540
ccaggagtgt ctgcccctct gaaggtttag ctctccctcc catgggattt gggtgcagag   81600
```

-continued

```
aactgttgag cagtcccttc aggtccgggc agcatctgga acgaggggga cctgctgctc   81660
cagtgcccct gtcttccagt tccaggaggc cctatacagt ttcctcttgg gccacggatg   81720
tgggcagggg tgggcagtgt tggtagtctc tcccactctg cagtctcagg agtgcccacc   81780
tgtctgggtg gtgagctctc tgtcccacag ggtttgggag ttgggagctg tgggccggga   81840
tcagtgaggt taggaggatg atactttcta gttccatcca tttgcctatg aatgtcatga   81900
atcattgttt ttagttgctg agtaatactc cattgtgtag atgtaccaca ttttctttat   81960
ttattccact gttgaggaac atctgggttc tttccagctt ctggttatta taaataaggt   82020
tgctatgaat ataggagaat atgtgtcctg gttatatgtt ggaacatctt ttgggtatat   82080
gcccaagaga ggtatagctg ggtactcagg taggtcaatg tccaatttc tgaggaacct   82140 ccagactgat ttccagaatg gttgtaacag cttgcaatcc caacaacaat ggaagagtgc   82200
tcctctttct ccacatcctt gccagcatct gttgtcacct gagtttttta tcttaagaat   82260
gtccattcag atactgcccc acctggggat ccagccaata tatatacagc caccaaaccc   82320
agtcactata tgccaagagc tgcatgctga caggaacctg gtatggaagt ctcctgagag   82380
gctctgccaa agcataacaa atacagagat ggactgagaa ctgggtgcat attggaggag   82440
ttagagaaag gattgaagga gctgaaggtg tttgcaaccc cctaagaaca acgatacca   82500 ccaaccagag ctttcaggaa ctaaatcact gtccaaagag tacacatgga cagacccatg   82560
gctccagttg catatgtagc agaggatggc cttgttggcc accaatggga ggagaaaccc   82620
ttggtcctgt caaggctcat cctccaaccc tttcctatct gacattccca ccccccccc   82680 cagtttaggc gactgtaaga taggaaaggg ttggaggatg ggcaggggaa caccctcata   82740
gaagaaagtg gagagggaat gggacagggg gtttgtgggc aggaaactgg aaagtgggat   82800
ggcatttgaa atgtaaaaat aaaaatatcc aataaaaaaa ctaatgaagg agaatcgggt   82860
atagttaaaa aaaaaagaa acgaagccat aattctagca tataaaaagt ttttgctgca   82920
taatttgaat gctggaagac aaatacgata tgagtcaaaa caaaattttt cctttccagc   82980
ccacctaagt tgttttttgtt ccatgtagtc tgagatatct gaattatcag aattctcaga   83040
atccaggaac acacaggctc ctctaaacag tctcatcact acaatgacag ttttagagca   83100
atgccactac aattacatat gctctaaatt tttcaaataa ttatgagtaa gttacatttt   83160
ataaagtcaa acataaatac tctaattttg gaaagtacaa gaaaaattga atgcaaaatt   83220
taaaatttca aaaattataa ccatcaggat tctgtgtcta tcttatttat tttcataaat   83280
atagaagaac gtcagtgtaa ctaagtaaaa aatggaaaac ctactgtatg tattgttttc   83340
tatgaagtta actattgttt catatatcgt atgttctaca acttcctgaa aacaaacacc   83400
cacatactct tttattttt taagaaactg attgtgacaa cttgcccaca tttgaaattg   83460
ccaaaccgac agaaaagaaa aaaaatcat acaggtcagg agaacaagtg acattcagat   83520
gtccacctcc gtatcgaatg gatggctctg acattgtcac atgtgttaat acgaagtgga   83580
ttggacagcc ggtatgcaaa ggtatttgaa tgggtttta acatgcattt attctagtgt   83640
caaagaatga cataactgaa aatggtgcag agattacttt taaagtaaga tcaagtttgt   83700
ttgtatcaaa taataaaagc attgaattaa aaaaactgat ggctaagctg atagcatgat   83760
ggtgttcaga gtttgatttc atggtcagca tcatcagtat cattagaata caaacatttt   83820
gaaaatgtaa attaacagct aggagtacat gctagatatc ctaaatagga cgacatctaa   83880
agatgagacc ttcaatctcc ttttagggat ctgtgtatga ctaagtttgg aatgtgctgt   83940
aggctgtcaa tatttgttaa tatgttgtta aataattagc cttcaattga aatcttgctt   84000
```

-continued

```
atatctcatt ttatcaaatt cattggaata ttaggatatt ttatttgatt atcactttct   84060
tatgactata ttattcttaa aacaatgttc tttttcctct aacattgcaa atagattttt   84120
ttctcacata atacatatcc tgattgtttt ctcttccctc cactcatttc agctccttcc   84180
tacccctttt ttcatctaat ttttcccctt tctgtatttc aggagaaagg aaagtcttct   84240
aaggagtaat actaataaaa caaaaatgaa acaaatacag taggaggtaa caaacaaata   84300
attttaggga aaacagcata agaaaataga taagaaacaa aatagacaaa atgtcccact   84360
ttatacacct aggaatccct taagaatact cacctgaaaa ccataatata tattgaacag   84420
catgcaaagt accttcctgt accaaagatg cttcccttag gggtgaaggc tctatgtagg   84480
catcagtgac actttgctat gatcagtgag ttgcatattt gttgtttttc acagtgtaga   84540
cttgccttca ggttgtgtgg tataatctgt agtcttctca acagcctgcc tgtgttattc   84600
ggaagtttcc atgtgacccc tctggtacac atttaattag atgtaacctt atcacagtac   84660
tagaagcttc attagtgaca tgatatgtcc ctcggggctc tgtctcctta cactttttggt   84720 gattgcactt atatttcctt tatatatgta tgtattttag aaagcttata ttgaattagg   84780
ttttgataat atccctcaaa tgacacttaa cttttgctgt tcctctctgt attctgattt   84840
ttgtctaccc ttcttgacat ccataactat ctactctatt tctccatcct aaggagacag   84900
tactttgccc ccaattcctt aggcctacac ctaaattctg ttgttctgtg gattgtaaag   84960
tgactttcat tggctttcag ctaatatcta catatcagca aatatataca tgtgtgtctt   85020
tctgggtctg agttcttcac tcaggatgaa tttttgtcta ttacccatca tttacctgtg   85080
acattcatga tttcatttttt gcatgtaaat aaatgtagca aattttcttt atccattcag   85140
caagtcagaa atatatttgg aatcttatgc attaattgga cactcaagat gagcaaatag   85200
gtactaatac tttatttttac tctttagata attcctgtgt gaatccacca catgtgccaa   85260
atgctactat actaacaagg cacaagacta aatatccatc tggtgacaaa gtacgttatg   85320
actgtaataa accttttgaa ttatttgggg aagtggaagt gatgtgccaa aacgggattt   85380
ggacagaacc accgaaatgc aaaggtaggg catcatttcc cctaatgttt atttgacaat   85440
gcaatttagt tattgtacat tagtgaaagg aaactgaagc aattttttaaa ctttttttaa   85500 cttttacaat tattttattt atttacatcc caaatgatgt cctctccctg tccccactcc   85560
aagaactctt tccccatac ccctctactt cacctctgag atggtgctta cccatccctc   85620
ttgcctgggg catcaatttt ttaaaggatt aggtgcatcc tatcccttcg aggccagaaa   85680
agggagtcct ctgctatatg tctgccagga gcttgtaatt agcctctgta tgctctttgg   85740
ttttgtggca tagtctgcga gctgcaagtg gtgagtggtc catgttagtt gacactgttg   85800
gtcttcctat ggggttccca ttcccctcaa cttctttaat acagccctg acacttccat   85860 aggtcaactg ctggtagagt ttattagagg aaagccatgc taggctcctg tctgcaagca   85920
caacatagca tcagtaatag catcagtgct tggtgaccct ccccacctcc atgagacaga   85980
actcacattg ggccagcaac tagtcaataa ttccttcagt ctctgctcct tttttgtctc   86040
tgcatttctt tcagagagga acaatttgga gtcaaaattt tgaagttggt ttggttgtca   86100
cacccctcct ctgggtgtcc tattgaacta ttggacttca ggttcctctt cccaccattg   86160
agtattttgc ttaaggtcac ccacattaaa acctgggagt ctctccaccc tgggtttcta   86220
ggattttaag cagtttctgt tgattccctg tctctggaaa atttatgttt ccacttattt   86280
ttctggtctg ctgggcttct cttccgtttt gccccatatc tgaccctgcc ccaccccatg   86340
```

-continued

```
ccccgttat cccttccct cccttctccc acctaggtaa ccccctccct ctacctccca   86400
tgattatttt gcctcatatt ctaaggtaaa tttgaagcat cccacatttg ggctttcctt   86460
cttgtttaac ttcttaagct atatgggga accccatggg aattctggac ttttaacta   86520 ataccctta ccaatgagtc cataccatga atgtcctttg agtcttggtt tctcagtcaa   86580 aataatttt ctttcttt tatattttgt ttactcttt ttacactcca aatttattc   86640 ccctctttgt ccaccctccg actgttccac atcacatatg tcctcccttc ccctgcccct   86700
gccttccatc taggaggatg tccctacac cccacccac ccccagatct ctaaactccc   86760
tggagcctcc agtctcttga aggttaggtg catcttcttt gattgaacac agacctggaa   86820
gtctagtgct gtatatttgt tgagggtctc atatcagctg gtgtatgcta ccaggttggt   86880
ggtacagtgt ctgagagatc tcaggggtcc aggttagttg agacagctgg tcttcctatg   86940
ggaccaccct aatcatcatc ttctttcaag catttcccta attcaaccac atggatcagc   87000
atcttctgtc cactggttga gtctaatatc tgcatctgaa ttttccagct tcttgttggg   87060
tctttcgggt ggcagtcatg agaggtccct ttttgtgagt gctccatatc cttagaatta   87120
ctgtcagacc ttatagcctc cccttgagct gggtcccaat ttgggcctat caacagattt   87180
cctttccctc aggctcttct ccatttttgt ccctgtagtt cttacagata ggaacatttc   87240
tgagttacag ttttttttgac tgtgggatag caaccccatc cctccacttt atcctttctc   87300
ttcctactgg aggtagactc tacaagttcc ctctccccac tgtagggcat ttcctctaag   87360
gtcctgcctt ttgggacctg agagtctctc atggccaagg tgtctggtaa tttatatagg   87420
gttccctcca tcttctacct ccagaggttg cttatttcca ttttttttctg ctaacccaaa   87480 ggacttcagt cctgtttttcc ctgcctccaa tatgtgatca tgtcatcctt ttcactcgct   87540
catccaagta cctctctctc ctgactgccc catgattgca tggggtgttc aaatctccta   87600
ttattattgt gtgaggtgtt atgtgtgctt caagcttcag taagttttt tttaataact   87660 gtatgttgcc ttgcatttgg agaatagata ttcaggatta agagttcatc cttggtagatt   87720 tttttccttt gatgaatatg aagtgtctgt tcttatcctt tttgataact tttggtagaa   87780
agttggtttt atttgctatt agaatgtcta ctccaacttg tttcttggaa ccaaatgctt   87840
ggaaaattgt ttttcagcct tttattctgc ggtagtatct atctacagtc actagagtgt   87900 gtttcctta ggcagcaaaa tgctgggtcc tctttctcta tccagtctgt tattggggaa   87960
ttgggtccat tggtgttaag agatattaag gaatagtgat tgttgttgtg tagctctctt   88020
cttttggttt cgttgtaagg agattacttt cttgctttt ctagggtgta gtttttnntg   88080
tggaaatata ttgtataaat ttggtttggt catggaatat ctttttttctc cacctgtgtt   88140 aatcaaaagt tttgctggat atagtagcat ggactggcat ttgtattctc ttagggtttg   88200
tatgaaatct gcccagtatc ttctggcttt catattctct ggtgagaagt ctggtgtaac   88260
tgttttaggt ctgtctttat atgttacttg accttttca cttactgctt ttaatattct   88320
ttcttcgttt tgtgcatttg gtgttttgtc tattacgtga caggaatttc ttttctgttc   88380
aaatctatat ggaattctgt aggcttcttg tatgtttatg ggaatttctt tctttaggtt   88440
agggaagttt tcttctataa ttttgttgaa gatattactg gccctttatg ttgggagtct   88500
ttggtctctt ctatgcctat tatccttagg ttgatcttct cattgcttcc tgaagtttct   88560
agaggttttg ggttaggagc tttttgcatt ttacattatc tttgacattt gtgtcgatgt   88620
tttctatggt atcttctgcc cctgagattc tctcttctat ctcctgaatc tctgttggtg   88680
atgcttgcat ctatgactcc tgatctcttt cctaggcttt ctgtctccct ttgtgatttc   88740
```

-continued

```
cttattgttt ctatttcaat ttttaaatcc tgaatagttt tgctcaattc cttcacctgt   88800
tcggttgtgt ttttctgtaa ctctttaagg aatttttggg tttcctcttt aagggcttct   88860
gcttgtttac ctgcattgtc ctgtatttct ttatgggagt tatttatgcc cttcttaaag   88920
ttctctatca tcaccatgag atgtaatttt aaatccaaat cttgctttc cagtgtgttt    88980 ggacatccag tattttcttt ggtgggagaa cttggctctg atgataccaa gtagtctttg   89040
tttctgttgc tttggttcct gtgcatgctt cttcccatca gtttgtctct gctgttagct   89100
tgtcttgctc tctctgacag tggtttgacc ctcctgtaag ctatgtgtca gcattcctgc   89160
agacctgttt cctttcagtc agatctggga agagagagct gttcctggtt gtgtgtcctg   89220
aagcctccaa gagggttgca tggagcagaa gagttggttt tacctctgtt ctctggtgtg   89280
tcagggctcc aggctattgg ctttcagctc tgggctcagg cagaaaccgg attgattctg   89340
cccctgacta ttcctaggtt cttgtattca gagggctcta gacagatttc tcttgggaca   89400
ggaatgtgag cagaagtggg ggtcttccct gatctctcag gattgtctgc acttctgagg   89460
gtccagctgt ctccctcaca ggatttgggt acagagaact gcaggacctg ttcaggacct   89520
tgtgcaggca gaaactggta gtggactgtc caagaagact tctgtctttg tgtgtcctga   89580
ggccaccagg tgtccacttg gagcagaaga gttggtctta cctctgctct ctggtgtgtc   89640
atcactcctg atgactggct ttcagttttg ggtgcaggca gaaacaggaa gagacctgcc   89700
cctgactgct ctaatttctt gtgcccagag agcagaggag gcactagaca ggttcctgtt   89760
gggccaagaa tgtgagcaga agtcggggtc tcccctgagc tctcaggatt atctgcactt   89820
ctgagggtcc agctgtctcc ccgataggat ttgggtacag agaactgcag gaccagttca   89880
ggtccttgtg caggcagaaa ctggaagtgt actgtcccag actgctcctg cctttgtgtg   89940
tcctgaggcc accaggcaga tttcttggag cagaagagtt ggccctccct ctgctcttag   90000
atgtgcaggc gctcctggaa accgactttc agctctggat acaggcaaaa accataagtt   90060
tcctccgctg aatgctccca ggttactgtg cttagaggtc acagagggca ctaggaaggt   90120
tcctgttggg ccaggaatgt gagcagaggt ggggtctct cctgagctct cgggattgtc    90180
tgcacttctg agagtccaat tctctctccc acgatatttg ggtacagaaa tgtgggacca   90240
ggtcagccct gggtgcaggt gcctatttct attattctta gatttgatat tttcattgta   90300
cctggatttc ctggatgctt catgttgcaa gatttttatg tcttgacttt tctttgacag   90360
tgtgtcaata tcttctaaaa tatcttctac atctgaaaat tctatataat atctcttata   90420
ttctgttgtt gatgctttca tccataattc ctgacctctt ttctaggttt tccaattcaa   90480
gcactgcctc tctttgtgtt ttctttatag tttctacttc cacttttagc tcttggacca   90540
cattcttcaa ttgcttcacc tgatttcttt cttttctttc ccccctgtat ttctttaagg   90600
aatttatttg tttccccttt aaaggcttct acccgtttac ctatgttttc ctgtttgtct   90660
ttccatgact tacttctatc ctctttaaag gatgctatta tcttcatgga tagtatatta   90720
ggtcagcttc ctgttttca agtttgttgt tgcacacaag gcttgctgaa gtgagagaat    90780
tggtttctga tgacgccaaa gtatattgac ttctgtttct tatggtcttg ggcttgcctc   90840
tagcaaactg gtcatctctg gtgttagctg ttctgggtgt ctctgtcttc atcctacttc   90900
ctatgtccct gggttgctag agttctctgg gtaggcttgt gtttctggct gtagctgacc   90960
actggtgaag acttcagaat gtgaggtctt aatagggggca tgtacactag tgacctgctg   91020
ccctggctac agagacaatc tgctgatctg ttgccctgtg tgcagcagat ctctttggag   91080
```

-continued

```
gccttcagac tgtggggtct gttgctcagt gtgtagcaga attcgcggag gacttcacac   91140
tggtcagtta tcctgcatgt accagaactc gtgagaggcc ttcagactgt agtatcttta   91200
gaggagcaga caagctgatg atctgccatt gcagaaggtg caggatggaa agcattcttg   91260
tttgggaggg tccccttactt attgccctgt gtgctgcaga actcctgaga ggccatcagg   91320
ctgtgatacc ttcagaagag cagccaagct ggtaggggtc ttatttctct ttttatttct   91380
tgttttggag gagtggttct caagaattta acagtggcat gcatttttat tactttttgaa   91440 cacatagtct gagtatgcta tctctaatag tttcctaacc atctgttact caagtcaacc   91500
aggctgatat tttatataag tagaaactga acttatcttc aaaatccaat tacatttttcc   91560 attttttgtg ttttccttaa aaattccttc ggagttttct cttacatata ttaaatgcca   91620 cccttttta ttttattt tttcagagtc catgatttat ttgtttactc tccttcctgg   91680
gattgccctt tcaataaatc cccttttcttt gcttttcatt gttattcatc aattttttct   91740
tcttattatt ttatttactt acattccaaa cattggcccc cttcccagta ccatatcctc   91800
aagttattca ttgtccccct ttccttttgct tctgagagtg tgctccctga cacacccacc   91860
tacctacacc tcacccctac cagcatccct tctcccctct tttcagattt ctacaggatt   91920
tggctgttcc tctcctactg aggtcagata aggcagccct ctgccacata tgtaccagga   91980
gctatggatc agtccatgaa tactctttttg ttggtggctt agactctggg atctctgagg   92040
tgttctggtt atttgatact gttgttcttt ctgtgatacc acaatcccct tcagcaccat   92100
caatcctttg cttaactcat ccatagacat cccagacctc attcactgtt ggctgtaaat   92160
atttccatct gtttcagtca gctgctaaat agagcctctc atgggacagc catgctgggc   92220
ttctctctgc aagtacaaca tggtgtcaaa gtttggtgcc tatacatggg atgcatctca   92280
agttgagagg gtcactggat gggctttcct tcaggctctc cacaattttt ctccctgtgt   92340
ttcctttaga caggaacaat tcttggtcga acatttataa ggtgactggg tgaccccatt   92400
cctcaactgg gtgccatgtc tacctactgt tggtctcttt aggttccaac tcctcacttt   92460
tggacattct gattaagctt atccccattg gatcctaaga gcccccctctc atatctttga   92520 tgtctgagtc tttctaggga ttctccagtt cccccaacca ttcactggtg catatttctg   92580
ttcattcttc tggccctcta gaattctgtc ctgtgtcccc ccatatttta tccagacctt   92640
cctcttctcc ctcctcatcc cctctgccat tcatgtccct ccctccctct gcctcctatg   92700
attattttta acactcttct tatatgcaag ttttcacttg aaacacaaat ctaattttat   92760
gaaaacaaag atcacctact atatagccct aatcttacag ttaaatttgt cctactctta   92820
atttttattt ttcacttata taatgaattc tggtagttat tctttaggga ggactctctg   92880
atggagataa atcccctttta tctctttttat ctgataatgt ctcatcaatg tctttattca   92940
aaaggcaaac aacacaggat atagaactta aggcttacac tcattttctt ttccttacta   93000
tggtctgcat ggtgagagga taggagtcac tttctttggg atctgggtcc agtgtggttg   93060
atgatgactt cctactgatt tttgtccaag atgttttctt taagcagttt cagtagagag   93120
atctccagga gtttcatggg acttgtccta tttgactttta ctcagttctt gaatatgtac   93180
agtcatctat tatggagaat tgttttcatt ttccttcata gtaaaacatt aattttgctt   93240
gaatattgaa tattttgttt ttacctaaaa atatttgaat tttttttcagt ttcatgatgt   93300 tcctcttgag gtcatactga acataatcag tacttttgat ttcatatttt tcctgtgtcc   93360
tcacaagaac aatcagtagt ctaaaagaaa aacatataac acaacagtgt gacattagat   93420
gagtttggaa tttctttgct agaatttttca atgtctcatc tcttcatata atgtttacta   93480
```

-continued

```
aaaattctat gtccaagctt ttcagatata cctagttaaa gtatatcata gatgtctatg  93540
cttattttaa ccatatcaga aacccagaaa acctcattag ccttctgtta cattataggc  93600
tttcaagtct tgtttttaaat gtacttatac aaaatgataa agagtgggaa tatatacagt  93660
catatactat tgagtttctt caaaaaaaaa tgcctatcta cattggccat agcacctaat  93720
ccttctcagg ttcagaagct gttaagagat ttactactac ttgaagtttt caggcagaca  93780
tgtttgctgt agttaagaaa tgtttcaggt gagaaaaaaa gaagaacttg taactctcag  93840
tttatatgat taatctttct tcaaataatc atttatacag ccagaaatca ctaaagactt  93900
aatacttaat gttttttggtt ctgcttgagc ctgtagtttt acttgatatt caaacattca  93960
aatgttgtct ccttagattc aacagggaaa tgtgggcctc ctccacctat tgacaatgga  94020
gacatcacct ccttgtcatt accagtatat gcaccattat catcagttga atatcaatgc  94080
cagaactatt atctacttaa gggaaataag atagtaacat gtagaaatgg aaagtggtct  94140
cagccaccaa cctgcttacg taagtacctt attcacatag attataagaa attctgtttt  94200
atattgtggg tattttttctg tttataatat aacattcaca aaataaaagt actgttttgt  94260
ttgtgtttca gtatcaaaca tcagcatgtg ataaaacaag attattagat tctttttata  94320
aaaaatacct gttaaataaa attgtatata ttattcttaa taattgtttt tttctaatat  94380
gtattaacat ctacaaaact gggtgccagc ataacattat ataactgttg tctcagtcag  94440
tgttctattg ttttaaagag gaactatgac catggcaact ctttttaaaag aaaccatttg  94500 ttgggggttg cttacaattt tggaaattta ttctactctc aacatgtttg ggagcatggt  94560
ggcacagagg taaacatgat ggtgaagaag tagctaagta ttccatatct ggctctgcag  94620
ggagcagaaa gtgataggca tacttctaac aagtctatgc aaactcccac aaggccgtag  94680
ccataatact tcacaagtac caccattctc caatgaaaaa tctgtatgtg tatctatgga  94740
ggtcattcct tttcaaataa gcacatctgt atacatcttg cagttattaa atccatacaa  94800
catctccttt ccttagataa ggcaactgac atctattaat cactgttatg cattctaaag  94860
taattctctc tgtgagaaag agcacaaagt agttgtctttt ctgtgttggt tatatttgac  94920
ttaatgtcct tcaatgccct tttctaagta aaataataaa atatatcttt aatgacttaa  94980
tattttacat ttaaatatac catgatgtca ttataaattc accaattagt attagttcag  95040
ctttcttcac cttaccaact tccatgtagc agtttagaat aaacatatag atccaggttg  95100
agtactttga ttttatttcc tttgcgtaca ttccagaaga aacaatagga acaatacata  95160
aatatctatt tttaaatttg taagaaatct caatttttat ccatagtaac ttcacaaaat  95220
catattcctg tcaatggttt gtgaagtgtt caccacacac taatgagcag ttgtaatttt  95280
tagggctcct tcctctggtg ctactttaac tgagttaaaa gatatcttac tatggctttt  95340
caatggaatg acagcaatga tatttatgtg tttttcttag aagtatctat tcatttatcc  95400
agatttgatc agcttatttt tcctttaaaa tgtgctttac cacagactaa tatagttcag  95460
cgaaaggtta tcagcagact ggaatatttt tcaattattt aagtataatt tatgacagat  95520
atagtgcaaa gccttttcac aatcaattta ctaaaaaagg tgttctaact tctaacagac  95580
cagcaaggcc caaagcaatg aaatcaaatt atataaaaac aaaacaaaag caaataaata  95640
tatttatgca ctttgtacga aatggaggtc acatctttat gctttcttga cccaggacac  95700 cccctaaaa gatatgtaaa tacctaaaaa taaagaatag acaaccatat acttcaatta  95760
aacttgctgc caatttctta ggtgtattga ctatgctctg tgatatgcac cagtaccaca  95820
```

-continued

```
atgggatcaa atccacaggt caaagtttgc tttttgcctt gtgatttgga gtcccagcca   95880
aacacacagt gtcaaaacca tgaaatgttt ccctgttgtg cttcctgata ctttcagtgg   95940
tttgttctta tatcaatgtc tttgaccaaa tttcagttga atttgcccat aatgacaaac   96000
agatataaaa tttcaatcat cgccatatgg atatcaatta tcattttatc atttattaaa   96060
tatgatatca gttcattaac ataagttttg ggaaagttta ttaagatcag taacctgtag   96120
atgcatagat caattttcaa atcacttttc tcattcattg gagtcttccg agtgttctgg   96180
ttactgtggg gttcctggtg tatattgaaa taaagtatta tggtatctcc tgattttcc    96240 tttctgttct agttacagtt gtctattcat tctattgtag ttccatacaa gttttagatt   96300
tttatcccta ttagtatgaa aaatgttatt gatatttcag tgtcagctca cagagtctgc   96360
tattagccat aggatatgtg gacatgtcta tacctatatt aattcttaca acccattaat   96420
atacaagctt tctctatttc tgtcttttca gattatttta ccagttaact aatatttttg   96480
attgaagttt tcacttctgt ttataaattc atagctgaat taattttgaa gatactgaaa   96540
atgacattgc atttatagtt aattctcaga aaaatggaat ttttctatag aaaggggtg    96600 atttctgtag gtttatatat taattgttga actttggtaa tttatctttc agatgcatgt   96660
gtgataccag aagatattat ggaaaaacat aatatagttc tcagatggag ggaaaatgca   96720
aagatttatt cccaatcagg ggagaatatt gaattcatgt gtaaacctgg atatagaaaa   96780
ttcagaggat cacctccgtt tcgtacaaag tgcattgagg gtcacatcaa ttatcccact   96840
tgtgtataaa atcgctatac aattattagt aaaccttatg gatgaacctt gtttttagaaa  96900 tgcacatgta tattactaat acagtttgaa tttacatttg aaatattgtt tagctcattt   96960
cttctaataa gtatataaac tttttttata tggtggttaa tcagtaactt tacagactgt   97020
tgccacaaag caagaacatt gcattcaaaa ctcctaatcc aaaatatgat atgtccaagg   97080
acaaactatg tctaagcaag aaaataaatg ttagttcttc aatgtctgtt tttattcagg   97140
acttttcaga ttttcttgga tacctttgt gttaggttc tgattcacag tgagtggaag     97200
acacactgac tctgacttca aattagtatt acttgccaat acataacaac caaactatca   97260
taatatcaca aatgtataca gctaattact gtgtcctacc tttgtatcaa taaagaaatc   97320
taagaaag                                                           97328
```

<210> SEQ ID NO 5
<211> LENGTH: 146
<212> TYPE: DNA
<213> ORGANISM: Rattus norvegicus

<400> SEQUENCE: 5

```
tcttcgagtc aactgctccc agatagatcc aagacatgag actgtcagca agaattattt      60
ggcttatatt atggactgtt tgtgtagcag aaggtaagct taaaaccacc acctttctcc     120
cttctgactg agccgcatta taaaac                                          146
```

<210> SEQ ID NO 6
<211> LENGTH: 4176
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Start Codon
<220> FEATURE:
<221> NAME/KEY: misc_feature -continued

```
<222> LOCATION: (10)..(30)
<223> OTHER INFORMATION: 5' NLS
<220> FEATURE:
<221> NAME/KEY: misc_feature
<222> LOCATION: (4126)..(4173)
<223> OTHER INFORMATION: 3' NLS
<220> FEATURE:
<221> NAME/KEY: misc_feature
<222> LOCATION: (4174)..(4176)
<223> OTHER INFORMATION: Stop Codon

<400> SEQUENCE: 6
atggacaagc ccaagaaaaa gcggaaagtg aagtacagca tcggcctgga catcggcacc          60
aactctgtgg gctgggccgt gatcaccgac gagtacaagg tgcccagcaa gaaattcaag         120
gtgctgggca acaccgacag gcacagcatc aagaagaacc tgatcggcgc cctgctgttc         180
gacagcggcg aaacagccga ggccaccaga ctgaagagaa ccgccagaag aagatacacc         240
aggcggaaga acaggatctg ctatctgcaa gagatcttca gcaacgagat ggccaaggtg         300
gacgacagct tcttccacag actggaagag tccttcctgg tggaagagga caagaagcac         360
gagagacacc ccatcttcgg caacatcgtg gacgaggtgg cctaccacga gaagtacccc         420
accatctacc acctgagaaa gaaactggtg gacagcaccg acaaggccga cctgagactg         480
atctacctgg ccctggccca tatgatcaag ttcagaggcc acttcctgat cgagggcgac         540
ctgaaccccg acaacagcga cgtggacaag ctgttcatcc agctggtgca gacctacaac         600
cagctgttcg aggaaaaccc catcaacgcc agcggcgtgg acgccaaggc tatcctgtct         660
gccagactga gcaagagcag aaggctggaa aatctgatcg cccagctgcc cggcgagaag         720
aagaacggcc tgttcggcaa cctgattgcc ctgagcctgg gcctgacccc caacttcaag         780
agcaacttcg acctggccga ggatgccaaa ctgcagctga gcaaggacac ctacgacgac         840
gacctggaca acctgctggc ccagatcggc gaccagtacg ccgacctgtt cctggccgcc         900
aagaacctgt ctgacgccat cctgctgagc gacatcctga gagtgaacac cgagatcacc         960 aaggccccc tgagcgcctc tatgatcaag agatacgacg agcaccacca ggacctgacc        1020
ctgctgaaag ctctcgtgcg gcagcagctg cctgagaagt acaaagaaat cttcttcgac        1080
cagagcaaga acggctacgc cggctacatc gatggcggcg ctagccagga agagttctac        1140
aagttcatca agcccatcct ggaaaagatg gacggcaccg aggaactgct cgtgaagctg        1200
aacagagagg acctgctgag aaagcagaga accttcgaca cggcagcat cccccaccag         1260 atccacctgg agagctgca cgctatcctg agaaggcagg aagatttta cccattcctg          1320 aaggacaacc gggaaaagat cgagaagatc ctgaccttca ggatcccta ctacgtgggc         1380 cccctggcca gaggcaacag cagattcgcc tggatgacca aaagagcga ggaaaccatc         1440 accccctgga acttcgagga agtggtggac aaggccgcca cgcccagag cttcatcgag         1500 agaatgacaa acttcgataa gaacctgccc aacgagaagg tgctgcccaa gcacagcctg        1560
ctgtacgagt acttcaccgt gtacaacgag ctgaccaaag tgaaatacgt gaccgaggga        1620
atgagaaagc ccgccttcct gagcggcgag cagaaaaagg ccatcgtgga cctgctgttc        1680
aagaccaaca aaaagtgac cgtgaagcag ctgaaagagg actacttcaa gaaaatcgag        1740
tgcttcgact ccgtggaaat ctccggcgtg aagatagat caacgcctc cctgggcaca        1800 taccacgatc tgctgaaaat tatcaaggac aaggacttcc tggataacga agagaacgag        1860
gacattctgg aagatatcgt gctgaccctg acactgtttg aggaccgcga gatgatcgag        1920
gaaaggctga aaacctacgc tcacctgttc gacgacaaag tgatgaagca gctgaagaga        1980
```

-continued

```
aggcggtaca ccggctgggg caggctgagc agaaagctga tcaacggcat cagagacaag      2040
cagagcggca agacaatcct ggatttcctg aagtccgacg gcttcgccaa ccggaacttc      2100
atgcagctga tccacgacga cagcctgaca ttcaaagagg acatccagaa agcccaggtg      2160
tccggccagg gcgactctct gcacgagcat atcgctaacc tggccggcag ccccgctatc      2220
aagaagggca tcctgcagac agtgaaggtg gtggacgagc tcgtgaaagt gatgggcaga      2280
cacaagcccg agaacatcgt gatcgagatg gctagagaga accagaccac ccagaaggga      2340
cagaagaact cccgcgagag gatgaagaga atcgaagagg gcatcaaaga gctgggcagc      2400
cagatcctga agaacaccc cgtggaaaac acccagctgc agaacgagaa gctgtacctg      2460
tactacctgc agaatggccg ggatatgtac gtggaccagg aactggacat caacagactg      2520
tccgactacg atgtggacca tatcgtgcct cagagctttc tgaaggacga ctccatcgat      2580
aacaaagtgc tgactcggag cgacaagaac agaggcaaga gcgacaacgt gccctccgaa      2640
gaggtcgtga agaagatgaa gaactactgg cgacagctgc tgaacgccaa gctgattacc      2700
cagaggaagt tcgataacct gaccaaggcc gagagaggcg gcctgagcga gctggataag      2760
gccggcttca tcaagaggca gctggtggaa accagacaga tcacaaagca cgtggcacag      2820
atcctggact cccggatgaa cactaagtac gacgaaacg ataagctgat ccgggaagtg      2880
aaagtgatca ccctgaagtc caagctggtg tccgatttcc ggaaggattt ccagtttttac     2940 aaagtgcgcg agatcaacaa ctaccaccac gcccacgacg cctacctgaa cgccgtcgtg      3000
ggaaccgccc tgatcaaaaa gtaccctaag ctggaaagcg agttcgtgta cggcgactac      3060
aaggtgtacg acgtgcggaa gatgatcgcc aagagcgagc aggaaatcgg caaggctacc      3120
gccaagtact tcttctacag caacatcatg aactttttca gaccgaaat caccctggcc      3180 aacgccgaga tcagaaagcg ccctctgatc gagacaaacg gcgaaaccgg ggagatcgtg      3240
tgggataagg gcagagactt cgccacagtg cgaaaggtgc tgagcatgcc ccaagtgaat      3300
atcgtgaaaa agaccgaggt gcagacaggc ggcttcagca agagtctat cctgcccaag      3360 aggaacagcg acaagctgat cgccagaaag aaggactggg accccaagaa gtacggcggc      3420
ttcgacagcc ctaccgtggc ctactctgtg ctggtggtgg ctaaggtgga aaagggcaag      3480
tccaagaaac tgaagagtgt gaaagagctg ctggggatca ccatcatgga agaagcagc      3540 tttgagaaga accctatcga ctttctggaa gccaagggct acaaagaagt gaaaaaggac      3600
ctgatcatca agctgcctaa gtactccctg ttcgagctgg aaaacggcag aaagagaatg      3660
ctggcctctg ccggcgaact gcagaaggga aacgagctgg ccctgcctag caaatatgtg      3720
aacttcctgt acctggcctc ccactatgag aagctgaagg gcagccctga ggacaacgaa      3780
cagaaacagc tgtttgtgga acagcataag cactacctgg acgagatcat cgagcagatc      3840
agcgagttct ccaagagagt gatcctggcc gacgccaatc tggacaaggt gctgtctgcc      3900
tacaacaagc acagggacaa gcctatcaga gagcaggccg agaatatcat ccacctgttc      3960
accctgacaa acctgggcgc tcctgccgcc ttcaagtact ttgacaccac catcgaccgg      4020
aagaggtaca ccagcaccaa agaggtgctg gacgccaccc tgatccacca gagcatcacc      4080
ggcctgtacg agacaagaat cgacctgtct cagctgggag cgacaagag acctgccgcc      4140 actaagaagg ccggacaggc caaaaagaag aagtga                                4176
```

<210> SEQ ID NO 7
<211> LENGTH: 1391
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (4)..(10)
<223> OTHER INFORMATION: 5' NLS
<220> FEATURE:
<221> NAME/KEY: MISC_FEATURE
<222> LOCATION: (1376)..(1391)
<223> OTHER INFORMATION: 3' NLS

<400> SEQUENCE: 7

Met Asp Lys Pro Lys Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60

Thr Ala Glu Ala Thr Arg Leu Lys Arg Thr Ala Arg Arg Arg Tyr Thr
65                  70                  75                  80

Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350
```

-continued

```
Lys Tyr Lys Glu Ile Phe Phe Asp Gln Ser Lys Asn Gly Tyr Ala Gly
        355             360             365

Tyr Ile Asp Gly Gly Ala Ser Gln Glu Glu Phe Tyr Lys Phe Ile Lys
        370             375             380

Pro Ile Leu Glu Lys Met Asp Gly Thr Glu Glu Leu Leu Val Lys Leu
385             390             395             400

Asn Arg Glu Asp Leu Leu Arg Lys Gln Arg Thr Phe Asp Asn Gly Ser
            405             410             415

Ile Pro His Gln Ile His Leu Gly Glu Leu His Ala Ile Leu Arg Arg
            420             425             430

Gln Glu Asp Phe Tyr Pro Phe Leu Lys Asp Asn Arg Glu Lys Ile Glu
        435             440             445

Lys Ile Leu Thr Phe Arg Ile Pro Tyr Tyr Val Gly Pro Leu Ala Arg
        450             455             460

Gly Asn Ser Arg Phe Ala Trp Met Thr Arg Lys Ser Glu Glu Thr Ile
465             470             475             480

Thr Pro Trp Asn Phe Glu Glu Val Val Asp Lys Gly Ala Ser Ala Gln
            485             490             495

Ser Phe Ile Glu Arg Met Thr Asn Phe Asp Lys Asn Leu Pro Asn Glu
            500             505             510

Lys Val Leu Pro Lys His Ser Leu Leu Tyr Glu Tyr Phe Thr Val Tyr
            515             520             525

Asn Glu Leu Thr Lys Val Lys Tyr Val Thr Glu Gly Met Arg Lys Pro
        530             535             540

Ala Phe Leu Ser Gly Glu Gln Lys Lys Ala Ile Val Asp Leu Leu Phe
545             550             555             560

Lys Thr Asn Arg Lys Val Thr Val Lys Gln Leu Lys Glu Asp Tyr Phe
            565             570             575

Lys Lys Ile Glu Cys Phe Asp Ser Val Glu Ile Ser Gly Val Glu Asp
            580             585             590

Arg Phe Asn Ala Ser Leu Gly Thr Tyr His Asp Leu Leu Lys Ile Ile
            595             600             605

Lys Asp Lys Asp Phe Leu Asp Asn Glu Glu Asn Glu Asp Ile Leu Glu
        610             615             620

Asp Ile Val Leu Thr Leu Thr Leu Phe Glu Asp Arg Glu Met Ile Glu
625             630             635             640

Glu Arg Leu Lys Thr Tyr Ala His Leu Phe Asp Asp Lys Val Met Lys
            645             650             655

Gln Leu Lys Arg Arg Arg Tyr Thr Gly Trp Gly Arg Leu Ser Arg Lys
            660             665             670

Leu Ile Asn Gly Ile Arg Asp Lys Gln Ser Gly Lys Thr Ile Leu Asp
            675             680             685

Phe Leu Lys Ser Asp Gly Phe Ala Asn Arg Asn Phe Met Gln Leu Ile
        690             695             700

His Asp Asp Ser Leu Thr Phe Lys Glu Asp Ile Gln Lys Ala Gln Val
705             710             715             720

Ser Gly Gln Gly Asp Ser Leu His Glu His Ile Ala Asn Leu Ala Gly
            725             730             735

Ser Pro Ala Ile Lys Lys Gly Ile Leu Gln Thr Val Lys Val Val Asp
            740             745             750

Glu Leu Val Lys Val Met Gly Arg His Lys Pro Glu Asn Ile Val Ile
            755             760             765

Glu Met Ala Arg Glu Asn Gln Thr Thr Gln Lys Gly Gln Lys Asn Ser
```

-continued

```
        770              775              780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                805                 810                 815

Lys Leu Tyr Leu Tyr Tyr Leu Gln Asn Gly Arg Asp Met Tyr Val Asp
                820                 825                 830

Gln Glu Leu Asp Ile Asn Arg Leu Ser Asp Tyr Asp Val Asp His Ile
            835                 840                 845

Val Pro Gln Ser Phe Leu Lys Asp Asp Ser Ile Asp Asn Lys Val Leu
        850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                885                 890                 895

Lys Leu Ile Thr Gln Arg Lys Phe Asp Asn Leu Thr Lys Ala Glu Arg
                900                 905                 910

Gly Gly Leu Ser Glu Leu Asp Lys Ala Gly Phe Ile Lys Arg Gln Leu
            915                 920                 925

Val Glu Thr Arg Gln Ile Thr Lys His Val Ala Gln Ile Leu Asp Ser
        930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
                980                 985                 990

Asp Ala Tyr Leu Asn Ala Val Val  Gly Thr Ala Leu Ile  Lys Lys Tyr
            995                 1000                1005

Pro Lys  Leu Glu Ser Glu Phe  Val Tyr Gly Asp Tyr  Lys Val Tyr
    1010                1015                1020

Asp Val  Arg Lys Met Ile Ala  Lys Ser Glu Gln Glu  Ile Gly Lys
    1025                1030                1035

Ala Thr  Ala Lys Tyr Phe Phe  Tyr Ser Asn Ile Met  Asn Phe Phe
    1040                1045                1050

Lys Thr  Glu Ile Thr Leu Ala  Asn Gly Glu Ile Arg  Lys Arg Pro
    1055                1060                1065

Leu Ile  Glu Thr Asn Gly Glu  Thr Gly Glu Ile Val  Trp Asp Lys
    1070                1075                1080

Gly Arg  Asp Phe Ala Thr Val  Arg Lys Val Leu Ser  Met Pro Gln
    1085                1090                1095

Val Asn  Ile Val Lys Lys Thr  Glu Val Gln Thr Gly  Gly Phe Ser
    1100                1105                1110

Lys Glu  Ser Ile Leu Pro Lys  Arg Asn Ser Asp Lys  Leu Ile Ala
    1115                1120                1125

Arg Lys  Lys Asp Trp Asp Pro  Lys Lys Tyr Gly Gly  Phe Asp Ser
    1130                1135                1140

Pro Thr  Val Ala Tyr Ser Val  Leu Val Val Ala Lys  Val Glu Lys
    1145                1150                1155

Gly Lys  Ser Lys Lys Leu Lys  Ser Val Lys Glu Leu  Leu Gly Ile
    1160                1165                1170

Thr Ile  Met Glu Arg Ser Ser  Phe Glu Lys Asn Pro  Ile Asp Phe
    1175                1180                1185
```

-continued

```
Leu Glu  Ala Lys Gly Tyr Lys  Glu Val Lys Lys Asp  Leu Ile Ile
    1190             1195              1200

Lys Leu  Pro Lys Tyr Ser Leu  Phe Glu Leu Glu Asn  Gly Arg Lys
    1205             1210              1215

Arg Met  Leu Ala Ser Ala Gly  Glu Leu Gln Lys Gly  Asn Glu Leu
    1220             1225              1230

Ala Leu  Pro Ser Lys Tyr Val  Asn Phe Leu Tyr Leu  Ala Ser His
    1235             1240              1245

Tyr Glu  Lys Leu Lys Gly Ser  Pro Glu Asp Asn Glu  Gln Lys Gln
    1250             1255              1260

Leu Phe  Val Glu Gln His Lys  His Tyr Leu Asp Glu  Ile Ile Glu
    1265             1270              1275

Gln Ile  Ser Glu Phe Ser Lys  Arg Val Ile Leu Ala  Asp Ala Asn
    1280             1285              1290

Leu Asp  Lys Val Leu Ser Ala  Tyr Asn Lys His Arg  Asp Lys Pro
    1295             1300              1305

Ile Arg  Glu Gln Ala Glu Asn  Ile Ile His Leu Phe  Thr Leu Thr
    1310             1315              1320

Asn Leu  Gly Ala Pro Ala Ala  Phe Lys Tyr Phe Asp  Thr Thr Ile
    1325             1330              1335

Asp Arg  Lys Arg Tyr Thr Ser  Thr Lys Glu Val Leu  Asp Ala Thr
    1340             1345              1350

Leu Ile  His Gln Ser Ile Thr  Gly Leu Tyr Glu Thr  Arg Ile Asp
    1355             1360              1365

Leu Ser  Gln Leu Gly Gly Asp  Lys Arg Pro Ala Ala  Thr Lys Lys
    1370             1375              1380

Ala Gly  Gln Ala Lys Lys Lys  Lys
    1385             1390
```

```
<210> SEQ ID NO 8
<211> LENGTH: 99
<212> TYPE: RNA
<213> ORGANISM: Artificial Sequence
<220> FEATURE:
<223> OTHER INFORMATION: Synthetic

<400> SEQUENCE: 8
cauagcagag aggaacugga ugguuuuaga gcuagaaaua gcaaguuaaa auaaggcuag      60
uccguuauca acuugaaaaa guggcaccga gucggugcu                             99

<210> SEQ ID NO 9
<211> LENGTH: 99
<212> TYPE: RNA
<213> ORGANISM: Artificial Sequence
<220> FEATURE:
<223> OTHER INFORMATION: Synthetic

<400> SEQUENCE: 9
auaaugcggc ucagucagaa ggguuuuaga gcuagaaaua gcaaguuaaa auaaggcuag      60
uccguuauca acuugaaaaa guggcaccga gucggugcu                             99

<210> SEQ ID NO 10
<211> LENGTH: 99
<212> TYPE: RNA
<213> ORGANISM: Artificial Sequence
<220> FEATURE:
<223> OTHER INFORMATION: Synthetic
```

-continued

```
<400> SEQUENCE: 10
gcaaagauuu auuccccauc agguuuuaga gcuagaaaua gcaaguuaaa auaaggcuag      60
uccguuauca acuugaaaaa guggcaccga gucggugcu                            99

<210> SEQ ID NO 11
<211> LENGTH: 99
<212> TYPE: RNA
<213> ORGANISM: Artificial Sequence
<220> FEATURE:
<223> OTHER INFORMATION: Synthetic

<400> SEQUENCE: 11
uuagauucaa cagggaaaug ugguuuuaga gcuagaaaua gcaaguuaaa auaaggcuag      60
uccguuauca acuugaaaaa guggcaccga gucggugcu                            99

<210> SEQ ID NO 12
<211> LENGTH: 20
<212> TYPE: DNA
<213> ORGANISM: Rattus norvegicus

<400> SEQUENCE: 12
catagcagag aggaactgga                                                 20

<210> SEQ ID NO 13
<211> LENGTH: 20
<212> TYPE: DNA
<213> ORGANISM: Rattus norvegicus

<400> SEQUENCE: 13
ataatgcggc tcagtcagaa                                                 20

<210> SEQ ID NO 14
<211> LENGTH: 20
<212> TYPE: DNA
<213> ORGANISM: Rattus norvegicus

<400> SEQUENCE: 14
gcaaagattt attccccatc                                                 20

<210> SEQ ID NO 15
<211> LENGTH: 20
<212> TYPE: DNA
<213> ORGANISM: Rattus norvegicus

<400> SEQUENCE: 15
ttagattcaa cagggaaatg                                                 20

<210> SEQ ID NO 16
<211> LENGTH: 4250
<212> TYPE: DNA
<213> ORGANISM: Rattus norvegicus

<400> SEQUENCE: 16
acagcacata cttctcttcg agtcaactgc tcccagatag atccaagaca tgagactgtc     60
agcaagaatt atttggctta tattatggac tgtttgtgta gcagaagatt gtaaaggtcc    120
tcctccaaga gaaaattcag aaattctctc aggttcgtgg tctgaacaac tatattcaga    180
aggcactcag gcaacctaca aatgccgccc tggataccga acacttggta ctattgtaaa    240
agtatgcaag aatggagaat gggtaccttc taacccatca aggatatgtc ggaaaaggcc    300
atgtgggcat cccggagaca caccctttgg gtcctttagg ctggcagttg gatctgaatt    360
```

-continued

```
tgaatttggt gcaaaggttg tttatacatg tgatgaaggg taccaactct taggtgaaat      420
tgattaccgt gaatgtgatg cagatgggtg gaccaatgat attccaatat gtgaagttgt      480
gaagtgcttg ccagtgacag aactggagaa tggaagaatt gtgagtggtg cagccgaacc      540
agaccaggaa tattattttg gacaggtggt acgctttgaa tgcaactccg gcttcaagat      600
tgaaggacag aaagaaatgc actgctcaga aaatggcctc tggagcaatg aaaagccaca      660
gtgtgtggaa atttcttgcc tgccaccacg agttgaaaat ggagatggta tatatctgaa      720
accagtttac aaggagaatg aaagattcca atataaatgt aagcaaggtt ttgtgtacaa      780
agaaagaggg gatgctgtct gcacgggttc tggatggaat cctcagcctt cctgtgaaga      840
aatgacatgt ttgactccat atattccaaa tggtatctac acacctcaca ggattaaaca      900
cagaattgat gatgaaatca gatatgaatg taaaaatggc ttctatcctg caacccgatc      960
acctgtttca aagtgtacaa ttactggctg gatccctgct ccaagatgta gcttgaaacc     1020
ttgtgatttt ccacaattca aacatggacg tctgtattat gaagaaagcc ggagaccta     1080 cttcccagta cctataggaa aggagtacag ctattactgt gacaacgggt ttacaacgcc     1140
ttcacagtca tactgggact accttcgttg cacagtaaat gggtgggagc ctgaagttcc     1200
atgcctcagg caatgtattt tccattatgt ggaatatgga gaatctttat actggcaaag     1260
aagatatata gagggtcagt ctgcaaaagt ccagtgtcac agtggctata gtcttccaaa     1320
tggtcaagat acaatattat gtacagaaaa tggctggtcc cctcctccca aatgcgtccg     1380
tatcaagact tgttcagtat cagatataga aattgaaaat gggttttttt ctgaatctga     1440
ttatacatat gctctaaata gaaaaacacg gtatagatgt aaacagggat atgtaacaaa     1500
taccggagaa atatcaggaa taattacttg tcttcaagat ggatggtcac ctcgaccctc     1560
atgcattaag tcttgtgata tgcctgtatt tgagaatgct atgactaaga ataataacac     1620
atggtttaaa ctcaatgaca aattagacta tgaatgtcac attggatatg aaaatgaata     1680
taaacatacc aaaggctcta aacatgtac ttatgatgga tggtctagta caccctcctg     1740
ttatgaaaga gaatgcagca ttcccctgtt acaccaagac ttagttgttt ttcccagaga     1800
agtaaaatac aaagttggag attcgttgag tttctcttgc cgttcaggac acagagttgg     1860
agcagattta gtgcaatgct accactttgg atggtcccct aatttcccaa cgtgtgaagg     1920
ccaagtaaaa tcatgtgacc aacctcttga aatcccgaat ggggaaataa agggaacaaa     1980
aaaagttgaa tacagccatg gtgacgtggt ggaatatgat tgcaaaccta gatttctact     2040
gaagggaccc aataaaatcc agtgtgttga cgggaagtgg acaaccttgc cgatatgcgt     2100
tgagtatgag agaacatgtg gagaccttcc tgcacttgag catggctctg tccagttatc     2160
tgtccctccc taccaccacg gagattcagt ggagttcact tgtgcagaaa ccttcacaat     2220
gattgggcat gcagtagttt ctgcattag tggaaggtgg accgagcttc ctcaatgtgt     2280
tgcaacagat caactggaga agtgtaaagc cccgaagtca actggcatag atgcaattca     2340
tccaaataag aatgaattta atcataactt tagtgtgagt tacagatgta gacaaaagca     2400
ggagtatgaa cattcaatct gcatcaatgg aagatgggat cctgaaccaa actgtacaag     2460
aaatgagaaa agattctgcc ctcctccccc acagattcca aatgcccaag tgattgaaac     2520
cacagtgaaa tacttggatg gagagaaagt atctgttctt tgccaagatg gttacctaac     2580
tcagggccca gaagaaatgg tgtgtaaaca tggaaggtgg cagtcgttac cacgctgcac     2640
ggaaaaaatt ccatgttccc agccccctaa aattgaacat ggatctatta gtcgcccag     2700
```

-continued

```
gtcctcagaa gagagagatt taattgagtc cagcagttat gaacacggaa ctacattcag    2760
ctatgtctgt gatgatggat tcaggatatc tgaagaaaat agggtaacct gcaacatggg    2820
aaaatggagc tctctgcctc gttgtgttgg aataccttgt ggacccccac cttcaattcc    2880
tcttggtatt gtttctcatg aactagaaag ttaccaatat ggagaggagg ttacatacaa    2940
ttgttctgaa ggctttggaa ttgatggacc agcatttatt aaatgtgtag gaggacagtg    3000
gtctgaacca cccaaatgca taaaaactga ttgtgacaac ttgcccacat ttgaaattgc    3060
caaaccgaca gaaaagaaaa aaaaatcata caggtcagga gaacaagtga cattcagatg    3120
tccacctccg tatcgaatgg atggctctga cattgtcaca tgtgttaata cgaagtggat    3180
tggacagccg gtatgcaaag ataattcctg tgtgaatcca ccacatgtgc caaatgctac    3240
tatactaaca aggcacaaga ctaaatatcc atctggtgac aaagtacgtt atgactgtaa    3300 taaaccttttt gaattatttg gggaagtgga agtgatgtgc caaaacggga tttggacaga    3360
accaccgaaa tgcaaagatt caacaggaa atgtgggcct cctccaccta ttgacaatgg    3420
agacatcacc tccttgtcat taccagtata tgcaccatta tcatcagttg aatatcaatg    3480
ccagaactat tatctactta agggaaataa gatagtaaca tgtagaaatg gaaagtggtc    3540
tcagccacca acctgcttac atgcatgtgt gataccagaa gatattatgg aaaaacataa    3600
tatagttctc agatggaggg aaaatgcaaa gatttattcc caatcagggg agaatattga    3660
attcatgtgt aaacctggat atagaaaatt cagaggatca cctccgtttc gtacaaagtg    3720
cattgagggt cacatcaatt atcccacttg tgtataaaat cgctatacaa ttattagtaa    3780
accttatgga tgaacctttg tttagaaatg cacatgtata ttactaatac agtttgaatt    3840
tacatttgaa atattgttta gctcatttct tctaataagt atataaactt tttttatatg    3900
gtggttaatc agtaacttta cagactgttg ccacaaagca agaacattgc attcaaaact    3960
cctaatccaa aatatgatat gtccaaggac aaactatgtc taagcaagaa aataaatgtt    4020
agttcttcaa tgtctgtttt tattcaggac ttttcagatt ttcttggata cctttttgttg    4080 ttaggttctg attcacagtg agtggaagac acactgactc tgacttcaaa ttagtattac    4140
ttgccaatac ataacaacca aactatcata atatcacaaa tgtatacagc taattactgt    4200
gtcctacctt tgtatcaata aagaaatcta agaaagttct tgcttatgaa                4250
```

```
<210> SEQ ID NO 17
<211> LENGTH: 24
<212> TYPE: DNA
<213> ORGANISM: Rattus norvegicus

<400> SEQUENCE: 17
catagcagag aggaactgga tggt                                              24

<210> SEQ ID NO 18
<211> LENGTH: 15
<212> TYPE: DNA
<213> ORGANISM: Rattus norvegicus

<400> SEQUENCE: 18
gcacatactt ctctt                                                        15

<210> SEQ ID NO 19
<211> LENGTH: 26
<212> TYPE: DNA
<213> ORGANISM: Rattus norvegicus

<400> SEQUENCE: 19
```

-continued

```
gtcaactgct cccagataga tccaag                                  26

<210> SEQ ID NO 20
<211> LENGTH: 26
<212> TYPE: DNA
<213> ORGANISM: Rattus norvegicus

<400> SEQUENCE: 20
accaccacct ttctcccttc tgactg                                  26

<210> SEQ ID NO 21
<211> LENGTH: 16
<212> TYPE: DNA
<213> ORGANISM: Rattus norvegicus

<400> SEQUENCE: 21
gccgcattat aaaaca                                             16

<210> SEQ ID NO 22
<211> LENGTH: 25
<212> TYPE: DNA
<213> ORGANISM: Rattus norvegicus

<400> SEQUENCE: 22
ttgctgataa tatttctcat agcaa                                   25

<210> SEQ ID NO 23
<211> LENGTH: 22
<212> TYPE: DNA
<213> ORGANISM: Rattus norvegicus

<400> SEQUENCE: 23
atttcctaaa ctaactttca ac                                      22

<210> SEQ ID NO 24
<211> LENGTH: 23
<212> TYPE: DNA
<213> ORGANISM: Rattus norvegicus

<400> SEQUENCE: 24
gtggtaagtt taaaaaccgt gaa                                     23

<210> SEQ ID NO 25
<211> LENGTH: 24
<212> TYPE: DNA
<213> ORGANISM: Rattus norvegicus

<400> SEQUENCE: 25
cgcctatgct gctggacttg tggt                                    24

<210> SEQ ID NO 26
<211> LENGTH: 25
<212> TYPE: DNA
<213> ORGANISM: Rattus norvegicus

<400> SEQUENCE: 26
ctttcacttg actattgtaa ttgat                                   25
```

COMPLEMENT FACTOR H GENE KNOCKOUT RAT AS A MODEL OF C3 GLOMERULOPATHY

CROSS-REFERENCE TO RELATED APPLICATIONS

This application is a 35 U.S.C. § 371 national stage of International Application No. PCT/US2019/050792, filed Sep. 12, 2019, which claims the benefit U.S. Application No. 62/730,690, filed Sep. 13, 2018, which are herein incorporated by reference in their entirety for all purposes.

REFERENCE TO A SEQUENCE LISTING SUBMITTED AS A TEXT FILE VIA EFS WEB

The Sequence Listing written in file 536658SEQLIST.txt is 294 kilobytes, was created on Sep. 6, 2019, and is hereby incorporated by reference.

BACKGROUND

C3 glomerulopathy (C3G) is characterized by hyperactivation of alternative pathway (AP) complement activation as a result of C3 nephritic factors and/or mutations in complement genes. Approximately 50% of patients develop end-stage renal disease (ESRD) within 10 years of diagnosis. There is a recurrence rate of approximately 80-90% after kidney transplantation. There is currently no FDA-approved treatment for C3G, nor are there therapies that attack the cause of C3G.

Complement factor H deficient ($Cfh^{-/-}$) mice have been used for experimental studies to understand the mechanisms underlying C3G. However, ESRD can take several months to manifest in $Cfh^{-/-}$ mice, requiring long preclinical studies to assess new therapeutics. Better C3G models are needed.

SUMMARY

Rats, rat cells, and rat genomes comprising an inactivated Cfh locus are provided, as well as methods of making and using such rats, rat cells, and rat genomes. Also provided are rat Cfh genes comprising a targeted genetic modification that inactivates the rat Cfh genes, nuclease agents for use in inactivating a rat Cfh gene, wherein the nuclease agents target and cleave a nuclease target site in the Cfh gene, and methods of making such rat Cfh genes.

In one aspect, provided are rats comprising an inactivated endogenous Cfh locus. Optionally, the start codon of the endogenous Cfh locus is mutated or deleted in the inactivated endogenous Cfh locus. Optionally, the start codon of the endogenous Cfh locus is deleted in the inactivated endogenous Cfh locus. Optionally, the coding sequence in the first exon in the endogenous Cfh locus is deleted in the inactivated endogenous Cfh locus. Optionally, the splice donor site in the first intron in the endogenous Cfh locus is deleted in the inactivated endogenous Cfh locus.

In some such rats, the rat is a male. In other such rats, the rat is a female. In some such rats, the rat is homozygous for the inactivated endogenous Cfh locus. In other such rats, the rat is heterozygous for the inactivated endogenous Cfh locus.

Some such rats have one or more symptoms of C3 glomerulopathy (C3G). Some such rats have decreased circulatory C3 levels compared to a wild type rat. Optionally, the circulatory C3 levels are less than about 200 µg/mL. Optionally, the circulatory C3 levels are less than about 100

µg/mL. Optionally, the genetically modified rat has decreased circulatory C3 levels compared to the wild type rat at an age of between about 7 weeks and about 17 weeks.

Some such rats have increased blood urea nitrogen levels compared to a wild type rat. Some such rats have increased blood urea nitrogen levels, increased serum cystatin C levels, or increased urinary albumin levels compared to a wild type rat. Some such rats have increased blood urea nitrogen levels, increased serum cystatin C levels, and increased urinary albumin levels compared to a wild type rat. Optionally, the blood urea nitrogen levels are more than about 10, more than about 20, more than about 30, more than about 40, more than about 50, more than about 60, more than about 70, more than about 80, more than about 90, or more than about 100 mg/dL. Optionally, the serum cystatin C levels are more than about 1000, more than about 1100, more than about 1200, more than about 1300, more than about 1400, more than about 1500, more than about 1600, more than about 1700, more than about 1800, more than about 1900, or more than about 2000 ng/mL. Optionally, the urinary albumin per day is more than about 1000, more than about 2000, more than about 3000, more than about 4000, more than about 5000, more than about 6000, more than about 7000, more than about 8000, more than about 9000, or more than about 10000 g/day. Optionally, the ratio of urinary albumin to urinary creatinine is more than about 100, more than about 200, more than about 300, more than about 400, more than about 500, more than about 600, more than about 700, more than about 800, more than about 900, more than about 1000, more than about 1100, more than about 1200, more than about 1300, more than about 1400, more than about 1500, more than about 1600, more than about 1700, more than about 1800, more than about 1900, or more than about 2000 µg:mg. Optionally, the genetically modified rat has increased blood urea nitrogen levels compared to the wild type rat at an age of between about 7 weeks and about 17 weeks. Optionally, the genetically modified rat has increased blood urea nitrogen levels, increased serum cystatin C levels, or increased urinary albumin levels compared to the wild type rat at an age of between about 7 weeks and about 17 weeks.

Some such rats have increased C3 deposition in the kidneys compared to a wild type rat. Optionally, the genetically modified rat has increased C3 deposition in the kidneys compared to the wild type rat at an age of between about 7 weeks and about 17 weeks. Some such rats have increased C5b-9 deposition in the kidneys compared to a wild type rat. Optionally, the genetically modified rat has increased C5b-9 deposition in the kidneys compared to the wild type rat at an age of between about 7 weeks and about 17 weeks.

Some such rats have increased glomerular pathology compared to a wild type rat. Optionally, the increased glomerular pathology comprises increased glomerular basement membrane thickness, increased podocyte foot process width, or decreased podocyte foot process number compared to the wild type rat. Optionally, the increased glomerular pathology comprises increased glomerular basement membrane thickness, increased podocyte foot process width, and decreased podocyte foot process number compared to the wild type rat. Optionally, the increase in glomerular basement membrane thickness is at least about 2-fold, at least about 3-fold, at least about 4-fold, at least about 5-fold, at least about 6-fold, at least about 7-fold, at least about 8-fold, at least about 9-fold, or at least about 10-fold compared to the wild type rat and/or the average glomerular basement membrane thickness in glomeruli in the genetically modified rat is at least about 0.2, at least about 0.3, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, or at least about 1.8 microns. Optionally, the increase in podocyte foot process width is at least about 2-fold, at least about 3-fold, at least about 4-fold, at least about 5-fold, at least about 6-fold, or at least about 7-fold compared to the wild type rat and/or the average width of foot process in glomeruli in the genetically modified rat is at least about 0.4, at least about 0.5, at least about 0.6, at least about 0.7, at least about 0.8, at least about 0.9, at least about 1.0, at least about 1.5, at least about 2.0, or at least about 2.5 microns. Optionally, the decrease in podocyte foot process number is at least about 2-fold, at least about 2.5-fold, at least about 3-fold, at least about 3.5-fold, or at least about 3.8-fold compared to the wild type rat and/or the average podocyte foot process number per micron length in the genetically modified rat is less than about 2.5, less than about 2, less than about 1.5, less than about 1, less than about 0.9, or less than about 0.8. Optionally, the genetically modified rat has increased glomerular pathology compared to the wild type rat at an age of between about 7 weeks and about 17 weeks.

Some such rats have a decreased lifespan compared to a wild type rat. Optionally, the median lifespan of the genetically modified rat is less than about 150 days.

In another aspect, provided are methods of assessing the in vivo therapeutic efficacy of an agent for use in a treatment of C3 glomerulopathy (C3G). Some such methods comprise: (a) administering the agent to any of the above genetically modified rats; and (b) assessing one or more symptoms of C3G in the genetically modified rat that has been administered the agent compared to a control genetically modified rat that has not been administered the agent. Optionally, step (b) comprises assessing one or more or all of the following: (i) circulatory C3 levels; (ii) blood urea nitrogen levels; (iii) C3 deposition in the kidneys; (iv) C5b-9 deposition in the kidneys; and (v) lifespan. Optionally, step (b) comprises assessing: (i) circulatory C3 levels; (ii) blood urea nitrogen levels; (iii) C3 deposition in the kidneys; (iv) C5b-9 deposition in the kidneys; (v) lifespan; or (vi) a combination thereof. Optionally, step (b) comprises assessing: (i) circulatory C3 levels; (ii) blood urea nitrogen levels; (iii) serum cystatin C levels; (iv) urinary albumin levels; (v) C3 deposition in the kidneys; (vi) C5b-9 deposition in the kidneys; (vii) glomerular basement membrane thickness; (viii) podocyte foot process width; (ix) podocyte foot number; (x) lifespan; or (xi) a combination thereof. Optionally, the age of the genetically modified rat is between about 7 weeks and about 17 weeks.

In some such methods, step (b) comprises assessing circulatory C3 levels, wherein increased circulatory C3 levels in the genetically modified rat administered the agent relative to the control genetically modified rat indicates a therapeutic effect for the putative C3G therapeutic agent. In some such methods, step (b) comprises assessing blood urea nitrogen levels, wherein decreased blood urea nitrogen levels in the genetically modified rat administered the agent relative to the control genetically modified rat indicates a therapeutic effect for the putative C3G therapeutic agent. In some such methods, step (b) comprises assessing serum cystatin C levels, wherein decreased serum cystatin C levels in the genetically modified rat administered the agent relative to the control genetically modified rat indicates a therapeutic effect for the putative C3G therapeutic agent. In some such methods, step (b) comprises assessing urinary albumin levels, wherein decreased urinary albumin levels in the genetically modified rat administered the agent relative to the control genetically modified rat indicates a therapeutic effect for the putative C3G therapeutic agent. In some such methods, step (b) comprises assessing C3 deposition in the kidney, wherein decreased levels of C3 deposition in the kidney in the genetically modified rat administered the agent relative to the control genetically modified rat indicates a therapeutic effect for the putative C3G therapeutic agent. In some such methods, wherein step (b) comprises assessing C5b-9 deposition in the kidney, wherein decreased levels of C5b-9 deposition in the kidney in the genetically modified rat administered the agent relative to the control genetically modified rat indicates a therapeutic effect for the putative C3G therapeutic agent. In some such methods, step (b) comprises assessing glomerular basement membrane thickness, wherein decreased glomerular basement membrane thickness in the genetically modified rat administered the agent relative to the control genetically modified rat indicates a therapeutic effect for the putative C3G therapeutic agent. In some such methods, step (b) comprises assessing podocyte foot process width, wherein decreased podocyte foot process width in the genetically modified rat administered the agent relative to the control genetically modified rat indicates a therapeutic effect for the putative C3G therapeutic agent. In some such methods, step (b) comprises assessing podocyte foot process number, wherein increased podocyte foot process number in the genetically modified rat administered the agent relative to the control genetically modified rat indicates a therapeutic effect for the putative C3G therapeutic agent. In some such methods, step (b) comprises assessing lifespan, wherein increased lifespan in the genetically modified rat administered the agent relative to the control genetically modified rat indicates a therapeutic effect for the putative C3G therapeutic agent.

In another aspect, provided are methods of making any of the above genetically modified rats. Some such methods comprise: (a) introducing into a rat embryonic stem (ES) cell a first nuclease agent that targets a first target sequence proximate to the start codon of the endogenous Cfh genomic locus, wherein the nuclease agent cleaves the first target sequence to produce a genetically modified rat ES cell comprising the inactivated endogenous Cfh locus; (b) introducing the genetically modified rat (ES) cell into a rat host embryo; and (c) gestating the rat host embryo in a surrogate mother, wherein the surrogate mother produces an F0 progeny genetically modified rat comprising the inactivated endogenous Cfh locus. Some such methods comprise: (a) introducing into a rat one-cell stage embryo a first nuclease agent that targets a first target sequence proximate to the start codon of the endogenous Cfh genomic locus, wherein the nuclease agent cleaves the first target sequence to produce a genetically modified rat one-cell stage embryo comprising the inactivated endogenous Cfh locus; and (b) gestating the genetically modified rat one-cell stage embryo in a surrogate mother, wherein the surrogate mother produces an F0 progeny genetically modified rat comprising the inactivated endogenous Cfh locus.

In some such methods, the first target sequence of the first nuclease agent is in the first exon, the first intron, or the 5' UTR of the endogenous Cfh locus. Optionally, the first nuclease agent is a Cas9 protein and a guide RNA. Optionally, the first target sequence comprises SEQ ID NO: 12 or 13.

In some such methods, step (a) further comprises introducing into the rat ES cell a second nuclease agent that targets a second target sequence proximate to the stop codon of the endogenous Cfh locus. In some such methods, step (a)

further comprises introducing into the rat ES cell or the rat one-cell stage embryo a second nuclease agent that targets a second target sequence proximate to the stop codon of the endogenous Cfh locus. Optionally, the second target sequence is in the penultimate intron, the penultimate exon, the last intron, the last exon, or the 3' UTR of the endogenous Cfh locus. Optionally, the second target sequence comprises SEQ ID NO: 14 or 15.

In some such methods, step (a) further comprises introducing into the rat ES cell a second nuclease agent that targets a second target sequence proximate to the start codon of the endogenous Cfh locus that is different from the first target sequence. In some such methods, step (a) further comprises introducing into the rat ES cell or the rat one-cell stage embryo a second nuclease agent that targets a second target sequence proximate to the start codon of the endogenous Cfh locus that is different from the first target sequence. Optionally, the first target sequence and the second target sequence flank the start codon of the endogenous Cfh locus. Optionally, the first target sequence is in the first exon or the 5' UTR of the endogenous Cfh locus, and the second target sequence is in the first exon or the first intron of the endogenous Cfh locus. Optionally, the first target sequence comprises SEQ ID NO: 12, and the second target sequence comprises SEQ ID NO: 13. Optionally, step (a) further comprises introducing into the rat ES cell a third nuclease agent and/or a fourth nuclease agent, wherein the third and fourth nuclease agents target third and fourth target sequences, respectively, proximate to the stop codon of the endogenous Cfh locus, and wherein the third and fourth target sequences are different. Optionally, step (a) further comprises introducing into the rat ES cell or the rat one-cell stage embryo a third nuclease agent and/or a fourth nuclease agent, wherein the third and fourth nuclease agents target third and fourth target sequences, respectively, proximate to the stop codon of the endogenous Cfh locus, and wherein the third and fourth target sequences are different. Optionally, the third and fourth target sequences are in the penultimate intron, the penultimate exon, the last intron, the last exon, or the 3' UTR of the endogenous Cfh locus. Optionally, the third and fourth target sequences comprise SEQ ID NOS: 14 and 15, respectively.

In some such methods, step (a) further comprises introducing into the rat ES cell an exogenous donor nucleic acid comprising a 5' homology arm that hybridizes to a 5' target sequence at the endogenous Cfh locus and a 3' homology arm that hybridizes to a 3' target sequence at the endogenous Cfh locus, wherein the exogenous donor nucleic acid is designed to mutate or delete the start codon of the endogenous Cfh locus. In some such methods, step (a) further comprises introducing into the rat ES cell or the rat one-cell stage embryo an exogenous donor nucleic acid comprising a 5' homology arm that hybridizes to a 5' target sequence at the endogenous Cfh locus and a 3' homology arm that hybridizes to a 3' target sequence at the endogenous Cfh locus, wherein the exogenous donor nucleic acid is designed to mutate or delete the start codon of the endogenous Cfh locus. Optionally, the 5' target sequence and the 3' target sequence flank the start codon of the endogenous Cfh locus. Optionally, the 5' target sequence and the 3' target sequence flank the coding sequence of the endogenous Cfh locus.

In another aspect, provided are genetically modified rat cells comprising an inactivated endogenous Cfh locus. In another aspect, provided are genetically modified rat genomes comprising an inactivated endogenous Cfh locus. In another aspect provided are rat Cfh genes comprising a targeted genetic modification that inactivates the rat Cfh genes. In another aspect, provided are nuclease agents for use in inactivating a rat Cfh gene, wherein the nuclease agents target and cleave a nuclease target site in the Cfh gene. In another aspect, provided are methods of making a genetically modified rat cell comprising an inactivated endogenous Cfh locus, comprising introducing into a rat cell a nuclease agent that targets a target sequence proximate to the start codon of the endogenous Cfh genomic locus, wherein the nuclease agent cleaves the target sequence to produce the genetically modified rat cell comprising the inactivated endogenous Cfh locus. In another aspect, provided are methods of making a genetically modified rat genome comprising an inactivated endogenous Cfh locus, comprising contacting a rat genome with a nuclease agent that targets a target sequence proximate to the start codon of the endogenous Cfh genomic locus, wherein the nuclease agent cleaves the target sequence to produce the genetically modified rat genome comprising the inactivated endogenous Cfh locus. In another aspect, provided are methods of making an inactivated rat Cfh gene, comprising contacting a rat Cfh gene with a nuclease agent that targets a target sequence proximate to the start codon of the endogenous Cfh genomic locus, wherein the nuclease agent cleaves the target sequence to produce the inactivated rat Cfh gene.

BRIEF DESCRIPTION OF THE FIGURES

FIGS. 9A-9D show urinary albumin measurements in male and female wild type and Cfh knockout rats. FIG. 9A shows urinary albumin per day in male wild type and Cfh knockout rats, FIG. 9B shows urinary albumin normalized to urinary creatinine in male wild type and Cfh knockout rats, FIG. 9C shows urinary albumin per day in female wild type and Cfh knockout rats, and FIG. 9D shows urinary albumin normalized to urinary creatinine in female wild type and Cfh knockout rats.

FIG. 11A is at a magnification of 12,000×, and FIG. 11B is a higher magnification from FIG. 11A.

FIG. 12A is at a magnification of 12,000×, and FIG. 12B is a higher magnification from FIG. 12A.

DEFINITIONS

Figure 1A:
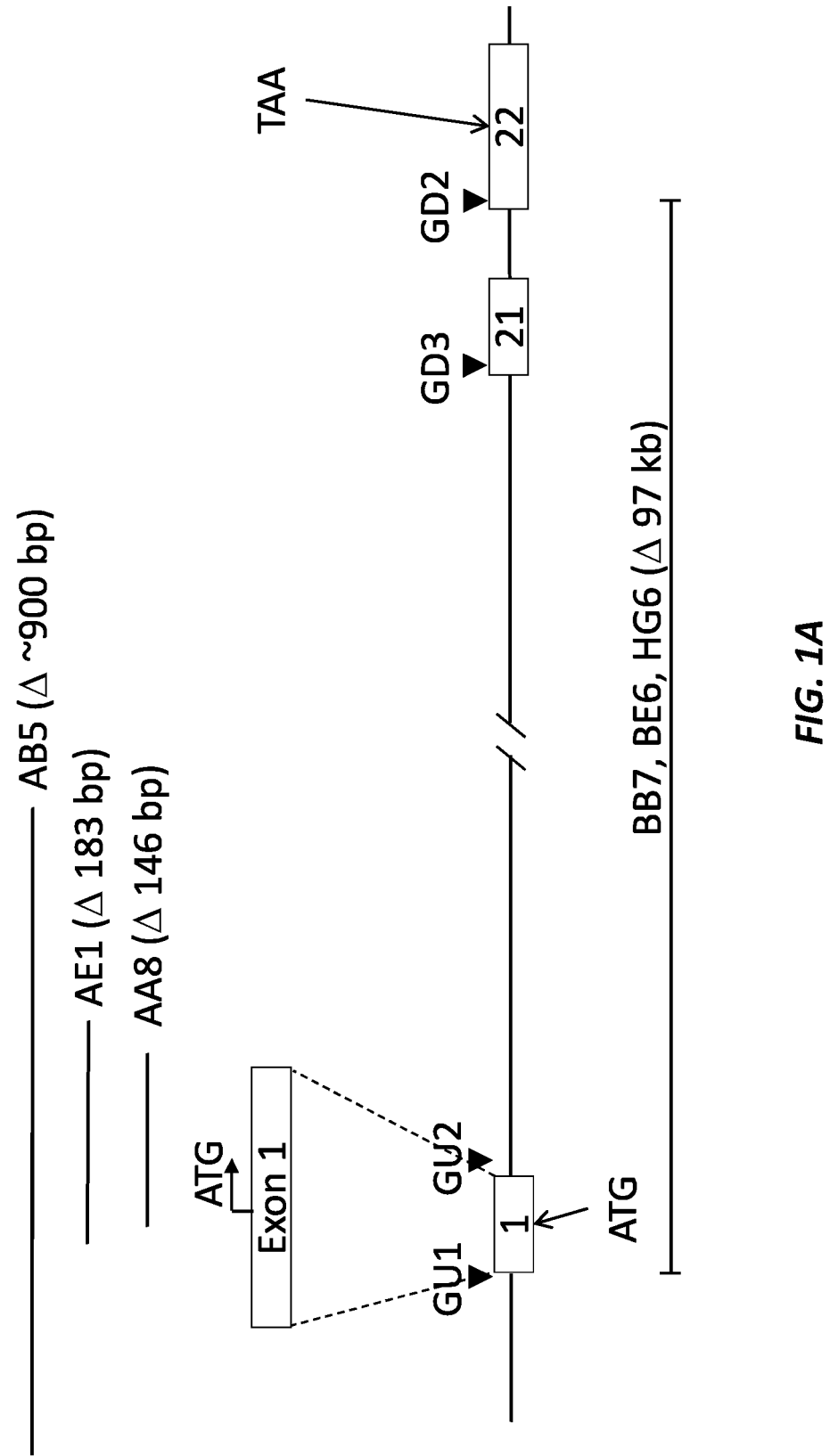
FIG. 1A (not to scale) shows a schematic of the targeting scheme for targeting the rat Cfh locus. The positions of the guide RNA target sequences for guide RNAs GU1, GU2, GD2, and GD3 are shown, along with the positions of exons 1, 21, and 22, and the ATG start codon and the TAA stop codon. Depictions of the regions deleted in rat ES cell clones AB5, AE1, AA8, BB7, BE6, and HG6 are also shown.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5′ ends" and "3′ ends" because mononucleotides are reacted to make oligonucleotides in a manner such that the 5′ phosphate of one mononucleotide pentose ring is attached to the 3′ oxygen of its neighbor in one direction via a phosphodiester linkage. An end of an oligonucleotide is referred to as the "5′ end" if its 5′ phosphate is not linked to the 3′ oxygen of a mononucleotide pentose ring. An end of an oligonucleotide is referred to as the "3′ end" if its 3′ oxygen is not linked to a 5′ phosphate of another mononucleotide pentose ring. A nucleic acid sequence, even if internal to a larger oligonucleotide, also may be said to have 5′ and 3′ ends. In either a linear or circular DNA molecule, discrete elements are referred to as being "upstream" or 5′ of the "downstream" or 3′ elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a rat cell or rat. For example, an endogenous Cfh sequence of a rat refers to a native Cfh sequence that naturally occurs at the Cfh locus in the rat.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

The term "locus" refers to a specific location of a gene (or significant sequence), DNA sequence, polypeptide-encoding sequence, or position on a chromosome of the genome of an organism. For example, a "Cfh locus" may refer to the specific location of a Cfh gene, Cfh DNA sequence, CFH-encoding sequence, or Cfh position on a chromosome of the genome of an organism that has been identified as to where such a sequence resides. A "Cfh locus" may comprise a regulatory element of a Cfh gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a rat cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

TABLE 1

| Amino Acid Categorizations. | | | | | |
| --- | --- | --- | --- | --- | --- |
| Alanine | Ala | A | Nonpolar | Neutral | 1.8 |
| Arginine | Arg | R | Polar | Positive | -4.5 |
| Asparagine | Asn | N | Polar | Neutral | -3.5 |
| Aspartic acid | Asp | D | Polar | Negative | -3.5 |
| Cysteine | Cys | C | Nonpolar | Neutral | 2.5 |
| Glutamic acid | Glu | E | Polar | Negative | -3.5 |
| Glutamine | Gln | Q | Polar | Neutral | -3.5 |
| Glycine | Gly | G | Nonpolar | Neutral | -0.4 |
| Histidine | His | H | Polar | Positive | -3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | -3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | -1.6 |
| Serine | Ser | S | Polar | Neutral | -0.8 |
| Threonine | Thr | T | Polar | Neutral | -0.7 |
| Tryptophan | Trp | W | Nonpolar | Neutral | -0.9 |
| Tyrosine | Tyr | Y | Polar | Neutral | -1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyl-transferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al.

(2013) Cell 153:910-918; Mandalos et al. (2012) *PLoS ONE* 7:e45768:1-9; and Wang et al. (2013) Nat. Biotechnol. 31:530-532, each of which is herein incorporated by reference in its entirety for all purposes.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means p≤0.05.

DETAILED DESCRIPTION

I. Overview

Disclosed herein are rat genomes, rat cells, and rats comprising an inactivated Cfh locus and methods of using such rat cells and rats. Also disclosed herein are rat Cfh genes comprising a targeted genetic modification that inactivates the rat Cfh genes and nuclease agents for use in inactivating a rat Cfh gene, wherein the nuclease agents target and cleave a nuclease target site in the Cfh gene. The rats disclosed herein are prone to high rates of spontaneous death and exhibit physiological, morphological, and histological symptoms that closely resemble C3 glomerulopathy (C3G). As such, the rats disclosed herein can be used to evaluate the therapeutic effectiveness of candidate compounds or agents for treatment of C3G.

C3G is a spectrum of disorders encompassing C3 glomerulonephritis and dense deposit disease. Unregulated alternative pathway (AP) complement activation as a result of acquired or genetic defects is the underlying cause of the C3G pathology. The acquired defects include development of C3 nephritic factors and autoantibodies stabilizing alternative pathway C3 convertase. The genetic defects include either mutations in C3 convertase components, complement component C3 and complement factor B, or regulatory proteins such as complement factor H (CFH), CFH-related 1, 2, 3 and 5, complement factor I, CD46, and others. About 50% percent of C3G patients progress to end-stage renal disease (ESRD) within 10 years after diagnosis with very few treatment options.

Histologically, kidneys of the C3G patients show predominant glomerular C3 deposition in the absence of immunoglobulins with a range of pathological features including mesangial matrix expansion, and membrane and endocapillary proliferation with crescent formation in few cases. There is also a histological evidence for kidney deposition of membrane attack complex (MAC), C5b-9, suggesting terminal complement component C5 activation. However, complete clinical response is not observed in C3G patients with eculizumab, a C5 blocking monoclonal antibody, suggesting a need for novel therapeutic strategies.

CFH is a critical negative regulator of alternative pathway. It controls complement activation both by decreasing the formation and increasing the dissociation of alternative pathway C3 convertase 2. CFH mutations leading to its loss-of function or deficiency were reported in C3G patients. The C3 levels are depleted in these patients due to uncontrolled complement activation. A spontaneous mutation in CFH was also identified in pigs leading to its deficiency and lethal C3G-like phenotype.

Complement factor H deficient (Cfh$^{-/-}$) mice have been a tool to understand the mechanisms underlying C3G. Similar to human patients, the Cfh$^{-/-}$ mice present unregulated alternative pathway complement activation and glomerular pathologies consistent with C3 and MAC deposition with minimal immunoglobulins, as well as hypercellularity, mesangial matrix expansion, and electron dense deposits. However, Cfh$^{-/-}$ mice do not show early mortality, and development of ESRD can take several months to manifest, requiring long preclinical studies to assess new therapeutics. Thus, alternative C3G models are needed.

Disclosed herein are Cfh$^{-/-}$ rats that were developed using VELOCIGENE® technology. Overall, our data indicate that Cfh$^{-/-}$ rats exhibited molecular and pathological features of C3G, including decreased circulatory C3 levels (suggesting a consumption of C3 due to hyperactivation of complement by the alternative pathway), elevation of blood urea nitrogen and serum cystatin C (suggesting kidney failure), elevated urinary albumin (albuminuria), deposition of C3 and C5b-9 in the glomeruli, glomerulosclerosis, tubular atrophy, and proteinaceous casts in the tubules. In addition, our data indicate that Cfh$^{-/-}$ rats exhibited marked glomerular pathology including podocyte effacement and contortion (epithelial effacement measured by increased width of foot processes and fewer foot processes), glomerular basement membrane (GBM) thickening with cellular interposition and electron dense deposits, mesangial expansion, and endothelial swelling with loss of fenestrae. Unlike Cfh$^{-/-}$ mice, however, a majority of the Cfh$^{-/-}$ rats succumb to ESRD and do so at a median age of 52 days in males and 103 days in females, thereby enabling shorter preclinical studies to assess new therapeutics.

II. Rats Comprising an Inactivated Cfh Locus

The rat cells and rats disclosed herein comprise an inactivated Cfh locus. Such rats recapitulate the phenotype of C3 glomerulopathy (C3G) and are advantageous over existing C3G models.

A. Complement Factor H (CFH), the Alternative Complement (AC) Pathway, and C3 Glomerulopathy (C3G)

The rat cells and rats described herein comprise an inactivated Cfh locus. Complement factor H (CFH; also known as factor H, complement component factor H, platelet complement factor H, complement inhibitory factor H, and adrenomedullin binding protein-1) is encoded by the Cfh gene (also known as Fh, Ambp-1, and Ambp1). Complement factor H functions as a cofactor in the inactivation of C3b by factor I and also increases the rate of dissociation of the C3bBb complex (C3 convertase) and the (C3b)NBB complex (C5 convertase) in the alternative complement pathway. Factor H is a member of the regulators of complement activation family and is a complement control protein. It is a large, soluble glycoprotein that circulates in plasma, and its principal function is to regulate the alternative pathway of the complement system, ensuring that the complement system is directed towards pathogens or other dangerous material and does not damage host tissue. Factor H regulates complement activation on self-cells and surfaces by possessing both cofactor activity for the factor-I-mediated C3b cleavage, and decay accelerating activity against the alternative pathway C3-convertase, C3bBb. Factor H exerts its protective action on self-cells and self surfaces but not on the surfaces of bacteria or viruses. This is may be the result of factor H having the ability to adopt either different conformations with lower or higher activity. The lower activity conformation is the predominant form in solution and is sufficient to control fluid phase amplification. The more active conformation is thought to be induced when factor H binds to glycosaminoglycans and or sialic acids that are generally present on host cells but not normally on pathogen surfaces, ensuring that self surfaces are protected while complement proceeds unabated on foreign surfaces.

Rat Cfh maps to rat 13q13 on chromosome 13 (NCBI RefSeq Gene ID 155012; Assembly Rnor_6.0 (GCF_000001895.5); location NC_005112.4 (56979155 . . . 57080540, complement)). The gene has been reported to have 22 exons. An exemplary rat Cfh genomic locus sequence is set forth in SEQ ID NO: 1. Reference to the rat Cfh genomic locus includes the wild type form (SEQ ID NO: 1) as well as all allelic forms and isoforms. Any other forms of the rat Cfh genomic locus have nucleotides numbered for maximal alignment with the wild type form, aligned nucleotides being designated the same number. Other rat Cfh genomic locus sequences can be homologs or allelic forms or isoforms at least about 90%, at least about 91%, at least about 92%, at least about 93%, at least about 94%, at least about 95%, at least about 96%, at least about 97%, at least about 98%, or at least about 99% identical to SEQ ID NO: 1. The wild type rat CFH protein has been assigned UniProt accession numbers Q5XJW6, G3V9R2, F1M983, and Q91YB6 and NCBI Accession No. NP_569093.2 (set forth in SEQ ID NO: 3). Reference to rat CFH protein includes the wild type form (NP_569093.2; SEQ ID NO: 3) as well as all allelic forms and isoforms. Any other forms of rat CFH have amino acids numbered for maximal alignment with the wild type form, aligned amino acids being designated the same number. Other rat CFH protein sequences can be homologs or allelic forms or isoforms at least about 90%, at least about 91%, at least about 92%, at least about 93%, at least about 94%, at least about 95%, at least about 96%, at least about 97%, at least about 98%, or at least about 99% identical to SEQ ID NO: 3. An mRNA (cDNA) encoding NP_569093.2 is assigned NCBI Accession No. NM_130409.2 (set forth in SEQ ID NO: 16). Other rat Cfh mRNA (cDNA) sequences can be homologs or allelic forms or isoforms at least about 90%, at least about 91%, at least about 92%, at least about 93%, at least about 94%, at least about 95%, at least about 96%, at least about 97%, at least about 98%, or at least about 99% identical to SEQ ID NO: 16. An exemplary coding sequence for the rat CFH protein is set forth in SEQ ID NO: 2. Other rat Cfh coding sequences can be homologs or allelic forms or isoforms at least about 90%, at least about 91%, at least about 92%, at least about 93%, at least about 94%, at least about 95%, at least about 96%, at least about 97%, at least about 98%, or at least about 99% identical to SEQ ID NO: 2. Reference to the rat Cfh mRNA (cDNA) and coding sequence includes the wild type forms (SEQ ID NOS: 16 and 2, respectively) as well as all allelic forms and isoforms. Any other forms of the rat Cfh mRNA (cDNA) and coding sequence have nucleotides numbered for maximal alignment with the wild type form, aligned nucleotides being designated the same number.

Figure 7:
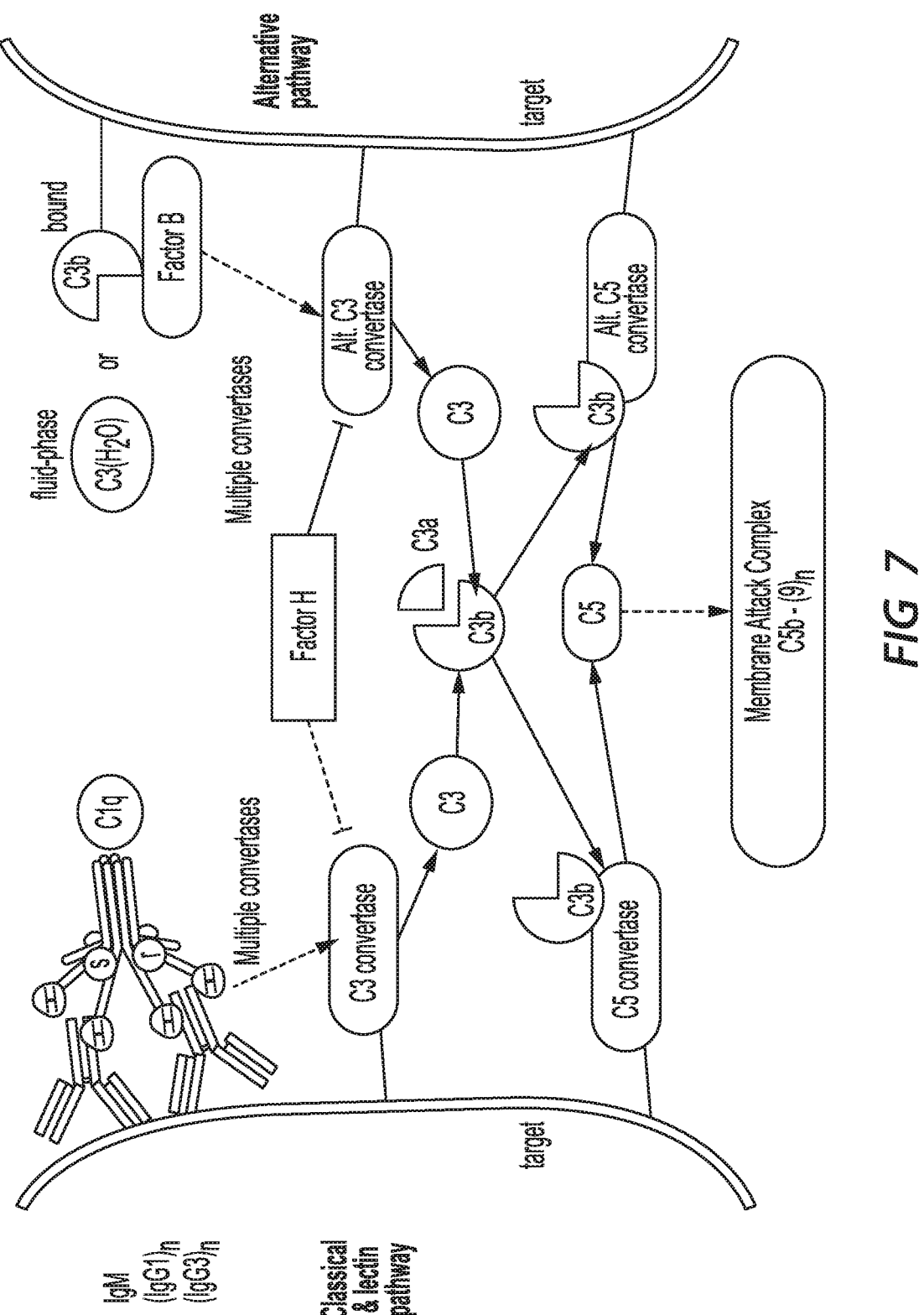
FIG. 7 shows a schematic of the complement pathways, including the classical and lectin pathways and the alternative pathway.

The complement system is a key component of innate immunity contributing to host defenses against invading pathogens through multiple mechanisms, which include opsonization, cell lysis, and inflammatory cell recruitment, an action principally mediated through the anaphylatoxin C5a. Complement activation is regulated by a complex group of membrane-bound and fluid-phase proteins. The complement system comprises three interrelated pathways, the classical pathway, lectin pathway, and the alternative pathway. See FIG. 7. However, dysregulation of the latter is characteristic of C3 glomerulopathy (C3G).

The alternative pathway (AP) of complement is unique. First, unlike the other pathways, it requires no specific triggering protein and remains continuously active through a process known as tickover. The initial alternative pathway protein, C3, is activated spontaneously through hydrolysis to form C3(H$_2$O). Tickover is responsible for constant, low-level activation of the alternative pathway. It is this feature that underscores the importance of proteins that control and protect self-tissues from perpetual complement activity.

Activated C3 recruits complement factor B (FB) and then factor D (FD). FD cleaves C3(H$_2$O) bound FB into Bb, releasing Ba and forming the alternative pathway C3 convertase [C3($H_2$O)Bb], a potent serine protease. This protease facilitates a process known as amplification, another unique feature of the alternative pathway. As a result of amplification, the convertase exponentially cleaves additional C3 into C3b and C3a, creating more C3 convertase enzymes (C3bBb). The alternative pathway functions as the effector arm of both the classical and the lectin pathway. Activity initiated from either of these pathways is amplified through the alternative pathway.

The association of additional C3b molecules with the C3 convertase complex creates the terminal pathway enzyme, the C5 convertase (C3bBbC3b). C5 convertase cleaves C5 into C5b, the first component of the terminal complement complex, and C5a. C5b associates with C6 and C7, with subsequent interaction with C8 inducing the binding of several C9 units to form the lytic complex C5b-C9 (C5b-9), also referred to as membrane attack complex. This lytic complex forms the basis of complement-mediated killing of target bacteria. Finally, in addition to the production of the terminal complement complex, the generation of the C3a and C5a anaphylotoxins during complement activation augments the immune role of the alternative pathway. Both anaphylotoxins play a central role in complement-mediated inflammation.

A number of complement control proteins have been identified. Those that act to control the activity of the alternative pathway (and indirectly the terminal complement pathway) include complement factor H (FH), membrane cofactor protein (MCP), decay accelerating factor (DAF), complement receptor 1 (CR1), and complement factor I (FI). Complement control is necessary to limit adverse, host cell damage from a continuously active complement system, or from an alternative pathway that has been triggered by an innate immune trigger. Factor H is an abundant serum complement regulatory protein that inhibits the alternative pathway of complement activation. It achieves this through several mechanisms, which include inhibition of the alternative pathway C3 convertase enzyme complex (C3bBb) and acting as a cofactor for the factor-I-mediated proteolytic degradation of activated C3 (termed C3b). Its critical importance as a regulator of C3 activation in vivo is illustrated by the complement profile reported in factor-H-deficient individuals, where alternative pathway activation proceeds unhindered, resulting in markedly reduced C3 levels.

C3 glomerulopathy (C3G) describes a spectrum of glomerular diseases defined by shared renal biopsy pathology: a predominance of C3 deposition on immunofluorescence with electron microscopy permitting disease subclassification. C3G is currently subdivided into two major electron microscopy subtypes: dense deposit disease (DDD) and C3 glomerulonephritis (C3GN). Before 2013, a portion of C3G patients carried the diagnosis of membranoproliferative glomerulonephritis (MPGN) or mesangioproliferative glomerulonephritis. These same patients would now be called C3G patients based on the microscopic appearance of their glomeruli. Complement dysregulation underlies the observed pathology, a causal relationship that is supported by studies of genetic and acquired drivers of disease. The complement system is a collection of proteins in the blood that, when functioning properly, help (complement) the immune system to fight invaders such as bacteria and viruses. However, when the complement system becomes abnormally activated, such as in C3G, normal complement proteins such as C3 can be broken down. Breakdown products of C3 become lodged in the kidney, setting off reactions that injure the glomeruli. Damaged glomeruli cannot filter the blood very well, and urine production is reduced. If this continues, toxins can build up in the blood, more kidney tissue can become damaged, and the ability of the kidney to perform other important functions may decline. Some common symptoms of C3G include blood in the urine (hematuria), excess protein in the urine (proteinuria), reduced glomerular filtration rate (GFR; reduced ability of the kidney to filter the blood and make urine), elevated creatinine, fatigue, and swelling (edema) of hands, feet, and ankles. Other symptoms include decreased circulatory C3 levels, increased blood urea nitrogen levels, increased C3 deposition in the kidneys, increased C5b-9 membrane attack complex deposition in the kidneys, and decreased lifespan (spontaneous mortality).

A mouse model with C3 predominance on renal biopsy and a C3GN pattern on renal histology was created by targeted disruption of CFH. This model remains the primary model used to study C3G today. However, end-stage renal disease (ESRD) can take several months to manifest in Cfh$^{-/-}$ mice, requiring long preclinical studies to assess new therapeutics. Better C3G models are needed that develop C3G and ESRD more rapidly and consistently.

B. Inactivated Cfh Loci

An inactivated endogenous Cfh locus or inactivated Cfh gene is a Cfh locus or Cfh gene that does not produce a complement factor H (CFH) protein or does not produce a functional CFH protein. The functions of CFH include inhibition of the alternative pathway C3 convertase enzyme complex (C3bBb) and acting as a cofactor for the factor-I-mediated proteolytic degradation of activated C3 (C3b). A CFH protein that is not functional is not able to inhibit the alternative pathway C3 convertase enzyme complex (C3bBb) or act as a cofactor for the factor-I-mediated proteolytic degradation of activated C3 (C3b).

As one example, an inactivated endogenous Cfh locus or inactivated Cfh gene can be one in which the start codon of the endogenous Cfh locus or Cfh gene has been deleted or has been disrupted or mutated such that the start codon is no longer functional. For example, the start codon can be disrupted by a deletion or insertion within the start codon. Alternatively the start codon can be mutated by, for example, by a substitution of one or more nucleotides.

As another example, the start codon of the endogenous Cfh locus or Cfh gene can be deleted or the coding sequence in the first exon of the endogenous Cfh locus or Cfh gene can be deleted. As a specific example, the start codon and the coding sequence in the first exon can be deleted, and the splice donor site in the first intron can be deleted.

As another example, some, most, or all of the coding sequence in the endogenous Cfh locus or Cfh gene can be deleted. For example, the coding sequence in exon 1, exons 1-2, exons 1-3, exons 1-4, exons 1-5, exons 1-6, exons 1-7, exons 1-8, exons 1-9, exons 1-10, exons 1-11, exons 1-12, exons 1-13, exons 1-14, exons 1-15, exons 1-16, exons 1-17, exons 1-18, exons 1-19, exons 1-20, exons 1-21, or exons 1-22 can be deleted. In a specific example, the coding sequence in exons 1-21 or exons 1-22 can be deleted. Alternatively, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the coding sequence in the endogenous Cfh locus or Cfh gene, including the start codon, can be deleted. In another example, all of the coding sequence in the endogenous Cfh locus or Cfh gene is deleted.

A specific example of a sequence deleted from an endogenous Cfh locus or Cfh gene to inactivate it is the sequence set forth in SEQ ID NO: 5 or a sequence corresponding to nucleotides 97-242 in SEQ ID NO: 1 (i.e., SEQ ID NO: 5) when optimally aligned with the rat Cfh genomic locus sequence set forth in SEQ ID NO: 1 (e.g., a homologous sequence at least about 90%, at least about 91%, at least about 92%, at least about 93%, at least about 94%, at least about 95%, at least about 96%, at least about 97%, at least about 98%, or at least about 99% identical to SEQ ID NO: 5). A specific example of an inactivated endogenous Cfh locus or Cfh gene is the sequence set forth in SEQ ID NO: 4 or a sequence with a deletion corresponding to the deletion in SEQ ID NO: 4 relative to SEQ ID NO: 1 when optimally aligned with SEQ ID NO: 1 (e.g., a homologous sequence at least about 90%, at least about 91%, at least about 92%, at least about 93%, at least about 94%, at least about 95%, at least about 96%, at least about 97%, at least about 98%, or at least about 99% identical to SEQ ID NO: 4).

C. Rat Genomes, Rat Cells, and Rats Comprising an Inactivated Cfh Locus

Rat genomes, rat cells and rats comprising an inactivated Cfh locus or inactivated Cfh gene as described elsewhere herein are provided. The genomes, cells, or rats can be male or female. The rat genomes, rat cells, or rats can be heterozygous or homozygous for the inactivated Cfh locus. Preferably, the genomes, cells, or rats, such as those used in the methods disclosed herein, are homozygous for the inactivated Cfh locus. A diploid organism has two alleles at each genetic locus. Each pair of alleles represents the genotype of a specific genetic locus. Genotypes are described as homozygous if there are two identical alleles at a particular locus and as heterozygous if the two alleles differ.

The rat genomes, rat cells, and rats provided herein can be, for example, any rat genome, rat cell, or rat comprising a Cfh locus. The rat cells can also be any type of undifferentiated or differentiated state. For example, a rat cell can be a totipotent cell, a pluripotent cell (e.g., rat pluripotent cell such as a rat embryonic stem (ES) cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be kidney cells.

Suitable cells provided herein also include primary cells. Primary cells include cells or cultures of cells that have been isolated directly from an organism, organ, or tissue. Primary cells include cells that are neither transformed nor immortal.

They include any cell obtained from an organism, organ, or tissue which was not previously passed in tissue culture or has been previously passed in tissue culture but is incapable of being indefinitely passed in tissue culture. Such cells can be isolated by conventional techniques and include, for example, kidney cells.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background, can be fresh or frozen, and can be derived from natural breeding or in vitro fertilization. The cells provided herein can be normal, healthy cells, or can be diseased or mutant-bearing cells.

Rats comprising an inactivated Cfh locus as described herein can be made by the methods described elsewhere herein. The rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an RTP $T^{av1}$ haplotype. Such strains are available from a variety of sources including Harlan Laboratories. The Dark Agouti (DA) rat strain is characterized as having an agouti coat and an RTP$^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

In a specific example, the Cfh gene is inactivated in embryonic stem cells of a Dark Agouti strain. In a specific example, those ES cells are then introduced into a Sprague Dawley rat host embryo to produce a chimera. The chimera can then, for example, be mated with a Sprague Dawley rat to produce F1 animals, which can then be interbred to establish a rat line with an inactivated Cfh locus. For example, the final rat Cfh knockout line can be 50% Dark Agouti and 50% Sprague Dawley.

Rats comprising an inactivated endogenous Cfh locus have one or more symptoms of C3 glomerulopathy (C3G) as disclosed elsewhere herein. The term "symptom" refers to objective evidence of a disease as observed by a physician.

As one example, rats comprising an inactivated endogenous Cfh locus can have decreased circulatory complement component 3 (C3) protein levels compared to a wild type rat (e.g., at about 7 weeks to about 17 weeks of age). For example, the circulatory C3 levels can be less than about 200 µg/mL or less than about 100 µg/mL. For example, the circulatory C3 levels can be less than about 200 µg/mL or less than about 100 µg/mL at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age. For example, the circulatory C3 levels can be between about 25 and about 200, between about 25 and about 175, between about 25 and about 150, between about 25 and about 125, between about 25 and about 100, or between about 25 and about 75 µg/mL (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age).

As another example, rats comprising an inactivated endogenous Cfh locus can have increased C3 deposition in the kidneys (e.g., in the glomeruli of the kidneys) compared to a wild type rat (e.g., at about 7 weeks to about 17 weeks of age). As another example, rats comprising an inactivated endogenous Cfh locus can have increased C5b-9 membrane attack complex (MAC; or terminal complement complex C5b-9) deposition in kidneys (e.g., in the glomeruli of the kidneys) compared to a wild type rat (e.g., at about 7 weeks to about 17 weeks of age).

As another example, rats comprising an inactivated endogenous Cfh locus can have increased blood urea nitrogen (BUN) levels compared to a wild type rat (e.g., at about 7 weeks to about 17 weeks of age). For example, the increased BUN levels can be at least about or more than about 10, at least about or more than about 20, at least about or more than about 30, at least about or more than about 40, at least about or more than about 50, at least about or more than about 60, at least about or more than about 70, at least about or more than about 80, at least about or more than about 90, or at least about or more than about 100 mg/dL (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the BUN levels can be between about 10 and about 400, between about 10 and about 350, between about 10 and about 300, between about 10 and about 250, between about 10 and about 200, between about 20 and about 400, between about 20 and about 350, between about 20 and about 300, between about 20 and about 250, between about 20 and about 200, between about 30 and about 400, between about 30 and about 350, between about 30 and about 300, between about 30 and about 250, between about 30 and about 200, between about 40 and about 400, between about 40 and about 350, between about 40 and about 300, between about 40 and about 250, between about 40 and about 200, between about 50 and about 400, between about 50 and about 350, between about 50 and about 300, between about 50 and about 250, or between about 50 and about 200 mg/dL (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age).

As another example, rats comprising an inactivated endogenous Cfh locus can have a decreased lifespan compared to a wild type rat. For example, the lifespan or median lifespan of a rat or populations of rats comprising an inactivated endogenous Cfh locus can be less than about 300 days, less than about 250 days, less than about 200 days, less than about 150 days, less than about 140 days, less than about 130 days, less than about 120 days, less than about 110 days, less than about 100 days, less than about 90 days, less than about 80 days, less than about 70 days, less than about 60 days, or less than about 50 days. In a specific example, the median lifespan is less than about 150 days or less than about 110 days. In a specific example, the lifespan is less than about 250 days, less than about 150 days, or less than about 130 days. For example, the lifespan or median lifespan of a rat or populations of rats comprising an inactivated endogenous Cfh locus can be between about 25 and about 75, between about 30 and about 70, between about 35 and about 65, between about 40 and about 60, between about 45 and about 55, between about 50 and about 55, between about 75 and about 125, between about 80 and about 120, between about 85 and about 115, between about 90 and about 110, between about 95 and about 105, between about 100 and about 105, between about 25 and about 125, between about 30 and about 120, between about 35 and about 115, between about 40 and about 110, between about 45 and about 105, or between about 50 and about 105 days.

As another example, rats comprising an inactivated endogenous Cfh locus can have increased serum cystatin C levels compared to a wild type rat (e.g., at about 7 weeks to about 17 weeks of age). For example, serum cystatin C levels can be at least about or more than about 1000, at least about or more than about 1100, at least about or more than about 1200, at least about or more than about 1300, at least about or more than about 1400, at least about or more than about 1500, at least about or more than about 1600, at least about or more than about 1700, at least about or more than about 1800, at least about or more than about 1900, or at least about or more than about 2000 ng/mL (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, serum cystatin C levels can be between about 1000 and about 5000, between about 1000 and about 4500, between about 1000 and about 4000, between about 1000 and about 3500, between about 1000 and about 3000, between about 1100 and about 5000, between about 1100 and about 4500, between about 1100 and about 4000, between about 1100 and about 3500, between about 1100 and about 3000, between about 1200 and about 5000, between about 1200 and about 4500, between about 1200 and about 4000, between about 1200 and about 3500, between about 1200 and about 3000, between about 1300 and about 5000, between about 1300 and about 4500, between about 1300 and about 4000, between about 1300 and about 3500, between about 1300 and about 3000, between about 1400 and about 5000, between about 1400 and about 4500, between about 1400 and about 4000, between about 1400 and about 3500, between about 1400 and about 3000, between about 1500 and about 5000, between about 1500 and about 4500, between about 1500 and about 4000, between about 1500 and about 3500, or between about 1500 and about 3000 ng/mL (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age).

As another example, rats comprising an inactivated endogenous Cfh locus can have increased urinary albumin levels (albuminuria) compared to a wild type rat (e.g., at about 7 weeks to about 17 weeks of age). For example, the increased urinary albumin can be as measured by urinary albumin per day or normalized to creatinine. For example, the urinary albumin/day can be, e.g., at least about or more than about 1000, at least about or more than about 2000, at least about or more than about 3000, at least about or more than about 4000, at least about or more than about 5000, at least about or more than about 6000, at least about or more than about 7000, at least about or more than about 8000, at least about or more than about 9000, or at least about or more than about 10000 g/day (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the urinary albumin/day can, e.g., be between about 1000 and about 40000, between about 2000 and about 40000, between about 3000 and about 40000, between about 4000 and about 40000, or between about 5000 and about 40000 g/day (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the urinary albumin normalized to urinary creatinine (i.e., the ratio of urinary albumin to urinary creatinine) can be, e.g., at least about or more than about 100, at least about or more than about 200, at least about or more than about 300, at least about or more than about 400, at least about or more than about 500, at least about or more than about 600, at least about or more than about 700, at least about or more than about 800, at least about or more than about 900, at least about or more than about 1000, at least about or more than about 1100, at least about or more than about 1200, at least about or more than about 1300, at least about or more than about 1400, at least about or more than about 1500, at least about or more than about 1600, at least about or more than about 1700, at least about or more than about 1800, at least about or more than about 1900, or at least about or more than about 2000 µg:mg (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the urinary albumin normalized to urinary creatinine (i.e., the ratio of urinary albumin to urinary creatinine) can be, e.g., between about 100 and about 6000, between about 200 and about 6000, between about 300 and about 6000, between about 400 and about 6000, between about 500 and about 6000, between about 1000 and about 6000, between about 100 and about 5000, between about 200 and about 5000, between about 300 and about 5000, between about 400 and about 5000, between about 500 and about 5000, or between about 1000 and about 5000 µg:mg (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age).

As another example, rats comprising an inactivated endogenous Cfh locus can exhibit marked glomerular pathology including podocyte effacement and contortion (epithelial effacement measured by increased width of foot processes and fewer foot processes), glomerular basement membrane (GBM) thickening (e.g., with cellular interposition and electron dense deposits), mesangial expansion, and/or endothelial swelling with loss of fenestrae (e.g., at about 7 weeks to about 17 weeks of age).

As one example, the increase in GBM thickness can be at least about 2-fold, at least about 3-fold, at least about 4-fold, at least about 5-fold, at least about 6-fold, at least about 7-fold, at least about 8-fold, at least about 9-fold, or at least about 10-fold compared to the wild type rat (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average GBM thickness in glomeruli can be at least about 0.2, at least about 0.3, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, or at least about 1.8 microns in length (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average GBM thickness in glomeruli can be between about 0.2 and about 2.5, between about 0.5 and about 2.5, between about 1.0 and about 2.5, between about 1.1 and about 2.5, between about 1.2 and about 2.4, between about 1.3 and about 2.3, between about 1.4 and about 2.2, between about 1.5 and about 2.1, between about 1.6 and about 2.0, or between about 1.7 and about 1.9 microns in length (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average GBM thickness in glomeruli can be about 1.8 microns in length (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age).

As another example, the increase in podocyte foot process width can be at least about 2-fold, at least about 3-fold, at least about 4-fold, at least about 5-fold, at least about 6-fold, or at least about 7-fold compared to the wild type rat (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average width of foot process in glomeruli can be at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.1, at least about 2.2, at least about 2.3, at least about 2.4, or at least about 2.5 microns (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average width of foot process in glomeruli can be between about 0.5 and about 5.5, between about 1.0 and about 5.5, between about 1.5 and about 5.5, between about 0.5 and about 3.5, between about 1.0 and about 3.5, between about 1.5 and about 3.5, between about 2.0 and about 3.5, between about 2.0 and about 3.0, between about 2.1 and about 2.9, between about 2.2 and about 2.8, between about 2.3 and about 2.7, or between about 2.4 and about 2.6 microns (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average width of foot process in glomeruli can be about 2.5 microns (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age).

As another example, the decrease in podocyte foot process number can be at least about 2-fold, at least about 2.5-fold, at least about 3-fold, at least about 3.5-fold, at least about 3.8-fold, or at least about 4-fold compared to the wild type rat (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average podocyte foot process number per micron length (e.g., average number of foot processes covering the capillary loops in glomeruli) can be less than about 2.5, less than about 2, less than about 1.5, less than about 1.4, less than about 1.3, less than about 1.2, less than about 1.1, less than about 1, less than about 0.9, or less than about 0.8 (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average podocyte foot process number per micron length can be between about 0.4 and about 2.5, between about 0.4 and about 2.0, between about 0.4 and about 1.5, between about 0.4 and about 1.4, between about 0.4 and about 1.3, between about 0.4 and about 1.2, between about 0.4 and about 1.1, between about 0.4 and about 1.0, between about 0.4 and about 0.9, between about 0.4 and about 0.8, between about 0.5 and about 2.5, between about 0.5 and about 2.0, between about 0.5 and about 1.5, between about 0.5 and about 1.4, between about 0.5 and about 1.3, between about 0.5 and about 1.2, between about 0.5 and about 1.1, between about 0.5 and about 1.0, between about 0.5 and about 0.9, between about 0.5 and about 0.8, between about 0.6 and about 2.5, between about 0.6 and about 2.0, between about 0.6 and about 1.5, between about 0.6 and about 1.4, between about 0.6 and about 1.3, between about 0.6 and about 1.2, between about 0.6 and about 1.1, between about 0.6 and about 1.0, between about 0.6 and about 0.9, or between about 0.6 and about 0.8 (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age). For example, the average podocyte foot process number per micron length can be about 0.7 (e.g., at about 7 weeks, about 8 weeks, about 9 weeks, about 10 weeks, about 11 weeks, about 12 weeks, about 13 weeks, about 14 weeks, about 15 weeks, about 16 weeks, or about 17 weeks of age).

III. Methods of Using Rats Comprising an Inactivated Cfh Locus for Assessing Efficacy of Putative C3G Therapeutic Agents In Vivo or Ex Vivo Various methods are provided for using the rats comprising an inactivated Cfh locus as described elsewhere herein for assessing efficacy of putative C3 glomerulopathy (C3G) therapeutic agents in vivo or ex vivo. Such methods can be methods for identifying a candidate agent (i.e. a compound or therapeutic molecule) or assessing the in vivo therapeutic efficacy of a candidate agent for use in the treatment of a C3G. The methods utilize any of the rats comprising an inactivated Cfh locus disclosed herein. In such methods, candidate compounds can be administered directly to rats exhibiting symptoms of C3G to determine if the agent or compound can reduce one or more symptoms of C3G.

A. Methods of Testing Efficacy of Putative C3G Therapeutic Agents In Vivo or Ex Vivo Various methods are provided for assessing the C3 glomerulopathy (C3G) therapeutic activity of an agent or compound (e.g., a putative C3G therapeutic agent) in vivo or ex vivo. Such methods can comprise administering the agent or compound to a rat comprising an inactivated Cfh locus and assessing the C3G therapeutic activity of the agent compound in the rat, or they can comprise administering a putative C3 therapeutic agent to a rat comprising an inactivated Cfh locus and assessing the activity of the putative C3 therapeutic agent in the rat. For example, such methods can be for assessing the in vivo therapeutic efficacy of an agent or compound for use in a treatment of C3 glomerulopathy (C3G). Such methods can comprise, for example, administering the agent or compound to a rat comprising an inactivated Cfh locus, and assessing one or more symptoms of C3G in the genetically modified rat that has been administered the agent or compound compared to a control genetically modified rat that has not been administered the agent or compound.

The agent or compound can be any biological or chemical agent. Examples of putative C3G therapeutic agents or compounds are disclosed elsewhere herein.

Such compounds or agents can be administered by any delivery method (e.g., injection, AAV, LNP, or HDD) as disclosed in more detail elsewhere herein and by any route of administration. Means of delivering therapeutic molecules and routes of administration are disclosed in more detail elsewhere herein.

Methods for assessing activity of a putative C3G therapeutic agent or for assessing the C3G therapeutic activity of an agent or compound are well-known and are provided elsewhere herein. Such assessing can comprise assessing readouts of activity of the Alternate Complement (AC) pathway or assessing kidney function. For example, such methods can comprise assessing any C3G symptom, such as one or more or all of the following: (i) circulatory C3 protein levels (decreased in C3G); (ii) blood urea nitrogen levels (increased in C3G); (iii) levels of C3 deposition in the kidneys (e.g., in the glomeruli of the kidneys) (increased in C3G); (iv) levels of C5b-9 deposition in the kidneys (e.g., in the glomeruli of the kidneys) (increased in C3G); and (v) lifespan of the rat (decreased in C3G). As another example, such methods can comprise assessing one or more or all of the following: (i) circulatory C3 protein levels (decreased in C3G); (ii) blood urea nitrogen levels (increased in C3G); (iii) levels of C3 deposition in the kidneys (e.g., in the glomeruli of the kidneys) (increased in C3G); (iv) levels of C5b-9 deposition in the kidneys (e.g., in the glomeruli of the kidneys) (increased in C3G); (v) serum cystatin C levels (increased in glomerular disease like C3G); (vi) urinary albumin (albuminuria) (increased in glomerular disease like C3G); (vii) glomerular basement membrane (GBM) thickness (increased in glomerular disease like C3G); (viii) podocyte foot process width (increased in glomerular disease like C3G); (ix) podocyte foot process number (decreased in glomerular disease like C3G); and (x) lifespan of the rat (decreased in C3G). Any other symptoms associated with glomerular disease that are described herein can also be used. The agent or compound can ameliorate or treat one or more symptoms of C3G compared to a control rat that has not been administered the candidate agent or compound. The terms "ameliorate" or "treat" mean to eliminate, delay the onset of, or reduce the prevalence, frequency, or severity of one or more r symptoms associated with C3G.

The one or more symptoms assessed can include decreased C3 circulatory levels. Such methods can comprise assessing circulatory C3 protein levels in the genetically modified rat administered the agent or compound. Circulatory C3 levels can be assessed, for example, in rats between about 2 weeks and about 17 weeks, between about 2 weeks and about 12 weeks, between about 3 weeks and about 11 weeks, between about 4 weeks and about 10 weeks, between about 5 weeks and about 9 weeks, or between about 6 weeks and about 8 weeks of age. In a specific example, circulatory C3 levels can be assessed at about 7 weeks of age. Alternatively, circulatory C3 levels can be assessed at between about 7 weeks and about 17 weeks, between about 7 weeks and about 16 weeks, between about 7 weeks and about 15 weeks, between about 7 weeks and about 14 weeks, between about 7 weeks and about 13 weeks, between about 7 weeks and about 12 weeks, between about 7 weeks and about 11 weeks, between about 7 weeks and about 10 weeks, between about 7 weeks and about 9 weeks, or between about 7 weeks and about 8 weeks of age. For example, the circulatory C3 protein levels in the genetically modified rat administered the agent or compound can be assessed relative to circulatory C3 protein levels in a control genetically modified rat that has not been administered the agent or compound, wherein increased circulatory C3 protein levels relative to the control genetically modified rat indicates a therapeutic effect for the agent or compound. For example, the amelioration of decreased circulatory C3 levels by the candidate agent or compound in any of the rats comprising an inactivated Cfh locus as described herein can be statistically significant. For example, the candidate agent or compound can ameliorate decreased circulatory C3 levels (e.g., increase circulatory C3 levels) in any of the rats comprising an inactivated Cfh locus as described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent. Assessing circulatory C3 levels can be accomplished using any number of well-known methods.

The one or more symptoms assessed can also include C3 deposition in the kidney (particularly in the nephron (for example, the in the glomerulus)). Such methods can comprise assessing levels of C3 deposition in the kidneys (e.g., in the glomeruli of the kidneys) in the genetically modified rat administered the agent or compound. C3 deposition can be assessed, for example, in rats between about 7 weeks and about 17 weeks, between about 8 weeks and about 17 weeks, or between about 9 weeks and about 17 weeks of age. Alternatively, levels of C3 deposition in the kidneys can be assessed at between about 7 weeks and about 17 weeks, between about 7 weeks and about 16 weeks, between about 7 weeks and about 15 weeks, between about 7 weeks and about 14 weeks, between about 7 weeks and about 13 weeks, between about 7 weeks and about 12 weeks, between about 7 weeks and about 11 weeks, between about 7 weeks and about 10 weeks, between about 7 weeks and about 9 weeks, or between about 7 weeks and about 8 weeks of age. For example, the C3 deposition levels in the genetically modified rat administered the agent or compound can be assessed relative to C3 deposition levels in a control genetically modified rat that has not been administered the agent or compound, wherein decreased C3 deposition levels relative to the control genetically modified rat indicates a therapeutic effect for the agent or compound. For example, the amelioration of kidney C3 deposition by the candidate agent or compound in any of the rats comprising an inactivated Cfh locus as described herein can be statistically significant. For example, the candidate agent or compound can ameliorate kidney C3 deposition (e.g., decrease kidney C3 deposition) in any of the rats comprising an inactivated Cfh locus as described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent. Determination of kidney C3 protein deposition can be analyzed by any number of known means, including, but not limited to, immunohistochemistry, immunofluorescence, and electron microscopy (including immunoelectron microscopy).

The one or more symptoms assessed can also include C5b-9 membrane attack complex deposition in the kidney (e.g., in the glomerulus)). Such methods can comprise assessing levels of C5b-9 deposition in the kidneys (e.g., in the glomeruli of the kidneys) in the genetically modified rat administered the agent or compound. C5b-9 deposition can be assessed, for example, in rats between about 7 weeks and about 17 weeks, between about 8 weeks and about 17 weeks, or between about 9 weeks and about 17 weeks of age. Alternatively, levels of C5b-9 deposition in the kidneys can be assessed at between about 7 weeks and about 17 weeks, between about 7 weeks and about 16 weeks, between about 7 weeks and about 15 weeks, between about 7 weeks and about 14 weeks, between about 7 weeks and about 13 weeks, between about 7 weeks and about 12 weeks, between about 7 weeks and about 11 weeks, between about 7 weeks and about 10 weeks, between about 7 weeks and about 9 weeks, or between about 7 weeks and about 8 weeks of age. For example, the C5b-9 deposition levels in the genetically modified rat administered the agent or compound can be assessed relative to C5b-9 deposition levels in a control genetically modified rat that has not been administered the agent or compound, wherein decreased C5b-9 deposition levels relative to the control genetically modified rat indicates a therapeutic effect for the agent or compound. For example, the amelioration of C5b-9 membrane attack complex formation and deposition in the kidney by the candidate agent or compound in any of the rats comprising an inactivated Cfh locus as described herein by a statistically significant amount. For example, the candidate agent or compound can ameliorate C5b-9 membrane attack complex formation and deposition in the kidney (e.g., decrease C5b-9 deposition levels) in any of the rats comprising an inactivated Cfh locus as described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% 40%, 4%1%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent. Determination of C5b-9 membrane attack complex formation and deposition in the kidney can be analyzed by any number of known means, including, but not limited to, immunohistochemistry, immunofluorescence (such as an immunofluorescently labeled anti-C9 antibody), and electron microscopy (including immunoelectron microscopy).

The one or more symptoms assessed can also include blood urea nitrogen (BUN) levels in the serum. Such methods can comprise assessing levels of blood urea nitrogen levels in the genetically modified rat administered the agent or compound. Blood urea nitrogen levels can be assessed, for example, in rats between about 7 weeks and about 17 weeks, between about 8 weeks and about 17 weeks, or between about 9 weeks and about 17 weeks of age. Alternatively, blood urea nitrogen levels can be assessed at between about 7 weeks and about 17 weeks, between about 7 weeks and about 16 weeks, between about 7 weeks and about 15 weeks, between about 7 weeks and about 14 weeks, between about 7 weeks and about 13 weeks, between about 7 weeks and about 12 weeks, between about 7 weeks and about 11 weeks, between about 7 weeks and about 10 weeks, between about 7 weeks and about 9 weeks, or between about 7 weeks and about 8 weeks of age. For example, the blood urea nitrogen levels in the genetically modified rat administered the agent or compound can be assessed relative to blood urea nitrogen levels in a control genetically modified rat that has not been administered the agent or compound, wherein decreased blood urea nitrogen levels relative to the control genetically modified rat indicates a therapeutic effect for the agent or compound. For example, the amelioration of elevated plasma or serum blood urea nitrogen levels by the candidate agent or compound in any of the rats comprising an inactivated Cfh locus as described herein can be statistically significant. For example, the candidate agent or compound can ameliorate elevated plasma or serum blood urea nitrogen levels (e.g., decrease plasma or serum blood urea nitrogen levels) in any of the rats comprising an inactivated Cfh locus as described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent. Assessing serum and/or plasma levels of BUN can be accomplished using any number of well-known methods.

The one or more symptoms assessed can also include serum cystatin C levels in the serum. Such methods can comprise assessing levels of serum cystatin C levels in the genetically modified rat administered the agent or compound. Serum cystatin C levels can be assessed, for example, in rats between about 7 weeks and about 17 weeks, between about 8 weeks and about 17 weeks, or between about 9 weeks and about 17 weeks of age. Alternatively, serum cystatin C levels can be assessed at between about 7 weeks and about 17 weeks, between about 7 weeks and about 16 weeks, between about 7 weeks and about 15 weeks, between about 7 weeks and about 14 weeks, between about 7 weeks and about 13 weeks, between about 7 weeks and about 12 weeks, between about 7 weeks and about 11 weeks, between about 7 weeks and about 10 weeks, between about 7 weeks and about 9 weeks, or between about 7 weeks and about 8 weeks of age. For example, the serum cystatin C levels in the genetically modified rat administered the agent or compound can be assessed relative to serum cystatin C levels in a control genetically modified rat that has not been administered the agent or compound, wherein decreased serum cystatin C levels relative to the control genetically modified rat indicates a therapeutic effect for the agent or compound. For example, the amelioration of elevated plasma or serum cystatin C levels by the candidate agent or compound in any of the rats comprising an inactivated Cfh locus as described herein can be statistically significant. For example, the candidate agent or compound can ameliorate elevated plasma or serum cystatin C levels (e.g., decrease plasma or serum cystatin C levels) in any of the rats comprising an inactivated Cfh locus as described herein by any of 1%, 2%, 3%, 4%, 5%, 6%, 7%, 8%, 9%, 10, 1%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 8100, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent. Assessing serum and/or plasma levels of serum cystatin C can be accomplished using any number of well-known methods.

The one or more symptoms assessed can also include urinary albumin levels (albuminuria). Such methods can comprise assessing levels of urinary albumin levels in the genetically modified rat administered the agent or compound. Urinary albumin levels can be assessed, for example, in rats between about 7 weeks and about 17 weeks, between about 8 weeks and about 17 weeks, or between about 9 weeks and about 17 weeks of age. Alternatively, urinary albumin levels can be assessed at between about 7 weeks and about 17 weeks, between about 7 weeks and about 16 weeks, between about 7 weeks and about 15 weeks, between about 7 weeks and about 14 weeks, between about 7 weeks and about 13 weeks, between about 7 weeks and about 12 weeks, between about 7 weeks and about 11 weeks, between about 7 weeks and about 10 weeks, between about 7 weeks and about 9 weeks, or between about 7 weeks and about 8 weeks of age. For example, the urinary albumin levels in the genetically modified rat administered the agent or compound can be assessed relative to urinary albumin levels in a control genetically modified rat that has not been administered the agent or compound, wherein decreased urinary albumin levels relative to the control genetically modified rat indicates a therapeutic effect for the agent or compound. For example, the amelioration of elevated urinary albumin levels by the candidate agent or compound in any of the rats comprising an inactivated Cfh locus as described herein can be statistically significant. For example, the candidate agent or compound can ameliorate elevated urinary albumin levels (e.g., decrease urinary albumin levels) in any of the rats comprising an inactivated Cfh locus as described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent. Assessing urinary albumin levels can be accomplished using any number of well-known methods and can be quantified, for example, as per day or normalized to urinary creatinine.

The one or more symptoms assessed can also include glomerulus pathology, such as thickness of glomerular basement membrane (GBM), width of podocyte foot processes, and number of podocyte foot processes. Such methods can comprise assessing glomerulus pathology in the genetically modified rat administered the agent or compound. Glomerulus pathology can be assessed, for example, in rats between about 7 weeks and about 17 weeks, between about 8 weeks and about 17 weeks, or between about 9 weeks and about 17 weeks of age. Alternatively, glomerulus pathology can be assessed at between about 7 weeks and about 17 weeks, between about 7 weeks and about 16 weeks, between about 7 weeks and about 15 weeks, between about 7 weeks and about 14 weeks, between about 7 weeks and about 13 weeks, between about 7 weeks and about 12 weeks, between about 7 weeks and about 11 weeks, between about 7 weeks and about 10 weeks, between about 7 weeks and about 9 weeks, or between about 7 weeks and about 8 weeks of age. For example, the glomerulus pathology in the genetically modified rat administered the agent or compound can be assessed relative to glomerulus pathology in a control genetically modified rat that has not been administered the agent or compound, wherein decreased GBM thickness, decreased podocyte foot process width, or increased podocyte foot process number (e.g., increased podocyte foot number/micron length) relative to the control genetically modified rat indicates a therapeutic effect for the agent or compound. For example, the amelioration of the increased GBM thickness, increased podocyte foot process width, or decreased podocyte foot process number by the candidate agent or compound in any of the rats comprising an inactivated Cfh locus as described herein can be statistically significant. For example, the candidate agent or compound can ameliorate increased GBM thickness, increased podocyte foot process width, or decreased podocyte foot process number (e.g., decrease GBM thickness, decrease podocyte foot process width, or increase podocyte foot process number) in any of the rats comprising an inactivated Cfh locus as described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent. Assessing glomerulus pathology can be accomplished using any number of well-known methods including those described herein.

The one or more symptoms assessed can also include spontaneous death (i.e. lifespan). Such methods can comprise assessing lifespan of the genetically modified rat administered the agent or compound. For example, the lifespan of the genetically modified rat administered the agent or compound can be assessed relative to lifespan of a control genetically modified rat that has not been administered the agent or compound, wherein increased lifespan relative to the control genetically modified rat indicates a therapeutic effect for the agent or compound. For example, the amelioration of the occurrence of spontaneous death by the candidate agent or compound in any of the rats comprising an inactivated Cfh locus as described herein can be statistically significant. For example, the candidate agent or compound can ameliorate the occurrence of spontaneous death (e.g., increase lifespan) in any of the rats comprising an inactivated Cfh locus as described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control rats that are not treated with the candidate compound or agent.

The control genetically modified rat in the examples above can be a rat otherwise identical to the one being treated with the agent or compound other than not being treated with the agent or compound. For example, the control rat can have the same inactivated Cfh locus, can be the same strain as the rat being treated, can be the same gender as the rat being treated, and/or can be the same age as the rat being treated. The control rat can be, for example, untreated or treated with a control substance (e.g., placebo) having no therapeutic effect.

The various methods provided above for assessing activity in vivo can also be used to assess the activity of putative C3G therapeutic agents or assessing the C3G therapeutic activity of compounds ex vivo as described elsewhere herein.

B. Candidate C3G Therapeutic Agents

Any candidate C3 glomerulopathy (C3G) therapeutic agent or compound can be tested in the rat cells and rats disclosed herein. Such putative therapeutic agents can be any agents designed or tailored to prevent or alleviate one or more symptoms associated with C3G as described elsewhere herein. Such putative therapeutic agents can be small molecules or can be biologics such as antibodies, antigen-binding proteins, or nucleic acids or proteins. Candidate therapeutic agents or compounds can be, for example, small molecule chemical compounds, antibodies, proteins, inhibitory nucleic acids, or any combination thereof.

As one example, putative C3G therapeutic agents can be designed to be complement inhibitors. Examples of complement inhibitors include eculizumab (a humanized anti-complement C5 monoclonal antibody approved for a different complement-mediated renal disease (atypical hemolytic uremic syndrome, aHUS); blocks cleavage of C5 thereby preventing both formation of C5b-9 and the production of the anaphylatoxin C5A), soluble complement receptor 1 (CR1), C3 inhibitors such as Cp40 (a peptidic C3 inhibitor), C5 inhibitors such as siRNA agents against C5, FB and FD inhibitors, and C5a receptor blockers. See, e.g., Nester and Smith (2016) *Seminars in Immunology* 28:241-249, herein incorporated by reference in its entirety for all purposes.

As another example, putative C3G therapeutic agents can be agents designed to slow the process of kidney damage from C3G. Such agents could include, for example, corticosteroids (used, for example, to calm subject's immune system, to which the complement system belongs, and stop it from attacking glomeruli), immunosuppressive drugs (used, for example, to inhibit function of subject's immune system, which contributes to kidney damage in C3G), ACE inhibitors and ARBs (blood pressure medications used, for example, to reduce protein loss and control blood pressure), diet changes (for example, reducing salt (sodium) and protein to lighten the load of wastes on the kidneys), and complement inhibitors.

The activity of any other known or putative C3G therapeutic agents can also be assessed using the rats disclosed herein. Similarly, any other molecule can be screened for C3G therapeutic activity using the rats disclosed herein.

C. Administering Putative C3G Therapeutic Agents to Rats or Rat Cells

The methods disclosed herein can comprise introducing into a rat or rat cell various agents or compounds (e.g., putative C3G therapeutic agents such as antibodies or small molecules), including nucleic acids, proteins, nucleic-acid-protein complexes, peptide mimetics, antigen-binding proteins, or small molecules. "Introducing" includes presenting to the rat cell or rat the molecule (e.g., nucleic acid or protein or small molecule) in such a manner that it gains access to the interior of the rat cell or to the interior of cells within the rat. The introducing can be accomplished by any means. If multiple components are introduced, they can be introduced simultaneously or sequentially in any combination. In addition, two or more of the components can be introduced into the rat cell or rat by the same delivery method or different delivery methods. Similarly, two or more of the components can be introduced into a rat by the same route of administration or different routes of administration.

Agents or compounds introduced into the rat or rat cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a putative C3G therapeutic agent or compound into a rat cell or rat. Methods for introducing agents into various cell types are known and include, for example, stable transfection methods, transient transfection methods, and virus-mediated methods.

Transfection protocols as well as protocols for introducing agents into cells may vary. Non-limiting transfection methods include chemical-based transfection methods using liposomes; nanoparticles; calcium phosphate (Graham et al. (1973) *Virology* 52(2):456-467, Bacchetti et al. (1977) *Proc. Natl. Acad. Sci. USA* 74(4):1590-1594, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Curr. Pharm. Biotechnol.* 7(4):277-285). Viral methods can also be used for transfection.

Introduction of putative C3G therapeutic agents or compounds into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of putative C3G therapeutic agents or compounds into a cell (e.g., a zygote) can also be accomplished by microinjection. In zygotes (i.e., one-cell stage embryos), microinjection can be into the maternal and/or paternal pronucleus or into the cytoplasm. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109: 9354-9359.

Other methods for introducing putative C3G therapeutic agents or compounds into a rat cell or rat can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a rat cell or rat in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a rat include hydrodynamic delivery, virus-mediated delivery (e.g., adeno-associated virus (AAV)-mediated delivery), and lipid-nanoparticle-mediated delivery.

Introduction of putative C3G therapeutic agents or compounds into rat cells or rats can be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of putative C3G therapeutic agents or compounds can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression. Exemplary viral titers (e.g., AAV titers) include $10^{12}$, $10^{13}$, $10^{14}$, $10^{15}$, and $10^{16}$ vector genomes/mL.

Introduction of putative C3G therapeutic agents or compounds can also be accomplished by lipid nanoparticle (LNP)-mediated delivery. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyrus, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically. In a particular example, the route of administration is subcutaneous or intravenous.

Compositions comprising putative C3G therapeutic agents or compounds can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can depend on the half-life of the putative C3G therapeutic agents or compounds and the route of administration among other factors. The introduction of putative C3G therapeutic agents or compounds into the rat cell or rat can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

IV. Methods of Making Rats Comprising an Inactivated Cfh Locus

Various methods are provided for making a rat comprising an inactivated Cfh locus as disclosed elsewhere herein. Likewise, various methods are provided for making an inactivated rat Cfh gene or locus or for making a rat genome or rat cell comprising an inactivated Cfh locus as disclosed elsewhere herein. Any convenient method or protocol for producing a genetically modified rat is suitable for producing such a genetically modified rat. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified rats can be generated, for example, through gene knock-out at a targeted Cfh locus.

For example, the method of producing a rat comprising an inactivated Cfh locus can comprise: (1) modifying the genome of a pluripotent cell to comprise the inactivated Cfh locus; (2) identifying or selecting the genetically modified pluripotent cell comprising the inactivated Cfh locus; (3) introducing the genetically modified pluripotent cell into a rat host embryo; and (4) implanting and gestating the host embryo in a surrogate mother. Alternatively, the method of producing a rat comprising an inactivated Cfh locus can comprise: (1) modifying the genome of a pluripotent cell to comprise the inactivated Cfh locus; (2) identifying or selecting the genetically modified pluripotent cell comprising the inactivated Cfh locus; (3) introducing the genetically modified pluripotent cell into a rat host embryo; and (4) gestating the host embryo in a surrogate mother. Optionally, the host embryo comprising modified pluripotent cell (e.g., a rat ES cell) can be incubated until the blastocyst stage before being implanted into and gestated in the surrogate mother to produce an F0 rat. The surrogate mother can then produce an F0 generation rat comprising the inactivated Cfh locus.

The methods can further comprise identifying a cell or animal having a modified target genomic locus. Various methods can be used to identify cells and animals having a targeted genetic modification.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. The loss-of-allele (*LOA*) assay inverts the conventional screening logic and quantifies the number of copies of the native locus to which the mutation was directed. In a correctly targeted cell clone, the *LOA* assay detects one of the two native alleles (for genes not on the X or Y chromosome), the other allele being disrupted by the targeted modification. For example, TAQMAN® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus(loci) which is replaced by successful targeting (i.e., a *LOA* assay). The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus(loci) has been replaced by homologous recombination will result in an increase of one Ct for the target TAQMAN® reaction without an increase in the Ct for the reference gene when compared to DNA from non-targeted cells.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes). Next generation sequencing (NGS) can also be used for screening. Next-generation sequencing can also be referred to as "NGS" or "massively parallel sequencing" or "high throughput sequencing." In the methods disclosed herein, it is not necessary to screen for targeted cells using selection markers. For example, the MOA (e.g. *LOA*) and NGS assays described herein can be relied on without using selection cassettes.

An example of a suitable pluripotent cell is a rat embryonic stem (ES) cell. The modified pluripotent cell can be generated, for example, through recombination by (a) introducing into the cell one or more targeting vectors or exogenous donor nucleic acids comprising 5' and 3' homology arms corresponding to 5' and 3' target sequences at the endogenous Cfh locus, wherein the exogenous donor nucleic acid or targeting vector is designed to mutate or delete the start codon of the endogenous Cfh locus or delete all or a portion of the coding sequence in the endogenous Cfh locus (optionally including the start codon). Likewise, a modified rat one-cell stage embryo can be generated, for example, through recombination by (a) introducing into the one-cell stage embryo one or more targeting vectors or exogenous donor nucleic acids comprising 5' and 3' homology arms corresponding to 5' and 3' target sequences at the endogenous Cfh locus, wherein the exogenous donor nucleic acid or targeting vector is designed to mutate or delete the start codon of the endogenous Cfh locus or delete all or a portion of the coding sequence in the endogenous Cfh locus (optionally including the start codon). Likewise, a modified rat genome or an inactivated rat Cfh gene or locus can be generated, for example, through recombination by (a) contacting the rat genome or the rat Cfh gene or locus with more targeting vectors or exogenous donor nucleic acids comprising 5' and 3' homology arms corresponding to 5' and 3' target sequences at the endogenous Cfh locus, wherein the exogenous donor nucleic acid or targeting vector is designed to mutate or delete the start codon of the endogenous Cfh locus or delete all or a portion of the coding sequence in the endogenous Cfh locus (optionally including the start codon). Optionally, the 5' and 3' homology arms can flank an insert nucleic acid comprising, for example, a reporter gene or selection marker, and the identifying can comprise identifying at least one cell comprising in its genome the insert nucleic acid integrated at the target genomic locus. Alternatively, the modified pluripotent cell can be generated by (a) introducing into the cell: (i) one or more nuclease agents, wherein the nuclease agents induce nicks or double-strand breaks at target sequences within the target genomic locus; and (b) identifying at least one cell comprising a modification (e.g., deletion of a target nucleic acid) at the target genomic locus. Likewise, a modified rat one-cell stage embryo can be generated by (a) introducing into the rat one-cell stage embryo: (i) one or more nuclease agents, wherein the nuclease agents induce nicks or double-strand breaks at target sequences within the target genomic locus; and (b) identifying at least one cell comprising a modification (e.g., deletion of a target nucleic acid) at the target genomic locus. Likewise, a modified rat genome or an inactivated rat Cfh gene or locus can be generated, for example, by contacting the rat genome or the rat Cfh gene or locus with one or more nuclease agents, wherein the nuclease agents induce nicks or double-strand breaks at target sequences within the target genomic locus in the rat Cfh gene or locus. Alternatively, the modified pluripotent cell can be generated by (a) introducing into the cell: (i) one or more nuclease agents, wherein the nuclease agents induce nicks or double-strand breaks at target sequences within the target genomic locus; and (ii) one or more targeting vectors or exogenous donor nucleic acids comprising 5' and 3' homology arms corresponding to 5' and 3' target sequences located in sufficient proximity to the nuclease target sequences; and (c) identifying at least one cell comprising the desired modification at the target genomic locus. Likewise, a modified rat one-cell stage embryo can be generated by (a) introducing into the rat one-cell stage embryo: (i) one or more nuclease agents, wherein the nuclease agents induce nicks or double-strand breaks at target sequences within the target genomic locus; and (ii) one or more targeting vectors or exogenous donor nucleic acids comprising 5' and 3' homology arms corresponding to 5' and 3' target sequences located in sufficient proximity to the nuclease target sequences; and (c) identifying at least one cell comprising the desired modification at the target genomic locus. Likewise, a modified rat genome or an inactivated rat Cfh gene or locus can be generated, for example, by contacting the rat genome or the rat Cfh gene or locus with (i) one or more nuclease agents, wherein the nuclease agents induce nicks or double-strand breaks at target sequences within the target genomic locus in the rat Cfh gene or locus; and (ii) one or more targeting vectors or exogenous donor nucleic acids comprising 5' and 3' homology arms corresponding to 5' and 3' target sequences located in sufficient proximity to the nuclease target sequences. Any nuclease agent that induces a nick or double-strand break into a desired target sequence can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

In a specific example, a method of making a rat comprising an inactivated endogenous Cfh locus can comprise: (a) introducing into a rat embryonic stem (ES) cell a first nuclease agent that targets a first target sequence in proximity to the start codon of the endogenous Cfh genomic locus, wherein the nuclease agent cleaves the first target sequence to produce a genetically modified rat ES cell comprising the inactivated endogenous Cfh locus; (b) introducing the genetically modified rat (ES) cell into a rat host embryo; and (c) gestating the rat host embryo in a surrogate mother, wherein the surrogate mother produces an F0 progeny genetically modified rat comprising the inactivated endogenous Cfh locus. In another specific example, a method of making a rat comprising an inactivated endogenous Cfh locus can comprise: (a) introducing into a rat one-cell stage embryo a first nuclease agent that targets a first target sequence in proximity to the start codon of the endogenous Cfh genomic locus, wherein the nuclease agent cleaves the first target sequence to produce a genetically modified rat one-cell stage embryo comprising the inactivated endogenous Cfh locus; and (b) gestating the genetically modified rat one-cell stage embryo in a surrogate mother, wherein the surrogate mother produces an F0 progeny genetically modified rat comprising the inactivated endogenous Cfh locus. The first target sequence of the first nuclease agent can be, for example, in the first exon, upstream of the first exon (e.g., in the 5' untranslated region (5' UTR)), or downstream of the first exon (e.g., in the first intron) of the endogenous Cfh locus. For example, the target sequence can be within about 10, about 20, about 30, about 40, about 50, about 100, about 200, about 300, about 400, about 500, or about 1000 nucleotides of the start codon. As a specific example, the target sequence can be within about 100 nucleotides of the start codon. Optionally, the first nuclease agent is a Cas9 protein and a guide RNA. The Cas9 protein can be delivered in the form of protein, mRNA, or DNA, and the guide RNA can be delivered in the form of RNA or DNA. For example, both the Cas9 protein and the guide RNA can be delivered in the form of DNA. For example, the DNA encoding the Cas9 protein can comprise, consist essentially of, or consist of SEQ ID NO: 6. The Cas9 protein sequence can comprise, consist essentially of, or consist of SEQ ID NO: 7. Optionally, the first target sequence comprises, consists essentially of, or consists of SEQ ID NO: 12 or 13. Optionally, the guide RNA sequence comprises, consists essentially of, or consists of SEQ ID NO: 8 or 9. The nuclease agent can cleave the first target sequence, which can be repaired by non-homologous end joining (NHEJ), resulting in additional deletions and/or insertions (indels) at the target genomic locus that disrupt the start codon.

Step (a) in such methods can further comprise introducing into the rat ES cell a second nuclease agent that targets a second target sequence in proximity to the stop codon of the endogenous Cfh locus. Likewise, step (a) in such methods can further comprise introducing into the rat one-cell stage embryo a second nuclease agent that targets a second target sequence in proximity to the stop codon of the endogenous Cfh locus. The second target sequence of the second nuclease agent can be, for example, in the penultimate intron, in the penultimate exon, in the last exon, upstream of the last exon (e.g., in the last intron), or downstream of the last exon (e.g., in the 3' untranslated region (3' UTR)) of the endogenous Cfh locus. For example, the target sequence can be within about 10, about 20, about 30, about 40, about 50, about 100, about 200, about 300, about 400, about 500, about 1000 nucleotides about 2000, about 3000, about 4000, or about 5000 nucleotides of the stop codon. In a specific example, the target sequence can be within about 200 nucleotides of the stop codon or within about 3000 nucleotides of the stop codon. Optionally, the second nuclease agent is a Cas9 protein and a guide RNA. The Cas9 protein can be delivered in the form of protein, mRNA, or DNA, and the guide RNA can be delivered in the form of RNA or DNA. Optionally, the second target sequence comprises, consists essentially of, or consists of SEQ ID NO: 14 or 15. Optionally, the guide RNA sequence comprises, consists essentially of, or consists of SEQ ID NO: 10 or 11. The first and second nuclease agents can cleave the first and second target sequences, respectively, which can be repaired by non-homologous end joining (NHEJ) to delete the sequence between the first and second target sequences, thereby deleting some or all of the coding sequence of the endogenous Cfh locus.

Alternatively, step (a) in such methods can further comprise introducing into the rat ES cell a second nuclease agent that targets a second target sequence in proximity to the start codon of the endogenous Cfh locus that is different from the first target sequence. Likewise, step (a) in such methods can further comprise introducing into the rat one-cell stage embryo a second nuclease agent that targets a second target sequence in proximity to the start codon of the endogenous Cfh locus that is different from the first target sequence. The first target sequence of the first nuclease agent can be, for example, in the first exon or upstream of the first exon (e.g., in the 5' UTR) of the endogenous Cfh locus, and the second target sequence of the second nuclease agent can be, for example, in the first exon or downstream of the first exon (e.g., in the first intron) of the endogenous Cfh locus. For example, the target sequence can be within about 10, about 20, about 30, about 40, about 50, about 100, about 200, about 300, about 400, about 500, or about 1000 nucleotides of the start codon. In a specific example, the target sequence can be within about 100 nucleotides of the start codon. Optionally, the second nuclease agent is a Cas9 protein and a guide RNA. The Cas9 protein can be delivered in the form of protein, mRNA, or DNA, and the guide RNA can be delivered in the form of RNA or DNA. Optionally, the first and second target sequences flank the start codon. Optionally, the first target sequence comprises, consists essentially of, or consists of SEQ ID NO: 12, and the second target sequence comprises, consists essentially of, or consists of SEQ ID NO: 13. Optionally, the first guide RNA comprises, consists essentially of, or consists of SEQ ID NO: 8, and the second guide RNA comprises, consists essentially of, or consists of SEQ ID NO: 9. The first and second nuclease agents can cleave the first and second target sequences, respectively, which can be repaired by non-homologous end joining (NHEJ) to delete the sequence between the first and second target sequences, thereby deleting the start codon.

Step (a) in such methods can further comprise introducing into the rat ES cell a third nuclease agent and/or a fourth nuclease agent that target third and fourth target sequences, respectively, in proximity to the stop codon of the endogenous Cfh locus, wherein the third and fourth target sequences are different. Likewise, step (a) in such methods can further comprise introducing into the rat one-cell stage embryo a third nuclease agent and/or a fourth nuclease agent that target third and fourth target sequences, respectively, in proximity to the stop codon of the endogenous Cfh locus, wherein the third and fourth target sequences are different. The third and/or fourth target sequence can be, for example, in the penultimate intron, in the penultimate exon (e.g., exon 21), in the last exon (e.g., exon 22), upstream of the last exon (e.g., in the last intron), or downstream of the last exon (e.g., in the 3' UTR) of the endogenous Cfh locus. For example, the target sequence can be within about 10, about 20, about 30, about 40, about 50, about 100, about 200, about 300, about 400, about 500, about 1000 nucleotides about 2000, about 3000, about 4000, or about 5000 nucleotides of the stop codon. In a specific example, the target sequence can be within about 200 nucleotides of the stop codon or within about 3000 nucleotides of the stop codon. Optionally, the third and/or fourth nuclease agent is a Cas9 protein and a guide RNA. The Cas9 protein can be delivered in the form of protein, mRNA, or DNA, and the guide RNA can be delivered in the form of RNA or DNA. Optionally, the third target sequence and/or fourth target sequence comprise, consist essentially of, or consist of SEQ ID NOS: 14 and/or 15, respectively. Optionally, the third guide RNA and/or fourth guide RNA comprise, consist essentially of, or consist of SEQ ID NOS: 10 and/or 11, respectively. The first and/or second nuclease agent can cleave the first and/or second target sequence, respectively, and the third and/or fourth nuclease agent can cleave the third and/or fourth target sequence, respectively, which can be repaired by non-homologous end joining (NHEJ) to delete the sequence between the first and second target sequences, the first and third target sequences, the first and fourth target sequences, the second and third target sequences, or the second and fourth target sequences, thereby deleting the most or all of the coding sequence of the endogenous Cfh locus.

Step (a) in such methods can further comprise introducing into the rat ES cell an exogenous donor nucleic acid or targeting vector comprising a 5' homology arm that hybridizes to a 5' target sequence at the endogenous Cfh locus and a 3' homology arm that hybridizes to a 3' target sequence at the endogenous Cfh locus, wherein the exogenous donor nucleic acid or targeting vector is designed to mutate or delete the start codon of the endogenous Cfh locus or is designed to delete some or all of the coding sequence of the endogenous Cfh locus (optionally including the start codon). Likewise, step (a) in such methods can further comprise introducing into the rat one-cell stage embryo an exogenous donor nucleic acid or targeting vector comprising a 5' homology arm that hybridizes to a 5' target sequence at the endogenous Cfh locus and a 3' homology arm that hybridizes to a 3' target sequence at the endogenous Cfh locus, wherein the exogenous donor nucleic acid or targeting vector is designed to mutate or delete the start codon of the endogenous Cfh locus or is designed to delete some or all of the coding sequence of the endogenous Cfh locus (optionally including the start codon). Alternatively or additionally, the exogenous donor nucleic acid or targeting vector can be designed to disrupt the start codon by inserting an insert sequence (flanked by the 5' and 3' homology arms) into the start codon or into the endogenous Cfh locus. In such methods, the exogenous donor nucleic acid or targeting vector can recombine with the target locus via homology directed repair or can be inserted via NHEJ-mediated insertion to generate the inactivated Cfh locus. For example, the exogenous donor sequence or targeting vector can function to delete the genome sequence between the 5' and 3' target sequences to generate the inactivated Cfh locus. In one example, the 5' and 3' target sequence can flank the start codon of the endogenous Cfh locus. In another example, the 5' and 3' target sequences can flank the first exon of the endogenous Cfh locus. In yet another example, the 5' and 3' target sequences can flank some or all of the coding sequence of the endogenous Cfh locus.

The donor cell can be introduced into a host embryo at any stage, such as the blastocyst stage or the pre-morula stage (i.e., the 4-cell stage or the 8-cell stage). Progeny that are capable of transmitting the genetic modification though the germline are generated. See, e.g., U.S. Pat. No. 7,294,754, herein incorporated by reference in its entirety for all purposes.

Alternatively, the method of producing the rats described elsewhere herein can comprise: (1) modifying the genome of a one-cell stage embryo to comprise the inactivated Cfh locus using the methods described above for modifying pluripotent cells; (2) selecting the genetically modified embryo; and (3) implanting and gestating the genetically modified embryo into a surrogate mother. Alternatively, the method of producing the rats described elsewhere herein can comprise: (1) modifying the genome of a one-cell stage embryo to comprise the inactivated Cfh locus using the methods described above for modifying pluripotent cells; (2) selecting the genetically modified embryo; and (3) gestating the genetically modified embryo into a surrogate mother. Progeny that are capable of transmitting the genetic modification though the germline are generated.

Nuclear transfer techniques can also be used to generate the rats. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified F0 rat wherein the cells of the genetically modified F0 rat comprise the inactivated Cfh locus. The cells of the genetically modified F0 rat can be heterozygous for the inactivated Cfh locus or can be homozygous for the inactivated Cfh locus.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | DNA | Rat Cfh Genome Sequence |
| 2 | DNA | Rat Cfh Coding Sequence |
| 3 | Protein | Rat CFH Protein Sequence (NP_569093.2) |
| 4 | DNA | Rat Cfh Modified Genomic Locus in Clone AA8 |
| 5 | DNA | Rat Genomic Cfh Sequence Deleted in Clone AA8 |
| 6 | DNA | Cas9 DNA Sequence |
| 7 | Protein | Cas9 Protein Sequence |
| 8 | RNA | rGU1 sgRNA |
| 9 | RNA | rGU2 sgRNA |
| 10 | RNA | rGD2 sgRNA |
| 11 | RNA | rGD3 sgRNA |
| 12 | DNA | rGU1 Target Sequence |
| 13 | DNA | rGU2 Target Sequence |
| 14 | DNA | rGD2 Target Sequence |
| 15 | DNA | rGD3 Target Sequence |
| 16 | DNA | Rat CFH mRNA (cDNA) Sequence Assigned Accession No. NM 130409.2 |
| 17 | DNA | rTUF |
| 18 | DNA | rTUP |
| 19 | DNA | rTUR |
| 20 | DNA | rTU2F |
| 21 | DNA | rTU2P |
| 22 | DNA | rTU2R |
| 23 | DNA | AmpF1 |
| 24 | DNA | AmpR1 |
| 25 | DNA | AmpF2 |
| 26 | DNA | AmpR2 |

EXAMPLES

Example 1. Generation of Rats Comprising an Inactivated Cfh Locus

To generate a knockout rat Cfh allele, guide RNAs were designed to cut at the ends of the Cfh gene to collapse (delete) the coding sequence or were designed to cut at sites that flank the start codon to delete the start codon. No targeting vector was used. The endogenous rat Cfh locus (from exon 1 to exon 22) is set forth in SEQ ID NO: 1. The rat Cfh coding sequence is set forth in SEQ ID NO: 2. The rat CFH protein sequence is set forth in SEQ ID NO: 3.

CRISPR/Cas9 components including four guide RNAs (guide RNA target sequences set forth in SEQ ID NOS: 12-15 for rGU1, rGU2, rGD2, and rGD3, respectively) were introduced into Dark Agouti rat embryonic stem cells. Specifically, $2 \times 10^6$ rat ES cells (Dark Agouti line DA2B) were electroporated with the following: 5 μg Cas9 expression plasmid (Cas9 coding sequence set forth in SEQ ID NO: 6); and 5 μg each of DNAs encoding the following gRNAs: rGU1, rGU2, rGD2, and rGD3 (guide RNA sequences set forth in SEQ ID NOS: 8-11, respectively, which target the rat Cfh sequences set forth in SEQ ID NOS: 12-15, respectively). The rGD2 target sequence has a one nucleotide difference (a "C" instead of an "A" at residue 17) from the target sequence annotated in the rat Cfh genome sequence set forth in SEQ ID NO: 1. The reason for this difference is that the guide RNA is specific to the Dark Agouti strain sequence (the strain of rat ES cell used), whereas the genomic sequence comes from the Brown Norway strain (the strain that was used to sequence the rat genome). The A/C variant is a SNP between Dark Agouti and Brown Norway. The electroporation conditions were: 400 V voltage; 100 mF capacitance; and 0 W resistance. Colonies were picked, expanded, and screened by TAQMAN® loss-of allele assays to detect loss of the endogenous rat allele. See FIG. 1B. The primers and probes for the loss-of-allele assays are set forth in Table 3.

TABLE 3

Screening Assays.

| Use | Primer/ Probe | Sequence | SEQ ID NO |
|---|---|---|---|
| TU LOA | rTUF | CATAGCAGAGAGGAACTGGATGGT | 17 |
| TU LOA | rTUP | GCACATACTTCTCTT | 18 |
| TU LOA | rTUR | GTCAACTGCTCCCAGATAGATCCAAG | 19 |
| TU2 LOA | rTU2F | ACCACCACCTTTCTCCCTTCTGACTG | 20 |
| TU2 LOA | rTU2P | GCCGCATTATAAAACA | 21 |
| TU2 LOA | rTU2R | TTGCTGATAATATTTCTCATAGCAA | 22 |
| NGS pair 1 | AmpF1 | ATTTCCTAAACTAACTTTCAAC | 23 |
| NGS pair 1 | AmpR1 | GTGGTAAGTTTAAAAACCGTGAA | 24 |
| NGS pair 2 | AmpF2 | CGCCTATGCTGCTGGACTTGTGGT | 25 |
| NGS pair 2 | AmpR2 | CTTTCACTTGACTATTGTAATTGAT | 26 |

Modification-of-allele (MOA) assays including loss-of-allele (*LOA*) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (*LOA*) assay inverts the conventional screening logic and quantifies the number of copies in a genomic DNA sample of the native locus to which the mutation was directed. In a correctly targeted heterozygous cell clone, the *LOA* assay detects one of the two native alleles (for genes not on the X or Y chromosome), the other allele being disrupted by the targeted modification.

Figure 1B:
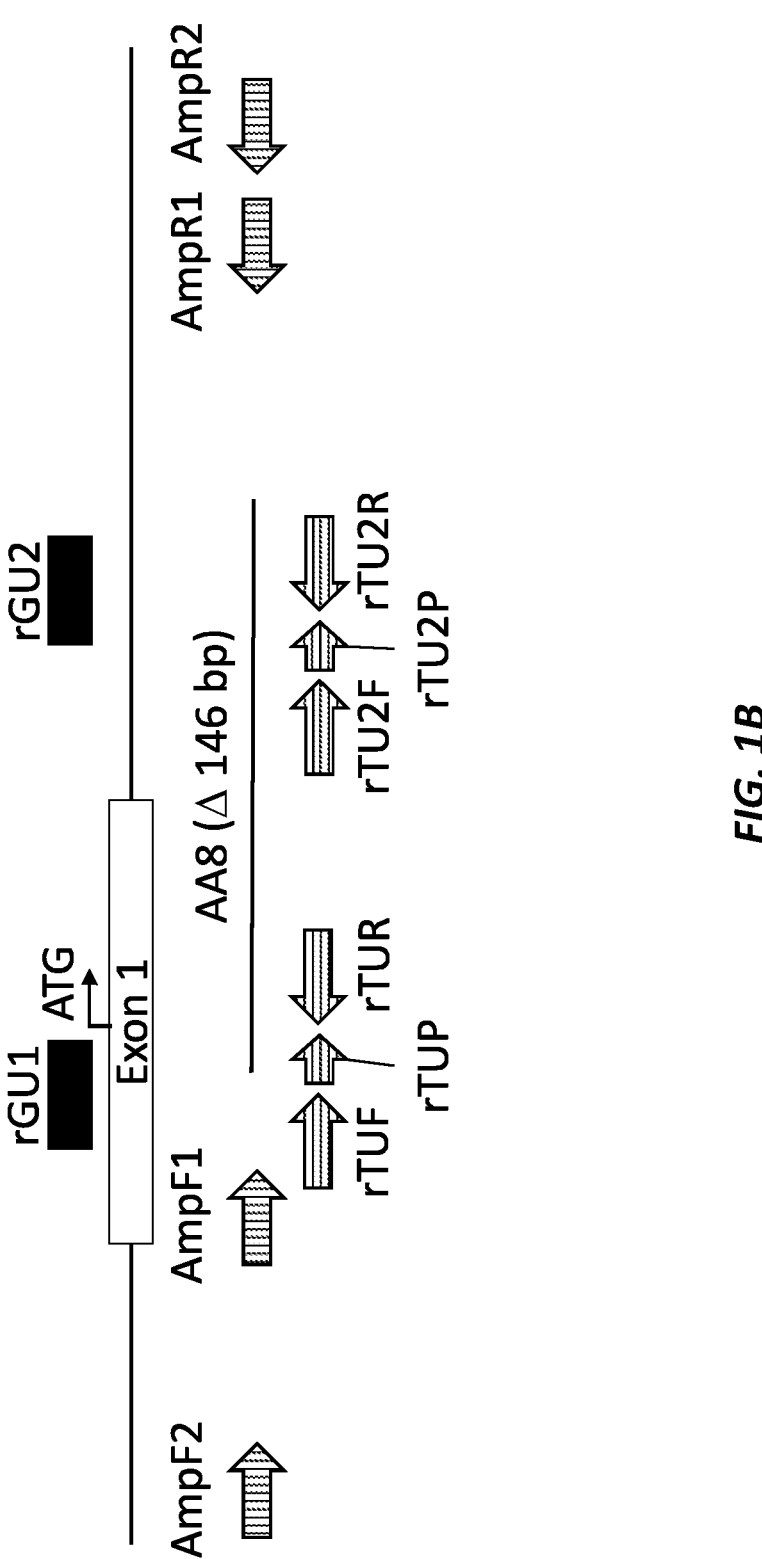
FIG. 1B (not to scale) shows a schematic of the TAQMAN® loss-of-allele (*LOA*) assays and next-generation sequencing (NGS) assays for screening the targeted rat Cfh locus. Primers and probes for *LOA* assays included rTUF, rTUP, rTUR, rTU2F, rTU2P, and rTU2R, and NGS primers included AmpF1, AmpF2, AmpR1, and AmpR2.

Six clones were screened and are shown in FIGS. 1A and 1*n* Table 4 below. Colonies were identified in which one allele of Cfh was collapsed. Colonies were also identified in which only exon 1 (containing the ATG start codon) was deleted. The Cfh knockout rat line was established using clone AA8, which had a heterozygous 146 bp deletion in exon 1 that deletes the ATG start codon, the exon 1 coding sequence, and the splice donor site in intron 1. The deleted sequence is set forth in SEQ ID NO: 5, and the modified Cfh genomic locus in clone AA8 is set forth in SEQ ID NO: 4. The positive clone AA8 was thawed, expanded, and reconfirmed by TAQMAN®. AA8 was also confirmed by next-generation sequencing (NGS).

TABLE 4

Rat Cfh Knockout Clones.

| Clone | Mutation | Microinjection Date | Chimeras | Germline Transmission |
|---|---|---|---|---|
| BE6 | ΔCDS (97 kb) | May 6, 2016; May 20, 2016 | 0 | N/A |
| HG6 | ΔCDS (97 kb) | May 6, 2016; May 20, 2016 | 0 | N/A |
| BB7 | ΔCDS (97 kb) | May 20, 2016 | 1M | No |
| AE1 | ΔExon 1 (183 bp) | Sep. 30, 2016 | 3F; 3 MPE | No |
| AA8 | ΔExon 1 (146 bp) | Sep. 30, 2016 | 1M | YES |
| AB5 | ΔExon 1 (~900 bp) | Sep. 30, 2016 | 2M | No |

F0 and F1 rats were generated using methods as described in US 2014/0235933, US 2014/0310828, WO 2014/130706, and WO 2014/172489, each of which is herein incorporated by reference in its entirety for all purposes. The confirmed heterozygous targeted rat ES cell clone AA8 (Dark Agouti) was microinjected into a Sprague Dawley (SD) blastocyst, which was then transferred to a pseudopregnant recipient female (SD recipient female) for gestation using standard techniques. Chimeras were identified by coat color, and male F0 chimeras were bred to female wild-type rats of the same strain (SD females). Germline (e.g., agouti) F1 pups were then genotyped for the presence of the homozygous modified allele. The homozygous F1 Cfh knockout rats were 50% Dark Agouti and 50% Sprague Dawley.

Example 2. Characterization of Rats Comprising an Inactivated Cfh Locus

Figure 2:
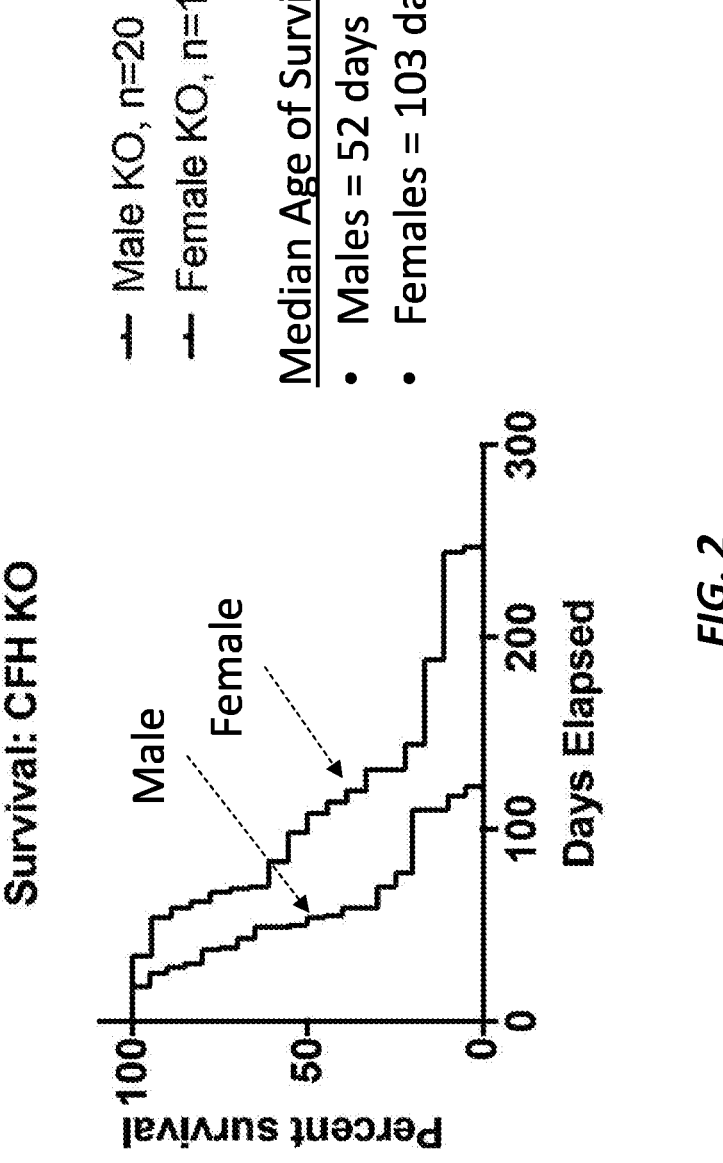
FIG. 2 shows percent survival of male and female Cfh knockout rats over time.

To assess whether the Cfh knockout rats recapitulate the phenotype of C3 glomerulopathy (C3G), various readouts related to alternative complement pathway activation, kidney pathology, and mortality were assessed. C3 glomerulopathy (C3G) is characterized by hyperactivation of alternative pathway (AP) complement activation as a result of C3 nephritic factors and/or mutations in complement genes. Because approximately 50% of patients develop end-stage renal disease (ESRD) within 10 years of diagnosis, survival of male and female Cfh knockout rats (20 male rats, 18 female rats) was assessed. As shown in FIG. 2, the median age at which the male Cfh knockout rats died was 52 days (~1.7 months), and the median age at which the female Cfh knockout rats died was 103 days (~3.4 months). The last male Cfh knockout rat died at 122 days (~4 months), and the last female Cfh knockout rat died at 247 days (~8.1 months). A difference was observed between females and males. Complement activity in female mice is lower than in male mice, and a similar gender difference may exist in rats. This spontaneous mortality occurs very early in the lifetime of the Cfh knockout rats and is dramatically lower than the average three-year lifespan of wild type laboratory rats. In addition, the spontaneous mortality observed in Cfh knockout rats is a much more dramatic and rapid phenotype than that observed in Cfh knockout mice, which have been reported to have only 23% mortality after 8 months. See Pickering et al. (2002) *Nat. Genet.* 31(4):424-428, herein incorporated by reference in its entirety for all purposes.

Figure 3:
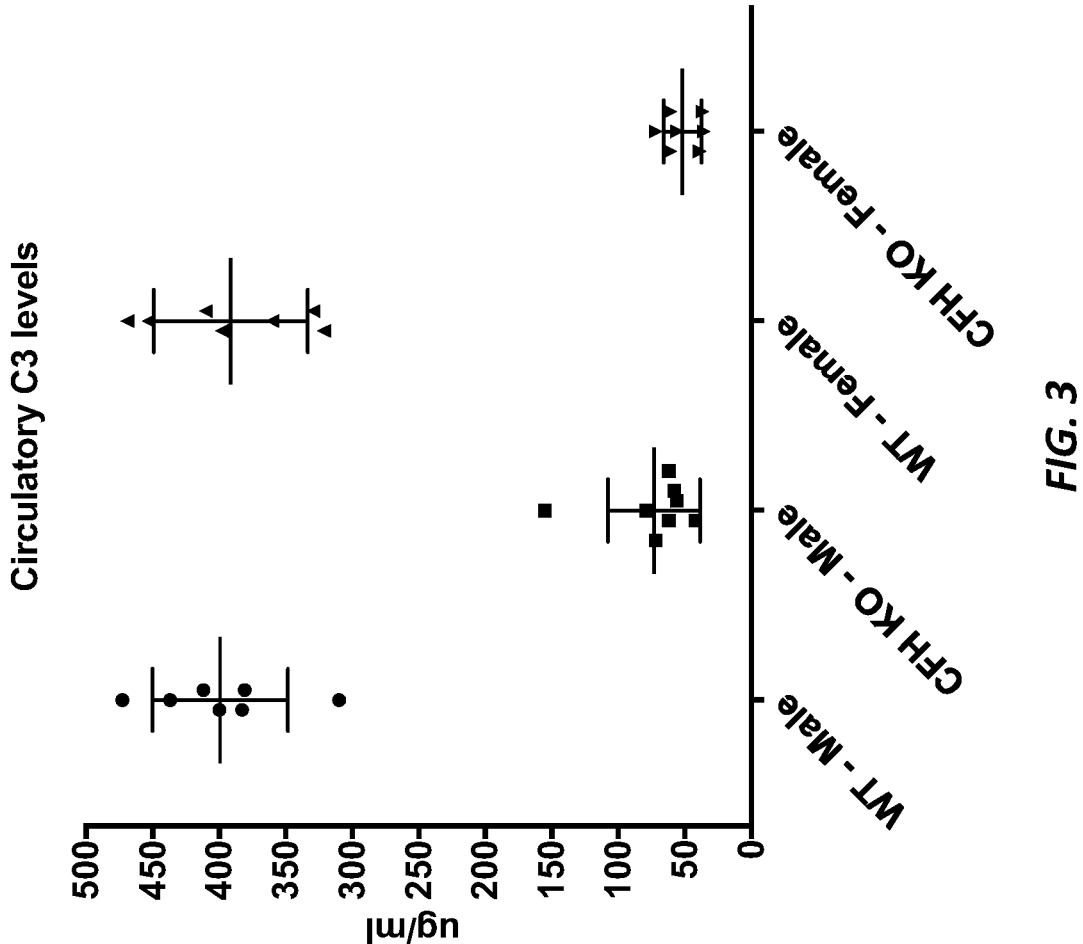
FIG. 3 shows circulatory C3 levels in 7-week-old male and female wild type and Cfh knockout rats.

Lower circulatory C3 levels were also observed in both male and female Cfh knockout rats compared to wild type counterparts. Circulatory C3 levels were measured in 7-week old male and female wild type (WT) and Cfh knockout rats using a sandwich ELISA from ABCAM. Samples and standards were diluted and added to a plate with bound C3 antibody. The plate was washed after incubation, and another C3 antibody was added. After another incubation, secondary antibody was used against the detection antibody and then exposed to a TMB solution to create a measurable color. The reaction was stopped with acid and the signal was measured at 450 nm. Complement C3 is constantly hydrolyzed, which can form fluid-phase C3 convertase that subsequently cleaves more molecules of C3. CFH is an endogenous negative regulator of alternative pathway and is required to inhibit C3 activation/cleavage. Without CFH, the C3 is continuously consumed leading to lower circulatory levels as shown in FIG. 3.

Figure 4:
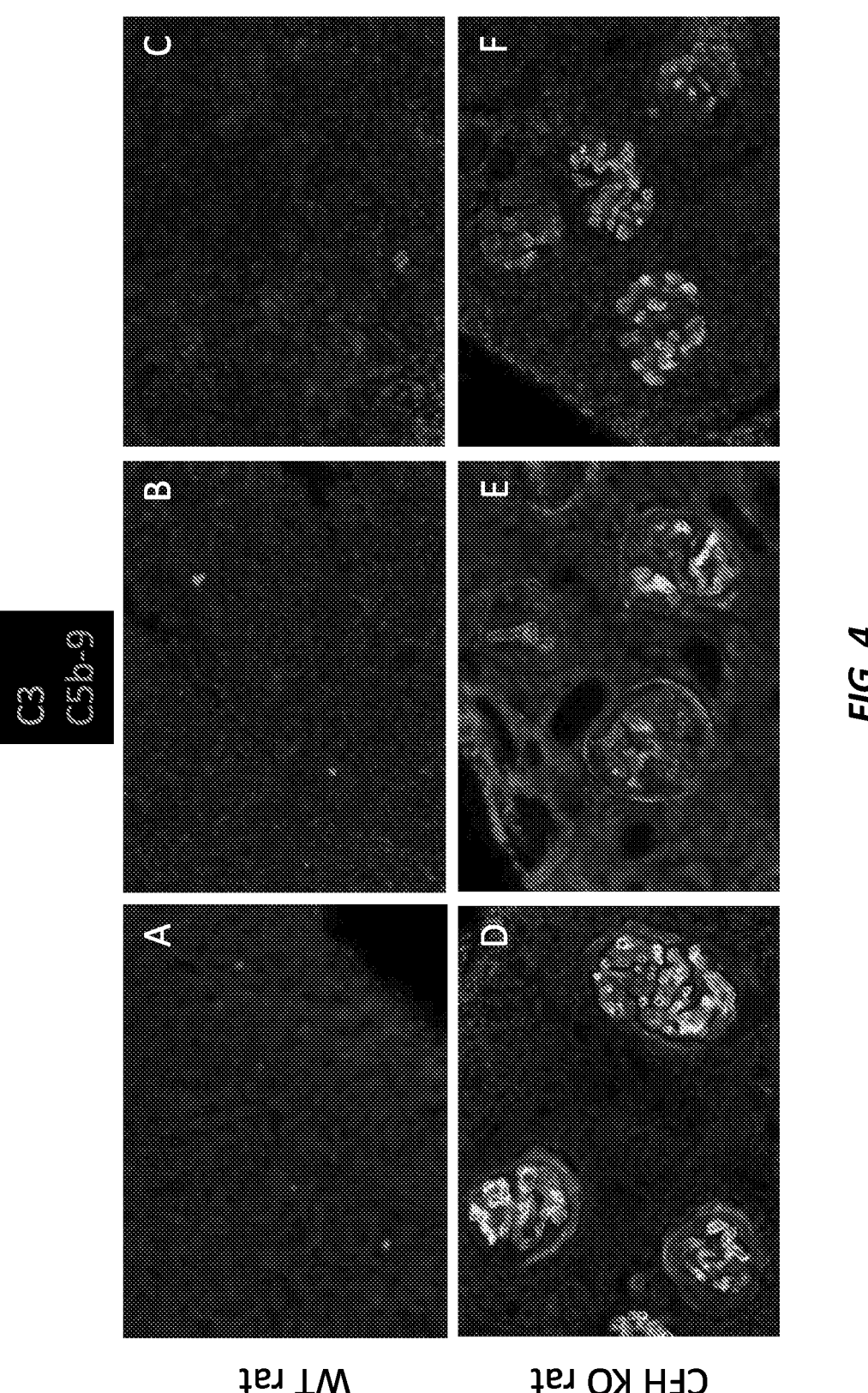
FIG. 4 shows staining for C3 and C5b-9 in frozen kidney sections from female wild type and Cfh knockout rats. Panels A-C are samples from female wild type rats aged 18 weeks, 17 weeks, and 17 weeks, respectively. Panels D-F are samples from female Cfh knockout rats aged 12 weeks, 17 weeks, and 9 weeks, respectively.

Increased C3 and C5b-9 deposition was also observed in the kidneys of Cfh knockout rats compared to wild type counterparts, consistent with what is observed in human C3G patients. See, e.g., Barbour et al. (2013) *Semin. Nephrol.* 33(6):493-507 and Vivarelli et al. (2012) *N. Engl. J. Med.* 366(12):1163-1165, each of which is herein incorporated by reference in its entirety for all purposes. C3 and C5b-9 deposition was measured in kidney samples from three female wild type rats with ages of 18 weeks, 17 weeks, and 17 weeks, respectively, and three female Cfh knockout rats with ages of 12 weeks, 17 weeks, and 9 weeks, respectively. Immunohistochemistry was done on the frozen sections of rat kidney using a 1:50 dilution of fluorescein-conjugated goat anti-C3 (MP Biomedicals #55191) and a 1:100 dilution of rabbit anti-C5b-9 (Abcam ab55811), along with a 1:333.3 dilution of Cy5-conjugated donkey anti-rabbit (Jackson Immunoresearch 711-605-152). The results are shown in FIG. 4. The Cfh knockout rats show spontaneous deposition of C3 and C5b-9 membrane attack complex (MAC) proteins far in excess of that observed in wild type rats.

Figure 5:
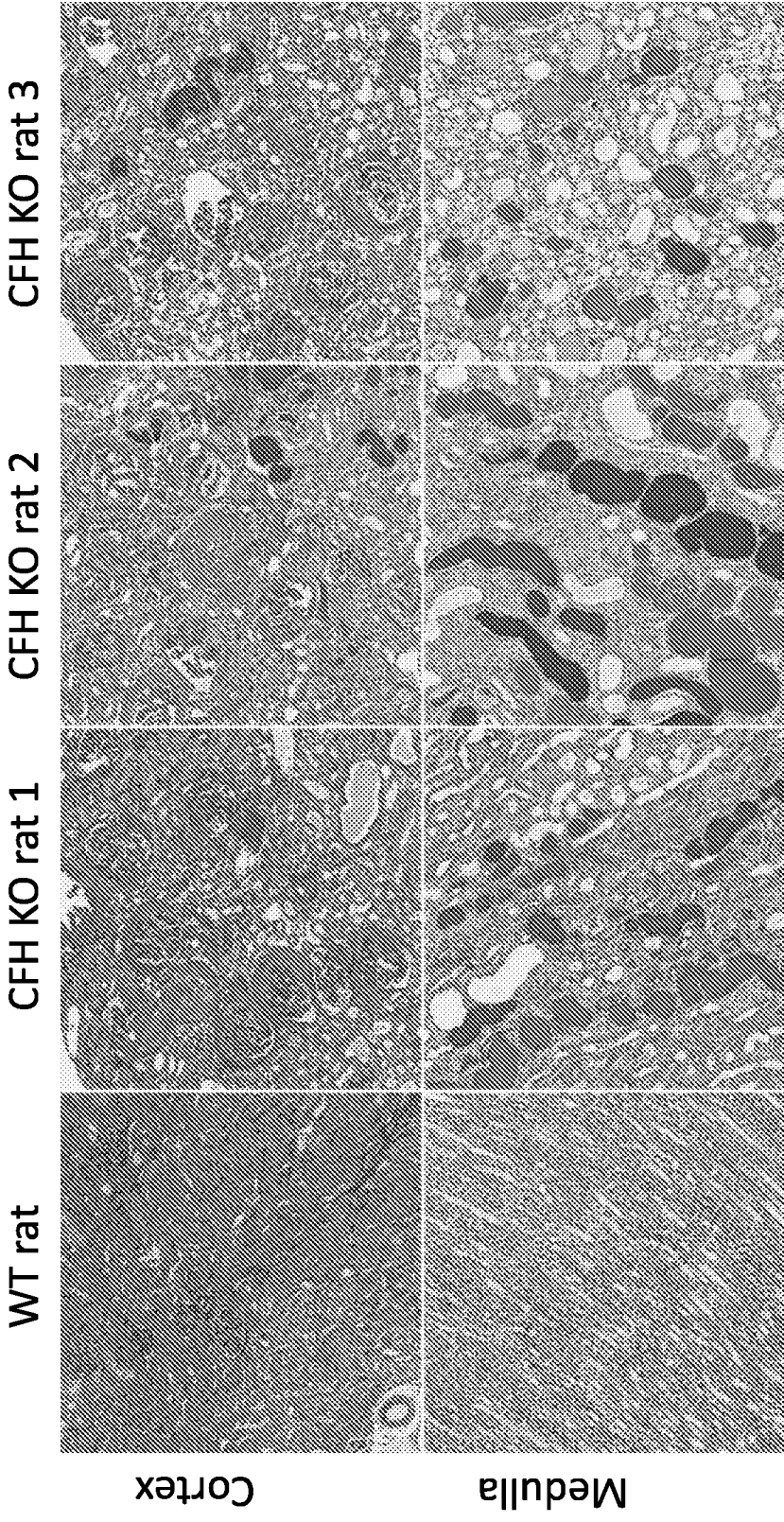
FIG. 5 shows periodic acid-Schiff (PAS) staining of medulla and cortex tissue in kidney samples from a female wild type rat aged 15 weeks and three female Cfh knockout rats (CFH KO rat 1, CFH KO rat 2, and CFH KO rat 3) aged 12 weeks, 13 weeks, and 15 weeks, respectively.

Severe glomerulosclerosis, tubular atrophy, and proteinaceous casts were also observed in Cfh knockout rats compared to wild type counterparts. Casts develop when there is proteinuria (when protein leaks into the urine). Casts are the result of solidification of protein in the lumen of the kidney tubules. Kidney samples were taken from one wild type female rat at 15 weeks of age and from three female Cfh knockout rats (CFH KO rat 1, CFH KO rat 2, and CFH KO rat 3) with ages of 12 weeks, 13 weeks, and 15 weeks, respectively. The kidney samples were stained with a periodic acid-Schiff stain. Briefly, slides were stained with Schiff's reagent after oxidation in 1% periodic acid and were then counterstained with hematoxylin. As shown in FIG. 5, the Cfh knockout rats showed dramatic expansion of mesangial cell matrix and glomerular tuft size, as well as prominent dilation of renal tubules. This pathology is more severe than the pathology that has been observed in Cfh knockout mice. There appear to be no tubular pathologies shown in published data on the Cfh knockout mice, whereas it is clear that Cfh knockout rats have tubular pathologies. The Cfh knockout rats also appear to have more glomerulosclerosis compared to published data on Cfh knockout mice. See, e.g., Pickering et al. (2002) *Nat. Genet.* 31(4):424-428, herein incorporated by reference in its entirety for all purposes. These findings are consistent with loss of kidney function and increased mortality.

Figures 6A, 6B:
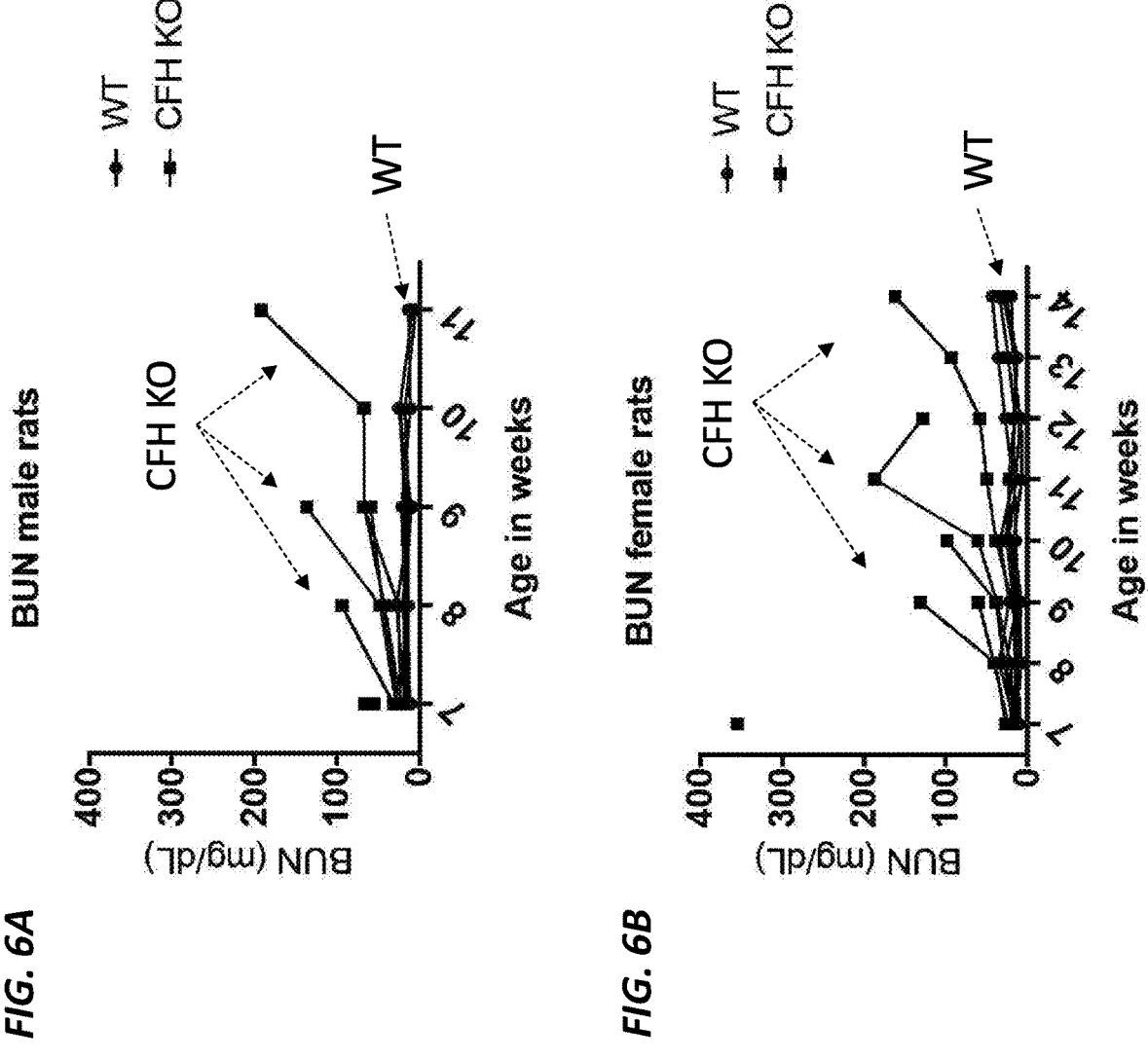
FIGS. 6A and 6B show blood urea nitrogen (BUN) levels in male wild type and Cfh knockout rats starting at 7 weeks of age until each Cfh knockout rat died (FIG. 6A) and in female wild type and Cfh knockout rats starting at 7 weeks of age until each Cfh knockout rat died (FIG. 6B). At baseline, there were 10 male wild type rats, 8 male Cfh knockout rats, 9 female wild type rats, and 7 female Cfh knockout rats.

Blood urea nitrogen (BUN), a glomerular filtration marker, was also elevated in Cfh knockout rats compared to wild type counterparts, suggesting a reduced glomerular filtration rate. Blood urea nitrogen levels were measured in male wild type and Cfh knockout rats (FIG. 6A) and female wild type and Cfh knockout rats (FIG. 6B) weekly starting at 7 weeks of age until all the Cfh knockout rats died. The assay kit used for blood urea nitrogen (BUN) levels was from BioAssay Systems. This assay uses the Jung method that utilizes a chromogenic reagent that forms a colored complex with urea. To accomplish this, serum was diluted by 5× and plated at a volume of 5 μL. A standard was added. In a 1:1 ratio, 200 μL of reagents A and B were added to the plate. After 20 minutes, the signal was read at 430 nm. Blood urea nitrogen (BUN) is a marker of kidney function. When kidneys start to fail, BUN gets accumulated in the blood. Increased BUN in the circulation, as was observed in both female and male Cfh knockout rats, means decreased kidney function. See FIGS. 6A and 6B. This phenotype is more dramatic then Cfh knockout mice. Although BUN levels were not measured in Cfh knockout mice, levels of another marker of kidney function, serum creatinine, were measured and did not differ between Cfh knockout mice and wild type mice. See, e.g., Pickering et al. (2002) *Nat. Genet.* 31(4): 424-428, herein incorporated by reference in its entirety for all purposes.

Figures 8A, 8B:
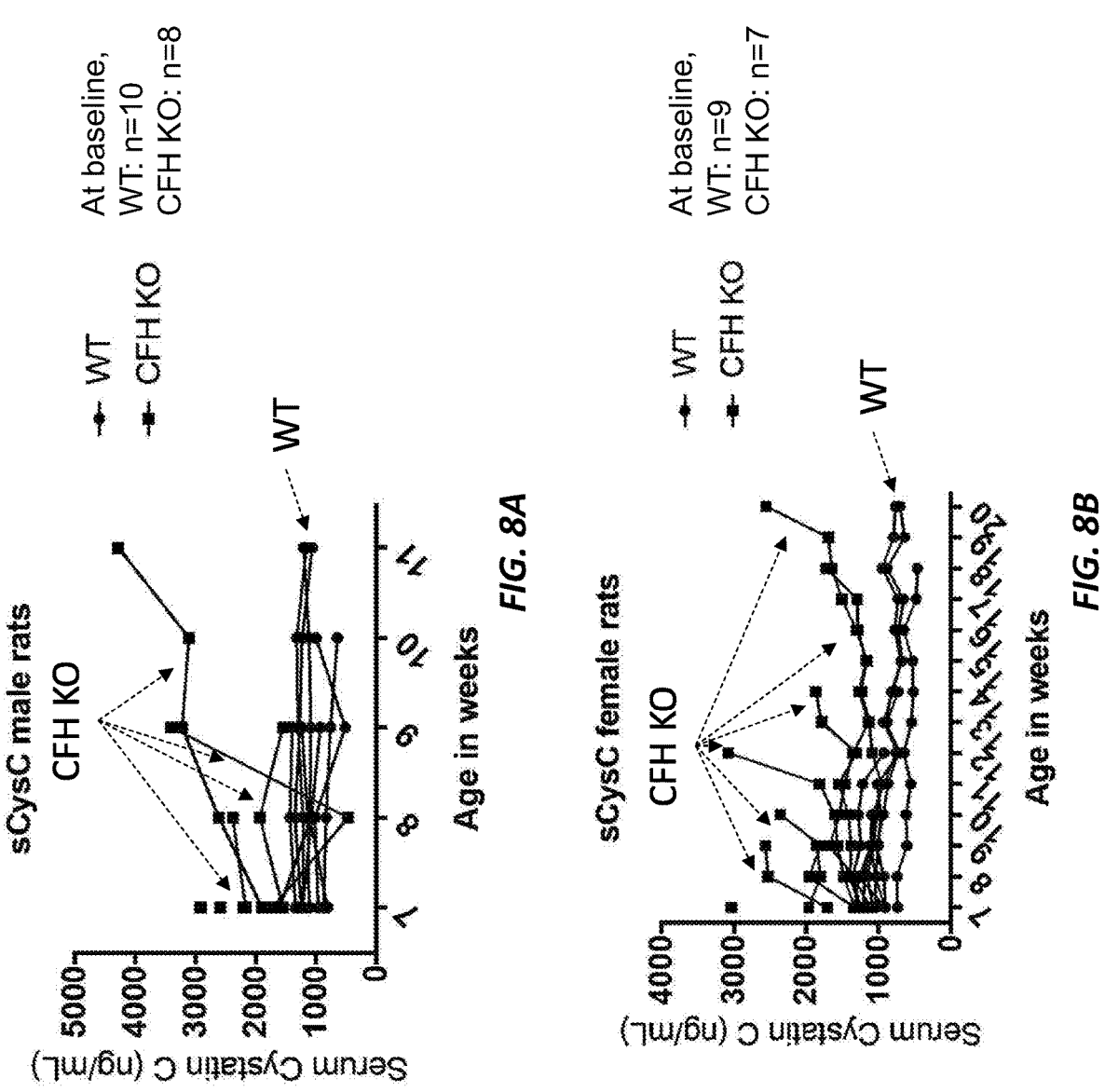
FIGS. 8A and 8B show serum cystatin C (sCysC) in male wild type and Cfh knockout rats (FIG. 8A) and in female wild type and Cfh knockout rats (FIG. 8B) starting at 7 weeks of age until each Cfh knockout rat died.

Serum cystatin C (sCysC), a glomerular filtration marker, was also measured in Cfh knockout rats and wild type counterparts. Serum cystatin C levels were measured in male wild type and Cfh knockout rats (FIG. 8A) and female wild type and Cfh knockout rats (FIG. 8B) weekly starting at 7 weeks of age until all the Cfh knockout rats died using a kit according to the manufacture's protocol (Biovendor #RD391009200R). Serum cystatin C was also elevated in Cfh knockout rats compared to wild type counterparts, suggesting a reduced glomerular filtration rate. See FIGS. 8A and 8B.

Next, urine was collected from wild type or Cfh knockout rats for 16-18 hours using diuresis cages (Tecniplast Inc.). Urinary albumin and urinary creatine were measured using kits from Exocell (Catalogue #NR002 and 1012 respectively) according to the manufacturer's protocol. Urinary albumin was quantified as per day or normalized to urinary creatinine and was measured both in male and female rats. As shown in FIGS. 9A-9D, urinary albumin per day or normalized to creatinine was elevated in both male (FIGS. 9A and 9B) and female (FIGS. 9C and 9D) Cfh knockout rats compared to wild type counterparts. Albuminuria is a marker of kidney injury suggesting a leaky glomerulus.

We next assessed glomerular injury by electron microscopy in Cfh knockout rats. The rats studied included 5 wild type controls (7 weeks old) and 7 Cfh knockout rats (7 weeks old). Cortical kidney tissue samples were fixed in glutaraldehyde. Fixed tissues were processed for electron microscopy sectioning and staining, and glomeruli in tissues obtained from a single time point were assessed by electron microscopy. Histological assessment included: measures of podocyte foot process effacement; glomerular basement membrane thickness (GBM); other GBM pathologic alterations (if evident); assessment of glomerular endothelial cell abnormalities qualitatively; and presence and location of any glomerular electron dense deposits.

Glomerular disease was assessed by the following criteria: (1) measurement of podocyte foot process effacement; (2) measurement of glomerular basement membrane thickness; and (3) qualitative assessment of glomerular endothelial cell abnormalities, presence and location of deposits or other ultrastructural abnormalities. For measurement of podocyte foot process effacement, glomeruli were assessed for foot process effacement by direct counting of the number of process profiles/m of capillary length. Average process width was also calculated using the linear measurement tool of Image-Pro Plus imaging software. Data were organized according to groups at the time of analysis. For measurement of glomerular basement membrane thickness, glomerular basement membrane thickness was measured by image analysis. Five separate measurements were made perpendicular to the linear axis along the basement membrane length in each image using a calibrated measurement tool of Image-Pro Plus software. Data were organized according to groups at the time of analysis.

Glomeruli from wild type rats showed normal ultrastructure where podocytes had uniform and regular interdigitation and width of foot processes, consistent thickness of GBM, and typical endothelial lining of the capillary loop. Cfh knockout rats showed substantial ultrastructural pathology including marked increase in the thickness of the glomerular basement membrane (GBM), cellular interposition, and electron dense deposits throughout the structure. Podocytes showed effacement (broadening of foot processes) with irregular contours. The mesangium was expanded and contained electron dense deposits. The endothelium was often swollen, vacuolated with loss of fenestrae (not quantitated). The results are shown in Table 5. The conclusion drawn from these data is that Cfh knockout rats have marked glomerular pathology including podocyte effacement and contortion, GBM thickening with cellular interposition and electron dense deposits, mesangial expansion, and endothelial swelling with loss of fenestrae.

TABLE 5

| | General Assessment of Samples. | | | | | | | |
| | Glomerular Basement Membrane | | | Podocyte Abnormalities | | Endothelial Abnormalities | |
| | Normal Appearance | Thickened GBM | Deposits | Inter-positioning | Effacement | Irregular Contours | Loss of Fenestrae | swelling |
|---|---|---|---|---|---|---|---|---|
| WT-2 | | | | | | | | |
| Glom 1 | ✓ | — | — | — | — | — | — | — |
| Glom 2 | ✓ | — | — | — | — | — | — | — |
| Glom 3 | ✓ | — | — | — | — | — | — | — |
| WT-3 | | | | | | | | |
| Glom 1 | ✓ | — | — | — | — | — | — | — |
| Glom 2 | ✓ | — | — | — | — | — | — | — |
| Glom 3 | ✓ | — | — | — | — | — | — | — |

TABLE 5-continued

General Assessment of Samples.

| | Normal Appearance | Glomerular Basement Membrane | | | Podocyte Abnormalities | | Endothelial Abnormalities | |
|---|---|---|---|---|---|---|---|---|
| | | Thickened GBM | Deposits | Inter-positioning | Effacement | Irregular Contours | Loss of Fenestrae | swelling |
| WT-7 | | | | | | | | |
| Glom 1 | ✓ | — | — | — | — | — | — | — |
| Glom 2 | ✓ | — | — | — | — | — | — | — |
| Glom 3 | ✓ | — | — | — | — | — | — | — |
| WT-8 | | | | | | | | |
| Glom 1 | ✓ | — | — | — | — | — | — | — |
| Glom 2 | ✓ | — | — | — | — | — | — | — |
| Glom 3 | ✓ | — | — | — | — | — | — | — |
| WT-10 | | | | | | | | |
| Glom 1 | ✓ | — | — | — | — | — | — | — |
| Glom 2 | ✓ | — | — | — | — | — | — | — |
| Glom 3 | ✓ | — | — | — | — | — | — | — |
| KO-1 | | | | | | | | |
| Glom 1 | | ✓ | ✓ | ✓ | ✓ | ✓ | ✓ | ✓ |
| Glom 2 | | ✓ | ✓ | ✓ | ✓ | ✓ | ✓ | ✓ |
| Glom 3 | | ✓ | ✓ | ✓ | ✓ | ✓ | ✓ | ✓ |
| KO-4 | | | | | | | | |
| Glom 1 | | ✓ | ✓ | ✓ | ✓ | ✓ | ✓ | ✓ |
| Glom 2 | | ✓ | ✓ | ✓ | ✓ | ✓ | ✓ | ✓ |
| Glom 3 | | ✓ | ✓ | ✓ | ✓ | ✓ | ✓ | ✓ |
| KO-5 | | | | | | | | |
| Glom 1 | | ✓ | ✓ | ✓ | ✓ | ✓ | ✓ | ✓ |
| Glom 2 | | ✓ | ✓ | ✓ | ✓ | ✓ | ✓ | ✓ |
| Glom 3 | | ✓ | ✓ | ✓ | ✓ | ✓ | ✓ | ✓ |
| KO-6 | | | | | | | | |
| Glom 1 | | ✓ | ✓ | ✓ | ✓ | ✓ | ✓ | ✓ |
| Glom 2 | | ✓ | ✓ | ✓ | ✓ | ✓ | ✓ | ✓ |
| Glom 3 | | ✓ | ✓ | ✓ | ✓ | ✓ | ✓ | ✓ |
| KO-9 | | | | | | | | |
| Glom 1 | | ✓ | ✓ | ✓ | ✓ | ✓ | ✓ | ✓ |
| Glom 2 | | ✓ | ✓ | ✓ | ✓ | ✓ | ✓ | ✓ |
| Glom 3 | | ✓ | ✓ | ✓ | ✓ | ✓ | ✓ | ✓ |
| KO-11 | | | | | | | | |
| Glom 1 | | ✓ | ✓ | ✓ | ✓ | ✓ | ✓ | ✓ |
| Glom 2 | | ✓ | ✓ | ✓ | ✓ | ✓ | ✓ | ✓ |
| Glom 3 | | ✓ | ✓ | ✓ | ✓ | ✓ | ✓ | ✓ |

Figures 10A, 10B:
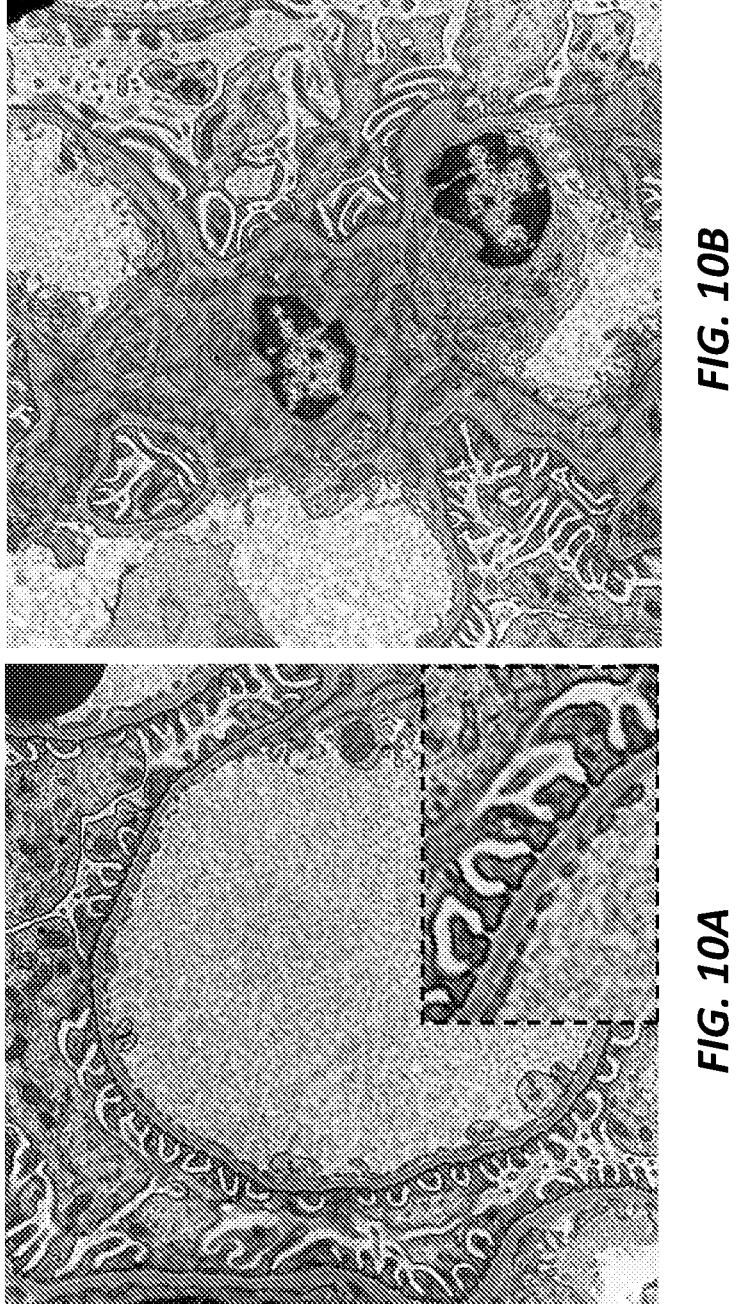
FIGS. 10A and 10B show electron micrographs of a glomerular capillary loop (FIG. 10A) and mesangium (FIG. 10B) of a glomerulus from a wild type rat (12,000×).

Representative images of these findings are shown in FIGS. 10A, 10B, 11A, 11B, 12A, and 12B. FIGS. 10A and 10B show electron micrographs of a glomerular capillary loop (FIG. 10A) and mesangium (FIG. 10B) of a glomerulus from a wild type rat (12,000×). The capillary loop shows normal ultrastructure where podocytes have regular inter-digitating foot processes placed on the outer aspect of an intact glomerular basement membrane (FIG. 10A, higher magnification in inset). The endothelium lining the capillary shows normally placed fenestra. The mesangium (FIG. 10B) is normal in appearance where cells occupy a sparse matrix.

Figures 11A, 11B:
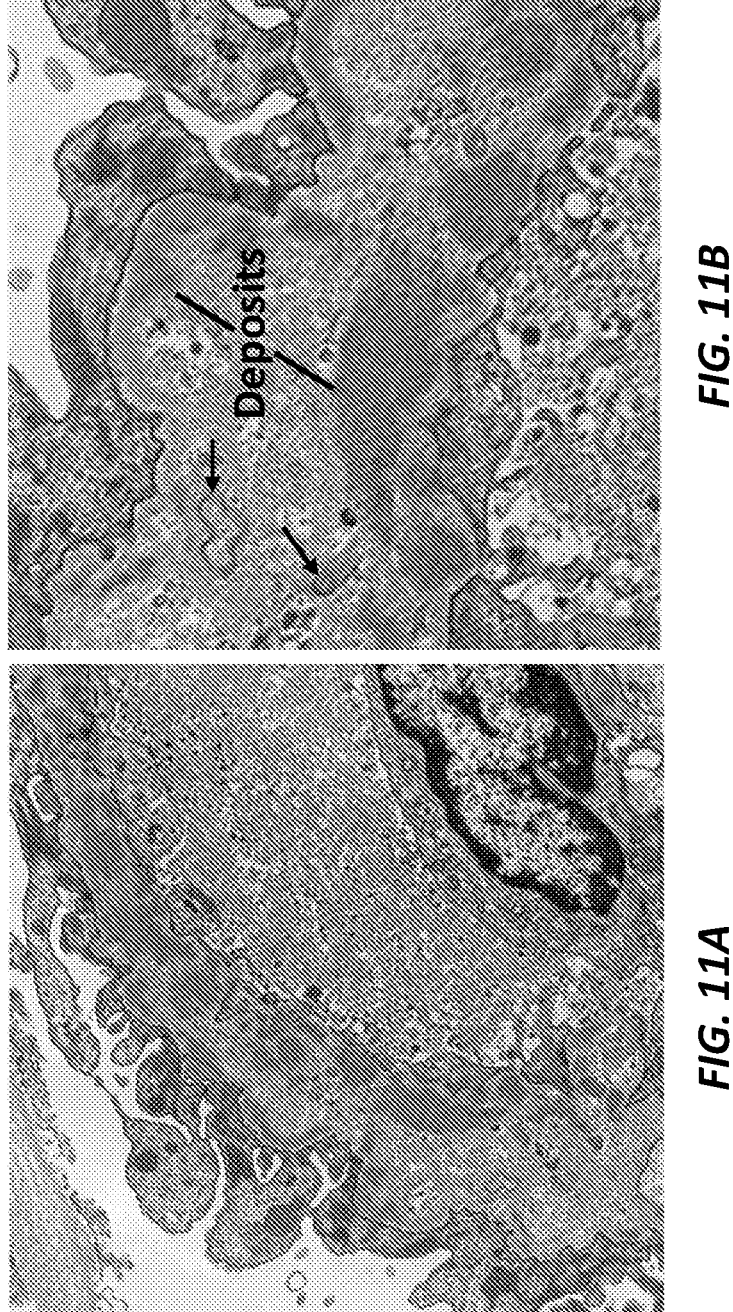
FIGS. 11A and 11B show electron micrographs of a glomerular capillary loop of a glomerulus from a Cfh knockout rat.

FIG. 11A shows electron micrographs of a glomerular capillary loop of a glomerulus from a Cfh knockout rat at the same magnification as above. FIG. 11B shows a higher magnification of FIG. 11A. The capillary loop illustrates abnormal ultrastructure where podocyte foot processes are effaced resting on a markedly thickened glomerular base-ment membrane. The GBM contains deposits of varying densities throughout the full thickness of the structure, but strongest in sub-endothelial and sub-epithelial locations. Interposition of cellular processes is also observed embed- B) had markedly thickened GBM and epithelial effacement measured by increased width and fewer foot processes. See Table 6.

TABLE 6

Detailed Ultrastructural Analysis.

| Group | Treatment | GBM Thickness (microns) | Foot Process Width (microns) | Number of Foot Processes/ Micron Length |
|---|---|---|---|---|
| A | WT + Vehicle | 0.182 | 0.369 | 2.671 |
| B | Cfh KO | 1.800 | 2.564 | 0.708 |

Group A vs. Group B, P < 0.05

GBM thickness was then assessed by image analysis. The average GBM thickness in glomeruli of wild type rats was measured at 0.182 microns (182 nm). There was a 10-fold increase in thickness of the GBM in glomeruli of Cfh knockout rats where average thickness reached 1.8 microns due to increase in matrix, electron dense deposits, and cellular inter-positioning. Differences between the two groups were statistically significant (P<0.0001). See Table 7.

TABLE 7

GBM Thickness.

Rearranged Data into Group Phenotypes (averages of each glomerulus)

| | | 100029 WT-2 | 100029 WT-3 | 100029 WT-7 | 100029 WT-8 | 100029 WT-10 | 100029 KO-1 | 100029 KO-4 | 100029 KO-5 | 100029 KO-6 | 100029 KO-9 | 100029 KO-11 |
|---|---|---|---|---|---|---|---|---|---|---|---|---|
| Avg | Glom 1 | 0.215 | 0.182 | 0.171 | 0.142 | 0.163 | 2.626 | 1.714 | 1.559 | 1.824 | 1.788 | 1.771 |
| Avg | Glom 2 | 0.244 | 0.175 | 0.188 | 0.151 | 0.173 | 1.483 | 1.199 | 2.853 | 1.952 | 1.742 | 1.032 |
| Avg | Glom 3 | 0.220 | 0.175 | 0.191 | 0.158 | 0.173 | 2.840 | 1.174 | 2.320 | 0.934 | 1.453 | 2.141 |
| | Avg | 0.226 | 0.177 | 0.184 | 0.151 | 0.170 | 2.316 | 1.362 | 2.244 | 1.570 | 1.661 | 1.648 | ded in the GBM (arrows). The endothelium is swollen with loss of fenestrae. As shown in FIG. 11B, the endothelium lining the capillary shows loss of fenestra.

Figures 12A, 12B:
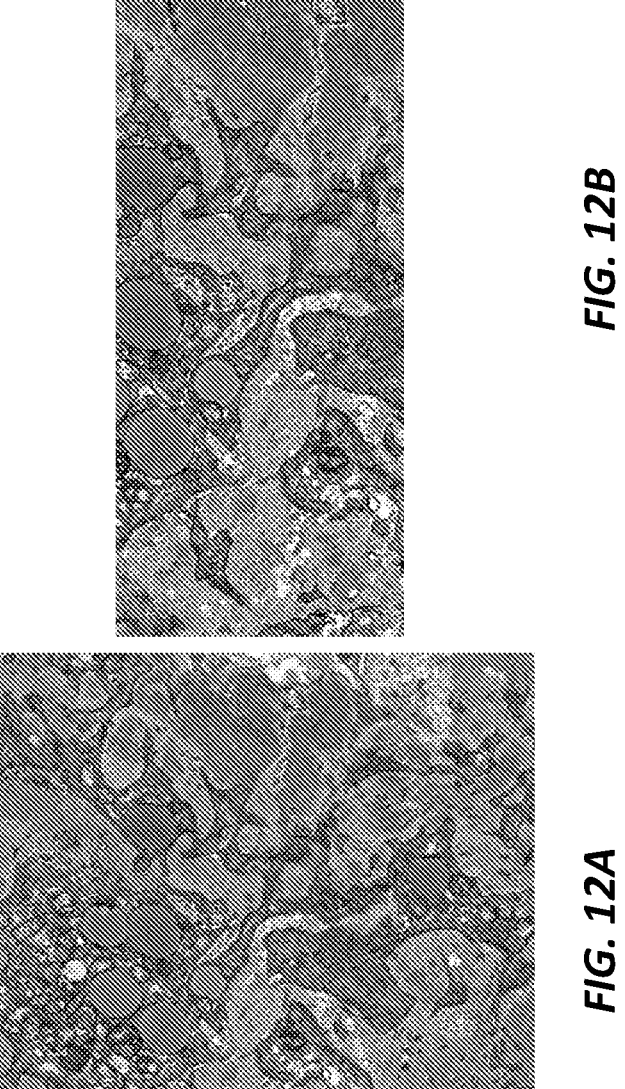
FIGS. 12A and 12B show electron micrographs of a mesangium of a glomerulus from a Cfh knockout rat.

FIG. 12A shows an electron micrograph of the mesangium from a glomerulus of a Cfh knockout rat at the same magnification as FIG. 10B. FIG. 12B shows a higher mag- Podocyte foot process width was then assessed by image analysis. The average width of foot process in glomeruli of wild type rats was measured at 0.369 microns (369 nm). There was an approximately 7-fold increase in width of foot processes in glomeruli of Cfh knockout rats where average width reached 2.564 microns. Differences between the two groups were statistically significant (P<0.0001). See Table 8.

TABLE 8

Podocyte Foot Process Width.

Rearranged Data into Group Phenotypes (averages of each glomerulus)

| | | 100029 WT-2 | 100029 WT-3 | 100029 WT-7 | 100029 WT-8 | 100029 WT-10 | 100029 KO-1 | 100029 KO-4 | 100029 KO-5 | 100029 KO-6 | 100029 KO-9 | 100029 KO-11 |
|---|---|---|---|---|---|---|---|---|---|---|---|---|
| Avg | Glom 1 | 0.373 | 0.294 | 0.366 | 0.439 | 0.315 | 1.432 | 2.422 | 1.142 | 8.836 | 4.930 | 1.336 |
| Avg | Glom 2 | 0.325 | 0.485 | 0.393 | 0.294 | 0.392 | 2.743 | 1.724 | 2.477 | 0.882 | 1.361 | 2.457 |
| Avg | Glom 3 | 0.280 | 0.328 | 0.396 | 0.463 | 0.386 | 1.986 | 1.014 | 1.477 | 6.071 | 1.190 | 2.679 |
| | Avg | 0.326 | 0.369 | 0.385 | 0.399 | 0.364 | 2.054 | 1.720 | 1.699 | 5.263 | 2.494 | 2.157 | nification of FIG. 12A. The mesangium illustrates abnormal ultrastructure where matrix is increased and embedded with electron dense deposits.

Glomeruli from wild type (WT)-vehicle (Group A) rats showed normal ultrastructure where podocytes showed uniform and regular interdigitation and width of foot processes, consistent thickness of GBM, and typical endothelial lining of the capillary loop. Glomeruli of Cfh knockout rats (Group Podocyte foot processes number/micron length was then assessed by image analysis. The average number of foot processes in glomeruli of wild type rats was measured at 2.67/micron length. There was an approximately 3.8-fold reduction in the number of foot processes covering the capillary loops in glomeruli of Cfh knockout rats where an average of 0.708 foot processes/micron length were measured. Differences between the two groups were statistically significant (P<0.0001). See Table 9.

TABLE 9

Podocyte Foot Processes Number/Micron Length.

Rearranged Data into Group Phenotypes (averages for each glomerulus)

| | | 100029 WT-2 | 100029 WT-3 | 100029 WT-7 | 100029 WT-8 | 100029 WT-10 | 100029 KO-1 | 100029 KO-4 | 100029 KO-5 | 100029 KO-6 | 100029 KO-9 | 100029 KO-11 |
|---|---|---|---|---|---|---|---|---|---|---|---|---|
| Avg | Glom 1 | 2.653 | 3.073 | 2.690 | 2.310 | 2.986 | 0.732 | 0.614 | 0.968 | 0.133 | 0.580 | 0.772 |
| Avg | Glom 2 | 2.684 | 2.272 | 2.472 | 3.091 | 2.485 | 0.641 | 0.699 | 0.480 | 1.149 | 0.826 | 0.818 |
| Avg | Glom 3 | 3.086 | 2.883 | 2.412 | 2.392 | 2.584 | 0.604 | 1.055 | 0.777 | 0.234 | 0.875 | 0.787 |
| | Avg | 2.808 | 2.742 | 2.524 | 2.598 | 2.685 | 0.659 | 0.789 | 0.742 | 0.505 | 0.760 | 0.793 |

In summary, spontaneous mortality was observed in Cfh knockout rats that occurs very early in the lifetime of the rats. Lower C3 levels in Cfh knockout rats suggests consumption via uncontrolled alternative complement pathway activation. Renal histopathology in the Cfh knockout rats is consistent with C3 and C5b-9 deposition, as well as glomerulosclerosis and tubular pathologies. Blood urea nitrogen and serum cystatin C, both of which are GFR markers, were elevated in Cfh knockout rats, suggesting kidney failure. Additionally, urinary albumin was elevated in Cfh knockout rats. Taken together, these phenotypes demonstrate that Cfh knockout rats present with C3 glomerulopathy (C3G)-like disease and show an accelerated disease course to enable more efficient and effective preclinical studies to assess new potential C3G therapeutics.

We claim:

1. A genetically modified rat with a modification consisting of an inactivated endogenous Cfh locus, wherein the genetically modified rat is homozygous for the inactivated endogenous Cfh locus, wherein the genetically modified rat has one or more symptoms of C3 glomerulopathy (C3G),
 wherein the genetically modified rat has increased blood urea nitrogen levels at an age of between about 7 weeks and about 17 weeks compared to a wild type rat at an age of between about 7 weeks and about 17 weeks,
 wherein the genetically modified rat has a decreased lifespan compared to a wild type rat, and
 wherein the median lifespan of the genetically modified rat is less than 150 days.

2. The genetically modified rat of claim 1, wherein the start codon of the endogenous Cfh locus is mutated or deleted in the inactivated endogenous Cfh locus.

3. The genetically modified rat of claim 2, wherein the start codon of the endogenous Cfh locus is deleted in the inactivated endogenous Cfh locus.

4. The genetically modified rat of claim 3, wherein the coding sequence in the first exon in the endogenous Cfh locus is deleted in the inactivated endogenous Cfh locus.

5. The genetically modified rat of claim 4, wherein the splice donor site in the first intron in the endogenous Cfh locus is deleted in the inactivated endogenous Cfh locus.

6. The genetically modified rat of claim 1, wherein the rat is a male.

7. The genetically modified rat of claim 1, wherein the rat is a female.

8. The genetically modified rat of claim 1, wherein the genetically modified rat has decreased circulatory C3 levels compared to a wild type rat.

9. The genetically modified rat of claim 8, wherein the circulatory C3 levels are less than 200 µg/mL.

10. The genetically modified rat of claim 9, wherein the circulatory C3 levels are less than 100 µg/mL.

11. The genetically modified rat of claim 8, wherein the genetically modified rat has decreased circulatory C3 levels at an age of between about 7 weeks and about 17 weeks compared to the wild type rat at an age of between about 7 weeks and about 17 weeks.

12. The genetically modified rat of claim 1, wherein the genetically modified rat has increased serum cystatin C levels or increased urinary albumin levels compared to a wild type rat.

13. The genetically modified rat of claim 12, wherein the genetically modified rat has increased serum cystatin C levels and increased urinary albumin levels compared to a wild type rat.

14. The genetically modified rat of claim 1, wherein the blood urea nitrogen levels are more than 10, more than 20, more than 30, more than 40, more than 50, more than 60, more than 70, more than 80, more than 90, or more than 100 mg/dL.

15. The genetically modified rat of claim 12, wherein the serum cystatin C levels are more than 1000, more than 1100, more than 1200, more than 1300, more than 1400, more than 1500, more than 1600, more than 1700, more than 1800, more than 1900, or more than 2000 ng/mL.

16. The genetically modified rat of claim 12, wherein:
 (I) the urinary albumin per day is more than 1000, more than 2000, more than 3000, more than 4000, more than 5000, more than 6000, more than 7000, more than 8000, more than 9000, or more than 10000 µg/day; and/or (II) the ratio of urinary albumin to urinary creatinine is more than 100, more than 200, more than 300, more than 400, more than 500, more than 600, more than 700, more than 800, more than 900, more than 1000, more than 1100, more than 1200, more than 1300, more than 1400, more than 1500, more than 1600, more than 1700, more than 1800, more than 1900, or more than 2000 µg:mg.

17. The genetically modified rat of claim 12, wherein the genetically modified rat has increased serum cystatin C levels at an age of between about 7 weeks and about 17 weeks or increased urinary albumin levels at an age of between about 7 weeks and about 17 weeks compared to the wild type rat at an age of between about 7 weeks and about 17 weeks.

18. The genetically modified rat of claim 1, wherein the genetically modified rat has increased C3 deposition in the kidneys compared to a wild type rat.

19. The genetically modified rat of claim 18, wherein the genetically modified rat has increased C3 deposition in the kidneys at an age of between about 7 weeks and about 17 weeks compared to the wild type rat at an age of between about 7 weeks and about 17 weeks.

20. The genetically modified rat of claim 1, wherein the genetically modified rat has increased C5b-9 deposition in the kidneys compared to a wild type rat.

21. The genetically modified rat of claim 20, wherein the genetically modified rat has increased C5b-9 deposition in the kidneys at an age of between about 7 weeks and about 17 weeks compared to the wild type rat at an age of between about 7 weeks and about 17 weeks.

22. The genetically modified rat of claim 1, wherein the genetically modified rat has increased glomerular pathology compared to a wild type rat.

23. The genetically modified rat of claim 22, wherein the increased glomerular pathology comprises increased glomerular basement membrane thickness, increased podocyte foot process width, or decreased podocyte foot process number compared to the wild type rat.

24. The genetically modified rat of claim 23, wherein the increased glomerular pathology comprises increased glomerular basement membrane thickness, increased podocyte foot process width, and decreased podocyte foot process number compared to the wild type rat.

25. The genetically modified rat of claim 23, wherein:
 (I) the increase in glomerular basement membrane thickness is at least 2-fold, at least 3-fold, at least 4-fold, at least 5-fold, at least 6-fold, at least 7-fold, at least 8-fold, at least 9-fold, or at least 10-fold compared to the wild type rat; and/or
 (II) the average glomerular basement membrane thickness in glomeruli in the genetically modified rat is at least 0.2, at least 0.3, at least 0.4, at least 0.5, at least 0.6, at least 0.7, at least 0.8, at least 0.9, at least 1.0, at least 1.1, at least 1.2, at least 1.3, at least 1.4, at least 1.5, at least 1.6, at least 1.7, or at least 1.8 microns.

26. The genetically modified rat of claim 23, wherein:
 (I) the increase in podocyte foot process width is at least 2-fold, at least 3-fold, at least 4-fold, at least 5-fold, at least 6-fold, or at least 7-fold compared to the wild type rat; and/or
 (II) the average width of podocyte foot process in glomeruli in the genetically modified rat is at least 0.4, at least 0.5, at least 0.6, at least 0.7, at least 0.8, at least 0.9, at least 1.0, at least 1.5, at least 2.0, or at least 2.5 microns.

27. The genetically modified rat of claim 23, wherein:

(I) the decrease in podocyte foot process number is at least 2-fold, at least 2.5-fold, at least 3-fold, at least 3.5-fold, or at least 3.8-fold compared to the wild type rat; and/or (II) the average podocyte foot process number per micron length in the genetically modified rat is less than 2.5, less than 2, less than 1.5, less than 1, less than 0.9, or less than 0.8.

28. The genetically modified rat of claim 22, wherein the genetically modified rat has increased glomerular pathology at an age of between about 7 weeks and about 17 weeks compared to the wild type rat at an age of between about 7 weeks and about 17 weeks.

\* \* \* \* \*